US012679890B2

(12) United States Patent
Li et al.

(10) Patent No.: US 12,679,890 B2
(45) Date of Patent: *Jul. 14, 2026

(54) ANTI-CLAUDIN 18 ANTIBODIES AND METHODS OF USE THEREOF

(71) Applicant: CSPC Megalith Biopharmaceutical Co., Ltd., Hebei (CN)

(72) Inventors: Han Li, Newtown, PA (US); Ming Lei, Princeton, NJ (US); Yi Pei, Paoli, PA (US); Haichun Huang, Fremont, CA (US)

(73) Assignee: CSPC Megalith Biopharmaceutical Co., Ltd., Hebei (CN)

( * ) Notice: Subject to any disclaimer, the term of this patent is extended or adjusted under 35 U.S.C. 154(b) by 920 days.

This patent is subject to a terminal disclaimer.

(21) Appl. No.: 17/846,709

(22) Filed: Jun. 22, 2022

(65) Prior Publication Data

US 2023/0067757 A1    Mar. 2, 2023

Related U.S. Application Data

(63) Continuation of application No. 17/427,909, filed as application No. PCT/US2020/016459 on Feb. 3, 2020, now Pat. No. 11,407,828.

(60) Provisional application No. 62/891,925, filed on Aug. 26, 2019, provisional application No. 62/800,359, filed on Feb. 1, 2019.

(51) Int. Cl.
*C07K 16/28*        (2006.01)

(52) U.S. Cl.
CPC .......... *C07K 16/28* (2013.01); *C07K 2317/52* (2013.01); *C07K 2317/565* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 6,602,684 | B1 | 8/2003 | Umaña et al. |
| 7,355,008 | B2 | 4/2008 | Stavenhagen et al. |
| 7,362,497 | B2 | 4/2008 | Hodder et al. |
| 7,939,637 | B2 | 5/2011 | Raeber |
| 8,003,774 | B2 | 8/2011 | Stavenhagen et al. |
| 8,039,592 | B2 | 10/2011 | Lazar et al. |
| 8,067,232 | B2 | 11/2011 | Kanda et al. |
| 8,093,359 | B2 | 1/2012 | Lazar et al. |
| 8,168,427 | B2 | 5/2012 | Sahin et al. |
| 8,217,147 | B2 | 7/2012 | Stavenhagen et al. |
| 8,586,047 | B2 | 11/2013 | Sahin et al. |
| 8,637,012 | B2 | 1/2014 | Sahin et al. |
| 8,652,466 | B2 | 2/2014 | Stavenhagen et al. |
| 8,697,071 | B2 | 4/2014 | Stavenhagen et al. |
| 9,044,382 | B2 | 6/2015 | Türeci et al. |
| 9,212,228 | B2 | 12/2015 | Sahin et al. |
| 9,499,609 | B2 | 11/2016 | Sahin et al. |
| 9,708,408 | B2 | 7/2017 | Stavenhagen et al. |
| 9,751,934 | B2 | 9/2017 | Sahin et al. |
| 9,775,785 | B2 | 10/2017 | Türeci et al. |
| 10,017,564 | B2 | 7/2018 | Sahin et al. |
| 10,053,512 | B2 | 8/2018 | Sahin et al. |
| 10,314,890 | B2 | 6/2019 | Sahin et al. |
| 10,421,817 | B1 | 9/2019 | Hu et al. |
| 10,738,108 | B2 | 8/2020 | Sahin et al. |
| 11,059,887 | B2 | 7/2021 | Li |
| 11,098,118 | B2 | 8/2021 | Li |
| 11,111,295 | B2 | 9/2021 | Wang et al. |
| 11,407,828 | B2 * | 8/2022 | Li ........................ C07K 16/28 |
| 2008/0050818 | A1 | 2/2008 | Dam |
| 2010/0080813 | A1 | 4/2010 | Lanzavecchia |
| 2011/0020369 | A1 | 1/2011 | De Waal Malefyt |
| 2011/0300156 | A1 | 12/2011 | Verpolegen |
| 2013/0096282 | A1 | 4/2013 | Neville |
| 2013/0209475 | A1 | 8/2013 | Richards |
| 2013/0251728 | A1 | 9/2013 | Harp |
| 2014/0056903 | A1 | 2/2014 | Croll |
| 2014/0056907 | A1 | 2/2014 | Macdonald |
| 2015/0252103 | A1 | 9/2015 | Sahin |
| 2016/0068591 | A1 | 3/2016 | Anderson |
| 2016/0130341 | A1 | 5/2016 | Johns |
| 2016/0176963 | A1 | 6/2016 | Maurer et al. |
| 2017/0210799 | A1 | 7/2017 | Anderson |
| 2017/0368168 | A1 | 12/2017 | Van Dijk |
| 2018/0117174 | A1 | 5/2018 | Sahin et al. |
| 2018/0237511 | A1 | 8/2018 | Beil |

(Continued)

FOREIGN PATENT DOCUMENTS

| | | |
|---|---|---|
| EP | 208049593 | 11/2018 |
| EP | 3483182 A1 | 5/2019 |

(Continued)

OTHER PUBLICATIONS

Arnold, A., et al. "Prognostic impact of Claudin 18.2 in gastric and esophageal adenocarcinomas." *Clinical and Translational Oncology* 22.12 (2020): 2357-2363.

Dottermusch, Matthias, et al. "Expression of the potential therapeutic target claudin-18.2 is frequently decreased in gastric cancer: results from a large Caucasian cohort study." *Virchows Archiv* 475.5 (2019): 563-571.

(Continued)

*Primary Examiner* — Ruixiang Li

(74) *Attorney, Agent, or Firm* — Morse, Barnes-Brown & Pendleton PC; Lisa M. Warren, Esq.; Erin E. Bryan, Esq.

(57)        ABSTRACT

Antibodies that specifically bind to the human tight junction molecule CLDN18.2 and have functional properties that make them suitable for use in antibody-based immunotherapies of a disease associated with aberrant expression of CLDN18.2 are disclosed.

10 Claims, 35 Drawing Sheets

Specification includes a Sequence Listing.

(56) References Cited

U.S. PATENT DOCUMENTS

| | | |
|---|---|---|
| 2018/0256713 A1 | 9/2018 | Yan |
| 2018/0282410 A1 | 10/2018 | Ast |
| 2018/0339042 A1 | 11/2018 | Wang |
| 2019/0023788 A1 | 1/2019 | Rønn |
| 2019/0233511 A1 | 8/2019 | Wang et al. |
| 2020/0040101 A1 | 2/2020 | Lu et al. |
| 2020/0055932 A1 | 2/2020 | Dahlhoff et al. |
| 2020/0207857 A1 | 7/2020 | Zhu et al. |
| 2020/0399364 A1 | 12/2020 | Wang et al. |
| 2021/0009686 A1 | 1/2021 | Song et al. |
| 2021/0230272 A1 | 7/2021 | Liu |
| 2021/0261658 A1 | 8/2021 | Wu et al. |
| 2021/0380680 A1 | 12/2021 | Li et al. |
| 2021/0403552 A1 | 12/2021 | Du et al. |
| 2022/0185880 A1 | 6/2022 | Wang et al. |
| 2023/0272063 A1 | 8/2023 | Li et al. |

FOREIGN PATENT DOCUMENTS

| | | |
|---|---|---|
| EP | 3878863 A1 | 9/2021 |
| EP | 3904386 A1 | 11/2021 |
| EP | 3929214 A1 | 12/2021 |
| EP | 3950716 A1 | 2/2022 |
| EP | 3960766 A1 | 3/2022 |
| WO | WO-2008/145338 A2 | 12/2008 |
| WO | WO-2011086001 A1 | 7/2011 |
| WO | WO-2011/107520 A1 | 9/2011 |
| WO | WO-2016/166122 A1 | 10/2016 |
| WO | WO-2017059095 A1 | 4/2017 |
| WO | 2018/006882 A1 | 1/2018 |
| WO | WO-2018175740 A1 | 9/2018 |
| WO | WO-2018195427 A2 | 10/2018 |
| WO | WO-2020200196 A1 | 10/2020 |
| WO | WO-2020205331 A1 | 10/2020 |
| WO | WO-2020211792 A1 | 10/2020 |
| WO | WO-2020228447 A1 | 11/2020 |
| WO | WO-2021008463 A1 | 1/2021 |
| WO | WO-2021011885 A1 | 1/2021 |
| WO | WO-2021032157 A1 | 2/2021 |

OTHER PUBLICATIONS

Gabrail, Nashat Y., et al. "A phase I clinical trial to evaluate the safety, tolerability, and pharmacokinetics of TST001 in patients with locally advanced or metastatic solid tumors." (2022): TPS375-TPS375.

Hewitt, Kyle J., Rachana Agarwal, and Patrice J. Morin. "The claudin gene family: expression in normal and neoplastic tissues." *BMC cancer* 6.1 (2006): 1-8.

Hong, Jung Yong, et al. "Claudin 18.2 expression in various tumor types and its role as a potential target in advanced gastric cancer." *Translational Cancer Research* 9.5 (2020): 3367-3374.

Jiang, Hua, et al. "Claudin18.2-specific chimeric antigen receptor engineered T cells for the treatment of gastric cancer." *JNCI: Journal of the National Cancer Institute* 111.4 (2019): 409-418.

Lei, et al., "NBL-015, a next-generation fully human anti-claudin 18.2 antibody with enhanced ADCC, CDC and ADCP for treating gastric and pancreatic cancers," AACR 2020, Poster 5195, 1 page, www.novarockbio.com.

Moentenich, Valeska, et al. "Claudin 18.2 expression in esophageal adenocarcinoma and its potential impact on future treatment strategies." *Oncology Letters* 19.6 (2020): 3665-3670.

Morin, Patrice J. "Claudin proteins in human cancer: promising new targets for diagnosis and therapy." *Cancer research* 65.21 (2005): 9603-9606.

Paluri, Ravi K., et al. "Second-line treatment for metastatic pancreatic cancer." *Clin Adv Hematol Oncol* 18 (2020): 106-115.

Rataj, Felicitas, et al. "High-affinity CD16-polymorphism and Fc-engineered antibodies enable activity of CD16-chimeric antigen receptor-modified T cells for cancer therapy." *British journal of cancer* 120.1 (2019): 79-87.

Rohde, Christoph, et al. "Comparison of Claudin 18.2 expression in primary tumors and lymph node metastases in Japanese patients with gastric adenocarcinoma." *Japanese Journal of Clinical Oncology* 49.9 (2019): 870-876.C13.

Sadilkova, Lenka Kyrych, et al. "SO-N102, a novel CLDN18.2-targeting antibody-drug conjugate with strong anti-tumor effect in various solid tumors expressing low target levels." (2021): 1204-1204.

Sahin, Ugur, et al. "Claudin-18 splice variant 2 is a pan-cancer target suitable for therapeutic antibody development." *Clinical Cancer Research* 14.23 (2008): 7624-7634.

Sahin, U., et al. "Fast: A randomised phase II study of zolbetuximab (IMAB362) plus EOX versus EOX alone for first-line treatment of advanced CLDN18. 2-positive gastric and gastro- oesophageal adenocarcinoma." *Annals of Oncology* 32.5 (2021): 609-619.

Singh, Prabhsimranjot, Sudhamshi Toom, and Yiwu Huang. "Anti-claudin 18.2 antibody as new targeted therapy for advanced gastric cancer." *Journal of hematology & oncology* 10.1 (2017): 1-5.

Teng, Fei, et al. "The precli nical characterization of TST001, a novel humanized anti-claudinl 8. 2 mAb with enhanced binding affinity and anti-tumor activity." (2020): 5183-5183.

Türeci, O., et al. "A multicentre, phase IIa study of zolbetuximab as a single agent in patients with recurrent or refractory advanced adenocarcinoma of the stomach or lower oesophagus: the MONO study." *Annals of Oncology* 30.9 (2019): 1487-1495.

Wöll, Stefan, et al. "Claudin 18.2 is a target for IMAB362 antibody in pancreatic neoplasms." *International journal of cancer* 134.3 (2014): 731-739.

Zhan, Xianbao, et al. "Phase I trial of Claudin 18.2-specific chimeric antigen receptor T cells for advanced gastric and pancreatic adenocarcinoma." (2019).

Zhang, Jianwei, Ruilan Dong, and Lin Shen. "Evaluation and reflection on claudin 18.2 targeting therapy in advanced gastric cancer." *Chinese Journal of Cancer Research* 32.2 (2020): 263.

Zhu, Guoyun, et al. "Targeting CLDN18. 2 by CDS bispecific and ADC modalities for the treatments of gastric and pancreatic cancer." *Scientific Reports* 9.1 (2019): 1-11.

International Search Report issued in International Application No. PCT/US2020/016459 dated Jul. 24, 2020.

Notice of Allowance of U.S. Appl. No. 17/427,909, Dated Mailed: Apr. 12, 2022.

Kellner et al., "Modulating Cytotoxic Effector Functions by Fc Engineering to Improve Cancer Therapy," Transfusion Medicine and Hemotherapy 44(5):327-336 (2017).

Heinz et al., "Preclinical evaluation of the anti-CLDN18.2 antibody, IMAB362, in pancreatic carcinoma", Annals of Oncology, vol. 28, Suppl 5, pp. 126-127, abstract 376P (2017).

Kreuzberg et al., "Preclinical characterization of IMAB362-vcMMAE, an anti-CLDN18.2 antibody-drug conjugate", Annals of Oncology, vol. 28, Suppl 5, p. 126, abstract 377P (2017).

Non-Final Office Action in U.S. Appl. No. 17/864,335 dated May 6, 2025.

* cited by examiner

Ms1_VH SEQ ID NO: 1
EIQLQQSGPELVKPGASVKVSCKASGYAYTRYNMYWVKQSHGKSLEWIGYIDPYNGGTNYN
QKFKGKATLTVDKSSSTAYMHLNSLTSEDSAVYYCARGGYYGNAMDYWGQGTSVTVSS

| GYAYTRYN | IDPYNGGT | ARGGYYGNAMDY |
|---|---|---|
| SEQ:47 | SEQ:48 | SEQ:49 |

Ms1_VL SEQ ID NO: 2
DIVMTQSPSSLTVTAGEKVTMSCKSSQSLLNSGNQKNYLTWYQQKPGQPPKLLIYWASTRES
GVPDRFTGSGSGTDFTLTISSVQAEDLSIYYCQSNYIYPFTFGAGTTLELQ

| QSLLNSGNQKNY | WAS | QSNYIYPFT |
|---|---|---|
| SEQ:50 | SEQ:51 | SEQ:52 |

Ms2_VH SEQ ID NO: 3
QVQLKESGPGLVAPSQSLSITCTVSGFSLTSYGVHWVRQPPGKGLEWLGVIWAGGSTNYNSA
LMSRLSISKDNSKSQVFLKMNSLQTDDTAMYYCARDFTTATGFDYWGQGTTLTVSS

| GFSLTSYG | IWAGGST | ARDFTTATGFDY |
|---|---|---|
| SEQ:53 | SEQ:54 | SEQ:55 |

Ms2_VL SEQ ID NO: 4
DIVMTQSPSSLSVSAGEKVTMSCKSSQSLLNSGNQKNYLAWYQQKPGQPPKLLIYGASTRES
GVPDRFTGSGSGTDFTLTISSVQAEDLAVYYCQNDHSYPFTFGSGTKLEIK

| QSLLNSGNQKNY | GAS | QNDHSYPFT |
|---|---|---|
| SEQ ID:56 | SEQ ID:57 | SEQ ID:58 |

Ms3-VH1 SEQ ID NO: 5
EVMLVESGGGIVKPGGSLKLSCAASGFTLSSYTMSWVRQTPERRLEWVATIIIGGSYTYYPDS
VKGRFTISRDNAKNTLYLQMSSLRSEDTAMYYCARQGYGNSFPYWGQGTLVTVSA

| GFTLSSYT | IIIGGSYT | ARQGYGNSFPY |
|---|---|---|
| SEQ ID:59 | SEQ ID:60 | SEQ ID:61 |

Ms3_VL SEQ ID NO: 6
DIVMTQSPSSLTVTAGEKVTMSCKSSQSLLNSGNQKNYLTWYQQKPGQPPKLLIYWASTRES
GVPDRFTGSGSGTDFTLTISSVQAEDLAVYYCQNDYSYPFTFGSGTKLEIK

| QSLLNSGNQKNY | WAS | QNDYSYPFT |
|---|---|---|
| SEQ ID:62 | SEQ ID:63 | SEQ ID:64 |

FIG. 1

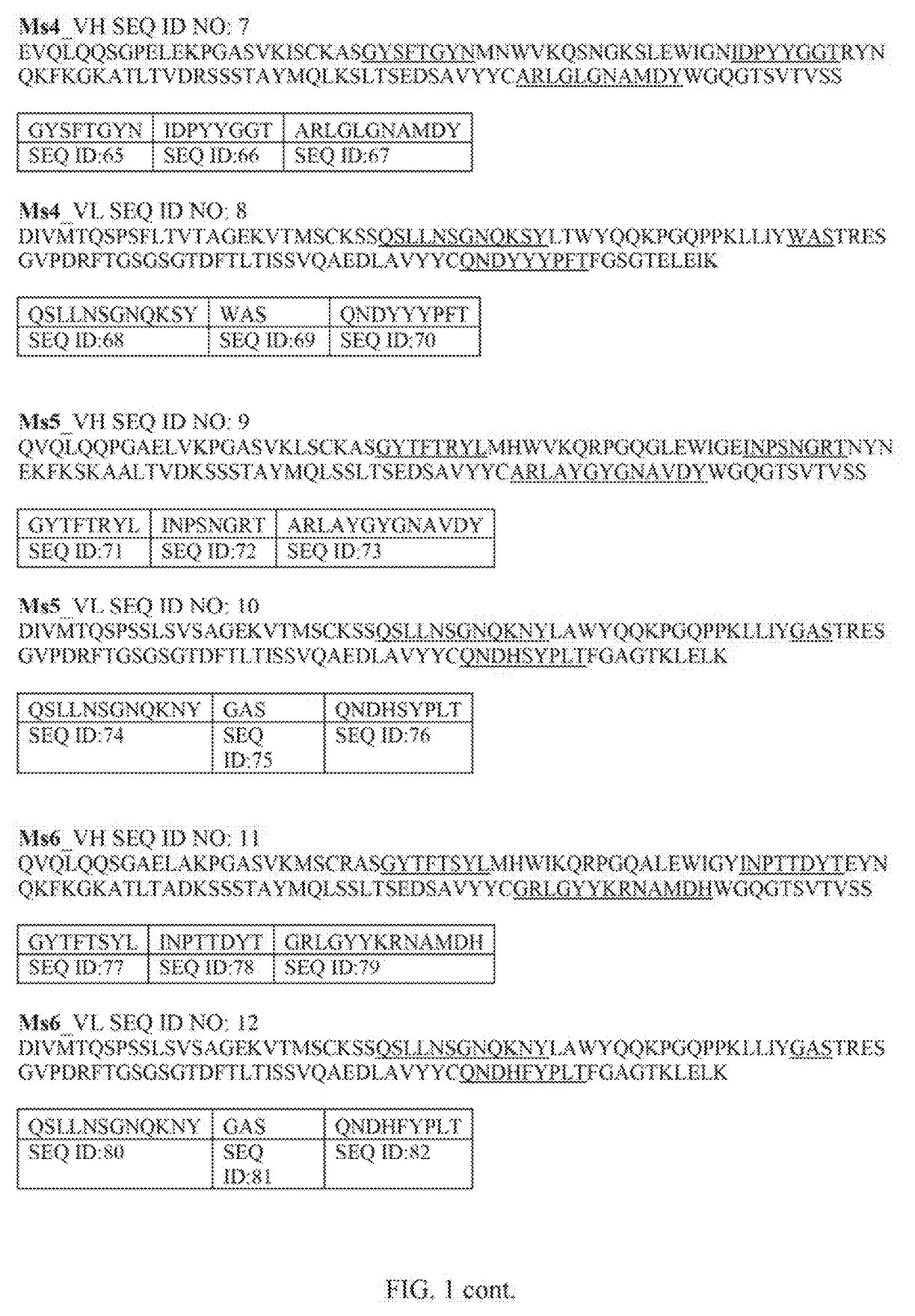

Ms4_VH SEQ ID NO: 7
EVQLQQSGPELEKPGASVKISCKASGYSFTGYNMNWVKQSNGKSLEWIGNIDPYYGGTRYN
QKFKGKATLTVDRSSSTAYMQLKSLTSEDSAVYYCARLGLGNAMDYWGQGTSVTVSS

| GYSFTGYN | IDPYYGGT | ARLGLGNAMDY |
|---|---|---|
| SEQ ID:65 | SEQ ID:66 | SEQ ID:67 |

Ms4_VL SEQ ID NO: 8
DIVMTQSPSFLTVTAGEKVTMSCKSSQSLLNSGNQKSYLTWYQQKPGQPPKLLIYWASTRES
GVPDRFTGSGSGTDFTLTISSVQAEDLAVYYCQNDYYYPFTFGSGTELEIK

| QSLLNSGNQKSY | WAS | QNDYYYPFT |
|---|---|---|
| SEQ ID:68 | SEQ ID:69 | SEQ ID:70 |

Ms5_VH SEQ ID NO: 9
QVQLQQPGAELVKPGASVKLSCKASGYTFTRYLMHWVKQRPGQGLEWIGEINPSNGRTNYN
EKFKSKAALTVDKSSSTAYMQLSSLTSEDSAVYYCARLAYGYGNAVDYWGQGTSVTVSS

| GYTFTRYL | INPSNGRT | ARLAYGYGNAVDY |
|---|---|---|
| SEQ ID:71 | SEQ ID:72 | SEQ ID:73 |

Ms5_VL SEQ ID NO: 10
DIVMTQSPSSLSVSAGEKVTMSCKSSQSLLNSGNQKNYLAWYQQKPGQPPKLLIYGASTRES
GVPDRFTGSGSGTDFTLTISSVQAEDLAVYYCQNDHSYPLTFGAGTKLELK

| QSLLNSGNQKNY | GAS | QNDHSYPLT |
|---|---|---|
| SEQ ID:74 | SEQ ID:75 | SEQ ID:76 |

Ms6_VH SEQ ID NO: 11
QVQLQQSGAELAKPGASVKMSCRASGYTFTSYLMHWIKQRPGQALEWIGYINPTTDYTEYN
QKFKGKATLTADKSSSTAYMQLSSLTSEDSAVYYCGRLGYYKRNAMDHWGQGTSVTVSS

| GYTFTSYL | INPTTDYT | GRLGYYKRNAMDH |
|---|---|---|
| SEQ ID:77 | SEQ ID:78 | SEQ ID:79 |

Ms6_VL SEQ ID NO: 12
DIVMTQSPSSLSVSAGEKVTMSCKSSQSLLNSGNQKNYLAWYQQKPGQPPKLLIYGASTRES
GVPDRFTGSGSGTDFTLTISSVQAEDLAVYYCQNDHFYPLTFGAGTKLELK

| QSLLNSGNQKNY | GAS | QNDHFYPLT |
|---|---|---|
| SEQ ID:80 | SEQ ID:81 | SEQ ID:82 |

FIG. 1 cont.

Ms7.2_VH1 SEQ ID NO: 13
EVKLVESGGDLVQPGGSLRLSCTTPGFTFSDFYMEWVRQPPGKRLEWIAASRNKANDYTTE
NSASVKGRFIVSRDTSQSILYLQMNALRAEDTAIYYCARDACPWDWFAYWGQGTLVTVSA

| GFTFSDFY | SRNKANDYTT | ARDACPWDWFAY |
|---|---|---|
| SEQ ID:83 | SEQ ID:84 | SEQ ID:85 |

Ms7.2_VL SEQ ID NO: 14
DIVMTQSPSSLTVTAGEKVTMSCKSSQSLLNSGNQKNYLTWYQQKPGQPPKLLIYWASTRES
GVPDRFTGSGSGTDFTLTISSVQAEDLAVYYCQNDYSYPFTFGSGTKLEIK

| QSLLNSGNQKNY | WAS | QNDYSYPFT |
|---|---|---|
| SEQ ID:86 | SEQ ID:87 | SEQ ID:88 |

Ms8_VH SEQ ID NO: 15
EIQLQQSGPELVKPGASVKVSCKASDYAFTRYNMYWVKQSHGKSLEWIGYIDPYNGGTNYN
QKFKGKATLTVDKSSSTAYMHLNSLTSEDSAVYYCARGGYYGNAMDYWGQGTSVTVSS

| DYAFTRYN | IDPYNGGT | ARGGYYGNAMDY |
|---|---|---|
| SEQ ID:89 | SEQ ID:90 | SEQ ID:91 |

Ms8_VL SEQ ID NO: 16
DIVMTQSPSSLTVTAGEKVTMSCKSSQSLLNSGNQKNYLTWYQQKPGQPPQLLIYWASTRES
GVPDRFTGSGSGTDFTLTISSVQAEDLSIYYCQSNYIYPFTFGAGTTLELQ

| QSLLNSGNQKNY | WAS | QSNYIYPFT |
|---|---|---|
| SEQ ID:92 | SEQ ID:93 | SEQ ID:94 |

Ms9_VH SEQ ID NO: 17
QVQLQQPGAEPVKPGASVKLSCKASGYTFTSYLIHWVKXRPGQGLEWIGEIIPSNGRTTYNE
KFKTKASLTVDKSSSTAYMQLSSLTSEDSAVYYCARLAYGYGNAVDYWGQGTSVTVSS

| GYTFTSYL | IIPSNGRT | ARLAYGYGNAVDY |
|---|---|---|
| SEQ ID:95 | SEQ ID:96 | SEQ ID:97 |

Ms9_VL SEQ ID NO: 18
DIVMTQSPSSLSVSAGEKVTMSCKSSQSLLNSGNQKNYLAWYQQKPGQPPKLLIYGASTRDS
GVPDRFTGSGSGTDFTLTISSVQAEDLAVYYCQNDHTYPLTFGAGTKLELK

| QSLLNSGNQKNY | GAS | QNDHTYPLT |
|---|---|---|
| SEQ ID:98 | SEQ ID:99 | SEQ ID:100 |

FIG. 1 cont.

Ms10_VH SEQ ID NO: 19
EVQLQQSGPELEKPGASVKISCKASGYSFTGYKMNWVKQSNGKSLEWIGHIDPYYGGPRYN
KKFMGKATLTVDRSSSTAYMQLKSLTSEDSAVYYCARLDYGNSFAYWGQGTLVTVSA

| GYSFTGYK | IDPYYGGP | ARLDYGNSFAY |
|---|---|---|
| SEQ ID:101 | SEQ ID:102 | SEQ ID:103 |

Ms10_VL SEQ ID NO: 20
DIVMTQSPSSLSVSAGEKVTMSCKSSQSLLNSGNQKNYLAWYQQKPGQPPKLLIYGASTRES
GVPDRFTGSGSGTDFTLTISSVQAEDLAVYYCQNDHSYPFTFGGGTKLEIK

| QSLLNSGNQKNY | GAS | QNDHSYPFT |
|---|---|---|
| SEQ ID:104 | SEQ ID:105 | SEQ ID:106 |

Ms11_VH SEQ ID NO:21
QVQLQQSGAELVKPGASVKMSCKAFGYTFTTYSIEWMKQNHGKSLEWIGNFRPYNDDTKC
NEKFKGKAKLTVEKSSSTVYLELSRLTSDDSAVYYCARGSYGNSFAYWGQGTLVTVSA

| GYTFTTYS | FRPYNDDT | ARGSYGNSFAY |
|---|---|---|
| SEQ ID:107 | SEQ ID:108 | SEQ ID:109 |

Ms11_VL SEQ ID NO:22
DIVMTQSPSSLSVSAGEKVTMSCKSSQSLLNSGNQKNYLAWYQQKPGQPPKLLIYGASTRES
GVPDRFTGSGSGTDFTLTISSVQAEDLAVYYCQNDHSYPFTFGSGTKLEIK

| QSLLNSGNQKNY | GAS | QNDHSYPFT |
|---|---|---|
| SEQ ID:110 | SEQ ID:111 | SEQ ID:112 |

Ms12_VH SEQ ID NO: 23
EIQLQQSGPELVKPGASVKVSCKASGYAFASYKMYWVKQSHGKSLEWIGYIDPYNGVTSYN
QKFRGKATLTVDKSSSTAYMHLNSLTSEDSAVYYCARGAYYGNSFDYWGQGTTLTVSS

| GYAFASYK | IDPYNGVT | ARGAYYGNSFDY |
|---|---|---|
| SEQ ID:113 | SEQ ID:114 | SEQ ID:115 |

Ms12_VL SEQ ID NO: 24
DIVMTQSPSSLTVTAGEKVTMSCKSSQSLLNSGNQKNYLTWYQQQPGQPPKLLIYWASTRES
GVPDRFTGSGSGTDFTLTISSVQAVDLAVYYCQSAYSFPYTFGGGTKLEVK

| QSLLNSGNQKNY | WAS | QSAYSFPYT |
|---|---|---|
| SEQ ID:116 | SEQ ID:117 | SEQ ID:118 |

FIG. 1 cont.

Ms13_VH SEQ ID NO: 25

EVQLQQSGPELVKPGASVKMSCKAS<u>GYTFTRYI</u>MHWVKQKPGQGLEWIGY<u>FNPYNDDS</u>KTS
EKFKGKATLTSDKSSSTAYMEINSLTSEDSAVYYC<u>AKLRQERIAY</u>WGQGTLVTVSA

| GYTFTRYI | FNPYNDDS | AKLRQERIAY |
|---|---|---|
| SEQ ID:119 | SEQ ID:120 | SEQ ID:121 |

Ms13_VL SEQ ID NO: 26

DIQMNQSPSSLSASLGDTITITCHAS<u>QNIDVW</u>LSWYQQKPGNFPKLLIY<u>KAS</u>NLHTGVPSRFSGSGSGTG
FTLTISSLQPEDIATYYC<u>QQGQSYPLT</u>FGAGTKLELK

| QNIDVW | KAS | QQGQSYPLT |
|---|---|---|
| SEQ ID:122 | SEQ ID:123 | SEQ ID:124 |

Ms14_VH SEQ ID NO: 27

EVQLQQSGPELVKPGASVKMSCKAS<u>GYTFTRYI</u>IHWVKQKPGQGLEWIGY<u>FNPYNDDS</u>KNN
EKFKGKATLTSDKSSSTAYMEISSLTSEDSAVYYC<u>AKLRQERIAY</u>WGQGTLVTVSA

| GYTFTRYI | FNPYNDDS | AKLRQERIAY |
|---|---|---|
| SEQ ID:125 | SEQ ID:126 | SEQ ID:127 |

Ms14_VL SEQ ID NO: 28

DIQMNQSPSSLSASLGDTITITCHVS<u>QNIDVW</u>LSWYQQKPGNIPKLLIY<u>KAS</u>NLHTGVPSRFSGSGSGTG
FTLTISSLQPEDIATYYC<u>QQGQSYPLT</u>FGAGTKLELK

| QNIDVW | KAS | QQGQSYPLT |
|---|---|---|
| SEQ ID:128 | SEQ ID:129 | SEQ ID:130 |

Ms15_VH SEQ ID NO: 29

EVQLQQSGPELVRPGASVKMSCRAS<u>GYTFTNYI</u>IHWVKQKPGQGLEWIGY<u>FNPYNDGT</u>KYN
EIFKDKATLTSDKSSSTAYMELRSLTSEDSAVYYC<u>AKLRQERIAY</u>WGQGTLVTVSA

| GYTFTNYI | FNPYNDGT | AKLRQERIAY |
|---|---|---|
| SEQ ID:131 | SEQ ID:132 | SEQ ID:133 |

Ms15_VL SEQ ID NO: 30

DIQMNQSPSSLSASLGDTITITCHVS<u>QNIDVW</u>LSWYQQKPGNIPKLLIY<u>KAS</u>NLHTGVPSRFSGSGSGTG
FTLTISSLQPEDIATYYC<u>QQGQSYPLT</u>FGAGTKLELK

| QNIDVW | KAS | QQGQSYPLT |
|---|---|---|
| SEQ ID:134 | SEQ ID:135 | SEQ ID:136 |

FIG. 1 cont.

Ms16_VH SEQ ID NO: 31
QVQLQQSGAELVRPGTSVKVSCKASGYAFTNYLIEWIKQRPGQGLEWIGVINPGSGGTNYNE
KLKGKATLTADKSSSTAYMQLSSLTSGDSAVYFCARYVKGNALDYWGQGTSVTVSS

| GYAFTNYL | INPGSGGT | ARYVKGNALDY |
|---|---|---|
| SEQ ID:137 | SEQ ID:138 | SEQ ID:139 |

Ms16_VL SEQ ID NO: 32
DIVMTQSPSSLTVTAGEKVTLSCKSSQSLFNSGNQKNYLTWYQQKPGQPPKLLIYWASTRESGVPDRFT
GSGSGTDFTLTISSVQAEDLAIYYCQNSYSFPLTFGAGTKLELT

| QSLFNSGNQKNY | WAS | QNSYSFPLT |
|---|---|---|
| SEQ ID:140 | SEQ ID:141 | SEQ ID:142 |

Ms17_VH SEQ ID NO: 33
EVQLQQSGPELVKPGASVKMSCKASGYTFTNYIIHWVKQKPGQGLEWIGYFNPYNDGIEYSE
KFKGKATLTSDKSSSTAYMELSSLTSEDSAVYYCSKLRQERFAYWGQGTLVTVSA

| GYTFTNYI | FNPYNDGI | SKLRQERFAY |
|---|---|---|
| SEQ ID:143 | SEQ ID:144 | SEQ ID:145 |

Ms17_VL SEQ ID NO: 34
DIQMNQSPSSLSASLGDTITITCHASQNINVWLSWYQQKPGNIPKLLIYKASNLHTGVPSRFSGSGSGTG
FTLTISSLQPEDIATYYCQQGQSYPLTFGAGTKLELK

| QNINVW | KAS | QQGQSYPLT |
|---|---|---|
| SEQ ID:146 | SEQ ID:147 | SEQ ID:148 |

Ms18_VH SEQ ID NO: 35
QVQLKESGPGLVAPSQSLSITCTVSGFSLISYGVHWVRQPPGKGLEWLGVIWAGGNTNYNSA
LMSRLSISKDNSKSQVFLKMNSLQTDDTAMYYCARVYYGNSFDYWGQGTTLTVSS

| GFSLISYG | IWAGGNT | ARVYYGNSFDY |
|---|---|---|
| SEQ ID:149 | SEQ ID:150 | SEQ ID:151 |

Ms18_VL SEQ ID NO: 36
DIVMTQSPSSLTVTAGEKVTMSCKSSQSLLNSGNQKNYLTWYQQKPGQPPKLLIYWASTRQSGVPDRF
TGSGSGTDFSLTISSVQAEDLAVYYCHNDYTYPLTFGAGTKLELK

| QSLLNSGNQKNY | WAS | HNDYTYPLT |
|---|---|---|
| SEQ ID:152 | SEQ ID:153 | SEQ ID:154 |

FIG. 1 cont.

Ms19_VH SEQ ID NO: 37

EVQLQQSGPELVKPGASVKMSCKAS GYTFTSYVIHWVKQKPGQGLEWIGY INPYNDGSKYN
EKFKGKATLTDKSSSTAYMELSSLTSEDSAVYYC AREGYGKRNALDY WGQGTSVTVSS

| GYTFTSYV | INPYNDGS | AREGYGKRNALDY |
|---|---|---|
| SEQ ID:155 | SEQ ID:156 | SEQ ID:157 |

Ms19_VL SEQ ID NO: 38

DIVMTQSPSSLSVSAGERVTMSCKSS QSLLNSGNQKNY LAWYQQKPGQPPKLLIY GAS TRESGVPDRFT
GSGSGTDFTLIISSVQVEDLAVYYC QNDHFYPLT FGAGTKLELK

| QSLLNSGNQKNY | GAS | QNDHFYPLT |
|---|---|---|
| SEQ ID:158 | SEQ ID:159 | SEQ ID:160 |

Ms20_VH SEQ ID NO: 39

EIQLQQSGPELMKPGASVKISCKAS GYSFTSYYMHWVKQSHGKSLEWIGY FDPYNGGTNYN
QKFKGKATLTADKSSSTAYMHLSSLTSEDSAVYYC ACYRFFAV WGAGTTVTVSS

| GYSFTSYY | FDPYNGGT | ACYRFFAV |
|---|---|---|
| SEQ ID:161 | SEQ ID:162 | SEQ ID:163 |

Ms20_VL SEQ ID NO: 40

DIVMTQSPSSLTVTAGEKVTMSCKSS QSLLNSGNQKNY LTWYQQKPGQPPKLLIY WAS TRESGVPDRF
TGSGSGTDFTLTISSVQAEDLAVYYC QNDYSYPLT FGAGTKLELK

| QSLLNSGNQKNY | WAS | QNDYSYPLT |
|---|---|---|
| SEQ ID:164 | SEQ ID:165 | SEQ ID:166 |

Ms21_VH SEQ ID NO: 41

DVQLVESGGGLVQPGGSRKLSCAAS GFTFSTFGMHWVRQAPEKGLEWVAF INGDSSSIYYA
DTVKGRFTISRDNPKNILFLQMTSLRSEDTAMYYC ARFARGNSFDY WGQGTTLTVSS

| GFTFSTFG | INGDSSSI | ARFARGNSFDY |
|---|---|---|
| SEQ ID:167 | SEQ ID:168 | SEQ ID:169 |

Ms21_VL SEQ ID NO: 42

DIVMTQSPSSLTVTAGEKVTMSCKSS QSLFNSGNQKNY LTWYQQKPWQPPKLLIY WAS TRESGVPDRF
TGSGSGTDFTLTITSVQTEDLAVYYC QIGYTYPLT FGAGTKLELK

| QSLFNSGNQKNY | WAS | QIGYTYPLT |
|---|---|---|
| SEQ ID:170 | SEQ ID:171 | SEQ ID:172 |

FIG. 1 cont.

Ms22_VH SEQ ID NO: 43

QVQLKESGPGLVAPSQSLSITCTVSGFSLTSNGVHWVRQPPGKGLEWLGVIWAGGSTNYNSALMSRLSI
SKDNSKSQVFLKMNSLQTHDTAMYYCARDKYDGTGFDYWGQGTTLTVSS

| GFSLTSNG | IWAGGST | ARDKYDGTGFDY |
|---|---|---|
| SEQ ID:173 | SEQ ID:174 | SEQ ID:175 |

Ms22_VL SEQ ID NO: 44

QIVLTQSPAIMSASPGEKVTMTCSASSSVSNMYWYQQKPGSSPRLLIYDTSNLASGVPVRFSGSGSGTS
YSLTISRMEAEDAATYYCQQWSSYPYTFGGGTKLEIK

| SSVSN | DTS | QQWSSYPYT |
|---|---|---|
| SEQ ID:176 | SEQ ID:177 | SEQ ID:178 |

Ms23_VH SEQ ID NO: 45

EIQLQQSGPELVKPGASVKVSCKASGYAFTRYNMYWVKQSHGKSLEWIGYIDPYNGGTNYN
QKFKGKATLTVDKSSSTAYMHLNSLTSEDSAVYYCARGGYYGNAMDYWGQGTSVTVSS

| GYAFTRYN | IDPYNGGT | ARGGYYGNAMDY |
|---|---|---|
| SEQ ID:179 | SEQ ID:180 | SEQ ID:181 |

Ms23_VL SEQ ID NO: 46

DIVMTQSPSSLTVTAGEKVTMSCKSSQSLLNSGNQKNYLTWYQQKPGQPPKLLIYWASTRES
GVPDRFTGSGSGTDFTLTISSVQAEDLSIYYCQSNYIYPFTFGAGTTLELQ

| QSLLNSGNQKNY | WAS | QSNYIYPFT |
|---|---|---|
| SEQ ID:182 | SEQ ID:183 | SEQ ID:184 |

FIG. 1 cont.

Hu-1_VH SEQ ID NO: 185
QVQLVESGGGVVQPGRSLRLSCAASGFTFSNYGMYWVRQAPGKGLEWVAVIWYDGSNKNYADSVK
GRFTISRDNSKNTLNLQMNSLRAEDTAVYYCARRGYDILTGYDYYGMDVWGQGTTVTVSA

| GFTFSNYG | IWYDGSNK | ARRGYDILTGYDYYGMDV |
|----------|----------|---------------------|
| SEQ ID:221 | SEQ ID:222 | SEQ ID:223 |

Hu-1_VL SEQ ID NO: 186
QTVVTQEPSFSVSPGGTVTLTCGLSSGSVSTSYYPSWYQQTPGQAPRTLIYRTNTRSSGVPDRFSGSILG
NKAALTISGAQAPDESNYYCVLYMGSGIWVFGGGTKLTVL

| SGSVSTSYY | RTN | VLYMGSGIWV |
|-----------|-----|------------|
| SEQ ID:224 | SEQ ID:225 | SEQ ID:226 |

Hu-2_VH SEQ ID NO: 187
QLRLQESGPGLVKPSETLSLTCAVSGGSISSSRSYWGWIRQPPGKGLELIGSIYYSGSTYYNPSLKSRVTI
SVDTSKNQFSLKLTSVTATDTAVYYCARQTLRYFDWLSPFDYWGQGTLVTVSS

| GGSISSSRSY | IYYSGST | ARQTLRYFDWLSPFDY |
|------------|---------|-------------------|
| SEQ ID:227 | SEQ ID:228 | SEQ ID:229 |

Hu-2_VL SEQ ID NO: 188
EIVMTQSPATLSLSPGERATLSCRASQSVRSNYLSWYQQKPGQAPRLLIYGTSTRATGIPARFSGSGSGT
DFTLTISSLQPEDFAVYFCQQDYNLPITFGQGTRLEIK

| QSVRSNY | GTS | QQDYNLPIT |
|---------|-----|-----------|
| SEQ ID:230 | SEQ ID:231 | SEQ ID:232 |

Hu-3_VH SEQ ID NO: 189
QLQLQESGPGLVKPSETLSLTCTVSDGPISSSRYYWGWIRQPPGKGLEWIGSFHYSGSTYYNPSLKSRVT
ISADTSKNQFSLKLSSVTAADTAVYYCARLVLRYFDWLGFFDLWGRGTLVTVSS

| DGPISSSRYY | FHYSGST | ARLVLRYFDWLGFFDL |
|------------|---------|-------------------|
| SEQ ID:233 | SEQ ID:234 | SEQ ID:235 |

Hu-3_VL SEQ ID NO: 190
EIVMTQSPAILSLSPGERAALSCRASQSVRSSYLSWYQQKPGQAPRLLIYGTSTRATGIPARFSGSGSGTD
FTLTISSLQPEDFAVYYCQQDYNLPITFGQGTRLEFK

| QSVRSSY | GTS | QQDYNLPIT |
|---------|-----|-----------|
| SEQ ID:236 | SEQ ID:237 | SEQ ID:238 |

FIG. 2

Hu-4_VH SEQ ID NO: 191
QVQLVESGGGVVQPGRSLRLSCAASGFTFSFYGMHWVRQAPGKGLEWVAVIWYDGSNKNYVDSVKG
RFTISRDNSKNTLYLQMNSLRAEDTAVYYCARRNYDILTGRDYYGMDVWGQGTTVTVSS

| GFTFSFYG | IWYDGSNK | ARRNYDILTGRDYYGMDV |
|---|---|---|
| SEQ ID:239 | SEQ ID:240 | SEQ ID:241 |

Hu-4_VL SEQ ID NO: 192
QTVVTQEPSFSVSPGGTVILTCGLNSGSVSTSYYPSWYQQTPGQAPRTLIYSTNTRSSGVPDRFSGSILG
NKAALTITGAQADDDSDYYCVLYMGSGIWVFGGGTKLTVL

| SGSVSTSYY | STN | VLYMGSGIWV |
|---|---|---|
| SEQ ID:242 | SEQ ID:243 | SEQ ID:244 |

Hu-5_VH SEQ ID NO: 193
QVQLVQSGAEVKKPGASVKVSCEASGYTFTSSYMHWVRQAPGQGLEWMGIINPSGGRTNYAQKFQG
RVTMTRDTSTSTVYMELSSLRSEDTAVYYCARDHYDIFTTYYPRGMDVWGQGTTVTVSS

| GYTFTSSY | INPSGGRT | ARDHYDIFTTYYPRGMDV |
|---|---|---|
| SEQ ID:245 | SEQ ID:246 | SEQ ID:247 |

Hu-5_VL SEQ ID NO: 194
DIQMTQSPSSLSASVGDRVTITCRASQGIRNDLGWYQQKPGKAPKRLIYAASSLQSGVPSRFSGSGSGTE
FTLTISSLQPEDFTTYYCLQHNSFPFTFGQGTELEIR

| QGIRND | AAS | LQHNSFPFT |
|---|---|---|
| SEQ ID:248 | SEQ ID:249 | SEQ ID:250 |

Hu-6_VH SEQ ID NO: 195
QMQLRESGPGLVKPSETLSLTCTVSNGPISSSRYYWGWIRQPPGKGLEWIGSEHYSGSTYYKPSLKSRV
TISADTSKNQLSLELSSVTAADTAVYYCARLVLRYFDWLGYFDLWGRGTLVTVSS

| NGPISSSRYY | EHYSGST | ARLVLRYFDWLGYFDL |
|---|---|---|
| SEQ ID:251 | SEQ ID:252 | SEQ ID:253 |

Hu-6_VL SEQ ID NO: 196
EFVMTQSPATLSLSPGERATLSCRASQSIRSNYLSWYQQKPGQAPRLLIYGASTRATAIPARFSGSGSGT
DFTLTISSLQPEDFAVYYCQQDYNLPITFGQGTRLEIK

| QSIRSNY | GAS | QQDYNLPIT |
|---|---|---|
| SEQ ID:254 | SEQ ID:255 | SEQ ID:256 |

FIG. 2 cont.

Hu-7_VH1 SEQ ID NO: 197
EVQLLESGGGLVQPGGSLRLSCAASGFTFSSYYMSWVRQAPGKGLEWVSTISGSGGSTYYADSVKDRF
TISRDNSKNTLYLQMNSLRAEDTAVYYCGKPLLGGTGLWDYWGQGTLVTVSS

| GFTFSSYV | ISGSGGST | GKPLLGGTGLWDY |
|---|---|---|
| SEQ ID:257 | SEQ ID:258 | SEQ ID:259 |

Hu-7_VL SEQ ID NO: 198
EIVLTQSPATLSLSPGERATLSCRASQSVSSYLAWYQQKPGQAPRLLIYDSSNRATGVPARFSGSGSGTD
FTLTISSLEPEDFAVYYCQQRSNWPLTFGGGTKVEIK

| QSVSSY | DSS | QQRSNWPLT |
|---|---|---|
| SEQ ID:260 | SEQ ID:261 | SEQ ID:262 |

Hu-8_VH SEQ ID NO: 199
QVQLVESGGGVVQPGRSLRLSCAASGFTFSSYGMHWVRQAPGKGLEWVAVIWYDGSNKKYADSVKG
RFTISRDNSKNTLYLQMNSLRAEDTAVYYCARRYDVLTAYPYYFYYNMDVWGPGTTVTVSS

| GFTFSSYG | IWYDGSNK | ARRYDVLTAYPYYFYYNMDV |
|---|---|---|
| SEQ ID:263 | SEQ ID:264 | SEQ ID:265 |

Hu-8_VL SEQ ID NO: 200
QTVVTQEPSFSVSPGGTVILTCGLNSGSVSTSYYPSWYQQTPGQAPRTLIYSTNTRSSGVPDRFSGSILG
NKAALTITGAQADDESDYYCVLYMGSGIWVFGGGTKLTVL

| SGSVSTSYY | STN | VLYMGSGIWV |
|---|---|---|
| SEQ ID:266 | SEQ ID:267 | SEQ ID:268 |

Hu-9_VH SEQ ID NO: 201
EVQLLESGGGLVQPGGSLRLSCAASGFTFSSFAMTWVRQAPGKGLEWVSSLSGSGRSTYYA
ASMKGRFTISRDNSKNTLYLQMNSLRAEDTAIYYCAKSLSYYHYYFDYWGQGTLVTVTS

| GFTFSSFA | LSGSGRST | AKSLSYYHYYFDY |
|---|---|---|
| SEQ ID:269 | SEQ ID:270 | SEQ ID:271 |

Hu-9_VL SEQ ID NO: 202
DIQLTQSPSFLSASVGDRVPITCRASQGISNFLAWYQQKPGKAPELLIHSASTLQSGVPSRFSGS
GSGTEFTLTISNLQPQDFATYYCQQVNSYPLTFGGGTKVEIK

| QGISNF | SAS | QQVNSYPLT |
|---|---|---|
| SEQ ID:272 | SEQ ID:273 | SEQ ID:274 |

FIG. 2 cont.

Hu-10_VH SEQ ID NO: 203
EVQLSESGGALVQPGESLRLSCAAS<u>GFTFSSYA</u>MTWVRQAPGKGLEWVSS<u>LSGSGRST</u>YYA
ASIKGRFTISRDNSKNTLYLQMSSLRAEDTAIYYC<u>AKSLSYYHYYFDY</u>WGQGTLVTVSS

| GFTFSSYA | LSGSGRST | AKSLSYYHYYFDY |
|---|---|---|
| SEQ ID:275 | SEQ ID:276 | SEQ ID:277 |

Hu-10_VL SEQ ID NO: 204
DIQLTQSPSFLSASVGDRVPITCRAS<u>QDISNY</u>LAWYQQKPGKAPKLLIYS<u>AST</u>LQSGVPSRFSG
SGSGTEFTLTISSLQPEDFASYHC<u>QQVKTYPLT</u>FGGGTKVEIK

| QDISNY | SAS | QQVKTYPLT |
|---|---|---|
| SEQ ID:278 | SEQ ID:279 | SEQ ID:280 |

Hu-11_VH SEQ ID NO: 205
QVHLVQSGAEVKKPGASVKVSCKAS<u>GYTFTSYY</u>IHWVRQAPGQGLEWMG<u>IINPSGGNT</u>IYA
QKFQGRVTMTRDTSTTTVYVELSSLRSEDTAVYYC<u>ARDHYDILTGYYPLYYGMDV</u>WGQGT
TVTVSS

| GYTFTSYY | INPSGGNT | ARDHYDILTGYYPLYYGMDV |
|---|---|---|
| SEQ ID:281 | SEQ ID:282 | SEQ ID:283 |

Hu-11_VL SEQ ID NO: 206
SYELTQPLSVSVALGQTARITCGGN<u>NIGSKN</u>VHWYQQKPGQAPVLVIY<u>RDS</u>NRPSGIPERFSG
SKSGNTATLTISRAQAGDEADYYC<u>QVWDSSTAV</u>FGGGTQLTAL

| NIGSKN | RDS | QVWDSSTAV |
|---|---|---|
| SEQ ID:284 | SEQ ID:285 | SEQ ID:286 |

Hu-12_VH SEQ ID NO: 207
EVRLLESGGGLVQPGGSLRLSCIAS<u>GFTFSSYV</u>MSWVRQAPGKGLEWVS<u>GISGSGGST</u>YYAD
SVKGRFTISRDNSKNTLYLQISSLRAEDTAVYYC<u>TKAPTLWWFFDL</u>WGRGTLVTVSS

| GFTFSSYV | ISGSGGST | TKAPTLWWFFDL |
|---|---|---|
| SEQ ID:287 | SEQ ID:288 | SEQ ID:289 |

Hu-12_VL SEQ ID NO: 208
DIQVTQSPSFLSASVGDRVTITCRAS<u>QGIRSY</u>LAWYQQKPGKAPKLLIY<u>AAS</u>TLQSGVPSRFSG
SGSGTEFTLTISSLLPEDFATYYC<u>QQLNSYPLT</u>FGGGTKVEIK

| QGIRSY | AAS | QQLNSYPLT |
|---|---|---|
| SEQ ID:290 | SEQ ID:291 | SEQ ID:292 |

FIG. 2 cont.

Hu-13_VH SEQ ID NO: 209
EVQLLESGGGLVQPGGSLRVACAASGFPLRSYAMSWVRQAPGKGLEWVSVTSGSGGSTYY
ADSVKGRFTISRDNSKSTVYLQMNSLRAEDTAVYYCAKDRGYDILTGYYDYFYGMDVWGQ
GTTVTVSS

| GFPLRSYA | TSGSGGST | AKDRGYDILTGYYDYFYGMDV |
|---|---|---|
| SEQ ID:293 | SEQ ID:294 | SEQ ID:295 |

Hu-13_VL SEQ ID NO: 210
DIQMTQSPSSLSASVGDRVTITCRASQGIRNDLGWFQQKPGKAPKRLIYAASSLQSGVPSRFS
GSGSGTEFTLTISSLQPEDFATYYCLQHNSYPYTFGQGTKLEIK

| QGIRND | AAS | LQHNSYPYT |
|---|---|---|
| SEQ ID:296 | SEQ ID:297 | SEQ ID:298 |

Hu-14_VH SEQ ID NO: 211
EVQLLESGGGLVQPGGSLRLSCAASGITFSSYAMSWVRQVPGKGLEWVSVISGSGGSTYYAD
SVKGRFTISRDNSKNTLYLQMNSLRAEDTAVYYCAKDRGYDILTTYYDYFYGMDVWGQPEF
QHTGG

| GITFSSYA | ISGSGGST | AKDRGYDILTTYYDYFYGMDV |
|---|---|---|
| SEQ ID:299 | SEQ ID:300 | SEQ ID:301 |

Hu-14_VL SEQ ID NO: 212
DIQMTQSPSSLSASVGDRVIITCRASQGIRNDLGWYQQKPGKAPKRLIYAASSLQSGVPSRFSG
SGSGTEFTLTISSLQPEDLASYYCLQHNSYPYTFGQGTKLEIK

| QGIRND | AAS | LQHNSYPYT |
|---|---|---|
| SEQ ID:302 | SEQ ID:303 | SEQ ID:304 |

Hu-16_VH SEQ ID NO: 215
EVQLLESGGGVVQPGGSLRLSCAASGLIFSSYAMSWVRQAPGKGLEWVSVIGGSGSNTFYAD
SVKGRFTISRDNSKNTLFLQMNSLRAEDTAVYYCAKDRGYDILTGYYNYYYGMDVWGQGI
TVTVSS

| GLIFSSYA | IGGSGSNT | AKDRGYDILTGYYNYYYGMDV |
|---|---|---|
| SEQ ID:311 | SEQ ID:312 | SEQ ID:313 |

Hu-16_VL SEQ ID NO: 216
DIQMTQSPSSLSASVGDRVTITCRASQGIRNDLGWYQQKPGKAPKRLIYAASSLQSGVPSRFS
GSGSGTEFTLTISSLQPEDFATYYCLQHNSYPYTFGQGTKLEIK

| QGIRND | AAS | LQHNSYPYT |
|---|---|---|
| SEQ ID:314 | SEQ ID:315 | SEQ ID:316 |

FIG. 2 cont.

HU-17_VH SEQ ID NO: 217

QVQLVQSGAEVKRPGASVKVSCRVSGYTLTALSMYWVRQAPGKGLEWMGGFDPEDGETIY
AQKFQGRVTMTEDTSTGTAYMELSSLKSEDTAVYYCATRLRYFDWNYWGQGTPVTVSS

| GYTLTALS | FDPEDGET | ATRLRYFDWNY |
|---|---|---|
| SEQ ID:317 | SEQ ID:318 | SEQ ID:319 |

Hu-17_VL  SEQ ID NO: 218
DIVMTQTPLSSPVTLGQPASISCRSSQSLVHSDGNTYLSWLQQRPGQPPRLLIYKVSKRFSGVPDRFSGS
GAGTDFTLKISRVEAEDVGVYYCTQGTQFPRTFGQGTKVEIK

| QSLVHSDGNTY | KVS | TQGTQFPRT |
|---|---|---|
| SEQ ID:320 | SEQ ID:321 | SEQ ID:322 |

Hu-18 17001.C8.2F9.1E1_VH SEQ ID NO: 219

QVQLVQSGAEVKKPGASVKVSCRVSGYTLSALSMYWVRQAPGKGLEWMGGFDPEDGKTIY
AQKFQGRVTMTEDTSTGTAYMELSSLRSEDTAIYYCATTLRYFDWNYWGQGTPVTVSS

| GYTLSALS | FDPEDGKT | ATTLRYFDWNY |
|---|---|---|
| SEQ ID:323 | SEQ ID:324 | SEQ ID:325 |

Hu-18_VL  SEQ ID NO: 220
DIVMTQTPLSSPVTLGQPASISCRSSQSLVHSDGNTYLSWLQQRPGQPPRLLIYKVSKRFSGVPDRFSGS
GAGTDFTLKISRVEAEDVGVYYCTQGTQFPRTFGQGTKVEIK

| QSLVHSDGNTY | KVS | TQGTQFPRT |
|---|---|---|
| SEQ ID:326 | SEQ ID:327 | SEQ ID:328 |

FIG. 2 cont.

| | Ms-4 CHO CLDN18.2 | Hu-3 CHO CLDN18.2 | Ms-4 CHO CLDN18.1 | Hu-3 CHO CLDN18.1 |
|---|---|---|---|---|
| EC50, nM | 0.75 | 1.34 | Inactive | Inactive |

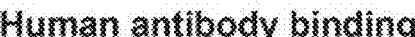
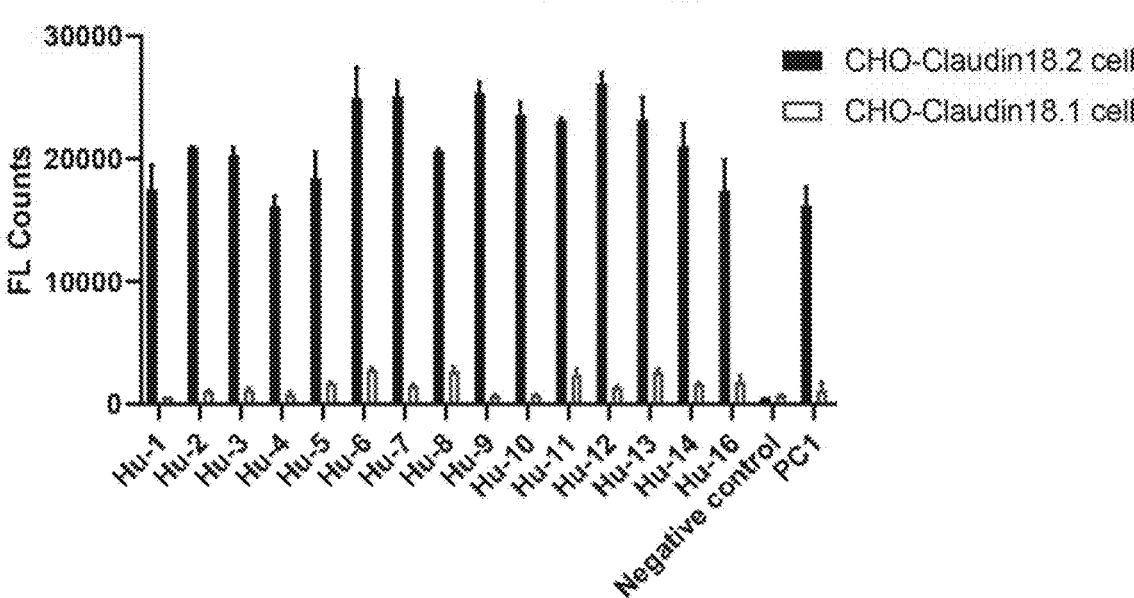
FIG. 4A
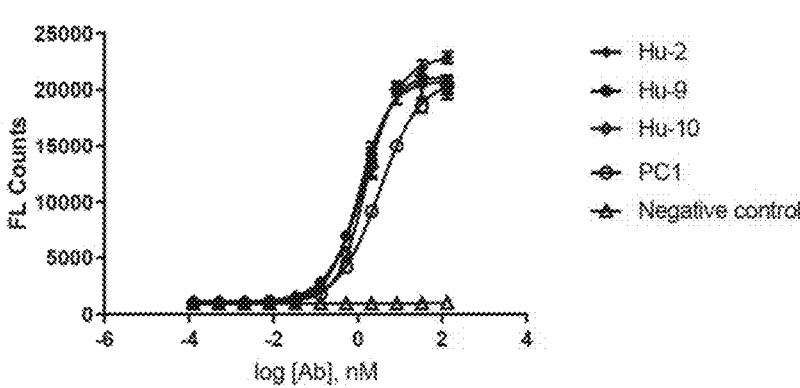
FIG. 4B

ADCC Activity of Anti-Claudin18.2 antibodies

| | Hu-2 | Hu-7 | Hu-9 | Unrelated Ab control |
|---|---|---|---|---|
| EC50, nM | 3.51 | 3.52 | 1.10 | Inactive |

Claudin-18.2 Antibody Endocytosis

| | Hu-2 | Hu-7 | Hu-9 | Hu-11 | Unrelated Ab control | PC1 |
|---|---|---|---|---|---|---|
| EC50, nM | 1.428 | 1.718 | 0.791 | 1.478 | >133.4 | 2.927 |

| SEQ IDENTIFIER | HUMAN IgG1 HEAVY CHAIN |
|---|---|
| SEQ ID NO: 331 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| SEQ ID NO: 332 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| SEQ ID NO: 333 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| SEQ ID NO: 334 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |

FIG. 11A

| SEQ IDENTIFIER | HUMAN KAPPA LIGHT CHAIN |
|---|---|
| SEQ ID NO: 335 | KRTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC |

FIG. 11B

| SEQ IDENTIFIER | NBL-014 HEAVY CHAINS AND LIGHT CHAIN |
|---|---|
| SEQ ID NO: 336 | EVQLLESGGGLVQPGGSLRLSCAASGFTFSSFAMTWVRQAPGKGLEW VSSLSGSGRSTYYAASMKGRFTISRDNSKNTLYLQMNSLRAEDTAIYY CAKSLSYYHYYFDYWGQGTLVTVTSASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELVG GPSVFLLPPKPKDTLMISRTPEVTCVVVDVSHEDPEVKFNWYVDGVEV HNAKTKPPEEQYNSTLRVVSVLTVLHQDWLNGKEYKCKVSNKALPAP IEKTISKAKGQPREPQVYTLPPSRDELTKNQVSLTCLVKGFYPSDIAVE WESNGQPENNYKTTPLVLDSDGSFFLYSKLTVDKSRWQQGNVFSCSV MHEALHNHYTQKSLSLSPGK |
| SEQ ID NO: 338 | EVQLLESGGGLVQPGGSLRLSCAASGFTFSSFAMTWVRQAPGKGLEW VSSLSGSGRSTYYAASMKGRFTISRDNSKNTLYLQMNSLRAEDTAIYY CAKSLSYYHYYFDYWGQGTLVTVTSASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKRVEPKSCDKTHTCPPCPAPELVG GPSVFLLPPKPKDTLMISRTPEVTCVVVDVSHEDPEVKFNWYVDGVEV HNAKTKPPEEQYNSTLRVVSVLTVLHQDWLNGKEYKCKVSNKALPAP IEKTISKAKGQPREPQVYTLPPSRDELTKNQVSLTCLVKGFYPSDIAVE WESNGQPENNYKTTPLVLDSDGSFFLYSKLTVDKSRWQQGNVFSCSV MHEALHNHYTQKSLSLSPGK |
| SEQ ID NO: 337 | DIQLTQSPSFLSASVGDRVPITCRASQGISNFLAWYQQKPGKAPELLIHS ASTLQSGVPSRFSGSGSGTEFTLTISNLQPQDFATYYCQQVNSYPLTFG GGTKVEIKRTVAAPSVFIFPPSDEQLKSGTASVVCLLNNFYPREAKVQ WKVDNALQSGNSQESVTEQDSKDSTYSLSSTLTLSKADYEKHKVYAC EVTHQGLSSPVTKSFNRGEC |

FIG. 12

CHO-Claudin18.2 Cell ADCC

| | NBL-014 | NBL-014P | NBL-014G | hIgG1 Control |
|---|---|---|---|---|
| EC50, nM | 0.73 | 0.06 | 0.02 | Inactive |

ADCC on CHO claudin18.2

| | NBL-014 | NBL-014P | NBL-014G | hIgG1 Control |
|---|---|---|---|---|
| EC50, nM | 0.12 | 0.06 | 0.04 | Inactive |

NUGC-4 cell ADCC

| | PC1 | NBL-014 | NBL-014P | NBL-014G | Isotype Ctl |
|---|---|---|---|---|---|
| EC50, nM | >133 | 0.4 | 0.06 | 0.04 | Inactive |

PATU8988S cell ADCC

| | PC1 | NBL-014 | NBL-014G | NBL-014P | Isotype Ctl |
|---|---|---|---|---|---|
| EC50, nM | 1.76 | 0.22 | 0.15 | 0.30 | Inactive |

| | PC1 | NBL-014 | NBL-014G | NBL-014P | Isotype Ctl |
|---|---|---|---|---|---|
| EC50, nM | In active | 1.62 | 1.76 | 1.67 | Inactive |

CHO-Claudin18.2 ADCP

| | PC1 | NBL-014 | NBL-014P | NBL-014G | Isotype Ctl |
|---|---|---|---|---|---|
| EC50, nM | 0.54 | 0.11 | 0.06 | 0.07 | Inactive |

| | PC1 | NBL-014 | NBL-014P | NBL-014G | Isotype Ctl |
|---|---|---|---|---|---|
| EC50, nM | 20.73 | 0.22 | 0.13 | 0.16 | Inactive |

Human claudin 18 isoform 2, Uni-Prot entry P56856 (CLD18_human) identified as P56856-2

MAVTACQGLGFVVSLIGIAGIIAATCMDQWSTQDLYNNPVTAVFNYQGLWRSCVRE
SSGFTECRGYFTLLGLPAMLQAVRALMIVGIVLGAIGLLVSIFALKCIRIGSMEDSAKA
NMTLTSGIMFIVSGLCAIAGVSVFANMLVTNFWMSTANMYTGMGGMVQTVQTRYT
FGAALFVGWVAGGLTLIGGVMMCIACRGLAPEETNYKAVSYHASGHSVAYKPGGF
KASTGFGSNTKNKKIYDGGARTEDEVQSYPSKHDYV (SEQ ID NO: 329)

Human claudin 18 isoform 1, Uni-Prot entry P56856 (CLD18_human) identified as P56856

MSTTTCQVVAFLLSILGLAGCIAATGMDMWSTQDLYDNPVTSVFQYEGLWRSCVRQ
SSGFTECRPYFTILGLPAMLQAVRALMIVGIVLGAIGLLVSIFALKCIRIGSMEDSAKA
NMTLTSGIMFIVSGLCAIAGVSVFANMLVTNFWMSTANMYTGMGGMVQTVQTRYT
FGAALFVGWVAGGLTLIGGVMMCIACRGLAPEETNYKAVSYHASGHSVAYKPGGF
KASTGFGSNTKNKKIYDGGARTEDEVQSYPSKHDYV (SEQ ID NO: 330)

FIG. 21

SEQUENCE LISTING

```
<160> NUMBER OF SEQ ID NOS: 338

<210> SEQ ID NO 1
<211> LENGTH: 119
<212> TYPE: PRT
<213> ORGANISM: Mus musculus

<400> SEQUENCE: 1

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Tyr Thr Arg Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Gly Gly Tyr Tyr Gly Asn Ala Met Asp Tyr Trp Gly Gln Gly
            100                 105                 110

Thr Ser Val Thr Val Ser Ser
        115

<210> SEQ ID NO 2
<211> LENGTH: 113
<212> TYPE: PRT
<213> ORGANISM: Mus musculus

<400> SEQUENCE: 2

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ser Ile Tyr Tyr Cys Gln Ser
                85                  90                  95

Asn Tyr Ile Tyr Pro Phe Thr Phe Gly Ala Gly Thr Thr Leu Glu Leu
            100                 105                 110

Gln
```

```
<210> SEQ ID NO 3
<211> LENGTH: 118
<212> TYPE: PRT
<213> ORGANISM: Mus musculus

<400> SEQUENCE: 3

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp Phe Thr Thr Ala Thr Gly Phe Asp Tyr Trp Gly Gln Gly Thr
            100                 105                 110

Thr Leu Thr Val Ser Ser
        115

<210> SEQ ID NO 4
<211> LENGTH: 113
<212> TYPE: PRT
<213> ORGANISM: Mus musculus

<400> SEQUENCE: 4

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
            100                 105                 110

Lys

<210> SEQ ID NO 5
<211> LENGTH: 118
<212> TYPE: PRT
<213> ORGANISM: Mus musculus

<400> SEQUENCE: 5

Glu Val Met Leu Val Glu Ser Gly Gly Gly Ile Val Lys Pro Gly Gly
1               5                   10                  15

Ser Leu Lys Leu Ser Cys Ala Ala Ser Gly Phe Thr Leu Ser Ser Tyr
            20                  25                  30

Thr Met Ser Trp Val Arg Gln Thr Pro Glu Arg Arg Leu Glu Trp Val
        35                  40                  45
```

-continued

```
Ala Thr Ile Ile Ile Gly Gly Ser Tyr Thr Tyr Tyr Pro Asp Ser Val
    50              55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Gly Tyr Gly Asn Ser Phe Pro Tyr Trp Gly Gln Gly Thr
                100                 105                 110

Leu Val Thr Val Ser Ala
        115

<210> SEQ ID NO 6
<211> LENGTH: 113
<212> TYPE: PRT
<213> ORGANISM: Mus musculus

<400> SEQUENCE: 6

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
                100                 105                 110

Lys

<210> SEQ ID NO 7
<211> LENGTH: 118
<212> TYPE: PRT
<213> ORGANISM: Mus musculus

<400> SEQUENCE: 7

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Asn Met Asn Trp Val Lys Gln Ser Asn Gly Lys Ser Leu Glu Trp Ile
            35                  40                  45

Gly Asn Ile Asp Pro Tyr Tyr Gly Gly Thr Arg Tyr Asn Gln Lys Phe
    50                  55                  60

Lys Gly Lys Ala Thr Leu Thr Val Asp Arg Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Leu Gly Leu Gly Asn Ala Met Asp Tyr Trp Gly Gln Gly Thr
                100                 105                 110

Ser Val Thr Val Ser Ser
        115
```

```
<210> SEQ ID NO 8
<211> LENGTH: 113
<212> TYPE: PRT
<213> ORGANISM: Mus musculus

<400> SEQUENCE: 8

Asp Ile Val Met Thr Gln Ser Pro Ser Phe Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Ser Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Phe Thr Phe Gly Ser Gly Thr Glu Leu Glu Ile
            100                 105                 110

Lys

<210> SEQ ID NO 9
<211> LENGTH: 120
<212> TYPE: PRT
<213> ORGANISM: Mus musculus

<400> SEQUENCE: 9

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Leu Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Ala Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Ala Tyr Gly Tyr Gly Asn Ala Val Asp Tyr Trp Gly Gln
            100                 105                 110

Gly Thr Ser Val Thr Val Ser Ser
        115                 120

<210> SEQ ID NO 10
<211> LENGTH: 113
<212> TYPE: PRT
<213> ORGANISM: Mus musculus

<400> SEQUENCE: 10

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45
```

Pro Pro Lys Leu Leu Ile Tyr Gly Ala Ser Thr Arg Glu Ser Gly Val
50                55                  60

Pro Asp Arg Phe Thr Gly Ser Gly Ser Gly Thr Asp Phe Thr Leu Thr
65                  70              75                  80

Ile Ser Ser Val Gln Ala Glu Asp Leu Ala Val Tyr Tyr Cys Gln Asn
                85              90                  95

Asp His Ser Tyr Pro Leu Thr Phe Gly Ala Gly Thr Lys Leu Glu Leu
            100                105                110

Lys

<210> SEQ ID NO 11
<211> LENGTH: 120
<212> TYPE: PRT
<213> ORGANISM: Mus musculus

<400> SEQUENCE: 11

Gln Val Gln Leu Gln Gln Ser Gly Ala Glu Leu Ala Lys Pro Gly Ala
1               5                  10                  15

Ser Val Lys Met Ser Cys Arg Ala Ser Gly Tyr Thr Phe Thr Ser Tyr
                20              25                  30

Leu Met His Trp Ile Lys Gln Arg Pro Gly Gln Ala Leu Glu Trp Ile
            35              40                  45

Gly Tyr Ile Asn Pro Thr Thr Asp Tyr Thr Glu Tyr Asn Gln Lys Phe
        50              55                  60

Lys Gly Lys Ala Thr Leu Thr Ala Asp Lys Ser Ser Ser Thr Ala Tyr
65                  70              75                  80

Met Gln Leu Ser Ser Leu Thr Ser Glu Asp Ser Ala Val Tyr Tyr Cys
                85              90                  95

Gly Arg Leu Gly Tyr Tyr Lys Arg Asn Ala Met Asp His Trp Gly Gln
            100                105                110

Gly Thr Ser Val Thr Val Ser Ser
        115                120

<210> SEQ ID NO 12
<211> LENGTH: 113
<212> TYPE: PRT
<213> ORGANISM: Mus musculus

<400> SEQUENCE: 12

Asp Ile Val Met Thr Gln Ser Pro Ser Ser Leu Ser Val Ser Ala Gly
1               5                  10                  15

Glu Lys Val Thr Met Ser Cys Lys Ser Ser Gln Ser Leu Leu Asn Ser
                20              25                  30

Gly Asn Gln Lys Asn Tyr Leu Ala Trp Tyr Gln Gln Lys Pro Gly Gln
            35              40                  45

Pro Pro Lys Leu Leu Ile Tyr Gly Ala Ser Thr Arg Glu Ser Gly Val
        50              55                  60

Pro Asp Arg Phe Thr Gly Ser Gly Ser Gly Thr Asp Phe Thr Leu Thr
65                  70              75                  80

Ile Ser Ser Val Gln Ala Glu Asp Leu Ala Val Tyr Tyr Cys Gln Asn
                85              90                  95

Asp His Phe Tyr Pro Leu Thr Phe Gly Ala Gly Thr Lys Leu Glu Leu
            100                105                110

Lys

<210> SEQ ID NO 13

<211> LENGTH: 121
<212> TYPE: PRT
<213> ORGANISM: Mus musculus

<400> SEQUENCE: 13

Glu Val Lys Leu Val Glu Ser Gly Gly Asp Leu Val Gln Pro Gly Gly
1               5                   10                  15

Ser Leu Arg Leu Ser Cys Thr Thr Pro Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Asn Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Ala Cys Pro Trp Asp Trp Phe Ala Tyr Trp Gly
            100                 105                 110

Gln Gly Thr Leu Val Thr Val Ser Ala
        115                 120

<210> SEQ ID NO 14
<211> LENGTH: 113
<212> TYPE: PRT
<213> ORGANISM: Mus musculus

<400> SEQUENCE: 14

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 15
<211> LENGTH: 119
<212> TYPE: PRT
<213> ORGANISM: Mus musculus

<400> SEQUENCE: 15

Glu Ile Gln Leu Gln Gln Ser Gly Pro Glu Leu Val Lys Pro Gly Ala
1               5                   10                  15

Ser Val Lys Val Ser Cys Lys Ala Ser Asp Tyr Ala Phe Thr Arg Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Asn Tyr Asn Gln Lys Phe

-continued

```
                50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Gly Gly Tyr Tyr Gly Asn Ala Met Asp Tyr Trp Gly Gln Gly
                100                 105                 110

Thr Ser Val Thr Val Ser Ser
        115

<210> SEQ ID NO 16
<211> LENGTH: 113
<212> TYPE: PRT
<213> ORGANISM: Mus musculus

<400> SEQUENCE: 16

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
        35                  40                  45

Pro Pro Gln Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ser Ile Tyr Tyr Cys Gln Ser
                85                  90                  95

Asn Tyr Ile Tyr Pro Phe Thr Phe Gly Ala Gly Thr Thr Leu Glu Leu
                100                 105                 110

Gln

<210> SEQ ID NO 17
<211> LENGTH: 120
<212> TYPE: PRT
<213> ORGANISM: Mus musculus
<220> FEATURE:
<221> NAME/KEY: misc_feature
<222> LOCATION: (39)..(39)
<223> OTHER INFORMATION: Xaa can be any naturally occurring amino acid

<400> SEQUENCE: 17

Gln Val Gln Leu Gln Gln Pro Gly Ala Glu Pro Val Lys Pro Gly Ala
1               5                   10                  15

Ser Val Lys Leu Ser Cys Lys Ala Ser Gly Tyr Thr Phe Thr Ser Tyr
                20                  25                  30

Leu Ile His Trp Val Lys Xaa Arg Pro Gly Gln Gly Leu Glu Trp Ile
        35                  40                  45

Gly Glu Ile Ile Pro Ser Asn Gly Arg Thr Thr Tyr Asn Glu Lys Phe
    50                  55                  60

Lys Thr Lys Ala Ser Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Ala Tyr Gly Tyr Gly Asn Ala Val Asp Tyr Trp Gly Gln
                100                 105                 110

Gly Thr Ser Val Thr Val Ser Ser
```

-continued

```
            115                    120
```

```
<210> SEQ ID NO 18
<211> LENGTH: 113
<212> TYPE: PRT
<213> ORGANISM: Mus musculus

<400> SEQUENCE: 18

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Thr Tyr Pro Leu Thr Phe Gly Ala Gly Thr Lys Leu Glu Leu
            100                 105                 110

Lys

<210> SEQ ID NO 19
<211> LENGTH: 118
<212> TYPE: PRT
<213> ORGANISM: Mus musculus

<400> SEQUENCE: 19

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Lys Met Asn Trp Val Lys Gln Ser Asn Gly Lys Ser Leu Glu Trp Ile
        35                  40                  45

Gly His Ile Asp Pro Tyr Tyr Gly Gly Pro Arg Tyr Asn Lys Lys Phe
    50                  55                  60

Met Gly Lys Ala Thr Leu Thr Val Asp Arg Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Leu Asp Tyr Gly Asn Ser Phe Ala Tyr Trp Gly Gln Gly Thr
            100                 105                 110

Leu Val Thr Val Ser Ala
        115

<210> SEQ ID NO 20
<211> LENGTH: 113
<212> TYPE: PRT
<213> ORGANISM: Mus musculus

<400> SEQUENCE: 20

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30
```

-continued

```
Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                    85                  90                  95

Asp His Ser Tyr Pro Phe Thr Phe Gly Gly Gly Thr Lys Leu Glu Ile
                100                 105                 110

Lys

<210> SEQ ID NO 21
<211> LENGTH: 118
<212> TYPE: PRT
<213> ORGANISM: Mus musculus

<400> SEQUENCE: 21

Gln Val Gln Leu Gln Gln Ser Gly Ala Glu Leu Val Lys Pro Gly Ala
1                   5                   10                  15

Ser Val Lys Met Ser Cys Lys Ala Phe Gly Tyr Thr Phe Thr Thr Tyr
                20                  25                  30

Ser Ile Glu Trp Met Lys Gln Asn His Gly Lys Ser Leu Glu Trp Ile
        35                  40                  45

Gly Asn Phe Arg Pro Tyr Asn Asp Asp Thr Lys Cys Asn Glu Lys Phe
        50                  55                  60

Lys Gly Lys Ala Lys Leu Thr Val Glu Lys Ser Ser Ser Thr Val Tyr
65                  70                  75                  80

Leu Glu Leu Ser Arg Leu Thr Ser Asp Asp Ser Ala Val Tyr Tyr Cys
                    85                  90                  95

Ala Arg Gly Ser Tyr Gly Asn Ser Phe Ala Tyr Trp Gly Gln Gly Thr
                100                 105                 110

Leu Val Thr Val Ser Ala
        115

<210> SEQ ID NO 22
<211> LENGTH: 113
<212> TYPE: PRT
<213> ORGANISM: Mus musculus

<400> SEQUENCE: 22

Asp Ile Val Met Thr Gln Ser Pro Ser Ser Leu Ser Val Ser Ala Gly
1                   5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                    85                  90                  95

Asp His Ser Tyr Pro Phe Thr Phe Gly Ser Gly Thr Lys Leu Glu Ile
                100                 105                 110

Lys
```

<210> SEQ ID NO 23
<211> LENGTH: 119
<212> TYPE: PRT
<213> ORGANISM: Mus musculus

<400> SEQUENCE: 23

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Ala Ser Tyr
                20                  25                  30

Lys Met Tyr Trp Val Lys Gln Ser His Gly Lys Ser Leu Glu Trp Ile
            35                  40                  45

Gly Tyr Ile Asp Pro Tyr Asn Gly Val Thr Ser Tyr Asn Gln Lys Phe
        50                  55                  60

Arg Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Gly Ala Tyr Tyr Gly Asn Ser Phe Asp Tyr Trp Gly Gln Gly
            100                 105                 110

Thr Thr Leu Thr Val Ser Ser
        115

<210> SEQ ID NO 24
<211> LENGTH: 113
<212> TYPE: PRT
<213> ORGANISM: Mus musculus

<400> SEQUENCE: 24

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Gln Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Val Asp Leu Ala Val Tyr Tyr Cys Gln Ser
                85                  90                  95

Ala Tyr Ser Phe Pro Tyr Thr Phe Gly Gly Gly Thr Lys Leu Glu Val
            100                 105                 110

Lys

<210> SEQ ID NO 25
<211> LENGTH: 117
<212> TYPE: PRT
<213> ORGANISM: Mus musculus

<400> SEQUENCE: 25

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
                20                  25                  30

Ile Met His Trp Val Lys Gln Lys Pro Gly Gln Gly Leu Glu Trp Ile

-continued

```
          35                  40                  45

Gly Tyr Phe Asn Pro Tyr Asn Asp Asp Ser Lys Thr Ser Glu Lys Phe
    50                  55                  60

Lys Gly Lys Ala Thr Leu Thr Ser Asp Lys Ser Ser Ser Thr Ala Tyr
65                  70                  75                  80

Met Glu Ile Asn Ser Leu Thr Ser Glu Asp Ser Ala Val Tyr Tyr Cys
                85                  90                  95

Ala Lys Leu Arg Gln Glu Arg Ile Ala Tyr Trp Gly Gln Gly Thr Leu
            100                 105                 110

Val Thr Val Ser Ala
        115

<210> SEQ ID NO 26
<211> LENGTH: 107
<212> TYPE: PRT
<213> ORGANISM: Mus musculus

<400> SEQUENCE: 26

Asp Ile Gln Met Asn Gln Ser Pro Ser Ser Leu Ser Ala Ser Leu Gly
1                   5                   10                  15

Asp Thr Ile Thr Ile Thr Cys His Ala Ser Gln Asn Ile Asp Val Trp
                20                  25                  30

Leu Ser Trp Tyr Gln Gln Lys Pro Gly Asn Phe Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
            100                 105

<210> SEQ ID NO 27
<211> LENGTH: 117
<212> TYPE: PRT
<213> ORGANISM: Mus musculus

<400> SEQUENCE: 27

Glu Val Gln Leu Gln Gln Ser Gly Pro Glu Leu Val Lys Pro Gly Ala
1                   5                   10                  15

Ser Val Lys Met Ser Cys Lys Ala Ser Gly Tyr Thr Phe Thr Arg Tyr
                20                  25                  30

Ile Ile His Trp Val Lys Gln Lys Pro Gly Gln Gly Leu Glu Trp Ile
            35                  40                  45

Gly Tyr Phe Asn Pro Tyr Asn Asp Asp Ser Lys Asn Asn Glu Lys Phe
    50                  55                  60

Lys Gly Lys Ala Thr Leu Thr Ser Asp Lys Ser Ser Ser Thr Ala Tyr
65                  70                  75                  80

Met Glu Ile Ser Ser Leu Thr Ser Glu Asp Ser Ala Val Tyr Tyr Cys
                85                  90                  95

Ala Lys Leu Arg Gln Glu Arg Ile Ala Tyr Trp Gly Gln Gly Thr Leu
            100                 105                 110

Val Thr Val Ser Ala
        115
```

-continued

<210> SEQ ID NO 28
<211> LENGTH: 107
<212> TYPE: PRT
<213> ORGANISM: Mus musculus

<400> SEQUENCE: 28

Asp Ile Gln Met Asn Gln Ser Pro Ser Ser Leu Ser Ala Ser Leu Gly
1               5                   10                  15

Asp Thr Ile Thr Ile Thr Cys His Val Ser Gln Asn Ile Asp Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
            100                 105

<210> SEQ ID NO 29
<211> LENGTH: 117
<212> TYPE: PRT
<213> ORGANISM: Mus musculus

<400> SEQUENCE: 29

Glu Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Asn Tyr
            20                  25                  30

Ile Ile His Trp Val Lys Gln Lys Pro Gly Gln Gly Leu Glu Trp Ile
        35                  40                  45

Gly Tyr Phe Asn Pro Tyr Asn Asp Gly Thr Lys Tyr Asn Glu Ile Phe
    50                  55                  60

Lys Asp Lys Ala Thr Leu Thr Ser Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Lys Leu Arg Gln Glu Arg Ile Ala Tyr Trp Gly Gln Gly Thr Leu
            100                 105                 110

Val Thr Val Ser Ala
        115

<210> SEQ ID NO 30
<211> LENGTH: 107
<212> TYPE: PRT
<213> ORGANISM: Mus musculus

<400> SEQUENCE: 30

Asp Ile Gln Met Asn Gln Ser Pro Ser Ser Leu Ser Ala Ser Leu Gly
1               5                   10                  15

Asp Thr Ile Thr Ile Thr Cys His Val Ser Gln Asn Ile Asp Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

-continued

```
Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
            100                 105

<210> SEQ ID NO 31
<211> LENGTH: 118
<212> TYPE: PRT
<213> ORGANISM: Mus musculus

<400> SEQUENCE: 31

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Ile Lys Gln Arg Pro Gly Gln Gly Leu Glu Trp Ile
            35                  40                  45

Gly Val Ile Asn Pro Gly Ser Gly Gly Thr Asn Tyr Asn Glu Lys Leu
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Gly Asp Ser Ala Val Tyr Phe Cys
                85                  90                  95

Ala Arg Tyr Val Lys Gly Asn Ala Leu Asp Tyr Trp Gly Gln Gly Thr
            100                 105                 110

Ser Val Thr Val Ser Ser
        115

<210> SEQ ID NO 32
<211> LENGTH: 113
<212> TYPE: PRT
<213> ORGANISM: Mus musculus

<400> SEQUENCE: 32

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Ser Leu Phe Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ser Tyr Ser Phe Pro Leu Thr Phe Gly Ala Gly Thr Lys Leu Glu Leu
            100                 105                 110

Thr

<210> SEQ ID NO 33
<211> LENGTH: 117
<212> TYPE: PRT
<213> ORGANISM: Mus musculus
```

<400> SEQUENCE: 33

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
                20                  25                  30

Ile Ile His Trp Val Lys Gln Lys Pro Gly Gln Gly Leu Glu Trp Ile
            35                  40                  45

Gly Tyr Phe Asn Pro Tyr Asn Asp Gly Ile Glu Tyr Ser Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Lys Leu Arg Gln Glu Arg Phe Ala Tyr Trp Gly Gln Gly Thr Leu
                100                 105                 110

Val Thr Val Ser Ala
            115
```

<210> SEQ ID NO 34
<211> LENGTH: 107
<212> TYPE: PRT
<213> ORGANISM: Mus musculus

<400> SEQUENCE: 34

```
Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
                20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys
                100                 105
```

<210> SEQ ID NO 35
<211> LENGTH: 117
<212> TYPE: PRT
<213> ORGANISM: Mus musculus

<400> SEQUENCE: 35

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
                20                  25                  30

Gly Val His Trp Val Arg Gln Pro Pro Gly Lys Gly Leu Glu Trp Leu
            35                  40                  45

Gly Val Ile Trp Ala Gly Gly Asn Thr Asn Tyr Asn Ser Ala Leu Met
        50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
```

```
                    85              90              95

Arg Val Tyr Tyr Gly Asn Ser Phe Asp Tyr Trp Gly Gln Gly Thr Thr
                100             105             110

Leu Thr Val Ser Ser
        115

<210> SEQ ID NO 36
<211> LENGTH: 113
<212> TYPE: PRT
<213> ORGANISM: Mus musculus

<400> SEQUENCE: 36

Asp Ile Val Met Thr Gln Ser Pro Ser Ser Leu Thr Val Thr Ala Gly
1               5               10              15

Glu Lys Val Thr Met Ser Cys Lys Ser Ser Gln Ser Leu Leu Asn Ser
                20              25              30

Gly Asn Gln Lys Asn Tyr Leu Thr Trp Tyr Gln Gln Lys Pro Gly Gln
        35              40              45

Pro Pro Lys Leu Leu Ile Tyr Trp Ala Ser Thr Arg Gln Ser Gly Val
        50              55              60

Pro Asp Arg Phe Thr Gly Ser Gly Ser Gly Thr Asp Phe Ser Leu Thr
65              70              75              80

Ile Ser Ser Val Gln Ala Glu Asp Leu Ala Val Tyr Tyr Cys His Asn
                85              90              95

Asp Tyr Thr Tyr Pro Leu Thr Phe Gly Ala Gly Thr Lys Leu Glu Leu
                100             105             110

Lys

<210> SEQ ID NO 37
<211> LENGTH: 120
<212> TYPE: PRT
<213> ORGANISM: Mus musculus

<400> SEQUENCE: 37

Glu Val Gln Leu Gln Gln Ser Gly Pro Glu Leu Val Lys Pro Gly Ala
1               5               10              15

Ser Val Lys Met Ser Cys Lys Ala Ser Gly Tyr Thr Phe Thr Ser Tyr
                20              25              30

Val Ile His Trp Val Lys Gln Lys Pro Gly Gln Gly Leu Glu Trp Ile
        35              40              45

Gly Tyr Ile Asn Pro Tyr Asn Asp Gly Ser Lys Tyr Asn Glu Lys Phe
        50              55              60

Lys Gly Lys Ala Thr Leu Thr Ser Asp Lys Ser Ser Ser Thr Ala Tyr
65              70              75              80

Met Glu Leu Ser Ser Leu Thr Ser Glu Asp Ser Ala Val Tyr Tyr Cys
                85              90              95

Ala Arg Glu Gly Tyr Gly Lys Arg Asn Ala Leu Asp Tyr Trp Gly Gln
                100             105             110

Gly Thr Ser Val Thr Val Ser Ser
        115             120

<210> SEQ ID NO 38
<211> LENGTH: 113
<212> TYPE: PRT
<213> ORGANISM: Mus musculus

<400> SEQUENCE: 38
```

```
Asp Ile Val Met Thr Gln Ser Pro Ser Ser Leu Ser Val Ser Ala Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Ile
65                  70                  75                  80

Ile Ser Ser Val Gln Val Glu Asp Leu Ala Val Tyr Tyr Cys Gln Asn
                85                  90                  95

Asp His Phe Tyr Pro Leu Thr Phe Gly Ala Gly Thr Lys Leu Glu Leu
                100                 105                 110

Lys

<210> SEQ ID NO 39
<211> LENGTH: 115
<212> TYPE: PRT
<213> ORGANISM: Mus musculus

<400> SEQUENCE: 39

Glu Ile Gln Leu Gln Gln Ser Gly Pro Glu Leu Met Lys Pro Gly Ala
1               5                   10                  15

Ser Val Lys Ile Ser Cys Lys Ala Ser Gly Tyr Ser Phe Thr Ser Tyr
            20                  25                  30

Tyr Met His Trp Val Lys Gln Ser His Gly Lys Ser Leu Glu Trp Ile
        35                  40                  45

Gly Tyr Phe Asp Pro Tyr Asn Gly Gly Thr Asn Tyr Asn Gln Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Cys Tyr Arg Phe Phe Ala Val Trp Gly Ala Gly Thr Thr Val Thr
                100                 105                 110

Val Ser Ser
        115

<210> SEQ ID NO 40
<211> LENGTH: 113
<212> TYPE: PRT
<213> ORGANISM: Mus musculus

<400> SEQUENCE: 40

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
```

-continued

```
                    85                  90                  95
Asp Tyr Ser Tyr Pro Leu Thr Phe Gly Ala Gly Thr Lys Leu Glu Leu
            100                 105                 110

Lys

<210> SEQ ID NO 41
<211> LENGTH: 118
<212> TYPE: PRT
<213> ORGANISM: Mus musculus

<400> SEQUENCE: 41

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Thr Phe
            20                  25                  30

Gly Met His Trp Val Arg Gln Ala Pro Glu Lys Gly Leu Glu Trp Val
            35                  40                  45

Ala Phe Ile Asn Gly Asp Ser Ser Ile Tyr Tyr Ala Asp Thr Val
        50                  55                  60

Lys Gly Arg Phe Thr Ile Ser Arg Asp Asn Pro Lys Asn Ile Leu Phe
65                  70                  75                  80

Leu Gln Met Thr Ser Leu Arg Ser Glu Asp Thr Ala Met Tyr Tyr Cys
                85                  90                  95

Ala Arg Phe Ala Arg Gly Asn Ser Phe Asp Tyr Trp Gly Gln Gly Thr
            100                 105                 110

Thr Leu Thr Val Ser Ser
        115

<210> SEQ ID NO 42
<211> LENGTH: 113
<212> TYPE: PRT
<213> ORGANISM: Mus musculus

<400> SEQUENCE: 42

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Asn Gln Lys Asn Tyr Leu Thr Trp Tyr Gln Lys Pro Trp Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Thr Ser Val Gln Thr Glu Asp Leu Ala Val Tyr Tyr Cys Gln Ile
                85                  90                  95

Gly Tyr Thr Tyr Pro Leu Thr Phe Gly Ala Gly Thr Lys Leu Glu Leu
            100                 105                 110

Lys

<210> SEQ ID NO 43
<211> LENGTH: 118
<212> TYPE: PRT
<213> ORGANISM: Mus musculus

<400> SEQUENCE: 43

Gln Val Gln Leu Lys Glu Ser Gly Pro Gly Leu Val Ala Pro Ser Gln
```

-continued

```
1             5                 10                15

Ser Leu Ser Ile Thr Cys Thr Val Ser Gly Phe Ser Leu Thr Ser Asn
             20                25                30

Gly Val His Trp Val Arg Gln Pro Pro Gly Lys Gly Leu Glu Trp Leu
             35                40                45

Gly Val Ile Trp Ala Gly Gly Ser Thr Asn Tyr Asn Ser Ala Leu Met
         50                55                60

Ser Arg Leu Ser Ile Ser Lys Asp Asn Ser Lys Ser Gln Val Phe Leu
65                70                75                80

Lys Met Asn Ser Leu Gln Thr His Asp Thr Ala Met Tyr Tyr Cys Ala
             85                90                95

Arg Asp Lys Tyr Asp Gly Thr Gly Phe Asp Tyr Trp Gly Gln Gly Thr
             100               105               110

Thr Leu Thr Val Ser Ser
             115
```

<210> SEQ ID NO 44
<211> LENGTH: 106
<212> TYPE: PRT
<213> ORGANISM: Mus musculus

<400> SEQUENCE: 44

```
Gln Ile Val Leu Thr Gln Ser Pro Ala Ile Met Ser Ala Ser Pro Gly
1             5                 10                15

Glu Lys Val Thr Met Thr Cys Ser Ala Ser Ser Ser Val Ser Asn Met
             20                25                30

Tyr Trp Tyr Gln Gln Lys Pro Gly Ser Ser Pro Arg Leu Leu Ile Tyr
             35                40                45

Asp Thr Ser Asn Leu Ala Ser Gly Val Pro Val Arg Phe Ser Gly Ser
         50                55                60

Gly Ser Gly Thr Ser Tyr Ser Leu Thr Ile Ser Arg Met Glu Ala Glu
65                70                75                80

Asp Ala Ala Thr Tyr Tyr Cys Gln Gln Trp Ser Ser Tyr Pro Tyr Thr
             85                90                95

Phe Gly Gly Gly Thr Lys Leu Glu Ile Lys
             100               105
```

<210> SEQ ID NO 45
<211> LENGTH: 119
<212> TYPE: PRT
<213> ORGANISM: Mus musculus

<400> SEQUENCE: 45

```
Glu Ile Gln Leu Gln Gln Ser Gly Pro Glu Leu Val Lys Pro Gly Ala
1             5                 10                15

Ser Val Lys Val Ser Cys Lys Ala Ser Gly Tyr Ala Phe Thr Arg Tyr
             20                25                30

Asn Met Tyr Trp Val Lys Gln Ser His Gly Lys Ser Leu Glu Trp Ile
             35                40                45

Gly Tyr Ile Asp Pro Tyr Asn Gly Gly Thr Asn Tyr Asn Gln Lys Phe
         50                55                60

Lys Gly Lys Ala Thr Leu Thr Val Asp Lys Ser Ser Ser Thr Ala Tyr
65                70                75                80

Met His Leu Asn Ser Leu Thr Ser Glu Asp Ser Ala Val Tyr Tyr Cys
             85                90                95

Ala Arg Gly Gly Tyr Tyr Gly Asn Ala Met Asp Tyr Trp Gly Gln Gly
```

-continued

```
                100                 105                 110

Thr Ser Val Thr Val Ser Ser
        115

<210> SEQ ID NO 46
<211> LENGTH: 113
<212> TYPE: PRT
<213> ORGANISM: Mus musculus

<400> SEQUENCE: 46

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ser Ile Tyr Tyr Cys Gln Ser
                85                  90                  95

Asn Tyr Ile Tyr Pro Phe Thr Phe Gly Ala Gly Thr Thr Leu Glu Leu
            100                 105                 110

Gln

<210> SEQ ID NO 47
<211> LENGTH: 8
<212> TYPE: PRT
<213> ORGANISM: Mus musculus

<400> SEQUENCE: 47

Gly Tyr Ala Tyr Thr Arg Tyr Asn
1               5

<210> SEQ ID NO 48
<211> LENGTH: 8
<212> TYPE: PRT
<213> ORGANISM: Mus musculus

<400> SEQUENCE: 48

Ile Asp Pro Tyr Asn Gly Gly Thr
1               5

<210> SEQ ID NO 49
<211> LENGTH: 12
<212> TYPE: PRT
<213> ORGANISM: Mus musculus

<400> SEQUENCE: 49

Ala Arg Gly Gly Tyr Tyr Gly Asn Ala Met Asp Tyr
1               5                   10

<210> SEQ ID NO 50
<211> LENGTH: 12
<212> TYPE: PRT
<213> ORGANISM: Mus musculus

<400> SEQUENCE: 50

Gln Ser Leu Leu Asn Ser Gly Asn Gln Lys Asn Tyr
1               5                   10
```

-continued

<210> SEQ ID NO 51
<211> LENGTH: 3
<212> TYPE: PRT
<213> ORGANISM: Mus musculus

<400> SEQUENCE: 51

Trp Ala Ser
1

<210> SEQ ID NO 52
<211> LENGTH: 9
<212> TYPE: PRT
<213> ORGANISM: Mus musculus

<400> SEQUENCE: 52

Gln Ser Asn Tyr Ile Tyr Pro Phe Thr
1               5

<210> SEQ ID NO 53
<211> LENGTH: 8
<212> TYPE: PRT
<213> ORGANISM: Mus musculus

<400> SEQUENCE: 53

Gly Phe Ser Leu Thr Ser Tyr Gly
1               5

<210> SEQ ID NO 54
<211> LENGTH: 7
<212> TYPE: PRT
<213> ORGANISM: Mus musculus

<400> SEQUENCE: 54

Ile Trp Ala Gly Gly Ser Thr
1               5

<210> SEQ ID NO 55
<211> LENGTH: 12
<212> TYPE: PRT
<213> ORGANISM: Mus musculus

<400> SEQUENCE: 55

Ala Arg Asp Phe Thr Thr Ala Thr Gly Phe Asp Tyr
1               5                   10

<210> SEQ ID NO 56
<211> LENGTH: 12
<212> TYPE: PRT
<213> ORGANISM: Mus musculus

<400> SEQUENCE: 56

Gln Ser Leu Leu Asn Ser Gly Asn Gln Lys Asn Tyr
1               5                   10

<210> SEQ ID NO 57
<211> LENGTH: 3
<212> TYPE: PRT
<213> ORGANISM: Mus musculus

<400> SEQUENCE: 57

Gly Ala Ser
1

```
<210> SEQ ID NO 58
<211> LENGTH: 9
<212> TYPE: PRT
<213> ORGANISM: Mus musculus

<400> SEQUENCE: 58

Gln Asn Asp His Ser Tyr Pro Phe Thr
1               5

<210> SEQ ID NO 59
<211> LENGTH: 8
<212> TYPE: PRT
<213> ORGANISM: Mus musculus

<400> SEQUENCE: 59

Gly Phe Thr Leu Ser Ser Tyr Thr
1               5

<210> SEQ ID NO 60
<211> LENGTH: 8
<212> TYPE: PRT
<213> ORGANISM: Mus musculus

<400> SEQUENCE: 60

Ile Ile Ile Gly Gly Ser Tyr Thr
1               5

<210> SEQ ID NO 61
<211> LENGTH: 11
<212> TYPE: PRT
<213> ORGANISM: Mus musculus

<400> SEQUENCE: 61

Ala Arg Gln Gly Tyr Gly Asn Ser Phe Pro Tyr
1               5                   10

<210> SEQ ID NO 62
<211> LENGTH: 12
<212> TYPE: PRT
<213> ORGANISM: Mus musculus

<400> SEQUENCE: 62

Gln Ser Leu Leu Asn Ser Gly Asn Gln Lys Asn Tyr
1               5                   10

<210> SEQ ID NO 63
<211> LENGTH: 3
<212> TYPE: PRT
<213> ORGANISM: Mus musculus

<400> SEQUENCE: 63

Trp Ala Ser
1

<210> SEQ ID NO 64
<211> LENGTH: 9
<212> TYPE: PRT
<213> ORGANISM: Mus musculus

<400> SEQUENCE: 64

Gln Asn Asp Tyr Ser Tyr Pro Phe Thr
1               5

<210> SEQ ID NO 65
<211> LENGTH: 8
```

-continued

```
<212> TYPE: PRT
<213> ORGANISM: Mus musculus

<400> SEQUENCE: 65

Gly Tyr Ser Phe Thr Gly Tyr Asn
1               5

<210> SEQ ID NO 66
<211> LENGTH: 8
<212> TYPE: PRT
<213> ORGANISM: Mus musculus

<400> SEQUENCE: 66

Ile Asp Pro Tyr Tyr Gly Gly Thr
1               5

<210> SEQ ID NO 67
<211> LENGTH: 11
<212> TYPE: PRT
<213> ORGANISM: Mus musculus

<400> SEQUENCE: 67

Ala Arg Leu Gly Leu Gly Asn Ala Met Asp Tyr
1               5                   10

<210> SEQ ID NO 68
<211> LENGTH: 12
<212> TYPE: PRT
<213> ORGANISM: Mus musculus

<400> SEQUENCE: 68

Gln Ser Leu Leu Asn Ser Gly Asn Gln Lys Ser Tyr
1               5                   10

<210> SEQ ID NO 69
<211> LENGTH: 3
<212> TYPE: PRT
<213> ORGANISM: Mus musculus

<400> SEQUENCE: 69

Trp Ala Ser
1

<210> SEQ ID NO 70
<211> LENGTH: 9
<212> TYPE: PRT
<213> ORGANISM: Mus musculus

<400> SEQUENCE: 70

Gln Asn Asp Tyr Tyr Tyr Pro Phe Thr
1               5

<210> SEQ ID NO 71
<211> LENGTH: 8
<212> TYPE: PRT
<213> ORGANISM: Mus musculus

<400> SEQUENCE: 71

Gly Tyr Thr Phe Thr Arg Tyr Leu
1               5

<210> SEQ ID NO 72
<211> LENGTH: 8
<212> TYPE: PRT
<213> ORGANISM: Mus musculus
```

-continued

<400> SEQUENCE: 72

Ile Asn Pro Ser Asn Gly Arg Thr
1               5

<210> SEQ ID NO 73
<211> LENGTH: 13
<212> TYPE: PRT
<213> ORGANISM: Mus musculus

<400> SEQUENCE: 73

Ala Arg Leu Ala Tyr Gly Tyr Gly Asn Ala Val Asp Tyr
1               5                   10

<210> SEQ ID NO 74
<211> LENGTH: 12
<212> TYPE: PRT
<213> ORGANISM: Mus musculus

<400> SEQUENCE: 74

Gln Ser Leu Leu Asn Ser Gly Asn Gln Lys Asn Tyr
1               5                   10

<210> SEQ ID NO 75
<211> LENGTH: 3
<212> TYPE: PRT
<213> ORGANISM: Mus musculus

<400> SEQUENCE: 75

Gly Ala Ser
1

<210> SEQ ID NO 76
<211> LENGTH: 9
<212> TYPE: PRT
<213> ORGANISM: Mus musculus

<400> SEQUENCE: 76

Gln Asn Asp His Ser Tyr Pro Leu Thr
1               5

<210> SEQ ID NO 77
<211> LENGTH: 8
<212> TYPE: PRT
<213> ORGANISM: Mus musculus

<400> SEQUENCE: 77

Gly Tyr Thr Phe Thr Ser Tyr Leu
1               5

<210> SEQ ID NO 78
<211> LENGTH: 8
<212> TYPE: PRT
<213> ORGANISM: Mus musculus

<400> SEQUENCE: 78

Ile Asn Pro Thr Thr Asp Tyr Thr
1               5

<210> SEQ ID NO 79
<211> LENGTH: 13
<212> TYPE: PRT
<213> ORGANISM: Mus musculus

<400> SEQUENCE: 79

```
Gly Arg Leu Gly Tyr Tyr Lys Arg Asn Ala Met Asp His
1               5               10

<210> SEQ ID NO 80
<211> LENGTH: 12
<212> TYPE: PRT
<213> ORGANISM: Mus musculus

<400> SEQUENCE: 80

Gln Ser Leu Leu Asn Ser Gly Asn Gln Lys Asn Tyr
1               5               10

<210> SEQ ID NO 81
<211> LENGTH: 3
<212> TYPE: PRT
<213> ORGANISM: Mus musculus

<400> SEQUENCE: 81

Gly Ala Ser
1

<210> SEQ ID NO 82
<211> LENGTH: 9
<212> TYPE: PRT
<213> ORGANISM: Mus musculus

<400> SEQUENCE: 82

Gln Asn Asp His Phe Tyr Pro Leu Thr
1               5

<210> SEQ ID NO 83
<211> LENGTH: 8
<212> TYPE: PRT
<213> ORGANISM: Mus musculus

<400> SEQUENCE: 83

Gly Phe Thr Phe Ser Asp Phe Tyr
1               5

<210> SEQ ID NO 84
<211> LENGTH: 10
<212> TYPE: PRT
<213> ORGANISM: Mus musculus

<400> SEQUENCE: 84

Ser Arg Asn Lys Ala Asn Asp Tyr Thr Thr
1               5               10

<210> SEQ ID NO 85
<211> LENGTH: 12
<212> TYPE: PRT
<213> ORGANISM: Mus musculus

<400> SEQUENCE: 85

Ala Arg Asp Ala Cys Pro Trp Asp Trp Phe Ala Tyr
1               5               10

<210> SEQ ID NO 86
<211> LENGTH: 12
<212> TYPE: PRT
<213> ORGANISM: Mus musculus

<400> SEQUENCE: 86

Gln Ser Leu Leu Asn Ser Gly Asn Gln Lys Asn Tyr
```

-continued

```
1               5                    10

<210> SEQ ID NO 87
<211> LENGTH: 3
<212> TYPE: PRT
<213> ORGANISM: Mus musculus

<400> SEQUENCE: 87

Trp Ala Ser
1

<210> SEQ ID NO 88
<211> LENGTH: 9
<212> TYPE: PRT
<213> ORGANISM: Mus musculus

<400> SEQUENCE: 88

Gln Asn Asp Tyr Ser Tyr Pro Phe Thr
1               5

<210> SEQ ID NO 89
<211> LENGTH: 8
<212> TYPE: PRT
<213> ORGANISM: Mus musculus

<400> SEQUENCE: 89

Asp Tyr Ala Phe Thr Arg Tyr Asn
1               5

<210> SEQ ID NO 90
<211> LENGTH: 8
<212> TYPE: PRT
<213> ORGANISM: Mus musculus

<400> SEQUENCE: 90

Ile Asp Pro Tyr Asn Gly Gly Thr
1               5

<210> SEQ ID NO 91
<211> LENGTH: 12
<212> TYPE: PRT
<213> ORGANISM: Mus musculus

<400> SEQUENCE: 91

Ala Arg Gly Gly Tyr Tyr Gly Asn Ala Met Asp Tyr
1               5                    10

<210> SEQ ID NO 92
<211> LENGTH: 12
<212> TYPE: PRT
<213> ORGANISM: Mus musculus

<400> SEQUENCE: 92

Gln Ser Leu Leu Asn Ser Gly Asn Gln Lys Asn Tyr
1               5                    10

<210> SEQ ID NO 93
<211> LENGTH: 3
<212> TYPE: PRT
<213> ORGANISM: Mus musculus

<400> SEQUENCE: 93

Trp Ala Ser
1
```

```
<210> SEQ ID NO 94
<211> LENGTH: 9
<212> TYPE: PRT
<213> ORGANISM: Mus musculus

<400> SEQUENCE: 94

Gln Ser Asn Tyr Ile Tyr Pro Phe Thr
1               5

<210> SEQ ID NO 95
<211> LENGTH: 8
<212> TYPE: PRT
<213> ORGANISM: Mus musculus

<400> SEQUENCE: 95

Gly Tyr Thr Phe Thr Ser Tyr Leu
1               5

<210> SEQ ID NO 96
<211> LENGTH: 8
<212> TYPE: PRT
<213> ORGANISM: Mus musculus

<400> SEQUENCE: 96

Ile Ile Pro Ser Asn Gly Arg Thr
1               5

<210> SEQ ID NO 97
<211> LENGTH: 13
<212> TYPE: PRT
<213> ORGANISM: Mus musculus

<400> SEQUENCE: 97

Ala Arg Leu Ala Tyr Gly Tyr Gly Asn Ala Val Asp Tyr
1               5                   10

<210> SEQ ID NO 98
<211> LENGTH: 12
<212> TYPE: PRT
<213> ORGANISM: Mus musculus

<400> SEQUENCE: 98

Gln Ser Leu Leu Asn Ser Gly Asn Gln Lys Asn Tyr
1               5                   10

<210> SEQ ID NO 99
<211> LENGTH: 3
<212> TYPE: PRT
<213> ORGANISM: Mus musculus

<400> SEQUENCE: 99

Gly Ala Ser
1

<210> SEQ ID NO 100
<211> LENGTH: 9
<212> TYPE: PRT
<213> ORGANISM: Mus musculus

<400> SEQUENCE: 100

Gln Asn Asp His Thr Tyr Pro Leu Thr
1               5

<210> SEQ ID NO 101
```

```
<211> LENGTH: 8
<212> TYPE: PRT
<213> ORGANISM: Mus musculus

<400> SEQUENCE: 101

Gly Tyr Ser Phe Thr Gly Tyr Lys
1               5

<210> SEQ ID NO 102
<211> LENGTH: 8
<212> TYPE: PRT
<213> ORGANISM: Mus musculus

<400> SEQUENCE: 102

Ile Asp Pro Tyr Tyr Gly Gly Pro
1               5

<210> SEQ ID NO 103
<211> LENGTH: 11
<212> TYPE: PRT
<213> ORGANISM: Mus musculus

<400> SEQUENCE: 103

Ala Arg Leu Asp Tyr Gly Asn Ser Phe Ala Tyr
1               5                   10

<210> SEQ ID NO 104
<211> LENGTH: 12
<212> TYPE: PRT
<213> ORGANISM: Mus musculus

<400> SEQUENCE: 104

Gln Ser Leu Leu Asn Ser Gly Asn Gln Lys Asn Tyr
1               5                   10

<210> SEQ ID NO 105
<211> LENGTH: 3
<212> TYPE: PRT
<213> ORGANISM: Mus musculus

<400> SEQUENCE: 105

Gly Ala Ser
1

<210> SEQ ID NO 106
<211> LENGTH: 9
<212> TYPE: PRT
<213> ORGANISM: Mus musculus

<400> SEQUENCE: 106

Gln Asn Asp His Ser Tyr Pro Phe Thr
1               5

<210> SEQ ID NO 107
<211> LENGTH: 8
<212> TYPE: PRT
<213> ORGANISM: Mus musculus

<400> SEQUENCE: 107

Gly Tyr Thr Phe Thr Thr Tyr Ser
1               5

<210> SEQ ID NO 108
<211> LENGTH: 8
<212> TYPE: PRT
```

-continued

```
<213> ORGANISM: Mus musculus

<400> SEQUENCE: 108

Phe Arg Pro Tyr Asn Asp Asp Thr
1               5

<210> SEQ ID NO 109
<211> LENGTH: 11
<212> TYPE: PRT
<213> ORGANISM: Mus musculus

<400> SEQUENCE: 109

Ala Arg Gly Ser Tyr Gly Asn Ser Phe Ala Tyr
1               5                   10

<210> SEQ ID NO 110
<211> LENGTH: 12
<212> TYPE: PRT
<213> ORGANISM: Mus musculus

<400> SEQUENCE: 110

Gln Ser Leu Leu Asn Ser Gly Asn Gln Lys Asn Tyr
1               5                   10

<210> SEQ ID NO 111
<211> LENGTH: 3
<212> TYPE: PRT
<213> ORGANISM: Mus musculus

<400> SEQUENCE: 111

Gly Ala Ser
1

<210> SEQ ID NO 112
<211> LENGTH: 9
<212> TYPE: PRT
<213> ORGANISM: Mus musculus

<400> SEQUENCE: 112

Gln Asn Asp His Ser Tyr Pro Phe Thr
1               5

<210> SEQ ID NO 113
<211> LENGTH: 8
<212> TYPE: PRT
<213> ORGANISM: Mus musculus

<400> SEQUENCE: 113

Gly Tyr Ala Phe Ala Ser Tyr Lys
1               5

<210> SEQ ID NO 114
<211> LENGTH: 8
<212> TYPE: PRT
<213> ORGANISM: Mus musculus

<400> SEQUENCE: 114

Ile Asp Pro Tyr Asn Gly Val Thr
1               5

<210> SEQ ID NO 115
<211> LENGTH: 12
<212> TYPE: PRT
<213> ORGANISM: Mus musculus
```

```
<400> SEQUENCE: 115

Ala Arg Gly Ala Tyr Tyr Gly Asn Ser Phe Asp Tyr
1               5                   10

<210> SEQ ID NO 116
<211> LENGTH: 12
<212> TYPE: PRT
<213> ORGANISM: Mus musculus

<400> SEQUENCE: 116

Gln Ser Leu Leu Asn Ser Gly Asn Gln Lys Asn Tyr
1               5                   10

<210> SEQ ID NO 117
<211> LENGTH: 3
<212> TYPE: PRT
<213> ORGANISM: Mus musculus

<400> SEQUENCE: 117

Trp Ala Ser
1

<210> SEQ ID NO 118
<211> LENGTH: 9
<212> TYPE: PRT
<213> ORGANISM: Mus musculus

<400> SEQUENCE: 118

Gln Ser Ala Tyr Ser Phe Pro Tyr Thr
1               5

<210> SEQ ID NO 119
<211> LENGTH: 8
<212> TYPE: PRT
<213> ORGANISM: Mus musculus

<400> SEQUENCE: 119

Gly Tyr Thr Phe Thr Arg Tyr Ile
1               5

<210> SEQ ID NO 120
<211> LENGTH: 8
<212> TYPE: PRT
<213> ORGANISM: Mus musculus

<400> SEQUENCE: 120

Phe Asn Pro Tyr Asn Asp Asp Ser
1               5

<210> SEQ ID NO 121
<211> LENGTH: 10
<212> TYPE: PRT
<213> ORGANISM: Mus musculus

<400> SEQUENCE: 121

Ala Lys Leu Arg Gln Glu Arg Ile Ala Tyr
1               5                   10

<210> SEQ ID NO 122
<211> LENGTH: 6
<212> TYPE: PRT
<213> ORGANISM: Mus musculus

<400> SEQUENCE: 122
```

-continued

```
Gln Asn Ile Asp Val Trp
1               5

<210> SEQ ID NO 123
<211> LENGTH: 3
<212> TYPE: PRT
<213> ORGANISM: Mus musculus

<400> SEQUENCE: 123

Lys Ala Ser
1

<210> SEQ ID NO 124
<211> LENGTH: 9
<212> TYPE: PRT
<213> ORGANISM: Mus musculus

<400> SEQUENCE: 124

Gln Gln Gly Gln Ser Tyr Pro Leu Thr
1               5

<210> SEQ ID NO 125
<211> LENGTH: 8
<212> TYPE: PRT
<213> ORGANISM: Mus musculus

<400> SEQUENCE: 125

Gly Tyr Thr Phe Thr Arg Tyr Ile
1               5

<210> SEQ ID NO 126
<211> LENGTH: 8
<212> TYPE: PRT
<213> ORGANISM: Mus musculus

<400> SEQUENCE: 126

Phe Asn Pro Tyr Asn Asp Asp Ser
1               5

<210> SEQ ID NO 127
<211> LENGTH: 10
<212> TYPE: PRT
<213> ORGANISM: Mus musculus

<400> SEQUENCE: 127

Ala Lys Leu Arg Gln Glu Arg Ile Ala Tyr
1               5                   10

<210> SEQ ID NO 128
<211> LENGTH: 6
<212> TYPE: PRT
<213> ORGANISM: Mus musculus

<400> SEQUENCE: 128

Gln Asn Ile Asp Val Trp
1               5

<210> SEQ ID NO 129
<211> LENGTH: 3
<212> TYPE: PRT
<213> ORGANISM: Mus musculus

<400> SEQUENCE: 129

Lys Ala Ser
1
```

```
<210> SEQ ID NO 130
<211> LENGTH: 9
<212> TYPE: PRT
<213> ORGANISM: Mus musculus

<400> SEQUENCE: 130

Gln Gln Gly Gln Ser Tyr Pro Leu Thr
1               5

<210> SEQ ID NO 131
<211> LENGTH: 9
<212> TYPE: PRT
<213> ORGANISM: Mus musculus

<400> SEQUENCE: 131

Gln Gln Gly Gln Ser Tyr Pro Leu Thr
1               5

<210> SEQ ID NO 132
<211> LENGTH: 8
<212> TYPE: PRT
<213> ORGANISM: Mus musculus

<400> SEQUENCE: 132

Phe Asn Pro Tyr Asn Asp Gly Thr
1               5

<210> SEQ ID NO 133
<211> LENGTH: 10
<212> TYPE: PRT
<213> ORGANISM: Mus musculus

<400> SEQUENCE: 133

Ala Lys Leu Arg Gln Glu Arg Ile Ala Tyr
1               5                   10

<210> SEQ ID NO 134
<211> LENGTH: 6
<212> TYPE: PRT
<213> ORGANISM: Mus musculus

<400> SEQUENCE: 134

Gln Asn Ile Asp Val Trp
1               5

<210> SEQ ID NO 135
<211> LENGTH: 3
<212> TYPE: PRT
<213> ORGANISM: Mus musculus

<400> SEQUENCE: 135

Lys Ala Ser
1

<210> SEQ ID NO 136
<211> LENGTH: 9
<212> TYPE: PRT
<213> ORGANISM: Mus musculus

<400> SEQUENCE: 136

Gln Gln Gly Gln Ser Tyr Pro Leu Thr
1               5
```

-continued

```
<210> SEQ ID NO 137
<211> LENGTH: 8
<212> TYPE: PRT
<213> ORGANISM: Mus musculus

<400> SEQUENCE: 137

Gly Tyr Ala Phe Thr Asn Tyr Leu
1               5

<210> SEQ ID NO 138
<211> LENGTH: 8
<212> TYPE: PRT
<213> ORGANISM: Mus musculus

<400> SEQUENCE: 138

Ile Asn Pro Gly Ser Gly Gly Thr
1               5

<210> SEQ ID NO 139
<211> LENGTH: 11
<212> TYPE: PRT
<213> ORGANISM: Mus musculus

<400> SEQUENCE: 139

Ala Arg Tyr Val Lys Gly Asn Ala Leu Asp Tyr
1               5                   10

<210> SEQ ID NO 140
<211> LENGTH: 12
<212> TYPE: PRT
<213> ORGANISM: Mus musculus

<400> SEQUENCE: 140

Gln Ser Leu Phe Asn Ser Gly Asn Gln Lys Asn Tyr
1               5                   10

<210> SEQ ID NO 141
<211> LENGTH: 3
<212> TYPE: PRT
<213> ORGANISM: Mus musculus

<400> SEQUENCE: 141

Trp Ala Ser
1

<210> SEQ ID NO 142
<211> LENGTH: 9
<212> TYPE: PRT
<213> ORGANISM: Mus musculus

<400> SEQUENCE: 142

Gln Asn Ser Tyr Ser Phe Pro Leu Thr
1               5

<210> SEQ ID NO 143
<211> LENGTH: 8
<212> TYPE: PRT
<213> ORGANISM: Mus musculus

<400> SEQUENCE: 143

Gly Tyr Thr Phe Thr Asn Tyr Ile
1               5

<210> SEQ ID NO 144
<211> LENGTH: 8
```

```
<212> TYPE: PRT
<213> ORGANISM: Mus musculus

<400> SEQUENCE: 144

Phe Asn Pro Tyr Asn Asp Gly Ile
1               5

<210> SEQ ID NO 145
<211> LENGTH: 10
<212> TYPE: PRT
<213> ORGANISM: Mus musculus

<400> SEQUENCE: 145

Ser Lys Leu Arg Gln Glu Arg Phe Ala Tyr
1               5                   10

<210> SEQ ID NO 146
<211> LENGTH: 6
<212> TYPE: PRT
<213> ORGANISM: Mus musculus

<400> SEQUENCE: 146

Gln Asn Ile Asn Val Trp
1               5

<210> SEQ ID NO 147
<211> LENGTH: 3
<212> TYPE: PRT
<213> ORGANISM: Mus musculus

<400> SEQUENCE: 147

Lys Ala Ser
1

<210> SEQ ID NO 148
<211> LENGTH: 9
<212> TYPE: PRT
<213> ORGANISM: Mus musculus

<400> SEQUENCE: 148

Gln Gln Gly Gln Ser Tyr Pro Leu Thr
1               5

<210> SEQ ID NO 149
<211> LENGTH: 8
<212> TYPE: PRT
<213> ORGANISM: Mus musculus

<400> SEQUENCE: 149

Gly Phe Ser Leu Ile Ser Tyr Gly
1               5

<210> SEQ ID NO 150
<211> LENGTH: 7
<212> TYPE: PRT
<213> ORGANISM: Mus musculus

<400> SEQUENCE: 150

Ile Trp Ala Gly Gly Asn Thr
1               5

<210> SEQ ID NO 151
<211> LENGTH: 11
<212> TYPE: PRT
<213> ORGANISM: Mus musculus
```

-continued

<400> SEQUENCE: 151

Ala Arg Val Tyr Tyr Gly Asn Ser Phe Asp Tyr
1                 5                   10

<210> SEQ ID NO 152
<211> LENGTH: 12
<212> TYPE: PRT
<213> ORGANISM: Mus musculus

<400> SEQUENCE: 152

Gln Ser Leu Leu Asn Ser Gly Asn Gln Lys Asn Tyr
1                 5                   10

<210> SEQ ID NO 153
<211> LENGTH: 3
<212> TYPE: PRT
<213> ORGANISM: Mus musculus

<400> SEQUENCE: 153

Trp Ala Ser
1

<210> SEQ ID NO 154
<211> LENGTH: 9
<212> TYPE: PRT
<213> ORGANISM: Mus musculus

<400> SEQUENCE: 154

His Asn Asp Tyr Thr Tyr Pro Leu Thr
1                 5

<210> SEQ ID NO 155
<211> LENGTH: 8
<212> TYPE: PRT
<213> ORGANISM: Mus musculus

<400> SEQUENCE: 155

Gly Tyr Thr Phe Thr Ser Tyr Val
1                 5

<210> SEQ ID NO 156
<211> LENGTH: 8
<212> TYPE: PRT
<213> ORGANISM: Mus musculus

<400> SEQUENCE: 156

Ile Asn Pro Tyr Asn Asp Gly Ser
1                 5

<210> SEQ ID NO 157
<211> LENGTH: 13
<212> TYPE: PRT
<213> ORGANISM: Mus musculus

<400> SEQUENCE: 157

Ala Arg Glu Gly Tyr Gly Lys Arg Asn Ala Leu Asp Tyr
1                 5                   10

<210> SEQ ID NO 158
<211> LENGTH: 12
<212> TYPE: PRT
<213> ORGANISM: Mus musculus

<400> SEQUENCE: 158

```
Gln Ser Leu Leu Asn Ser Gly Asn Gln Lys Asn Tyr
1               5                   10

<210> SEQ ID NO 159
<211> LENGTH: 3
<212> TYPE: PRT
<213> ORGANISM: Mus musculus

<400> SEQUENCE: 159

Gly Ala Ser
1

<210> SEQ ID NO 160
<211> LENGTH: 9
<212> TYPE: PRT
<213> ORGANISM: Mus musculus

<400> SEQUENCE: 160

Gln Asn Asp His Phe Tyr Pro Leu Thr
1               5

<210> SEQ ID NO 161
<211> LENGTH: 8
<212> TYPE: PRT
<213> ORGANISM: Mus musculus

<400> SEQUENCE: 161

Gly Tyr Ser Phe Thr Ser Tyr Tyr
1               5

<210> SEQ ID NO 162
<211> LENGTH: 8
<212> TYPE: PRT
<213> ORGANISM: Mus musculus

<400> SEQUENCE: 162

Phe Asp Pro Tyr Asn Gly Gly Thr
1               5

<210> SEQ ID NO 163
<211> LENGTH: 8
<212> TYPE: PRT
<213> ORGANISM: Mus musculus

<400> SEQUENCE: 163

Ala Cys Tyr Arg Phe Phe Ala Val
1               5

<210> SEQ ID NO 164
<211> LENGTH: 12
<212> TYPE: PRT
<213> ORGANISM: Mus musculus

<400> SEQUENCE: 164

Gln Ser Leu Leu Asn Ser Gly Asn Gln Lys Asn Tyr
1               5                   10

<210> SEQ ID NO 165
<211> LENGTH: 3
<212> TYPE: PRT
<213> ORGANISM: Mus musculus

<400> SEQUENCE: 165

Trp Ala Ser
```

-continued

1

<210> SEQ ID NO 166
<211> LENGTH: 9
<212> TYPE: PRT
<213> ORGANISM: Mus musculus

<400> SEQUENCE: 166

Gln Asn Asp Tyr Ser Tyr Pro Leu Thr
1               5

<210> SEQ ID NO 167
<211> LENGTH: 8
<212> TYPE: PRT
<213> ORGANISM: Mus musculus

<400> SEQUENCE: 167

Gly Phe Thr Phe Ser Thr Phe Gly
1               5

<210> SEQ ID NO 168
<211> LENGTH: 8
<212> TYPE: PRT
<213> ORGANISM: Mus musculus

<400> SEQUENCE: 168

Ile Asn Gly Asp Ser Ser Ser Ile
1               5

<210> SEQ ID NO 169
<211> LENGTH: 11
<212> TYPE: PRT
<213> ORGANISM: Mus musculus

<400> SEQUENCE: 169

Ala Arg Phe Ala Arg Gly Asn Ser Phe Asp Tyr
1               5                   10

<210> SEQ ID NO 170
<211> LENGTH: 12
<212> TYPE: PRT
<213> ORGANISM: Mus musculus

<400> SEQUENCE: 170

Gln Ser Leu Phe Asn Ser Gly Asn Gln Lys Asn Tyr
1               5                   10

<210> SEQ ID NO 171
<211> LENGTH: 3
<212> TYPE: PRT
<213> ORGANISM: Mus musculus

<400> SEQUENCE: 171

Trp Ala Ser
1

<210> SEQ ID NO 172
<211> LENGTH: 9
<212> TYPE: PRT
<213> ORGANISM: Mus musculus

<400> SEQUENCE: 172

Gln Ile Gly Tyr Thr Tyr Pro Leu Thr
1               5

```
<210> SEQ ID NO 173
<211> LENGTH: 8
<212> TYPE: PRT
<213> ORGANISM: Mus musculus

<400> SEQUENCE: 173

Gly Phe Ser Leu Thr Ser Asn Gly
1               5

<210> SEQ ID NO 174
<211> LENGTH: 7
<212> TYPE: PRT
<213> ORGANISM: Mus musculus

<400> SEQUENCE: 174

Ile Trp Ala Gly Gly Ser Thr
1               5

<210> SEQ ID NO 175
<211> LENGTH: 12
<212> TYPE: PRT
<213> ORGANISM: Mus musculus

<400> SEQUENCE: 175

Ala Arg Asp Lys Tyr Asp Gly Thr Gly Phe Asp Tyr
1               5                   10

<210> SEQ ID NO 176
<211> LENGTH: 5
<212> TYPE: PRT
<213> ORGANISM: Mus musculus

<400> SEQUENCE: 176

Ser Ser Val Ser Asn
1               5

<210> SEQ ID NO 177
<211> LENGTH: 3
<212> TYPE: PRT
<213> ORGANISM: Mus musculus

<400> SEQUENCE: 177

Asp Thr Ser
1

<210> SEQ ID NO 178
<211> LENGTH: 9
<212> TYPE: PRT
<213> ORGANISM: Mus musculus

<400> SEQUENCE: 178

Gln Gln Trp Ser Ser Tyr Pro Tyr Thr
1               5

<210> SEQ ID NO 179
<211> LENGTH: 8
<212> TYPE: PRT
<213> ORGANISM: Mus musculus

<400> SEQUENCE: 179

Gly Tyr Ala Phe Thr Arg Tyr Asn
1               5

<210> SEQ ID NO 180
```

```
<211> LENGTH: 8
<212> TYPE: PRT
<213> ORGANISM: Mus musculus

<400> SEQUENCE: 180

Ile Asp Pro Tyr Asn Gly Gly Thr
1               5

<210> SEQ ID NO 181
<211> LENGTH: 12
<212> TYPE: PRT
<213> ORGANISM: Mus musculus

<400> SEQUENCE: 181

Ala Arg Gly Gly Tyr Tyr Gly Asn Ala Met Asp Tyr
1               5                   10

<210> SEQ ID NO 182
<211> LENGTH: 12
<212> TYPE: PRT
<213> ORGANISM: Mus musculus

<400> SEQUENCE: 182

Gln Ser Leu Leu Asn Ser Gly Asn Gln Lys Asn Tyr
1               5                   10

<210> SEQ ID NO 183
<211> LENGTH: 3
<212> TYPE: PRT
<213> ORGANISM: Mus musculus

<400> SEQUENCE: 183

Trp Ala Ser
1

<210> SEQ ID NO 184
<211> LENGTH: 9
<212> TYPE: PRT
<213> ORGANISM: Mus musculus

<400> SEQUENCE: 184

Gln Ser Asn Tyr Ile Tyr Pro Phe Thr
1               5

<210> SEQ ID NO 185
<211> LENGTH: 125
<212> TYPE: PRT
<213> ORGANISM: Homo sapiens

<400> SEQUENCE: 185

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
            35                  40                  45

Ala Val Ile Trp Tyr Asp Gly Ser Asn Lys Asn Tyr Ala Asp Ser Val
        50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95
```

Ala Arg Arg Gly Tyr Asp Ile Leu Thr Gly Tyr Asp Tyr Tyr Gly Met
            100                     105                     110

Asp Val Trp Gly Gln Gly Thr Thr Val Thr Val Ser Ala
        115                     120                 125

<210> SEQ ID NO 186
<211> LENGTH: 110
<212> TYPE: PRT
<213> ORGANISM: Homo sapiens

<400> SEQUENCE: 186

Gln Thr Val Val Thr Gln Glu Pro Ser Phe Ser Val Ser Pro Gly Gly
1                   5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Arg Thr Asn Thr Arg Ser Ser Gly Val Pro Asp Arg Phe
    50                  55                  60

Ser Gly Ser Ile Leu Gly Asn Lys Ala Ala Leu Thr Ile Ser Gly Ala
65                  70                  75                  80

Gln Ala Pro Asp Glu Ser Asn Tyr Tyr Cys Val Leu Tyr Met Gly Ser
                85                  90                  95

Gly Ile Trp Val Phe Gly Gly Gly Thr Lys Leu Thr Val Leu
            100                 105                 110

<210> SEQ ID NO 187
<211> LENGTH: 124
<212> TYPE: PRT
<213> ORGANISM: Homo sapiens

<400> SEQUENCE: 187

Gln Leu Arg Leu Gln Glu Ser Gly Pro Gly Leu Val Lys Pro Ser Glu
1                   5                   10                  15

Thr Leu Ser Leu Thr Cys Ala Val Ser Gly Gly Ser Ile Ser Ser Ser
            20                  25                  30

Arg Ser Tyr Trp Gly Trp Ile Arg Gln Pro Pro Gly Lys Gly Leu Glu
        35                  40                  45

Leu Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Thr Asp Thr Ala Val Tyr Tyr
                85                  90                  95

Cys Ala Arg Gln Thr Leu Arg Tyr Phe Asp Trp Leu Ser Pro Phe Asp
            100                 105                 110

Tyr Trp Gly Gln Gly Thr Leu Val Thr Val Ser Ser
        115                 120

<210> SEQ ID NO 188
<211> LENGTH: 108
<212> TYPE: PRT
<213> ORGANISM: Homo sapiens

<400> SEQUENCE: 188

Glu Ile Val Met Thr Gln Ser Pro Ala Thr Leu Ser Leu Ser Pro Gly
1                   5                   10                  15

Glu Arg Ala Thr Leu Ser Cys Arg Ala Ser Gln Ser Val Arg Ser Asn

-continued

```
             20              25              30

Tyr Leu Ser Trp Tyr Gln Gln Lys Pro Gly Gln Ala Pro Arg Leu Leu
         35              40              45

Ile Tyr Gly Thr Ser Thr Arg Ala Thr Gly Ile Pro Ala Arg Phe Ser
     50              55              60

Gly Ser Gly Ser Gly Thr Asp Phe Thr Leu Thr Ile Ser Ser Leu Gln
65              70              75              80

Pro Glu Asp Phe Ala Val Tyr Phe Cys Gln Gln Asp Tyr Asn Leu Pro
                 85              90              95

Ile Thr Phe Gly Gln Gly Thr Arg Leu Glu Ile Lys
             100             105
```

```
<210> SEQ ID NO 189
<211> LENGTH: 124
<212> TYPE: PRT
<213> ORGANISM: Homo sapiens

<400> SEQUENCE: 189

Gln Leu Gln Leu Gln Glu Ser Gly Pro Gly Leu Val Lys Pro Ser Glu
1               5               10              15

Thr Leu Ser Leu Thr Cys Thr Val Ser Asp Gly Pro Ile Ser Ser Ser
             20              25              30

Arg Tyr Tyr Trp Gly Trp Ile Arg Gln Pro Pro Gly Lys Gly Leu Glu
         35              40              45

Trp Ile Gly Ser Phe His Tyr Ser Gly Ser Thr Tyr Tyr Asn Pro Ser
     50              55              60

Leu Lys Ser Arg Val Thr Ile Ser Ala Asp Thr Ser Lys Asn Gln Phe
65              70              75              80

Ser Leu Lys Leu Ser Ser Val Thr Ala Ala Asp Thr Ala Val Tyr Tyr
                 85              90              95

Cys Ala Arg Leu Val Leu Arg Tyr Phe Asp Trp Leu Gly Phe Phe Asp
             100             105             110

Leu Trp Gly Arg Gly Thr Leu Val Thr Val Ser Ser
         115             120
```

```
<210> SEQ ID NO 190
<211> LENGTH: 108
<212> TYPE: PRT
<213> ORGANISM: Homo sapiens

<400> SEQUENCE: 190

Glu Ile Val Met Thr Gln Ser Pro Ala Ile Leu Ser Leu Ser Pro Gly
1               5               10              15

Glu Arg Ala Ala Leu Ser Cys Arg Ala Ser Gln Ser Val Arg Ser Ser
             20              25              30

Tyr Leu Ser Trp Tyr Gln Gln Lys Pro Gly Gln Ala Pro Arg Leu Leu
         35              40              45

Ile Tyr Gly Thr Ser Thr Arg Ala Thr Gly Ile Pro Ala Arg Phe Ser
     50              55              60

Gly Ser Gly Ser Gly Thr Asp Phe Thr Leu Thr Ile Ser Ser Leu Gln
65              70              75              80

Pro Glu Asp Phe Ala Val Tyr Tyr Cys Gln Gln Asp Tyr Asn Leu Pro
                 85              90              95

Ile Thr Phe Gly Gln Gly Thr Arg Leu Glu Phe Lys
             100             105
```

```
<210> SEQ ID NO 191
<211> LENGTH: 125
<212> TYPE: PRT
<213> ORGANISM: Homo sapiens

<400> SEQUENCE: 191

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asn Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Asn Tyr Asp Ile Leu Thr Gly Arg Asp Tyr Tyr Gly Met
            100                 105                 110

Asp Val Trp Gly Gln Gly Thr Thr Val Thr Val Ser Ser
        115                 120                 125

<210> SEQ ID NO 192
<211> LENGTH: 110
<212> TYPE: PRT
<213> ORGANISM: Homo sapiens

<400> SEQUENCE: 192

Gln Thr Val Val Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Ser
            20                  25                  30

Tyr Tyr Pro Ser Trp Tyr Gln Gln Thr Pro Gly Gln Ala Pro Arg Thr
            35                  40                  45

Leu Ile Tyr Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Asp Ser Asp Tyr Tyr Cys Val Leu Tyr Met Gly Ser
                85                  90                  95

Gly Ile Trp Val Phe Gly Gly Gly Thr Lys Leu Thr Val Leu
            100                 105                 110

<210> SEQ ID NO 193
<211> LENGTH: 125
<212> TYPE: PRT
<213> ORGANISM: Homo sapiens

<400> SEQUENCE: 193

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Ser Ser
            20                  25                  30

Tyr Met His Trp Val Arg Gln Ala Pro Gly Gln Gly Leu Glu Trp Met
        35                  40                  45

Gly Ile Ile Asn Pro Ser Gly Gly Arg Thr Asn Tyr Ala Gln Lys Phe
        50                  55                  60
```

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Tyr Asp Ile Phe Thr Thr Tyr Tyr Pro Arg Gly Met
            100                 105                 110

Asp Val Trp Gly Gln Gly Thr Thr Val Thr Val Ser Ser
        115                 120                 125
```

<210> SEQ ID NO 194
<211> LENGTH: 107
<212> TYPE: PRT
<213> ORGANISM: Homo sapiens

<400> SEQUENCE: 194

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Phe Pro Phe
                85                  90                  95

Thr Phe Gly Gln Gly Thr Glu Leu Glu Ile Arg
            100                 105
```

<210> SEQ ID NO 195
<211> LENGTH: 124
<212> TYPE: PRT
<213> ORGANISM: Homo sapiens

<400> SEQUENCE: 195

```
Gln Met Gln Leu Arg Glu Ser Gly Pro Gly Leu Val Lys Pro Ser Glu
1               5                   10                  15

Thr Leu Ser Leu Thr Cys Thr Val Ser Asn Gly Pro Ile Ser Ser Ser
            20                  25                  30

Arg Tyr Tyr Trp Gly Trp Ile Arg Gln Pro Pro Gly Lys Gly Leu Glu
        35                  40                  45

Trp Ile Gly Ser Phe His Tyr Ser Gly Ser Thr Tyr Tyr Lys Pro Ser
    50                  55                  60

Leu Lys Ser Arg Val Thr Ile Ser Ala Asp Thr Ser Lys Asn Gln Leu
65                  70                  75                  80

Ser Leu Glu Leu Ser Ser Val Thr Ala Ala Asp Thr Ala Val Tyr Tyr
                85                  90                  95

Cys Ala Arg Leu Val Leu Arg Tyr Phe Asp Trp Leu Gly Tyr Phe Asp
            100                 105                 110

Leu Trp Gly Arg Gly Thr Leu Val Thr Val Ser Ser
        115                 120
```

<210> SEQ ID NO 196
<211> LENGTH: 108
<212> TYPE: PRT
<213> ORGANISM: Homo sapiens

<400> SEQUENCE: 196

Glu Phe Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Arg Ser Asn
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Ala Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Ile Thr Phe Gly Gln Gly Thr Arg Leu Glu Ile Lys
            100                 105

<210> SEQ ID NO 197
<211> LENGTH: 120
<212> TYPE: PRT
<213> ORGANISM: Homo sapiens

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Thr Ile Ser Gly Ser Gly Ser Thr Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Lys Pro Leu Leu Gly Gly Thr Gly Leu Trp Asp Tyr Trp Gly Gln
            100                 105                 110

Gly Thr Leu Val Thr Val Ser Ser
        115                 120

<210> SEQ ID NO 198
<211> LENGTH: 107
<212> TYPE: PRT
<213> ORGANISM: Homo sapiens

<400> SEQUENCE: 198

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 199
<211> LENGTH: 127
<212> TYPE: PRT
<213> ORGANISM: Homo sapiens

<400> SEQUENCE: 199

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Tyr Asp Val Leu Thr Ala Tyr Pro Tyr Tyr Phe Tyr Tyr
                100                 105                 110

Asn Met Asp Val Trp Gly Pro Gly Thr Thr Val Thr Val Ser Ser
            115                 120                 125

<210> SEQ ID NO 200
<211> LENGTH: 110
<212> TYPE: PRT
<213> ORGANISM: Homo sapiens

<400> SEQUENCE: 200

Gln Thr Val Val Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Ser
                20                  25                  30

Tyr Tyr Pro Ser Trp Tyr Gln Gln Thr Pro Gly Gln Ala Pro Arg Thr
            35                  40                  45

Leu Ile Tyr Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu
            100                 105                 110

<210> SEQ ID NO 201
<211> LENGTH: 120
<212> TYPE: PRT
<213> ORGANISM: Homo sapiens

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30
```

-continued

```
              20                  25                  30

Ala Met Thr Trp Val Arg Gln Ala Pro Gly Lys Gly Leu Glu Trp Val
          35                  40                  45

Ser Ser Leu Ser Gly Ser Gly Arg Ser Thr Tyr Tyr Ala Ala Ser Met
      50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
              85                  90                  95

Ala Lys Ser Leu Ser Tyr Tyr His Tyr Tyr Phe Asp Tyr Trp Gly Gln
          100                 105                 110

Gly Thr Leu Val Thr Val Thr Ser
          115                 120

<210> SEQ ID NO 202
<211> LENGTH: 107
<212> TYPE: PRT
<213> ORGANISM: Homo sapiens

<400> SEQUENCE: 202

Asp Ile Gln Leu Thr Gln Ser Pro Ser Phe Leu Ser Ala Ser Val Gly
1                   5                  10                  15

Asp Arg Val Pro Ile Thr Cys Arg Ala Ser Gln Gly Ile Ser Asn Phe
              20                  25                  30

Leu Ala Trp Tyr Gln Gln Lys Pro Gly Lys Ala Pro Glu Leu Leu Ile
          35                  40                  45

His Ser Ala Ser Thr Leu Gln Ser Gly Val Pro Ser Arg Phe Ser Gly
      50                  55                  60

Ser Gly Ser Gly Thr Glu Phe Thr Leu Thr Ile Ser Asn Leu Gln Pro
65                  70                  75                  80

Gln Asp Phe Ala Thr Tyr Tyr Cys Gln Gln Val Asn Ser Tyr Pro Leu
              85                  90                  95

Thr Phe Gly Gly Gly Thr Lys Val Glu Ile Lys
          100                 105

<210> SEQ ID NO 203
<211> LENGTH: 120
<212> TYPE: PRT
<213> ORGANISM: Homo sapiens

<400> SEQUENCE: 203

Glu Val Gln Leu Ser Glu Ser Gly Gly Ala Leu Val Gln Pro Gly Glu
1                   5                  10                  15

Ser Leu Arg Leu Ser Cys Ala Ala Ser Gly Phe Thr Phe Ser Ser Tyr
              20                  25                  30

Ala Met Thr Trp Val Arg Gln Ala Pro Gly Lys Gly Leu Glu Trp Val
          35                  40                  45

Ser Ser Leu Ser Gly Ser Gly Arg Ser Thr Tyr Tyr Ala Ala Ser Ile
      50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Ile Tyr Tyr Cys
              85                  90                  95

Ala Lys Ser Leu Ser Tyr Tyr His Tyr Tyr Phe Asp Tyr Trp Gly Gln
          100                 105                 110

Gly Thr Leu Val Thr Val Ser Ser
```

-continued

```
             115                 120

<210> SEQ ID NO 204
<211> LENGTH: 107
<212> TYPE: PRT
<213> ORGANISM: Homo sapiens

<400> SEQUENCE: 204

Asp Ile Gln Leu Thr Gln Ser Pro Ser Phe Leu Ser Ala Ser Val Gly
1               5                   10                  15

Asp Arg Val Pro Ile Thr Cys Arg Ala Ser Gln Asp Ile Ser Asn Tyr
                20                  25                  30

Leu Ala Trp Tyr Gln Gln Lys Pro Gly Lys Ala Pro Lys Leu Leu Ile
            35                  40                  45

Tyr Ser Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Ser Tyr His Cys Gln Gln Val Lys Thr Tyr Pro Leu
                85                  90                  95

Thr Phe Gly Gly Gly Thr Lys Val Glu Ile Lys
            100                 105

<210> SEQ ID NO 205
<211> LENGTH: 127
<212> TYPE: PRT
<213> ORGANISM: Homo sapiens

<400> SEQUENCE: 205

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Ile Ile Asn Pro Ser Gly Gly Asn Thr Ile Tyr Ala Gln Lys Phe
        50                  55                  60

Gln Gly Arg Val Thr Met Thr Arg Asp Thr Ser Thr Thr Thr Val Tyr
65                  70                  75                  80

Val Glu Leu Ser Ser Leu Arg Ser Glu Asp Thr Ala Val Tyr Tyr Cys
                85                  90                  95

Ala Arg Asp His Tyr Asp Ile Leu Thr Gly Tyr Tyr Pro Leu Tyr Tyr
            100                 105                 110

Gly Met Asp Val Trp Gly Gln Gly Thr Thr Val Thr Val Ser Ser
        115                 120                 125

<210> SEQ ID NO 206
<211> LENGTH: 106
<212> TYPE: PRT
<213> ORGANISM: Homo sapiens

<400> SEQUENCE: 206

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
                20                  25                  30

His Trp Tyr Gln Gln Lys Pro Gly Gln Ala Pro Val Leu Val Ile Tyr
            35                  40                  45
```

-continued

```
Arg Asp Ser Asn Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala Val
                85                  90                  95

Phe Gly Gly Gly Thr Gln Leu Thr Ala Leu
            100                 105

<210> SEQ ID NO 207
<211> LENGTH: 119
<212> TYPE: PRT
<213> ORGANISM: Homo sapiens

<400> SEQUENCE: 207

Glu Val Arg Leu Leu Glu Ser Gly Gly Gly Leu Val Gln Pro Gly Gly
1               5                   10                  15

Ser Leu Arg Leu Ser Cys Ile Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Ser Ser Leu Arg Ala Glu Asp Thr Ala Val Tyr Tyr Cys
                85                  90                  95

Thr Lys Ala Pro Thr Leu Trp Trp Phe Phe Asp Leu Trp Gly Arg Gly
            100                 105                 110

Thr Leu Val Thr Val Ser Ser
        115

<210> SEQ ID NO 208
<211> LENGTH: 107
<212> TYPE: PRT
<213> ORGANISM: Homo sapiens

<400> SEQUENCE: 208

Asp Ile Gln Val Thr Gln Ser Pro Ser Phe Leu Ser Ala Ser Val Gly
1               5                   10                  15

Asp Arg Val Thr Ile Thr Cys Arg Ala Ser Gln Gly Ile Arg Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Leu Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 209
<211> LENGTH: 128
<212> TYPE: PRT
<213> ORGANISM: Homo sapiens
```

<400> SEQUENCE: 209

```
Glu Val Gln Leu Leu Glu Ser Gly Gly Gly Leu Val Gln Pro Gly Gly
1               5                   10                  15

Ser Leu Arg Val Ala Cys Ala Ala Ser Gly Phe Pro Leu Arg Ser Tyr
            20                  25                  30

Ala Met Ser Trp Val Arg Gln Ala Pro Gly Lys Gly Leu Glu Trp Val
        35                  40                  45

Ser Val Thr Ser Gly Ser Gly Gly Ser Thr Tyr Tyr Ala Asp Ser Val
    50                  55                  60

Lys Gly Arg Phe Thr Ile Ser Arg Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Tyr Asp Ile Leu Thr Gly Tyr Tyr Asp Tyr Phe
            100                 105                 110

Tyr Gly Met Asp Val Trp Gly Gln Gly Thr Thr Val Thr Val Ser Ser
        115                 120                 125
```

<210> SEQ ID NO 210
<211> LENGTH: 107
<212> TYPE: PRT
<213> ORGANISM: Homo sapiens

<400> SEQUENCE: 210

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105
```

<210> SEQ ID NO 211
<211> LENGTH: 128
<212> TYPE: PRT
<213> ORGANISM: Homo sapiens

<400> SEQUENCE: 211

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Ala Met Ser Trp Val Arg Gln Val Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Arg Gly Tyr Asp Ile Leu Thr Thr Tyr Tyr Asp Tyr Phe
            100                 105                 110

Tyr Gly Met Asp Val Trp Gly Gln Pro Glu Phe Gln His Thr Gly Gly
        115                 120                 125

<210> SEQ ID NO 212
<211> LENGTH: 107
<212> TYPE: PRT
<213> ORGANISM: Homo sapiens

<400> SEQUENCE: 212

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 213

<400> SEQUENCE: 213

000

<210> SEQ ID NO 214

<400> SEQUENCE: 214

000

<210> SEQ ID NO 215
<211> LENGTH: 128
<212> TYPE: PRT
<213> ORGANISM: Homo sapiens

<400> SEQUENCE: 215

Glu Val Gln Leu Leu Glu Ser Gly Gly Gly Val Val Gln Pro Gly Gly
1               5                   10                  15

Ser Leu Arg Leu Ser Cys Ala Ala Ser Gly Leu Ile Phe Ser Ser Tyr
            20                  25                  30

Ala Met Ser Trp Val Arg Gln Ala Pro Gly Lys Gly Leu Glu Trp Val
        35                  40                  45

Ser Val Ile Gly Gly Ser Gly Ser Asn Thr Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Arg Gly Tyr Asp Ile Leu Thr Gly Tyr Tyr Asn Tyr Tyr
```

-continued

```
          100               105               110

Tyr Gly Met Asp Val Trp Gly Gln Gly Ile Thr Val Thr Val Ser Ser
        115               120               125

<210> SEQ ID NO 216
<211> LENGTH: 107
<212> TYPE: PRT
<213> ORGANISM: Homo sapiens

<400> SEQUENCE: 216

Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Arg Asn Asp
                20              25              30

Leu Gly Trp Tyr Gln Gln Lys Pro Gly Lys Ala Pro Lys Arg Leu Ile
        35              40              45

Tyr Ala Ala Ser Ser Leu Gln Ser Gly Val Pro Ser Arg Phe Ser Gly
    50              55              60

Ser Gly Ser Gly Thr Glu Phe Thr Leu Thr Ile Ser Ser Leu Gln Pro
65              70              75              80

Glu Asp Phe Ala Thr Tyr Tyr Cys Leu Gln His Asn Ser Tyr Pro Tyr
                85              90              95

Thr Phe Gly Gln Gly Thr Lys Leu Glu Ile Lys
                100             105

<210> SEQ ID NO 217
<211> LENGTH: 118
<212> TYPE: PRT
<213> ORGANISM: Homo sapiens

<400> SEQUENCE: 217

Gln Val Gln Leu Val Gln Ser Gly Ala Glu Val Lys Arg Pro Gly Ala
1               5               10              15

Ser Val Lys Val Ser Cys Arg Val Ser Gly Tyr Thr Leu Thr Ala Leu
                20              25              30

Ser Met Tyr Trp Val Arg Gln Ala Pro Gly Lys Gly Leu Glu Trp Met
        35              40              45

Gly Gly Phe Asp Pro Glu Asp Gly Glu Thr Ile Tyr Ala Gln Lys Phe
    50              55              60

Gln Gly Arg Val Thr Met Thr Glu Asp Thr Ser Thr Gly Thr Ala Tyr
65              70              75              80

Met Glu Leu Ser Ser Leu Lys Ser Glu Asp Thr Ala Val Tyr Tyr Cys
                85              90              95

Ala Thr Arg Leu Arg Tyr Phe Asp Trp Asn Tyr Trp Gly Gln Gly Thr
                100             105             110

Pro Val Thr Val Ser Ser
        115

<210> SEQ ID NO 218
<211> LENGTH: 112
<212> TYPE: PRT
<213> ORGANISM: Homo sapiens

<400> SEQUENCE: 218

Asp Ile Val Met Thr Gln Thr Pro Leu Ser Ser Pro Val Thr Leu Gly
1               5               10              15

Gln Pro Ala Ser Ile Ser Cys Arg Ser Ser Gln Ser Leu Val His Ser
                20              25              30
```

-continued

Asp Gly Asn Thr Tyr Leu Ser Trp Leu Gln Gln Arg Pro Gly Gln Pro
        35                  40                  45

Pro Arg Leu Leu Ile Tyr Lys Val Ser Lys Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Gly
                85                  90                  95

Thr Gln Phe Pro Arg Thr Phe Gly Gln Gly Thr Lys Val Glu Ile Lys
            100                 105                 110

<210> SEQ ID NO 219
<211> LENGTH: 118
<212> TYPE: PRT
<213> ORGANISM: Homo sapiens

<400> SEQUENCE: 219

Gln Val Gln Leu Val Gln Ser Gly Ala Glu Val Lys Lys Pro Gly Ala
1               5                   10                  15

Ser Val Lys Val Ser Cys Arg Val Ser Gly Tyr Thr Leu Ser Ala Leu
            20                  25                  30

Ser Met Tyr Trp Val Arg Gln Ala Pro Gly Lys Gly Leu Glu Trp Met
        35                  40                  45

Gly Gly Phe Asp Pro Glu Asp Gly Lys Thr Ile Tyr Ala Gln Lys Phe
        50                  55                  60

Gln Gly Arg Val Thr Met Thr Glu Asp Thr Ser Thr Gly Thr Ala Tyr
65                  70                  75                  80

Met Glu Leu Ser Ser Leu Arg Ser Glu Asp Thr Ala Ile Tyr Tyr Cys
                85                  90                  95

Ala Thr Thr Leu Arg Tyr Phe Asp Trp Asn Tyr Trp Gly Gln Gly Thr
            100                 105                 110

Pro Val Thr Val Ser Ser
        115

<210> SEQ ID NO 220
<211> LENGTH: 112
<212> TYPE: PRT
<213> ORGANISM: Homo sapiens

<400> SEQUENCE: 220

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Val Ser Lys Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Gly
                85                  90                  95

Thr Gln Phe Pro Arg Thr Phe Gly Gln Gly Thr Lys Val Glu Ile Lys
            100                 105                 110

<210> SEQ ID NO 221

```
<211> LENGTH: 8
<212> TYPE: PRT
<213> ORGANISM: Homo sapiens

<400> SEQUENCE: 221

Gly Phe Thr Phe Ser Asn Tyr Gly
1               5

<210> SEQ ID NO 222
<211> LENGTH: 8
<212> TYPE: PRT
<213> ORGANISM: Homo sapiens

<400> SEQUENCE: 222

Ile Trp Tyr Asp Gly Ser Asn Lys
1               5

<210> SEQ ID NO 223
<211> LENGTH: 18
<212> TYPE: PRT
<213> ORGANISM: Homo sapiens

<400> SEQUENCE: 223

Ala Arg Arg Gly Tyr Asp Ile Leu Thr Gly Tyr Asp Tyr Tyr Gly Met
1               5                   10                  15

Asp Val

<210> SEQ ID NO 224
<211> LENGTH: 9
<212> TYPE: PRT
<213> ORGANISM: Homo sapiens

<400> SEQUENCE: 224

Ser Gly Ser Val Ser Thr Ser Tyr Tyr
1               5

<210> SEQ ID NO 225
<211> LENGTH: 3
<212> TYPE: PRT
<213> ORGANISM: Homo sapiens

<400> SEQUENCE: 225

Arg Thr Asn
1

<210> SEQ ID NO 226
<211> LENGTH: 10
<212> TYPE: PRT
<213> ORGANISM: Homo sapiens

<400> SEQUENCE: 226

Val Leu Tyr Met Gly Ser Gly Ile Trp Val
1               5                   10

<210> SEQ ID NO 227
<211> LENGTH: 10
<212> TYPE: PRT
<213> ORGANISM: Homo sapiens

<400> SEQUENCE: 227

Gly Gly Ser Ile Ser Ser Ser Arg Ser Tyr
1               5                   10

<210> SEQ ID NO 228
```

-continued

```
<211> LENGTH: 7
<212> TYPE: PRT
<213> ORGANISM: Homo sapiens

<400> SEQUENCE: 228

Ile Tyr Tyr Ser Gly Ser Thr
1               5

<210> SEQ ID NO 229
<211> LENGTH: 16
<212> TYPE: PRT
<213> ORGANISM: Homo sapiens

<400> SEQUENCE: 229

Ala Arg Gln Thr Leu Arg Tyr Phe Asp Trp Leu Ser Pro Phe Asp Tyr
1               5                   10                  15

<210> SEQ ID NO 230
<211> LENGTH: 7
<212> TYPE: PRT
<213> ORGANISM: Homo sapiens

<400> SEQUENCE: 230

Gln Ser Val Arg Ser Asn Tyr
1               5

<210> SEQ ID NO 231
<211> LENGTH: 3
<212> TYPE: PRT
<213> ORGANISM: Homo sapiens

<400> SEQUENCE: 231

Gly Thr Ser
1

<210> SEQ ID NO 232
<211> LENGTH: 9
<212> TYPE: PRT
<213> ORGANISM: Homo sapiens

<400> SEQUENCE: 232

Gln Gln Asp Tyr Asn Leu Pro Ile Thr
1               5

<210> SEQ ID NO 233
<211> LENGTH: 10
<212> TYPE: PRT
<213> ORGANISM: Homo sapiens

<400> SEQUENCE: 233

Asp Gly Pro Ile Ser Ser Ser Arg Tyr Tyr
1               5                   10

<210> SEQ ID NO 234
<211> LENGTH: 7
<212> TYPE: PRT
<213> ORGANISM: Homo sapiens

<400> SEQUENCE: 234

Phe His Tyr Ser Gly Ser Thr
1               5

<210> SEQ ID NO 235
<211> LENGTH: 16
<212> TYPE: PRT
```

<213> ORGANISM: Homo sapiens

<400> SEQUENCE: 235

Ala Arg Leu Val Leu Arg Tyr Phe Asp Trp Leu Gly Phe Phe Asp Leu
1               5                   10                  15

<210> SEQ ID NO 236
<211> LENGTH: 7
<212> TYPE: PRT
<213> ORGANISM: Homo sapiens

<400> SEQUENCE: 236

Gln Ser Val Arg Ser Ser Tyr
1               5

<210> SEQ ID NO 237
<211> LENGTH: 3
<212> TYPE: PRT
<213> ORGANISM: Homo sapiens

<400> SEQUENCE: 237

Gly Thr Ser
1

<210> SEQ ID NO 238
<211> LENGTH: 9
<212> TYPE: PRT
<213> ORGANISM: Homo sapiens

<400> SEQUENCE: 238

Gln Gln Asp Tyr Asn Leu Pro Ile Thr
1               5

<210> SEQ ID NO 239
<211> LENGTH: 8
<212> TYPE: PRT
<213> ORGANISM: Homo sapiens

<400> SEQUENCE: 239

Gly Phe Thr Phe Ser Phe Tyr Gly
1               5

<210> SEQ ID NO 240
<211> LENGTH: 8
<212> TYPE: PRT
<213> ORGANISM: Homo sapiens

<400> SEQUENCE: 240

Ile Trp Tyr Asp Gly Ser Asn Lys
1               5

<210> SEQ ID NO 241
<211> LENGTH: 18
<212> TYPE: PRT
<213> ORGANISM: Homo sapiens

<400> SEQUENCE: 241

Ala Arg Arg Asn Tyr Asp Ile Leu Thr Gly Arg Asp Tyr Tyr Gly Met
1               5                   10                  15

Asp Val

<210> SEQ ID NO 242
<211> LENGTH: 9
<212> TYPE: PRT

-continued

```
<213> ORGANISM: Homo sapiens

<400> SEQUENCE: 242

Ser Gly Ser Val Ser Thr Ser Tyr Tyr
1               5

<210> SEQ ID NO 243
<211> LENGTH: 3
<212> TYPE: PRT
<213> ORGANISM: Homo sapiens

<400> SEQUENCE: 243

Ser Thr Asn
1

<210> SEQ ID NO 244
<211> LENGTH: 10
<212> TYPE: PRT
<213> ORGANISM: Homo sapiens

<400> SEQUENCE: 244

Val Leu Tyr Met Gly Ser Gly Ile Trp Val
1               5                   10

<210> SEQ ID NO 245
<211> LENGTH: 8
<212> TYPE: PRT
<213> ORGANISM: Homo sapiens

<400> SEQUENCE: 245

Gly Tyr Thr Phe Thr Ser Ser Tyr
1               5

<210> SEQ ID NO 246
<211> LENGTH: 8
<212> TYPE: PRT
<213> ORGANISM: Homo sapiens

<400> SEQUENCE: 246

Ile Asn Pro Ser Gly Gly Arg Thr
1               5

<210> SEQ ID NO 247
<211> LENGTH: 18
<212> TYPE: PRT
<213> ORGANISM: Homo sapiens

<400> SEQUENCE: 247

Ala Arg Asp His Tyr Asp Ile Phe Thr Thr Tyr Tyr Pro Arg Gly Met
1               5                   10                  15

Asp Val

<210> SEQ ID NO 248
<211> LENGTH: 6
<212> TYPE: PRT
<213> ORGANISM: Homo sapiens

<400> SEQUENCE: 248

Gln Gly Ile Arg Asn Asp
1               5

<210> SEQ ID NO 249
<211> LENGTH: 3
<212> TYPE: PRT
```

-continued

<213> ORGANISM: Homo sapiens

<400> SEQUENCE: 249

Ala Ala Ser
1

<210> SEQ ID NO 250
<211> LENGTH: 9
<212> TYPE: PRT
<213> ORGANISM: Homo sapiens

<400> SEQUENCE: 250

Leu Gln His Asn Ser Phe Pro Phe Thr
1               5

<210> SEQ ID NO 251
<211> LENGTH: 10
<212> TYPE: PRT
<213> ORGANISM: Homo sapiens

<400> SEQUENCE: 251

Asn Gly Pro Ile Ser Ser Ser Arg Tyr Tyr
1               5                   10

<210> SEQ ID NO 252
<211> LENGTH: 7
<212> TYPE: PRT
<213> ORGANISM: Homo sapiens

<400> SEQUENCE: 252

Phe His Tyr Ser Gly Ser Thr
1               5

<210> SEQ ID NO 253
<211> LENGTH: 16
<212> TYPE: PRT
<213> ORGANISM: Homo sapiens

<400> SEQUENCE: 253

Ala Arg Leu Val Leu Arg Tyr Phe Asp Trp Leu Gly Tyr Phe Asp Leu
1               5                   10                  15

<210> SEQ ID NO 254
<211> LENGTH: 7
<212> TYPE: PRT
<213> ORGANISM: Homo sapiens

<400> SEQUENCE: 254

Gln Ser Ile Arg Ser Asn Tyr
1               5

<210> SEQ ID NO 255
<211> LENGTH: 3
<212> TYPE: PRT
<213> ORGANISM: Homo sapiens

<400> SEQUENCE: 255

Gly Ala Ser
1

<210> SEQ ID NO 256
<211> LENGTH: 9
<212> TYPE: PRT
<213> ORGANISM: Homo sapiens

```
<400> SEQUENCE: 256

Gln Gln Asp Tyr Asn Leu Pro Ile Thr
1               5

<210> SEQ ID NO 257
<211> LENGTH: 8
<212> TYPE: PRT
<213> ORGANISM: Homo sapiens

<400> SEQUENCE: 257

Gly Phe Thr Phe Ser Ser Tyr Val
1               5

<210> SEQ ID NO 258
<211> LENGTH: 8
<212> TYPE: PRT
<213> ORGANISM: Homo sapiens

<400> SEQUENCE: 258

Ile Ser Gly Ser Gly Gly Ser Thr
1               5

<210> SEQ ID NO 259
<211> LENGTH: 13
<212> TYPE: PRT
<213> ORGANISM: Homo sapiens

<400> SEQUENCE: 259

Gly Lys Pro Leu Leu Gly Gly Thr Gly Leu Trp Asp Tyr
1               5                   10

<210> SEQ ID NO 260
<211> LENGTH: 6
<212> TYPE: PRT
<213> ORGANISM: Homo sapiens

<400> SEQUENCE: 260

Gln Ser Val Ser Ser Tyr
1               5

<210> SEQ ID NO 261
<211> LENGTH: 3
<212> TYPE: PRT
<213> ORGANISM: Homo sapiens

<400> SEQUENCE: 261

Asp Ser Ser
1

<210> SEQ ID NO 262
<211> LENGTH: 9
<212> TYPE: PRT
<213> ORGANISM: Homo sapiens

<400> SEQUENCE: 262

Gln Gln Arg Ser Asn Trp Pro Leu Thr
1               5

<210> SEQ ID NO 263
<211> LENGTH: 8
<212> TYPE: PRT
<213> ORGANISM: Homo sapiens

<400> SEQUENCE: 263
```

```
Gly Phe Thr Phe Ser Ser Tyr Gly
1               5

<210> SEQ ID NO 264
<211> LENGTH: 8
<212> TYPE: PRT
<213> ORGANISM: Homo sapiens

<400> SEQUENCE: 264

Ile Trp Tyr Asp Gly Ser Asn Lys
1               5

<210> SEQ ID NO 265
<211> LENGTH: 20
<212> TYPE: PRT
<213> ORGANISM: Homo sapiens

<400> SEQUENCE: 265

Ala Arg Arg Tyr Asp Val Leu Thr Ala Tyr Pro Tyr Tyr Phe Tyr Tyr
1               5                   10                  15

Asn Met Asp Val
            20

<210> SEQ ID NO 266
<211> LENGTH: 9
<212> TYPE: PRT
<213> ORGANISM: Homo sapiens

<400> SEQUENCE: 266

Ser Gly Ser Val Ser Thr Ser Tyr Tyr
1               5

<210> SEQ ID NO 267
<211> LENGTH: 3
<212> TYPE: PRT
<213> ORGANISM: Homo sapiens

<400> SEQUENCE: 267

Ser Thr Asn
1

<210> SEQ ID NO 268
<211> LENGTH: 10
<212> TYPE: PRT
<213> ORGANISM: Homo sapiens

<400> SEQUENCE: 268

Val Leu Tyr Met Gly Ser Gly Ile Trp Val
1               5                   10

<210> SEQ ID NO 269
<211> LENGTH: 8
<212> TYPE: PRT
<213> ORGANISM: Homo sapiens

<400> SEQUENCE: 269

Gly Phe Thr Phe Ser Ser Phe Ala
1               5

<210> SEQ ID NO 270
<211> LENGTH: 8
<212> TYPE: PRT
<213> ORGANISM: Homo sapiens

<400> SEQUENCE: 270
```

```
Leu Ser Gly Ser Gly Arg Ser Thr
1               5

<210> SEQ ID NO 271
<211> LENGTH: 13
<212> TYPE: PRT
<213> ORGANISM: Homo sapiens

<400> SEQUENCE: 271

Ala Lys Ser Leu Ser Tyr Tyr His Tyr Tyr Phe Asp Tyr
1               5                   10

<210> SEQ ID NO 272
<211> LENGTH: 6
<212> TYPE: PRT
<213> ORGANISM: Homo sapiens

<400> SEQUENCE: 272

Gln Gly Ile Ser Asn Phe
1               5

<210> SEQ ID NO 273
<211> LENGTH: 3
<212> TYPE: PRT
<213> ORGANISM: Homo sapiens

<400> SEQUENCE: 273

Ser Ala Ser
1

<210> SEQ ID NO 274
<211> LENGTH: 9
<212> TYPE: PRT
<213> ORGANISM: Homo sapiens

<400> SEQUENCE: 274

Gln Gln Val Asn Ser Tyr Pro Leu Thr
1               5

<210> SEQ ID NO 275
<211> LENGTH: 8
<212> TYPE: PRT
<213> ORGANISM: Homo sapiens

<400> SEQUENCE: 275

Gly Phe Thr Phe Ser Ser Tyr Ala
1               5

<210> SEQ ID NO 276
<211> LENGTH: 8
<212> TYPE: PRT
<213> ORGANISM: Homo sapiens

<400> SEQUENCE: 276

Leu Ser Gly Ser Gly Arg Ser Thr
1               5

<210> SEQ ID NO 277
<211> LENGTH: 13
<212> TYPE: PRT
<213> ORGANISM: Homo sapiens

<400> SEQUENCE: 277

Ala Lys Ser Leu Ser Tyr Tyr His Tyr Tyr Phe Asp Tyr
```

```
1               5                 10
```

<210> SEQ ID NO 278
<211> LENGTH: 6
<212> TYPE: PRT
<213> ORGANISM: Homo sapiens

<400> SEQUENCE: 278

Gln Asp Ile Ser Asn Tyr
1               5

<210> SEQ ID NO 279
<211> LENGTH: 3
<212> TYPE: PRT
<213> ORGANISM: Homo sapiens

<400> SEQUENCE: 279

Ser Ala Ser
1

<210> SEQ ID NO 280
<211> LENGTH: 9
<212> TYPE: PRT
<213> ORGANISM: Homo sapiens

<400> SEQUENCE: 280

Gln Gln Val Lys Thr Tyr Pro Leu Thr
1               5

<210> SEQ ID NO 281
<211> LENGTH: 8
<212> TYPE: PRT
<213> ORGANISM: Homo sapiens

<400> SEQUENCE: 281

Gly Tyr Thr Phe Thr Ser Tyr Tyr
1               5

<210> SEQ ID NO 282
<211> LENGTH: 8
<212> TYPE: PRT
<213> ORGANISM: Homo sapiens

<400> SEQUENCE: 282

Ile Asn Pro Ser Gly Gly Asn Thr
1               5

<210> SEQ ID NO 283
<211> LENGTH: 20
<212> TYPE: PRT
<213> ORGANISM: Homo sapiens

<400> SEQUENCE: 283

Ala Arg Asp His Tyr Asp Ile Leu Thr Gly Tyr Tyr Pro Leu Tyr Tyr
1               5                 10                15

Gly Met Asp Val
            20

<210> SEQ ID NO 284
<211> LENGTH: 6
<212> TYPE: PRT
<213> ORGANISM: Homo sapiens

<400> SEQUENCE: 284

-continued

```
Asn Ile Gly Ser Lys Asn
1               5

<210> SEQ ID NO 285
<211> LENGTH: 3
<212> TYPE: PRT
<213> ORGANISM: Homo sapiens

<400> SEQUENCE: 285

Arg Asp Ser
1

<210> SEQ ID NO 286
<211> LENGTH: 9
<212> TYPE: PRT
<213> ORGANISM: Homo sapiens

<400> SEQUENCE: 286

Gln Val Trp Asp Ser Ser Thr Ala Val
1               5

<210> SEQ ID NO 287
<211> LENGTH: 8
<212> TYPE: PRT
<213> ORGANISM: Homo sapiens

<400> SEQUENCE: 287

Gly Phe Thr Phe Ser Ser Tyr Val
1               5

<210> SEQ ID NO 288
<211> LENGTH: 8
<212> TYPE: PRT
<213> ORGANISM: Homo sapiens

<400> SEQUENCE: 288

Ile Ser Gly Ser Gly Gly Ser Thr
1               5

<210> SEQ ID NO 289
<211> LENGTH: 12
<212> TYPE: PRT
<213> ORGANISM: Homo sapiens

<400> SEQUENCE: 289

Thr Lys Ala Pro Thr Leu Trp Trp Phe Phe Asp Leu
1               5                   10

<210> SEQ ID NO 290
<211> LENGTH: 6
<212> TYPE: PRT
<213> ORGANISM: Homo sapiens

<400> SEQUENCE: 290

Gln Gly Ile Arg Ser Tyr
1               5

<210> SEQ ID NO 291
<211> LENGTH: 3
<212> TYPE: PRT
<213> ORGANISM: Homo sapiens

<400> SEQUENCE: 291

Ala Ala Ser
1
```

```
<210> SEQ ID NO 292
<211> LENGTH: 9
<212> TYPE: PRT
<213> ORGANISM: Homo sapiens

<400> SEQUENCE: 292

Gln Gln Leu Asn Ser Tyr Pro Leu Thr
1               5

<210> SEQ ID NO 293
<211> LENGTH: 8
<212> TYPE: PRT
<213> ORGANISM: Homo sapiens

<400> SEQUENCE: 293

Gly Phe Pro Leu Arg Ser Tyr Ala
1               5

<210> SEQ ID NO 294
<211> LENGTH: 8
<212> TYPE: PRT
<213> ORGANISM: Homo sapiens

<400> SEQUENCE: 294

Thr Ser Gly Ser Gly Gly Ser Thr
1               5

<210> SEQ ID NO 295
<211> LENGTH: 21
<212> TYPE: PRT
<213> ORGANISM: Homo sapiens

<400> SEQUENCE: 295

Ala Lys Asp Arg Gly Tyr Asp Ile Leu Thr Gly Tyr Tyr Asp Tyr Phe
1               5                   10                  15

Tyr Gly Met Asp Val
            20

<210> SEQ ID NO 296
<211> LENGTH: 6
<212> TYPE: PRT
<213> ORGANISM: Homo sapiens

<400> SEQUENCE: 296

Gln Gly Ile Arg Asn Asp
1               5

<210> SEQ ID NO 297
<211> LENGTH: 3
<212> TYPE: PRT
<213> ORGANISM: Homo sapiens

<400> SEQUENCE: 297

Ala Ala Ser
1

<210> SEQ ID NO 298
<211> LENGTH: 9
<212> TYPE: PRT
<213> ORGANISM: Homo sapiens

<400> SEQUENCE: 298

Leu Gln His Asn Ser Tyr Pro Tyr Thr
```

```
1                  5

<210> SEQ ID NO 299
<211> LENGTH: 8
<212> TYPE: PRT
<213> ORGANISM: Homo sapiens

<400> SEQUENCE: 299

Gly Ile Thr Phe Ser Ser Tyr Ala
1                  5

<210> SEQ ID NO 300
<211> LENGTH: 8
<212> TYPE: PRT
<213> ORGANISM: Homo sapiens

<400> SEQUENCE: 300

Ile Ser Gly Ser Gly Gly Ser Thr
1                  5

<210> SEQ ID NO 301
<211> LENGTH: 21
<212> TYPE: PRT
<213> ORGANISM: Homo sapiens

<400> SEQUENCE: 301

Ala Lys Asp Arg Gly Tyr Asp Ile Leu Thr Thr Tyr Tyr Asp Tyr Phe
1                  5                  10                  15

Tyr Gly Met Asp Val
            20

<210> SEQ ID NO 302
<211> LENGTH: 6
<212> TYPE: PRT
<213> ORGANISM: Homo sapiens

<400> SEQUENCE: 302

Gln Gly Ile Arg Asn Asp
1                  5

<210> SEQ ID NO 303
<211> LENGTH: 3
<212> TYPE: PRT
<213> ORGANISM: Homo sapiens

<400> SEQUENCE: 303

Ala Ala Ser
1

<210> SEQ ID NO 304
<211> LENGTH: 9
<212> TYPE: PRT
<213> ORGANISM: Homo sapiens

<400> SEQUENCE: 304

Leu Gln His Asn Ser Tyr Pro Tyr Thr
1                  5

<210> SEQ ID NO 305

<400> SEQUENCE: 305

000
```

-continued

```
<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311
<211> LENGTH: 8
<212> TYPE: PRT
<213> ORGANISM: Homo sapiens

<400> SEQUENCE: 311

Gly Leu Ile Phe Ser Ser Tyr Ala
1               5

<210> SEQ ID NO 312
<211> LENGTH: 8
<212> TYPE: PRT
<213> ORGANISM: Homo sapiens

<400> SEQUENCE: 312

Ile Gly Gly Ser Gly Ser Asn Thr
1               5

<210> SEQ ID NO 313
<211> LENGTH: 21
<212> TYPE: PRT
<213> ORGANISM: Homo sapiens

<400> SEQUENCE: 313

Ala Lys Asp Arg Gly Tyr Asp Ile Leu Thr Gly Tyr Tyr Asn Tyr Tyr
1               5                   10                  15

Tyr Gly Met Asp Val
            20

<210> SEQ ID NO 314
<211> LENGTH: 6
<212> TYPE: PRT
<213> ORGANISM: Homo sapiens

<400> SEQUENCE: 314

Gln Gly Ile Arg Asn Asp
```

-continued

```
1               5

<210> SEQ ID NO 315
<211> LENGTH: 3
<212> TYPE: PRT
<213> ORGANISM: Homo sapiens

<400> SEQUENCE: 315

Ala Ala Ser
1

<210> SEQ ID NO 316
<211> LENGTH: 9
<212> TYPE: PRT
<213> ORGANISM: Homo sapiens

<400> SEQUENCE: 316

Leu Gln His Asn Ser Tyr Pro Tyr Thr
1               5

<210> SEQ ID NO 317
<211> LENGTH: 8
<212> TYPE: PRT
<213> ORGANISM: Homo sapiens

<400> SEQUENCE: 317

Gly Tyr Thr Leu Thr Ala Leu Ser
1               5

<210> SEQ ID NO 318
<211> LENGTH: 8
<212> TYPE: PRT
<213> ORGANISM: Homo sapiens

<400> SEQUENCE: 318

Phe Asp Pro Glu Asp Gly Glu Thr
1               5

<210> SEQ ID NO 319
<211> LENGTH: 11
<212> TYPE: PRT
<213> ORGANISM: Homo sapiens

<400> SEQUENCE: 319

Ala Thr Arg Leu Arg Tyr Phe Asp Trp Asn Tyr
1               5                   10

<210> SEQ ID NO 320
<211> LENGTH: 11
<212> TYPE: PRT
<213> ORGANISM: Homo sapiens

<400> SEQUENCE: 320

Gln Ser Leu Val His Ser Asp Gly Asn Thr Tyr
1               5                   10

<210> SEQ ID NO 321
<211> LENGTH: 3
<212> TYPE: PRT
<213> ORGANISM: Homo sapiens

<400> SEQUENCE: 321

Lys Val Ser
1
```

<210> SEQ ID NO 322
<211> LENGTH: 9
<212> TYPE: PRT
<213> ORGANISM: Homo sapiens

<400> SEQUENCE: 322

Thr Gln Gly Thr Gln Phe Pro Arg Thr
1               5

<210> SEQ ID NO 323
<211> LENGTH: 8
<212> TYPE: PRT
<213> ORGANISM: Homo sapiens

<400> SEQUENCE: 323

Gly Tyr Thr Leu Ser Ala Leu Ser
1               5

<210> SEQ ID NO 324
<211> LENGTH: 8
<212> TYPE: PRT
<213> ORGANISM: Homo sapiens

<400> SEQUENCE: 324

Phe Asp Pro Glu Asp Gly Lys Thr
1               5

<210> SEQ ID NO 325
<211> LENGTH: 11
<212> TYPE: PRT
<213> ORGANISM: Homo sapiens

<400> SEQUENCE: 325

Ala Thr Thr Leu Arg Tyr Phe Asp Trp Asn Tyr
1               5                   10

<210> SEQ ID NO 326
<211> LENGTH: 11
<212> TYPE: PRT
<213> ORGANISM: Homo sapiens

<400> SEQUENCE: 326

Gln Ser Leu Val His Ser Asp Gly Asn Thr Tyr
1               5                   10

<210> SEQ ID NO 327
<211> LENGTH: 3
<212> TYPE: PRT
<213> ORGANISM: Homo sapiens

<400> SEQUENCE: 327

Lys Val Ser
1

<210> SEQ ID NO 328
<211> LENGTH: 9
<212> TYPE: PRT
<213> ORGANISM: Homo sapiens

<400> SEQUENCE: 328

Thr Gln Gly Thr Gln Phe Pro Arg Thr
1               5

<210> SEQ ID NO 329

-continued

```
<211> LENGTH: 261
<212> TYPE: PRT
<213> ORGANISM: Homo sapiens

<400> SEQUENCE: 329

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
        50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 330
<211> LENGTH: 261
<212> TYPE: PRT
<213> ORGANISM: Homo sapiens

<400> SEQUENCE: 330

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
            35                  40                  45

Leu Trp Arg Ser Cys Val Arg Gln Ser Ser Gly Phe Thr Glu Cys Arg
        50                  55                  60

Pro Tyr Phe Thr Ile Leu Gly Leu Pro Ala Met Leu Gln Ala Val Arg
65                  70                  75                  80
```

-continued

```
Ala Leu Met Ile Val Gly Ile Val Leu Gly Ala Ile Gly Leu Leu Val
                85              90              95

Ser Ile Phe Ala Leu Lys Cys Ile Arg Ile Gly Ser Met Glu Asp Ser
            100             105             110

Ala Lys Ala Asn Met Thr Leu Thr Ser Gly Ile Met Phe Ile Val Ser
            115             120             125

Gly Leu Cys Ala Ile Ala Gly Val Ser Val Phe Ala Asn Met Leu Val
        130             135             140

Thr Asn Phe Trp Met Ser Thr Ala Asn Met Tyr Thr Gly Met Gly Gly
145             150             155             160

Met Val Gln Thr Val Gln Thr Arg Tyr Thr Phe Gly Ala Ala Leu Phe
                165             170             175

Val Gly Trp Val Ala Gly Gly Leu Thr Leu Ile Gly Gly Val Met Met
            180             185             190

Cys Ile Ala Cys Arg Gly Leu Ala Pro Glu Glu Thr Asn Tyr Lys Ala
            195             200             205

Val Ser Tyr His Ala Ser Gly His Ser Val Ala Tyr Lys Pro Gly Gly
        210             215             220

Phe Lys Ala Ser Thr Gly Phe Gly Ser Asn Thr Lys Asn Lys Lys Ile
225             230             235             240

Tyr Asp Gly Gly Ala Arg Thr Glu Asp Glu Val Gln Ser Tyr Pro Ser
                245             250             255

Lys His Asp Tyr Val
                260
```

```
<210> SEQ ID NO 331
<211> LENGTH: 330
<212> TYPE: PRT
<213> ORGANISM: Homo sapiens

<400> SEQUENCE: 331

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
        50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
        130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
```

```
                180               185               190

His Gln Asp Trp Leu Asn Gly Lys Glu Tyr Lys Cys Lys Val Ser Asn
        195               200               205

Lys Ala Leu Pro Ala Pro Ile Glu Lys Thr Ile Ser Lys Ala Lys Gly
    210               215               220

Gln Pro Arg Glu Pro Gln Val Tyr Thr Leu Pro Pro Ser Arg Glu Glu
225               230               235               240

Met Thr Lys Asn Gln Val Ser Leu Thr Cys Leu Val Lys Gly Phe Tyr
                245               250               255

Pro Ser Asp Ile Ala Val Glu Trp Glu Ser Asn Gly Gln Pro Glu Asn
                260               265               270

Asn Tyr Lys Thr Thr Pro Pro Val Leu Asp Ser Asp Gly Ser Phe Phe
            275               280               285

Leu Tyr Ser Lys Leu Thr Val Asp Lys Ser Arg Trp Gln Gln Gly Asn
        290               295               300

Val Phe Ser Cys Ser Val Met His Glu Ala Leu His Asn His Tyr Thr
305               310               315               320

Gln Lys Ser Leu Ser Leu Ser Pro Gly Lys
                325               330

<210> SEQ ID NO 332
<211> LENGTH: 330
<212> TYPE: PRT
<213> ORGANISM: Homo sapiens

<400> SEQUENCE: 332

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 333
<211> LENGTH: 330
<212> TYPE: PRT
<213> ORGANISM: Homo sapiens

<400> SEQUENCE: 333

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 334
<211> LENGTH: 330
<212> TYPE: PRT
<213> ORGANISM: Homo sapiens

<400> SEQUENCE: 334

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
```

-continued

```
305              310              315              320

Gln Lys Ser Leu Ser Leu Ser Pro Gly Lys
                 325              330

<210> SEQ ID NO 335
<211> LENGTH: 108
<212> TYPE: PRT
<213> ORGANISM: Homo sapiens

<400> SEQUENCE: 335

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
                100                 105

<210> SEQ ID NO 336
<211> LENGTH: 450
<212> TYPE: PRT
<213> ORGANISM: Artificial
<220> FEATURE:
<223> OTHER INFORMATION: NBL-014 heavy chain

<400> SEQUENCE: 336

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ala Met Thr Trp Val Arg Gln Ala Pro Gly Lys Gly Leu Glu Trp Val
            35                  40                  45

Ser Ser Leu Ser Gly Ser Gly Arg Ser Thr Tyr Tyr Ala Ala Ser Met
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Ser Leu Ser Tyr Tyr His Tyr Tyr Phe Asp Tyr Trp Gly Gln
                100                 105                 110

Gly Thr Leu Val Thr Val Thr Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Val Gly Gly
225                 230                 235                 240

Pro Ser Val Phe Leu Leu Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Pro Glu Glu Gln Tyr Asn Ser Thr Leu Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

```
<210> SEQ ID NO 337
<211> LENGTH: 214
<212> TYPE: PRT
<213> ORGANISM: Artificial
<220> FEATURE:
<223> OTHER INFORMATION: NBL-014 light chain

<400> SEQUENCE: 337
```

```
Asp Ile Gln Leu Thr Gln Ser Pro Ser Phe Leu Ser Ala Ser Val Gly
1               5                   10                  15

Asp Arg Val Pro Ile Thr Cys Arg Ala Ser Gln Gly Ile Ser Asn Phe
            20                  25                  30

Leu Ala Trp Tyr Gln Gln Lys Pro Gly Lys Ala Pro Glu Leu Leu Ile
        35                  40                  45

His Ser Ala Ser Thr Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Gln Asp Phe Ala Thr Tyr Tyr Cys Gln Gln Val Asn Ser Tyr Pro Leu
            85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 338
<211> LENGTH: 450
<212> TYPE: PRT
<213> ORGANISM: Homo sapiens

<400> SEQUENCE: 338

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Thr Trp Val Arg Gln Ala Pro Gly Lys Gly Leu Glu Trp Val
            35                  40                  45

Ser Ser Leu Ser Gly Ser Gly Arg Ser Thr Tyr Tyr Ala Ala Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Ser Leu Ser Tyr Tyr His Tyr Tyr Phe Asp Tyr Trp Gly Gln
            100                 105                 110

Gly Thr Leu Val Thr Val Thr Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Val Gly Gly
225                 230                 235                 240

Pro Ser Val Phe Leu Leu Pro Pro Lys Pro Lys Asp Thr Leu Met Ile
```

-continued

```
              245              250              255

Ser Arg Thr Pro Glu Val Thr Cys Val Val Val Asp Val Ser His Glu
            260              265              270

Asp Pro Glu Val Lys Phe Asn Trp Tyr Val Asp Gly Val Glu Val His
            275              280              285

Asn Ala Lys Thr Lys Pro Pro Glu Glu Gln Tyr Asn Ser Thr Leu Arg
        290              295              300

Val Val Ser Val Leu Thr Val Leu His Gln Asp Trp Leu Asn Gly Lys
305              310              315              320

Glu Tyr Lys Cys Lys Val Ser Asn Lys Ala Leu Pro Ala Pro Ile Glu
            325              330              335

Lys Thr Ile Ser Lys Ala Lys Gly Gln Pro Arg Glu Pro Gln Val Tyr
            340              345              350

Thr Leu Pro Pro Ser Arg Asp Glu Leu Thr Lys Asn Gln Val Ser Leu
            355              360              365

Thr Cys Leu Val Lys Gly Phe Tyr Pro Ser Asp Ile Ala Val Glu Trp
        370              375              380

Glu Ser Asn Gly Gln Pro Glu Asn Asn Tyr Lys Thr Thr Pro Leu Val
385              390              395              400

Leu Asp Ser Asp Gly Ser Phe Phe Leu Tyr Ser Lys Leu Thr Val Asp
            405              410              415

Lys Ser Arg Trp Gln Gln Gly Asn Val Phe Ser Cys Ser Val Met His
            420              425              430

Glu Ala Leu His Asn His Tyr Thr Gln Lys Ser Leu Ser Leu Ser Pro
            435              440              445

Gly Lys
    450
```

ANTI-CLAUDIN 18 ANTIBODIES AND METHODS OF USE THEREOF

RELATED APPLICATION(S)

This application is a continuation of U.S. application Ser. No. 17/427,909, filed on Aug. 2, 2021, which is a national stage filing under 35 U.S.C. 371 of International Application No.: PCT/US2020/016459, filed Feb. 3, 2020, which claims the benefit of U.S. Provisional Application No. 62/800,359, filed on Feb. 1, 2019, and U.S. Provisional Application No. 62/891,925 filed on Aug. 26, 2019. The entire teachings of the above applications are incorporated herein by reference. International Application No. PCT/US2020/016459 was published under PCT Article 21(2) in English.

STATEMENT REGARDING SEQUENCE LISTING

Sequence Listing associated with this application is provided in text format in lieu of a paper copy and is hereby incorporated by reference into the specification. The name of the text file containing the Sequence Listing is NVRB-001-102—sequence listing.txt. The text file is 143 KB, was created on Jun. 15, 2022, and is being submitted electronically via EFS-Web, concurrent with the filing of the specification.

FIELD OF THE DISCLOSURE

The present disclosure generally relates to claudin 18.2 (CLDN18.2)-specific antibodies and antibody fragments thereof. The antibodies are useful for immunotherapy of a disease associated with aberrant expression of CLDN18.2, including epithelial cell-derived primary and metastatic cancer.

BACKGROUND OF THE INVENTION

Two alternatively spliced human claudin 18 transcript variants, encoding distinct isoforms that exhibit lung-restricted (CLDN18.1) and stomach-restricted (CLDN18.2) expression (Niimi et al., Mol. Cell. Biol. 21:7380-90, 2001), in a promoter-dependent manner, have previously been described. The primary protein sequences of the splice variants differ in the N-terminal portion that comprises the N-terminal intracellular region, first transmembrane region (TMD1), and extracellular loop one (ECL1). CLDN18.2 is one of a few members of the human claudin family with strict restriction to one cell lineage (Türeci et al.). More specifically, it provides a highly selective gastric lineage (e.g., gastrocyte-specific) marker with an expression pattern that is restricted to short-lived differentiated epithelial cells and absent from the stem cell zone of gastric glands (Sahin et al., Clin. Cancer Res. 14 (23) 7624-7634, 2008).

CLDN18.2 is retained in malignant transformation and is expressed in a significant portion of primary tumors and their metastasis. Sahin et al. also reported that CLDN18.2, but not CLDN18.1, is frequently overexpressed in several different types of cancers, including pancreatic, stomach, esophageal, lung, and ovarian cancers. Therefore, in the context of cancer, CLDN18.2 does not remain restricted to the gastric cell lineage (Sahin et al.). Considered together, the findings of published reports establish that CLDN18.2 provides both a diagnostic tool and a druggable target for the development of cancer immunotherapies of diseases associated with epithelial cell-derived tumors.

It has been reported that tight junction permeability is often higher in tumor tissues than in normal tissues, leading to the speculation that claudin proteins on tumor cells may be more accessible than in normal tissues with intact tight junctions. This possibility makes claudin proteins attractive targets for therapeutic cancer interventions. In addition, published expression profiling results suggest that cancer therapies targeting CLDN18.2 will have favorable systemic toxicity profiles because normal turnover and homeostasis processes replenish gastrointestinal epithelial cells every two to seven days (Sahin et al.). Transient gastrointestinal toxicity of limited duration is a common and manageable adverse event for cancer immunotherapeutics.

Pancreatic and gastroesophageal cancers are among the malignancies with the highest unmet medical need (Sahin, et al.). Despite the fact that gastric cancer and pancreatic cancer contribute to significant cancer-related morbidity and mortality, the treatment options are limited. Thus, the need exists for anti-CLDN18.2 specific antibodies and binding agents for use in the immunotherapy of cancer associated with epithelial cell-derived primary and metastatic solid tumors.

SUMMARY OF THE INVENTION

The present disclosure addresses the above need by providing antibodies and antibody fragments that specifically bind to the human tight junction molecule CLDN18 isoform 2 (CLDN18.2) and have desirable functional properties. The anti-CLDN18.2 antibodies or antibody fragments thereof, or bispecific molecules, or fusion proteins comprising the CLDN18.2 antibodies or antibody fragments may be used for antibody-based therapies of diseases associated with dysregulation of CLDN18.2 expression. For example, the antibodies may be used for treating solid tumor cancer diseases associated with cells expressing CLDN18.2, such as gastric, pancreatic and esophageal, lung, ovarian, colon, and hepatic cancers.

In some embodiments, the antibody of the invention may be a monoclonal, chimeric, humanized or human antibody, a component of a bispecific or multispecific antibody, or an antigen-binding portion of an antibody, which binds to the first extracellular domain/loop of CLDN18.2 and exhibits one or more of the following properties: (a) specificity for CLDN18.2 (e.g. binding to human CLDN18.2 but not to CLDN18.1); (b) ability to mediate ADCC killing of cells expressing CLDN18.2; and (c) efficiently internalized upon CLDN18.2 binding on CLDN18.2 expressing cells and therefore suitable for ADC development.

In some embodiments, the anti-CLDN18.2 specific antibodies or antibody fragments thereof bind preferentially to CLDN18.2 (isoform 2) naturally expressed by human tumor cells and do not bind to CLDN18 isoform 1 (CLDN18.1). As a consequence of binding CLDN18.2 expressed on the surface of a target cell, the disclosed antibodies can mediate target cell killing by one or more mechanisms of action, such as induction of apoptosis, inhibition of proliferation, CDC lysis, ADCC lysis or delivery of a cytotoxic agent. In one embodiment, the target cells are primary or metastatic cancer cells.

In some embodiments, the anti-CLDN18.2 antibody is a full-length antibody.

In some embodiments, the anti-CLDN18.2 antibody is an antibody fragment. In further embodiments, the antibody fragment is selected from the group consisting of: Fab, Fab', F(ab)2, Fd, Fv, scFv, and scFv-Fc fragment, a single-chain antibody, a minibody, and a diabody.

In some embodiments, the anti-CLDN18.2 antibody is a monoclonal antibody.

In some embodiments, the anti-CLDN18.2 antibody is a murine antibody.

In some embodiments, the anti-CLDN18.2 antibody is a human antibody. In some embodiments, the anti-CLDN18.2 antibody is a humanized antibody.

In some embodiments, the anti-CLDN18.2 antibody is a chimeric antibody.

In some embodiments, the anti-CLDN18.2 antibody is a bispecific antibody comprising either an unmodified (e.g., naturally occurring) Fc fragment or a modified Fc fragment designed to optimize, or in the alternative to eliminate, particular Fc-mediated functions.

In some embodiments, the anti-CLDN18.2 antibodies or antibody fragments thereof comprise a heavy chain variable region having SEQ ID NO: 47 (HCDR1), SEQ ID NO: 48 (HCDR2), and SEQ ID NO: 49 (HCDR3); and/or a light chain variable region having SEQ ID NO: 50 (LCDR1), SEQ ID NO: 51 (LCDR2), and SEQ ID NO: 52 (LCDR3).

In some embodiments, the anti-CLDN18.2 antibodies or antibody fragments thereof comprise a heavy chain variable region having SEQ ID NO: 53 (HCDR1), SEQ ID NO: 54 (HCDR2), and SEQ ID NO: 55 (HCDR3); and/or a light chain variable region having SEQ ID NO: 56(LCDR1), SEQ ID NO: 57 (LCDR2), and SEQ ID NO: 58 (LCDR3).

In some embodiments, the anti-CLDN18.2 antibodies or antibody fragments thereof comprise a heavy chain variable region having SEQ ID NO: 59 (HCDR1), SEQ ID NO: 60 (HCDR2), and SEQ ID NO: 61 (HCDR3); and/or a light chain variable region having SEQ ID NO: 62 (LCDR1), SEQ ID NO: 63 (LCDR2), and SEQ ID NO: 64 (LCDR3).

In some embodiments, the anti-CLDN18.2 antibodies or antibody fragments thereof comprise a heavy chain variable region having SEQ ID NO: 65 (HCDR1), SEQ ID NO: 66 (HCDR2), and SEQ ID NO: 67 (HCDR3); and/or a light chain variable region having SEQ ID NO:68 (LCDR1), SEQ ID NO: 69 (LCDR2), and SEQ ID NO:70 (LCDR3).

In some embodiments, the anti-CLDN18.2 antibodies or antibody fragments thereof comprise a heavy chain variable region having SEQ ID NO: 71 (HCDR1), SEQ ID NO: 72 (HCDR2), and SEQ ID NO: 73 (HCDR3); and/or a light chain variable region having SEQ ID NO: 74 (LCDR1), SEQ ID NO: 75 (LCDR2), and SEQ ID NO: 76 (LCDR3).

In some embodiments, the anti-CLDN18.2 antibodies or antibody fragments thereof comprise a heavy chain variable region having SEQ ID NO: 77 (HCDR1), SEQ ID NO: 78 (HCDR2), and SEQ ID NO: 79 (HCDR3); and/or a light chain variable region having SEQ ID NO:80 (LCDR1), SEQ ID NO: 81 (LCDR2), and SEQ ID NO: 82 (LCDR3).

In some embodiments, the anti-CLDN18.2 antibodies or antibody fragments thereof comprise a heavy chain variable region having SEQ ID NO: 83 (HCDR1), SEQ ID NO: 84 (HCDR2), and SEQ ID NO: 85 (HCDR3); and/or a light chain variable region having SEQ ID NO: 86 (LCDR1), SEQ ID NO: 87 (LCDR2), and SEQ ID NO: 88 (LCDR3).

In some embodiments, the anti-CLDN18.2 antibodies or antibody fragments thereof comprise a heavy chain variable region having SEQ ID NO: 89 (HCDR1), SEQ ID NO: 90 (HCDR2), and SEQ ID NO: 91 (HCDR3); and/or a light chain variable region having SEQ ID NO: 92 (LCDR1), SEQ ID NO: 93 (LCDR2), and SEQ ID NO: 94 (LCDR3).

In some embodiments, the anti-CLDN18.2 antibodies or antibody fragments thereof comprise a heavy chain variable region having SEQ ID NO: 95 (HCDR1), SEQ ID NO: 96 (HCDR2), and SEQ ID NO: 97 (HCDR3); and/or a light chain variable region having SEQ ID NO: 98 (LCDR1), SEQ ID NO: 99 (LCDR2), and SEQ ID NO: 100 (LCDR3).

In some embodiments, the anti-CLDN18.2 antibodies or antibody fragments thereof comprise a heavy chain variable region having SEQ ID NO: 101 (HCDR1), SEQ ID NO: 102 (HCDR2), and SEQ ID NO: 103 (HCDR3); and/or a light chain variable region having SEQ ID NO: 104 (LCDR1), SEQ ID NO: 105 (LCDR2), and SEQ ID NO: 106 (LCDR3).

In some embodiments, the anti-CLDN18.2 antibodies or antibody fragments thereof comprise a heavy chain variable region having SEQ ID NO: 107 (HCDR1), SEQ ID NO: 108 (HCDR2), and SEQ ID NO: 109 (HCDR3); and/or a light chain variable region having SEQ ID NO:110 (LCDR1), SEQ ID NO: 111 (LCDR2), and SEQ ID NO: 112 (LCDR3).

In some embodiments, the anti-CLDN18.2 antibodies or antibody fragments thereof comprise a heavy chain variable region having SEQ ID NO: 113 (HCDR1), SEQ ID NO: 114 (HCDR2), and SEQ ID NO: 115 (HCDR3); and/or a light chain variable region having SEQ ID NO: 116 (LCDR1), SEQ ID NO: 117 (LCDR2), and SEQ ID NO: 118 (LCDR3).

In some embodiments, the anti-CLDN18.2 antibodies or antibody fragments thereof comprise a heavy chain variable region having SEQ ID NO: 119 (HCDR1), SEQ ID NO: 120 (HCDR2), and SEQ ID NO: 121 (HCDR3); and/or a light chain variable region having SEQ ID NO: 122 (LCDR1), SEQ ID NO: 123 (LCDR2), and SEQ ID NO: 124 (LCDR3).

In some embodiments, the anti-CLDN18.2 antibodies or antibody fragments thereof comprise a heavy chain variable region having SEQ ID NO: 125 (HCDR1), SEQ ID NO: 126 (HCDR2), and SEQ ID NO: 127 (HCDR3); and/or a light chain variable region having SEQ ID NO: 128 (LCDR1), SEQ ID NO: 129 (LCDR2), and SEQ ID NO: 130 (LCDR3).

In some embodiments, the anti-CLDN18.2 antibodies or antibody fragments thereof comprise a heavy chain variable region having SEQ ID NO: 131 (HCDR1), SEQ ID NO: 132 (HCDR2), and SEQ ID NO: 133 (HCDR3); and/or a light chain variable region having SEQ ID NO: 134 (LCDR1), SEQ ID NO: 135 (LCDR2), and SEQ ID NO: 136 (LCDR3).

In some embodiments, the anti-CLDN18.2 antibodies or antibody fragments thereof comprise a heavy chain variable region having SEQ ID NO: 137 (HCDR1), SEQ ID NO: 138 (HCDR2), and SEQ ID NO:139 (HCDR3); and/or a light chain variable region having SEQ ID NO:140 (LCDR1), SEQ ID NO:141 (LCDR2), and SEQ ID NO: 142 (LCDR3).

In some embodiments, the anti-CLDN18.2 antibodies or antibody fragments thereof comprise a heavy chain variable region having SEQ ID NO: 143 (HCDR1), SEQ ID NO: 144 (HCDR2), and SEQ ID NO: 145 (HCDR3); and/or a light chain variable region having SEQ ID NO:146 (LCDR1), SEQ ID NO: 147 (LCDR2), and SEQ ID NO: 148 (LCDR3).

In some embodiments, the anti-CLDN18.2 antibodies or antibody fragments thereof comprise a heavy chain variable region having SEQ ID NO: 149 (HCDR1), SEQ ID NO: 150 (HCDR2), and SEQ ID NO: 151 (HCDR3); and/or a light chain variable region having SEQ ID NO: 152 (LCDR1), SEQ ID NO: 153 (LCDR2), and SEQ ID NO: 154 (LCDR3).

In some embodiments, the anti-CLDN18.2 antibodies or antibody fragments thereof comprise a heavy chain variable region having SEQ ID NO: 155 (HCDR1), SEQ ID NO: 156 (HCDR2), and SEQ ID NO: 157 (HCDR3); and/or a light chain variable region having SEQ ID NO: 158 (LCDR1), SEQ ID NO: 159 (LCDR2), and SEQ ID NO: 160 (LCDR3).

In some embodiments, the anti-CLDN18.2 antibodies or antibody fragments thereof comprise a heavy chain variable region having SEQ ID NO:161 (HCDR1), SEQ ID NO: 162 (HCDR2), and SEQ ID NO: 163 (HCDR3); and/or a light chain variable region having SEQ ID NO: 164 (LCDR1), SEQ ID NO: 165 (LCDR2), and SEQ ID NO: 166 (LCDR3).

In some embodiments, the anti-CLDN18.2 antibodies or antibody fragments thereof comprise a heavy chain variable region having SEQ ID NO: 167 (HCDR1), SEQ ID NO: 168 (HCDR2), and SEQ ID NO: 169 (HCDR3); and/or a light chain variable region having SEQ ID NO: 170 (LCDR1), SEQ ID NO:171 (LCDR2), and SEQ ID NO: 172 (LCDR3).

In some embodiments, the anti-CLDN18.2 antibodies or antibody fragments thereof comprise a heavy chain variable region having SEQ ID NO:173 (HCDR1), SEQ ID NO: 174 (HCDR2), and SEQ ID NO: 175 (HCDR3); and/or a light chain variable region having SEQ ID NO: 176 (LCDR1), SEQ ID NO: 177 (LCDR2), and SEQ ID NO: 178 (LCDR3).

In some embodiments, the anti-CLDN18.2 antibodies or antibody fragments thereof comprise a heavy chain variable region having SEQ ID NO: 179 (HCDR1), SEQ ID NO: 180 (HCDR2), and SEQ ID NO:181 (HCDR3); and/or a light chain variable region having SEQ ID NO: 182 (LCDR1), SEQ ID NO: 183 (LCDR2), and SEQ ID NO: 184 (LCDR3).

In some embodiments, the anti-CLDN18.2 antibodies or antibody fragments thereof comprise a heavy chain variable region having SEQ ID NO: 221 (HCDR1), SEQ ID NO: 222 (HCDR2), and SEQ ID NO: 223 (HCDR3); and/or a light chain variable region having SEQ ID NO: 224 (LCDR1), SEQ ID NO: 225 (LCDR2), and SEQ ID NO: 226 (LCDR3).

In some embodiments, the anti-CLDN18.2 antibodies or antibody fragments thereof comprise a heavy chain variable region having SEQ ID NO: 227 (HCDR1), SEQ ID NO: 228 (HCDR2), and SEQ ID NO:229 (HCDR3); and/or a light chain variable region having SEQ ID NO: 230 (LCDR1), SEQ ID NO: 231(LCDR2), and SEQ ID NO: 232 (LCDR3).

In some embodiments, the anti-CLDN18.2 antibodies or antibody fragments thereof comprise a heavy chain variable region having SEQ ID NO: 233 (HCDR1), SEQ ID NO: 234 (HCDR2), and SEQ ID NO: 235 (HCDR3); and/or a light chain variable region having SEQ ID NO: 236 (LCDR1), SEQ ID NO: 237 (LCDR2), and SEQ ID NO: 238 (LCDR3).

In some embodiments, the anti-CLDN18.2 antibodies or antibody fragments thereof comprise a heavy chain variable region having SEQ ID NO: 239 (HCDR1), SEQ ID NO: 240 (HCDR2), and SEQ ID NO: 241 (HCDR3); and/or a light chain variable region having SEQ ID NO: 242 (LCDR1), SEQ ID NO: 243 (LCDR2), and SEQ ID NO: 244 (LCDR3).

In some embodiments, the anti-CLDN18.2 antibodies or antibody fragments thereof comprise a heavy chain variable region having SEQ ID NO: 245 (HCDR1), SEQ ID NO: 246 (HCDR2), and SEQ ID NO: 247 (HCDR3); and/or a light chain variable region having SEQ ID NO: 248 (LCDR1), SEQ ID NO: 249 (LCDR2), and SEQ ID NO: 250 (LCDR3).

In some embodiments, the anti-CLDN18.2 antibodies or antibody fragments thereof comprise a heavy chain variable region having SEQ ID NO: 251 (HCDR1), SEQ ID NO: 252 (HCDR2), and SEQ ID NO: 253 (HCDR3); and/or a light chain variable region having SEQ ID NO: 254 (LCDR1), SEQ ID NO: 255 (LCDR2), and SEQ ID NO: 256 (LCDR3).

In some embodiments, the anti-CLDN18.2 antibodies or antibody fragments thereof comprise a heavy chain variable region having SEQ ID NO: 257 (HCDR1), SEQ ID NO: 258 (HCDR2), and SEQ ID NO: 259 (HCDR3); and/or a light chain variable region having SEQ ID NO: 260 (LCDR1), SEQ ID NO: 261 (LCDR2), and SEQ ID NO: 262 (LCDR3).

In some embodiments, the anti-CLDN18.2 antibodies or antibody fragments thereof comprise a heavy chain variable region having SEQ ID NO: 263 (HCDR1), SEQ ID NO: 264 (HCDR2), and SEQ ID NO: 265 (HCDR3); and/or a light chain variable region having SEQ ID NO: 266 (LCDR1), SEQ ID NO: 267 (LCDR2), and SEQ ID NO: 268 (LCDR3).

In some embodiments, the anti-CLDN18.2 antibodies or antibody fragments thereof comprise a heavy chain variable region having SEQ ID NO: 269 (HCDR1), SEQ ID NO: 270 (HCDR2), and SEQ ID NO: 271 (HCDR3); and/or a light chain variable region having SEQ ID NO: 272 (LCDR1), SEQ ID NO: 273 (LCDR2), and SEQ ID NO: 274 (LCDR3).

In some embodiments, the anti-CLDN18.2 antibodies or antibody fragments thereof comprise a heavy chain variable region having SEQ ID NO: 275 (HCDR1), SEQ ID NO: 276 (HCDR2), and SEQ ID NO: 277 (HCDR3); and/or a light chain variable region having SEQ ID NO: 278 (LCDR1), SEQ ID NO: 279 (LCDR2), and SEQ ID NO: 280 (LCDR3).

In some embodiments, the anti-CLDN18.2 antibodies or antibody fragments thereof comprise a heavy chain variable region having SEQ ID NO: 281 (HCDR1), SEQ ID NO: 282 (HCDR2), and SEQ ID NO: 283 (HCDR3); and/or a light chain variable region having SEQ ID NO: 284 (LCDR1), SEQ ID NO: 285 (LCDR2), and SEQ ID NO: 286 (LCDR3).

In some embodiments, the anti-CLDN18.2 antibodies or antibody fragments thereof comprise a heavy chain variable region having SEQ ID NO: 287 (HCDR1), SEQ ID NO: 288 (HCDR2), and SEQ ID NO: 289 (HCDR3); and/or a light chain variable region having SEQ ID NO: 290 (LCDR1), SEQ ID NO: 291 (LCDR2), and SEQ ID NO: 292 (LCDR3).

In some embodiments, the anti-CLDN18.2 antibodies or antibody fragments thereof comprise a heavy chain variable region having SEQ ID NO: 293 (HCDR1), SEQ ID NO: 294 (HCDR2), and SEQ ID NO: 295 (HCDR3); and/or a light chain variable region having SEQ ID NO: 296 (LCDR1), SEQ ID NO: 297 (LCDR2), and SEQ ID NO: 298 (LCDR3).

In some embodiments, the anti-CLDN18.2 antibodies or antibody fragments thereof comprise a heavy chain variable region having SEQ ID NO: 299 (HCDR1), SEQ ID NO: 300 (HCDR2), and SEQ ID NO: 301 (HCDR3); and/or a light chain variable region having SEQ ID NO: 302 (LCDR1), SEQ ID NO: 303 (LCDR2), and SEQ ID NO: 304 (LCDR3).

In some embodiments, the anti-CLDN18.2 antibodies or antibody fragments thereof comprise a heavy chain variable region having SEQ ID NO: 311 (HCDR1), SEQ ID NO: 312 (HCDR2), and SEQ ID NO: 313(HCDR3); and/or a light chain variable region having SEQ ID NO: 314 (LCDR1), SEQ ID NO: 315 (LCDR2), and SEQ ID NO: 316 (LCDR3).

In some embodiments, the anti-CLDN18.2 antibodies or antibody fragments thereof comprise a heavy chain variable region having SEQ ID NO: 317 (HCDR1), SEQ ID NO: 318 (HCDR2), and SEQ ID NO: 319 (HCDR3); and/or a light chain variable region having SEQ ID NO: 320 (LCDR1), SEQ ID NO: 321 (LCDR2), and SEQ ID NO: 322 (LCDR3).

In some embodiments, the anti-CLDN18.2 antibodies or antibody fragments thereof comprise a heavy chain variable region having SEQ ID NO: 323 (HCDR1), SEQ ID NO: 324 (HCDR2), and SEQ ID NO: 325 (HCDR3); and/or a light chain variable region having SEQ ID NO: 326 (LCDR1), SEQ ID NO: 327 (LCDR2), and SEQ ID NO: 328 (LCDR3).

In some embodiments, the anti-CLDN18.2 antibodies or antibody fragments thereof comprise a variable heavy chain sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 185, 187, 189, 191, 193, 195, 197, 199, 201, 203, 205, 207, 09, 211, 215, 217, and 219.

In some embodiments, the anti-CLDN18.2 antibodies or antibody fragments thereof comprise a variable light chain sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 186, 188, 190, 192, 194, 196, 198, 200, 202, 204, 206, 208, 210, 212, 216, 218, and 220.

The present invention further provides anti-CLDN18.2 specific antibodies or binding fragments thereof comprising an antibody or CLDN18.2 binding fragment comprising a specific combination or pair of variable heavy and variable light chain sequences.

In an embodiment, an anti-CLDN18.2 specific antibodies or binding fragments thereof comprise an antibody or CLDN18.2 binding fragment thereof comprising a variable heavy chain sequence selected from the group consisting of SEQ ID NOS: 1, 3, 5, 7, 9, 11, 13, 15, 17, 19, 21, 23, 25, 27, 29, 31, 33, 35, 37, 39, 41, 43, and 45, respectively, paired with a variable light chain sequence selected from the group consisting of SEQ ID NOS: 2, 4, 6, 8, 10, 12, 14, 16, 18, 20, 22, 24, 26, 28, 30, 32, 34, 36, 38, 40, 42, 44, and 46, respectively.

In an embodiment, the anti-CLDN18.2 specific antibodies or binding fragments thereof comprise an antibody or CLDN18.2 binding fragment thereof comprising a variable heavy chain sequence selected from the group consisting of SEQ ID NOS: 185, 187, 189, 191, 193, 195, 197, 199, 201, 203, 205, 207, 209, 211, 215, 217, and 219, respectively, paired with a and a variable light chain sequence selected from the group consisting of SEQ ID NOS: 186, 188, 190, 192, 194, 196, 198, 200, 202, 204, 206, 208, 210, 212, 216, 218, and 220, respectively.

In an embodiment, the anti-CLDN18.2 specific antibodies or binding fragments thereof comprise an antibody or CLDN18.2 binding fragment comprising a specific combination or pair of variable heavy and variable light chain sequences. In an alternative embodiment, the anti-CLDN18.2 specific antibodies or binding fragments thereof comprise an antibody or CLDN18.2 binding fragment or binding agent comprising defined sets or combinations of CDR sequences derived from the VH and/or VL domain regions of the anti-CLDN18.2 antibodies of the invention.

In some embodiments, the anti-CLDN18.2 antibody or antigen-binding fragment thereof comprises a specific pair of variable heavy chain and variable light chain sequences, selected from the following combinations.

(a) a variable heavy chain sequence comprising SEQ ID NO:1 and a variable light chain sequence comprising SEQ ID NO:2;

(b) a variable heavy chain sequence comprising SEQ ID NO:3 and a variable light chain sequence comprising SEQ ID NO:4;

(c) a variable heavy chain sequence comprising SEQ ID NO:5 and a variable light chain sequence comprising SEQ ID NO:6;

(d) a variable heavy chain sequence comprising SEQ ID NO:7 and a variable light chain sequence comprising SEQ ID NO:8;

(e) a variable heavy chain sequence comprising SEQ ID NO:9 and a variable light chain sequence comprising SEQ ID NO:10;

(f) a variable heavy chain sequence comprising SEQ ID NO:11 and a variable light chain sequence comprising SEQ ID NO:12;

(g) a variable heavy chain sequence comprising SEQ ID NO:13 and a variable light chain sequence comprising SEQ ID NO:14;

(h) a variable heavy chain sequence comprising SEQ ID NO:15 and a variable light chain sequence comprising SEQ ID NO:16;

(i) a variable heavy chain sequence comprising SEQ ID NO:17 and a variable light chain sequence comprising SEQ ID NO:18;

(j) a variable heavy chain sequence comprising SEQ ID NO:19 and a variable light chain sequence comprising SEQ ID NO:20;

(k) a variable heavy chain sequence comprising SEQ ID NO:21 and a variable light chain sequence comprising SEQ ID NO:22;

(l) a variable heavy chain sequence comprising SEQ ID NO:23 and a variable light chain sequence comprising SEQ ID NO:24;

(m) a variable heavy chain sequence comprising SEQ ID NO:25 and a variable light chain sequence comprising SEQ ID NO:26;

(n) a variable heavy chain sequence comprising SEQ ID NO:27 and a variable light chain sequence comprising SEQ ID NO:28;

(o) a variable heavy chain sequence comprising SEQ ID NO:29 and a variable light chain sequence comprising SEQ ID NO:30;

(p) a variable heavy chain sequence comprising SEQ ID NO:31 and a variable light chain sequence comprising SEQ ID NO:32;

(q) a variable heavy chain sequence comprising SEQ ID NO:33 and a variable light chain sequence comprising SEQ ID NO:34;

(r) a variable heavy chain sequence comprising SEQ ID NO:35 and a variable light chain sequence comprising SEQ ID NO:36;

(s) a variable heavy chain sequence comprising SEQ ID NO:37 and a variable light chain sequence comprising SEQ ID NO:38;

(t) a variable heavy chain sequence comprising SEQ ID NO:39 and a variable light chain sequence comprising SEQ ID NO:40;

(u) a variable heavy chain sequence comprising SEQ ID NO:41 and a variable light chain sequence comprising SEQ ID NO:42;

(v) a variable heavy chain sequence comprising SEQ ID NO:43 and a variable light chain sequence comprising SEQ ID NO:44; and (w) a variable heavy chain sequence comprising SEQ ID NO:45 and a variable light chain sequence comprising SEQ ID NO:46.

In some embodiments, the provided antibodies are fully human anti-CLDN18.2 antibodies, or antigen-binding fragment thereof, comprising a specific pair of variable heavy chain and variable light chain sequences, selected from the following combinations:

(aa) a variable heavy chain sequence comprising SEQ ID NO: 185 and a variable light chain sequence comprising SEQ ID NO: 186;

(bb) a variable heavy chain sequence comprising SEQ ID NO: 187 and a variable light chain sequence comprising SEQ ID NO: 188;

(cc) a variable heavy chain sequence comprising SEQ ID NO: 189 and a variable light chain sequence comprising SEQ ID NO: 190;

(dd) a variable heavy chain sequence comprising SEQ ID NO: 191 and a variable light chain sequence comprising SEQ ID NO: 192;

(ee) a variable heavy chain sequence comprising SEQ ID NO: 193 and a variable light chain sequence comprising SEQ ID NO: 194;

(ff) a variable heavy chain sequence comprising SEQ ID NO: 195 and a variable light chain sequence comprising SEQ ID NO: 196;

(gg) a variable heavy chain sequence comprising SEQ ID NO: 197 and a variable light chain sequence comprising SEQ ID NO: 198;

(hh) a variable heavy chain sequence comprising SEQ ID NO: 199 and a variable light chain sequence comprising SEQ ID NO: 200;

(ii) a variable heavy chain sequence comprising SEQ ID NO: 201 and a variable light chain sequence comprising SEQ ID NO: 202;

(jj) a variable heavy chain sequence comprising SEQ ID NO: 203 and a variable light chain sequence comprising SEQ ID NO: 204;

(kk) a variable heavy chain sequence comprising SEQ ID NO: 205 and a variable light chain sequence comprising SEQ ID NO: 206;

(ll) a variable heavy chain sequence comprising SEQ ID NO: 207 and a variable light chain sequence comprising SEQ ID NO: 208;

(mm) a variable heavy chain sequence comprising SEQ ID NO: 209 and a variable light chain sequence comprising SEQ ID NO: 210;

(nn) a variable heavy chain sequence comprising SEQ ID NO: 211 and a variable light chain sequence comprising SEQ ID NO: 212;

(oo) a variable heavy chain sequence comprising SEQ ID NO: 215 and a variable light chain sequence comprising SEQ ID NO: 216;

(pp) a variable heavy chain sequence comprising SEQ ID NO: 217 and a variable light chain sequence comprising SEQ ID NO: 218; and (qq) a variable heavy chain sequence comprising SEQ ID NO: 219 and a variable light chain sequence comprising SEQ ID NO: 220.

The skilled person will further understand that the variable light and variable heavy chains may be independently selected, or mixed and matched, from the antibodies provided herein.

In some embodiments, the anti-CLDN18.2 antibodies or antibody fragments thereof comprise a combination of CDR sequences derived from a variable heavy chain sequence selected from the group consisting of SEQ ID NOs: 1, 3, 5, 7, 9, 11, 13, 15, 17, 19, 21, 23, 25, 27, 29, 31, 33, 35, 37, 39, 41, 43 and 45 and a variable light chain sequence selected from the group consisting of SEQ ID NOs: 2, 4, 6, 8, 10, 12, 14, 16, 18, 20, 22, 24, 26, 28, 30, 32, 34, 36, 38, 40, 42, 44 and 46.

In some embodiments, the anti-CLDN18.2 antibodies or antibody fragments thereof comprise a combination of CDR sequences derived from a variable heavy chain sequence selected from the group consisting of SEQ ID NOs: 185, 187, 189, 191, 193, 195, 197, 199, 201, 203, 205, 207, 209, 211, 215, 217 and 219 and a variable light chain sequence selected from the group consisting of SEQ ID NOs: 186, 188, 190, 192, 194, 196, 198, 200, 202, 204, 206, 208, 210, 212, 216, 218 and 220.

In some embodiments, the anti-CLDN18 antibodies and antibody fragments thereof comprise one or more heavy chain variable region CDRs disclosed in Table 1 and/or one or more light chain variable region CDRs disclosed in Table 3.

In some embodiments, the anti-CLDN18 antibodies and antibody fragments thereof comprise one or more heavy chain variable region CDRs disclosed in Table 2 and/or one or more light chain variable region CDRs disclosed in Table 4.

In some embodiments, the anti-CLDN18.2 antibody or antibody fragment is a recombinant antibody (e.g., a chimeric antibody, humanized antibody, or a bispecific antibody) comprising six (6) CDRs, all derived from the VH or VL domain of a single anti-CLDN18.2 antibody disclosed herein. For example, a binding agent may comprise all six of the CDR regions for the anti-CLDN18.2 antibody designated as Hu-1. In this instance, the antibody or binding agent would comprise the amino acid sequences of SEQ ID NOS: 221-223 and SEQ ID NOS: 224-226, representing the CDR1, CDR2 and CDR3 of the variable heavy and the CDR1, CDR2 and CDR3 sequences of the variable light domains, respectively, of the Hu-1 antibody.

In some embodiments, the anti-CLDN18 antibodies or antibody fragments thereof bind to the first extracellular domain/loop of CLDN18.2 and exhibit one or more of the following properties binding preferentially to CLDN18 isoform 2 being naturally expressed by human tumor cells, not binding to CLDN18 isoform 1 (CLDN18.1), efficiently internalized from the surface of CLDN18.2 positive cells after binding, capable of directing the killing of CLDN18.2 positive cells by inducing antibody-dependent cellular cytotoxicity (ADCC) mediated lysis, complement-dependent cytotoxicity (CDC), or antibody-dependent phagocytosis (ADPC).

The present disclosure also provides methods for the treatment of epithelial cell-derived primary and metastatic cancer comprising administering a composition or formulation that comprises an anti-CLDN18.2 antibody, a bispecific antibody comprising an anti-CLDN18.2-specific binding agent, or an antibody fragment thereof, and optionally another immune-based therapy, to a subject in need thereof. In some embodiments, the cancer is selected from solid tumor, gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer. In some instances the other immune-based therapy is a checkpoint inhibitor.

The anti-CLDN18.2 antibodies of the disclosure can also be used for developing antibody-based immunotherapeutics that rely on CLDN18.2-specific binding to direct patient effector cells (e.g., T cells or NK cells) to tumors including bispecific T cell engaging antibodies, or bispecific molecules that redirect NK cells, or cell therapies, such as CAR-T therapy or for delivery to toxic payloads (e.g., a conjugated cytotoxic drug) to CLDN18.2 positive solid tumors.

The anti-CLDN18.2 antibodies of the disclosure can also be used for diagnosis of gastric cancer, esophageal cancer, cancer of the gastroesophageal junction, pancreatic cancer, cancer of the bile duct, lung cancer, ovarian cancer, colon cancer, hepatic cancer, head and neck cancer, gallbladder cancer.

BRIEF DESCRIPTION OF THE OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples, and instrumentalities shown.

FIG. 1 provides the amino acid sequences of the VH and VL domains of the murine anti-CLDN18.2 antibodies and their respective CDR sequences. Sequence identifiers are provided and the CDRs are underlined in the variable domain sequences.

FIG. 2 provides the amino acid sequences of the VH and VL domains of the human anti-CLDN18.2 antibodies and their respective CDR sequences. Sequence identifiers are provided and the CDRs are underlined in the variable domain sequences.

FIGS. 3A, 3B and 3C demonstrate the binding of mouse anti-Claudin18.2 antibodies to CHO-Claudin18.2 cells. FIG. 3A shows the binding intensity counts of murine anti-Claudin18.2 antibodies. FIG. 3B shows the binding curves of murine anti-Claudin18.2 antibodies Ms-1, Ms-2, and Ms-3 to CHO-Claudin18.2 cells. FIG. 3C shows the binding of Claudin18.2 antibodies Ms-4 and Hu-3 to CHO-Cladin18.2 cells, but not to CHO-Cladin18.1.

FIGS. 4A and 4B are graphs showing the binding of human anti-Claudin18.2 antibodies to CHO-Claudin18.2 and CHO-Claudin18.1 cells. FIG. 4A shows the binding of human anti-Claudin18.2 antibodies. FIG. 4B shows the binding curves of human anti-Claudin18.2 antibodies Hu-2, Hu-9, and Hu-10 to CHO-Claudin18.2 cells.

FIG. 5 is a bar graph showing the comparison of the surface Claudin18.2 expression level on CHO-Claudin18.2 and tumor cell lines PATU8988S and NUGC-4.

FIGS. 6A and 6B are bar graphs showing the binding of anti-Claudin18.2 antibodies to tumor cell line PATU8988S. FIG. 6A shows the binding intensity counts of murine anti-Claudin18.2 antibodies. FIG. 6B shows the binding of human anti-Claudin18.2 antibodies.

Figure 9:
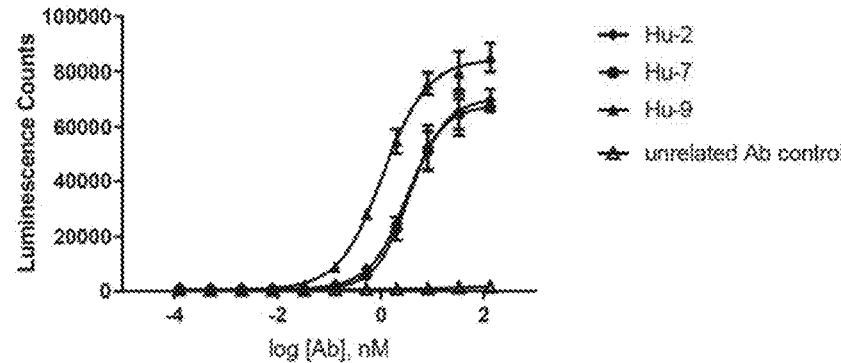

FIG. 9 demonstrates Hu-2-, Hu-7-, and Hu-9-mediated antibody-dependent cellular cytotoxicity (ADCC).

Figure 10:
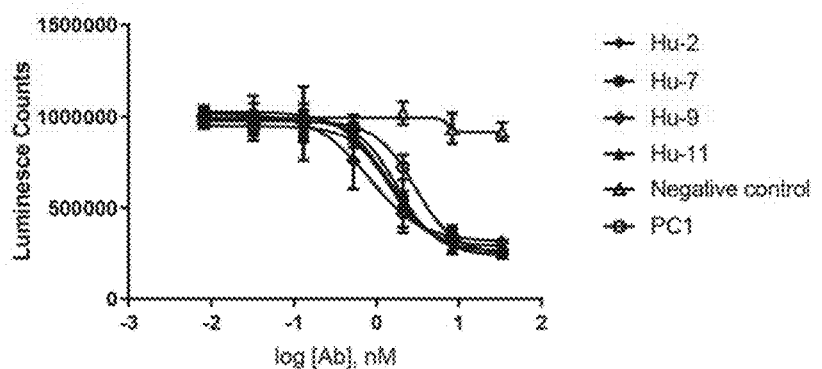

FIG. 10 demonstrates antibody-mediated endocytosis induced by anti-Claudin18.2 antibodies Hu-2, Hu-7, Hu-9, and Hu-11.

FIGS. 11A and 11B provide the amino acid sequences of four human immunoglobulin IgG1 CH domains (FIG. 11A) and a human immunoglobulin kappa light chain CL domain (FIG. 11B) suitable for use in combination with the disclosed anti-CLDN18.2 VH and VL domains and/or CDR sequences. Sequence identifiers are provided.

FIG. 12 provides the amino acid sequence of two representative full-length anti-CLDN18.2 antibody) recombinant heavy chains comprising the amino acid sequence provided in SEQ ID NO: 336 or SEQ ID NO: 338, either of which can be paired with a recombinant kappa light chain having the amino acid sequence provided in SEQ ID NO: 337 to provide a full-length human IgG1 anti-CLDN18.2 antibody.

Figure 13A:
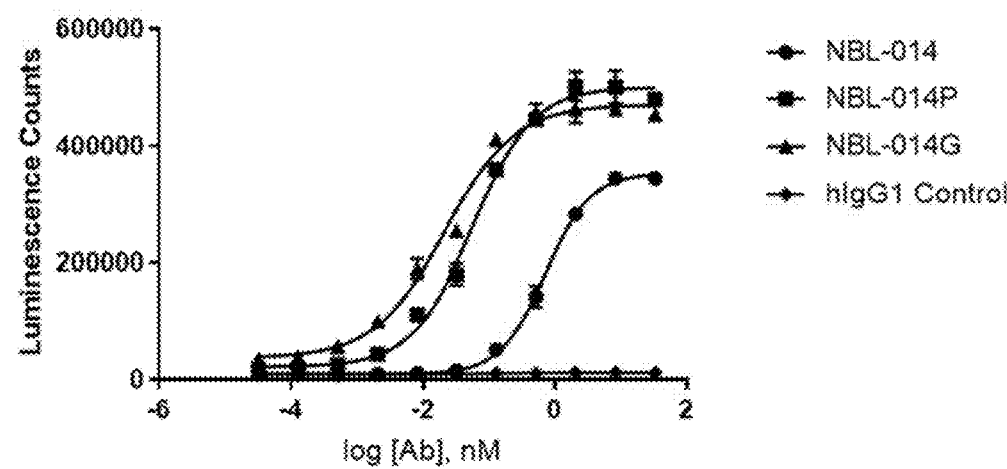
Figure 13B:
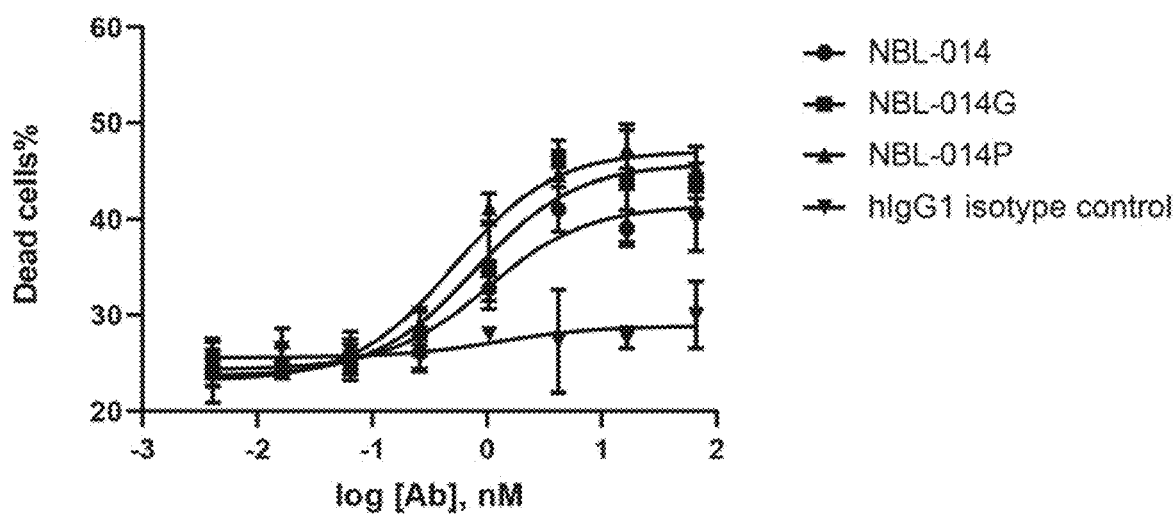

FIGS. 13A and 13B demonstrate Fc modified Claudin18.2 antibodies NBL-014P and NBL-014G induce enhanced ADCC against CHO cells overexpressing human claudin18.2. using Promega surrogate effector cells (FIG. 13A) or NK92MI cells overexpressing CD16A (FIG. 13B).

Figure 14A:
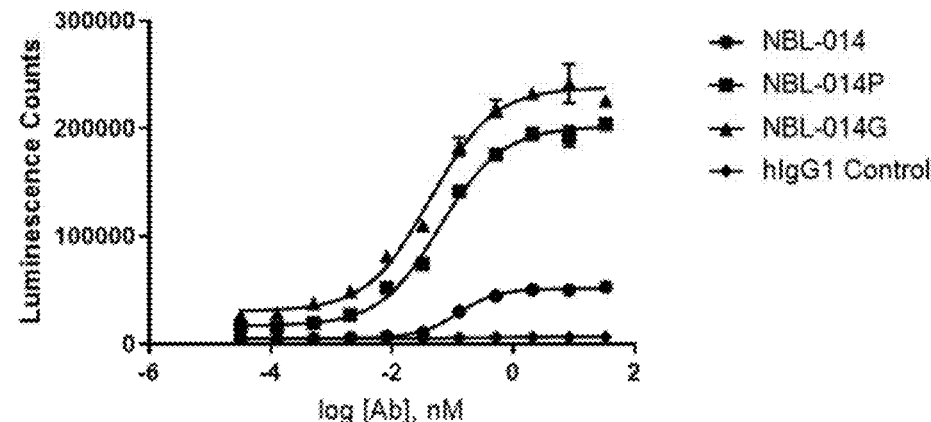
Figure 14B:
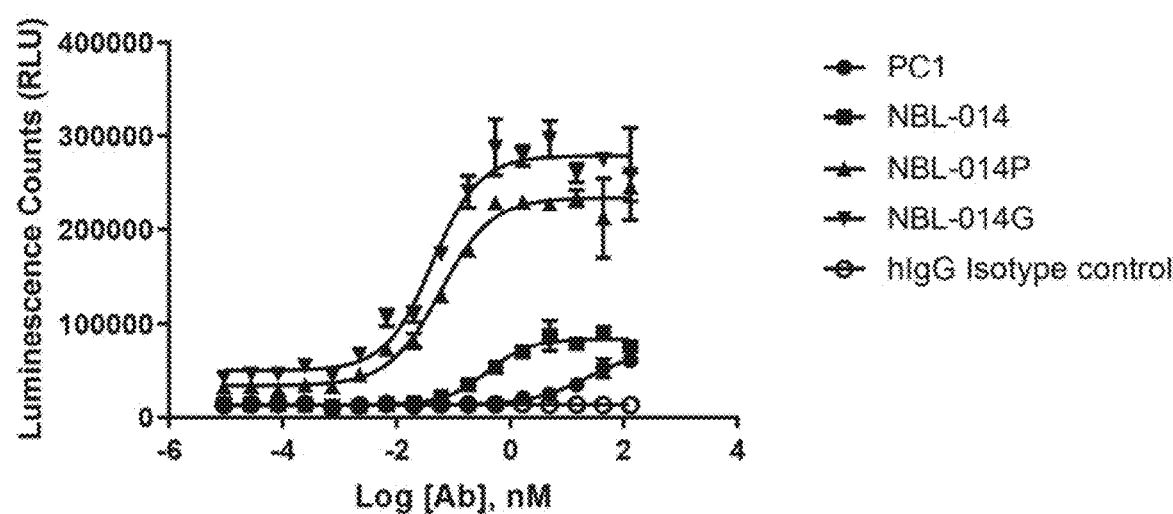

FIGS. 14A and 14B show the Fc modified anti-Claudin18.2 antibodies NBL-014P and NBL-014G induce enhanced ADCC against NUGC-4 cells (FIG. 14A) and PATU8988S cells (FIG. 14B).

Figure 15:
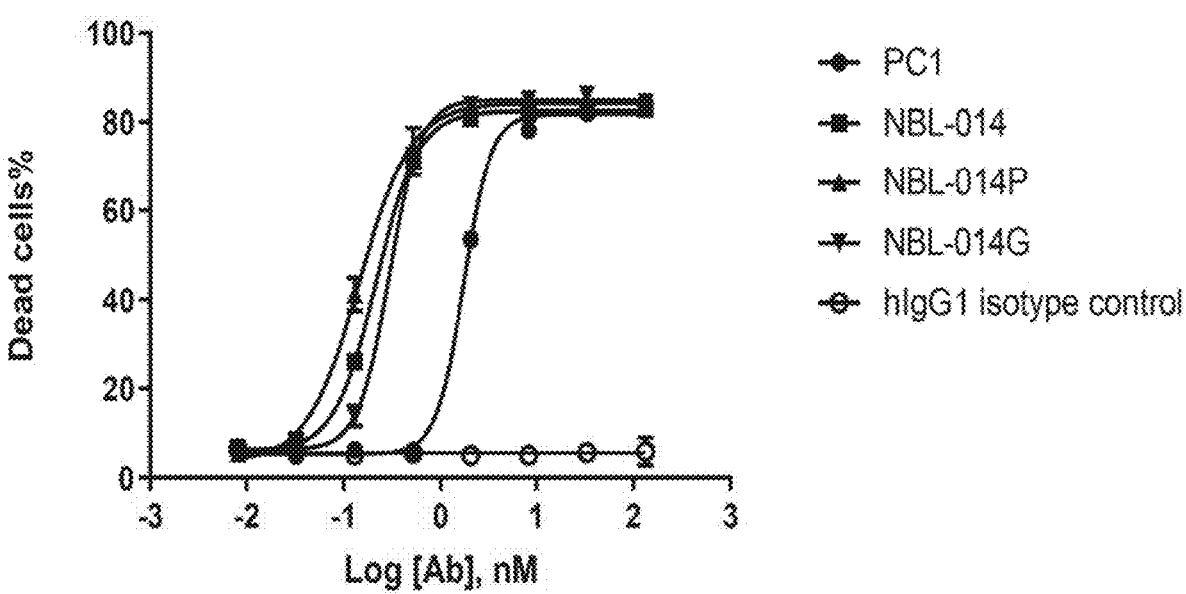

FIG. 15 shows the Fc modified anti-Claudin18.2 antibodies NBL-014P and NBL-014G induce enhanced CDC, compared to the CDC activity of PC1, against CHO cells overexpressing human claudin18.2.

Figure 16:
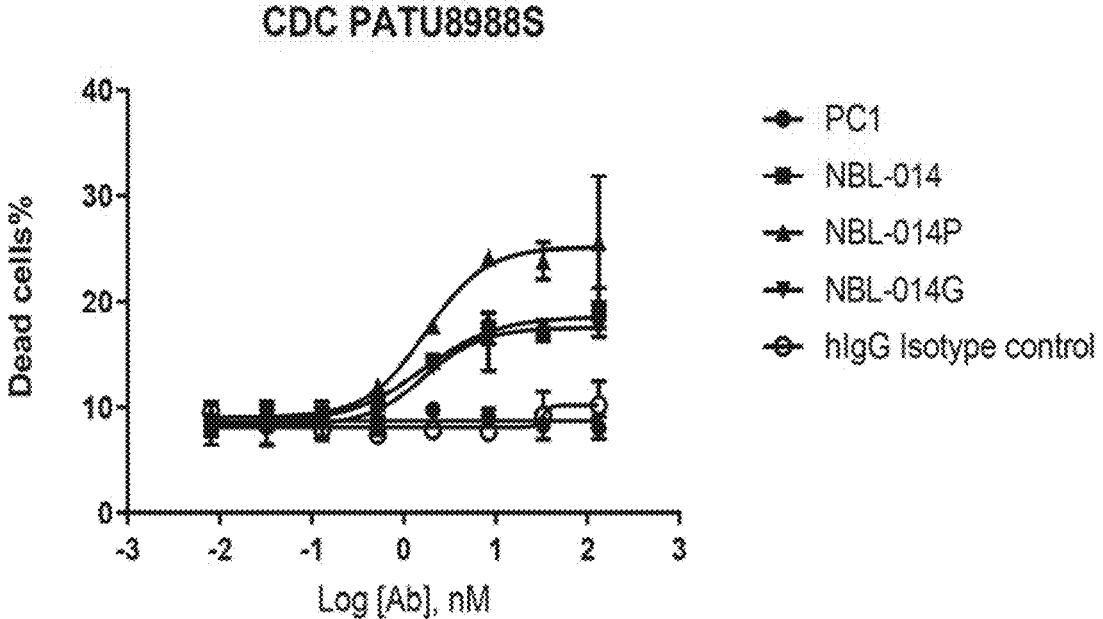

FIG. 16 shows the Fc modified anti-Claudin18.2 antibodies NBL-014P and NBL-014G induce enhanced CDC activity, compared to the CDC activity of PC1, against PATU8988S cells.

Figure 17A:
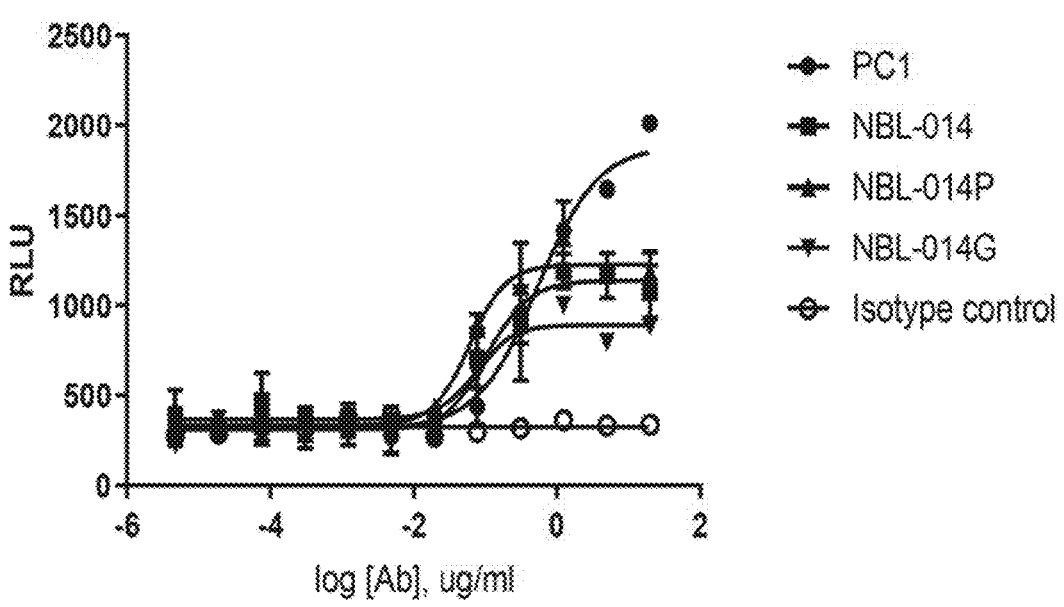
Figure 17B:
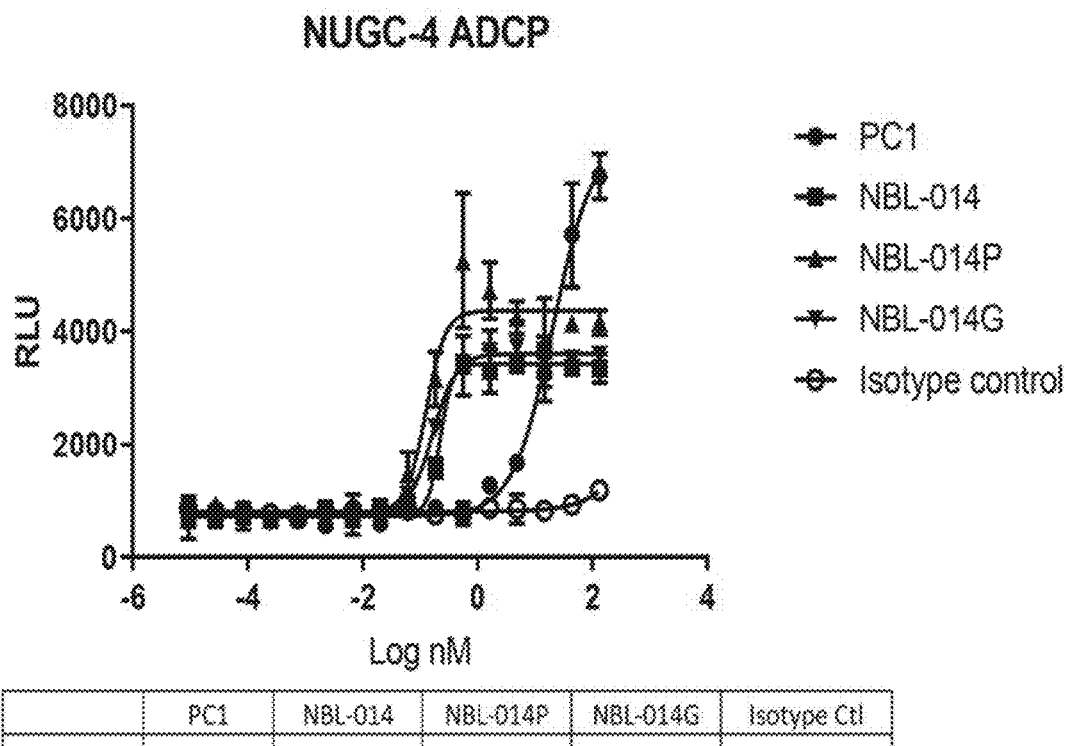

FIGS. 17A-17B show ADCP activity of anti-Claudin18.2 antibodies against CHO cells overexpressing human claudin18.2 (FIG. 17A) and NUGC-4 cells (FIG. 17B).

Figure 18A:
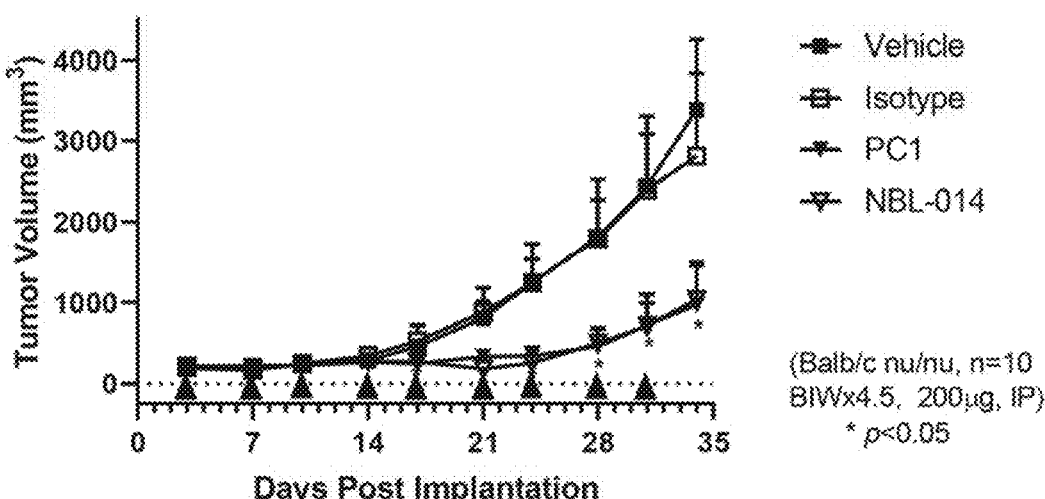
Figure 18B:
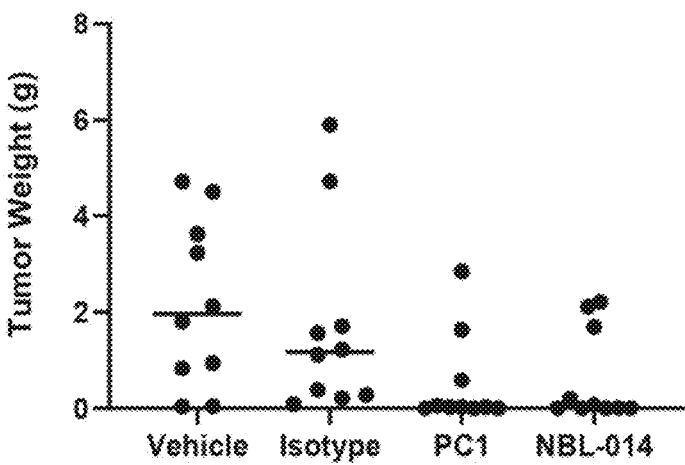

FIGS. 18A and 18B demonstrate the anti-tumor efficacy of anti-Claudin 18.2 antibodies NBL-014 and PC1 in a subcutaneous PATU8988S overexpressing human Claudin 18.2 model based on determination of changes in tumor volume over time (FIG. 18A) and tumor weight on day 34 (FIG. 18B).

Figure 19:
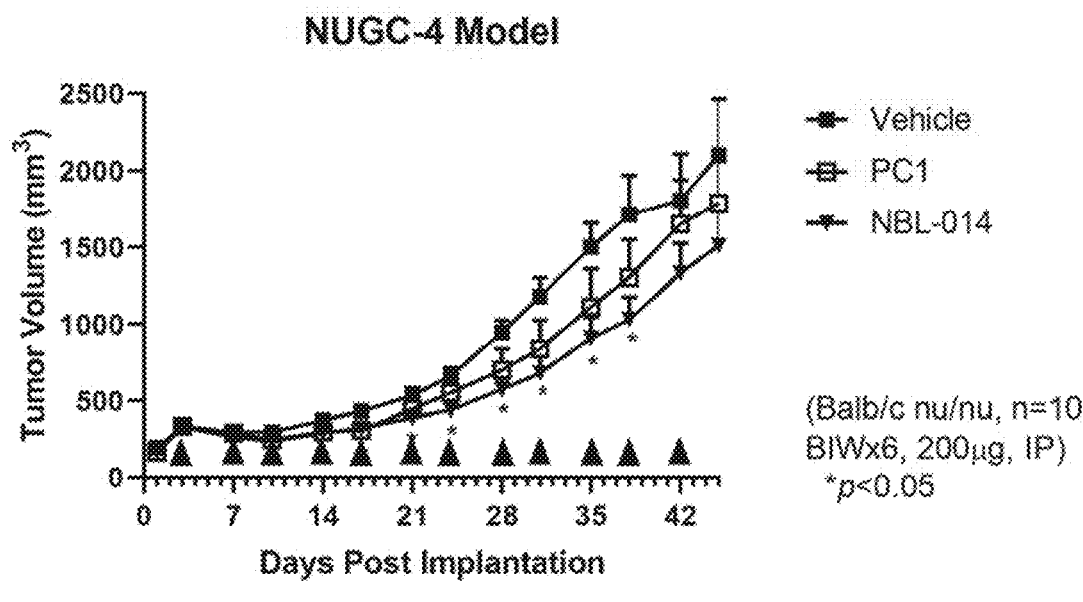

FIG. 19 is a graph showing the anti-tumor efficacy of anti-Claudin 18.2 antibodies NBL-014 and PC1 in a subcutaneous NUGC-4 model based on changes in tumor volume over time.

Figure 20A:
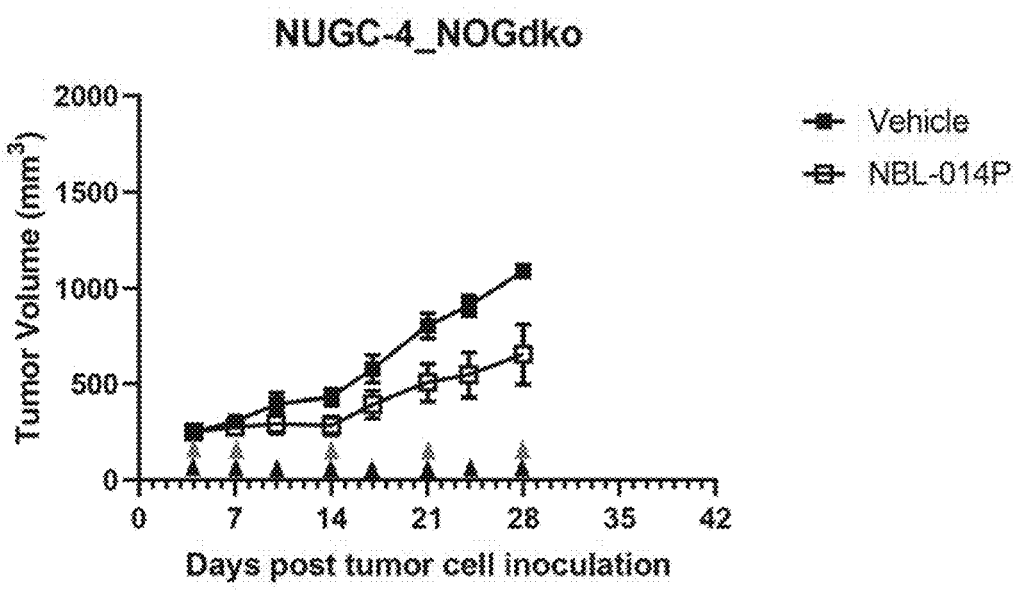
Figure 20B:
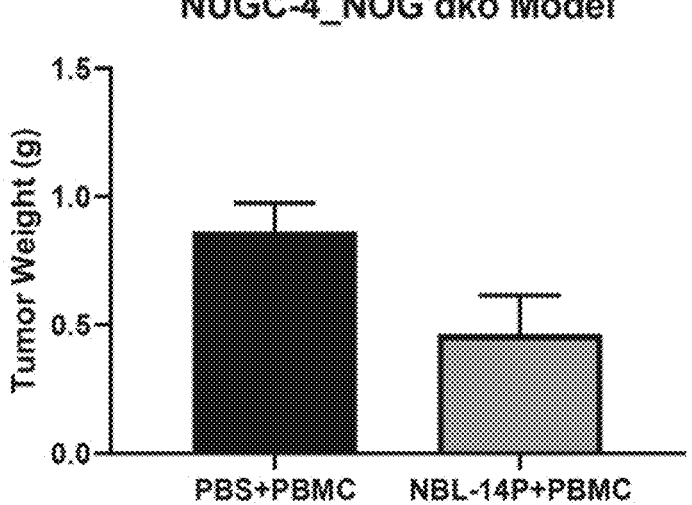

FIGS. 20A and 20B demonstrate the anti-tumor efficacy of anti-Claudin 18.2 antibody NBL-014P in a subcutaneous NUGC-4 model implanted in human PBMC engrafted NOGdKO mice based on determination of changes in tumor volume over time (FIG. 20A) and tumor weight on day 28 (FIG. 20B).

FIG. 21 provides the amino sequence of Human claudin 18 isoform 2 (claudin 18.2) (SEQ ID NO: 329) and Human claudin 18 isoform 1 (claudin 18.1) (SEQ ID NO: 330).

DETAILED DESCRIPTION OF THE INVENTION

The present disclosure generally relates to claudin 18.2 (CLDN18.2)-specific antibodies and antibody fragments thereof. The anti-CLDN18.2 antibodies or antibody fragments thereof, or bispecific molecules, or fusion proteins comprising the CDRs or VH and VL sequences of the disclosed anti-CLDN18.2 antibodies may be used for antibody-based therapies of diseases associated with dysregulation of CLDN18.2 expression. More specifically, the anti-CLDN18.2 antibodies can be used for immunotherapy of epithelial cell-derived primary and metastatic cancer, including gastric, pancreatic and esophageal, lung, ovarian, colon, and hepatic cancers.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

Throughout this disclosure the following abbreviations will be used.

ADC—Antibody drug conjugate.

ADCC—Antibody-dependent cellular cytotoxicity.

CDC—Complement-dependent cytotoxicity.

CDR—Complementarity determining region in the immunoglobulin variable regions.

ECD—Extracellular domain.

FR—Antibody framework region, the immunoglobulin variable regions excluding the CDR regions.

EC50—the concentration of antibody that gives half-maximal binding or the efficient concentration of an antibody which produces 50% of its maximum response.

IC50—the concentration resulting in 50% inhibition.

mAb or Mab or MAb—Monoclonal antibody.

VH or $V_H$—Immunoglobulin heavy chain variable region.

VL or $V_L$—Immunoglobulin light chain variable region.

eADCC—Enhanced Antibody-dependent cellular cytotoxicity.

ADCP—Antibody-dependent cellular phagocytosis.

Fc—Fragment crystallizable region.

FcRn—the neonatal Fc receptor.

As used herein the term "CLDN" means claudin and includes CLDN18.2 and CLDN 18.1. Preferably, a claudin is a human claudin.

As used herein, the term "claudin 18 isoform 2" (used interchangeably with CLDN18.2) refers to a peptide comprising or consisting of the amino acid sequence provided in Uni-Prot entry P56856 (CLD18_human) identified as P56856-2, isoform (splice variant 2) including post-translationally modified variants and species homologs present on the surface of normal or transformed cancer cells or are expressed on cells transfected with a CLDN18.2 gene. Claudin 18.2 preferably has the amino acid sequence according to SEQ ID NO: 329.

As used herein, the term "claudin 18 isoform 1" (used interchangeably with CLDN18.1) refers to a peptide comprising or consisting of the amino acid sequence provided in Uni-Prot entry P56856 (CLD18_human) identified as P56856-1 isoform (splice variant 1), including post-translationally modified variants and species homologs of present on the surface of normal or transformed cancer cells or are expressed on cells transfected with a CLDN18.1 gene. Claudin 18.1 preferably has the amino acid sequence according to SEQ ID NO: 330.

The term "extracellular domain" or "extracellular portion" as used herein refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

As used herein, the term "CLDN18-associated disease or disorder" includes disease states and/or symptoms associated with a disease state, where altered levels or activity, or accessibility of CLDN18.2 are found. Exemplary CLDN18.2-associated diseases or disorders include, but are not limited to, cancer diseases associated with epithelial tumors expressing CLDN18.2, such as pancreatic and gastroesophageal cancers.

The term "antibody" herein is used in the broadest sense and encompasses various antibody structures, including but not limited to monoclonal antibodies, polyclonal antibodies, and multispecific antibodies (e.g., bispecific antibodies).

An exemplary antibody such as an IgG comprises two heavy chains and two light chains. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order: FR1, CDR1, FR2, CDR2, FR3, CDR3, FR4.

The "class" or "isotype" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called a, 6, F, 7, and, respectively.

As used herein the term "IgG" refers to the isotype of human immunoglobulin comprising antibodies belonging to the four subclasses IgG1, IgG2, IgG3 and IgG4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35 (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) *J. Mol. Biol.* 196:901-917.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to a recombinant antibody in which a portion of the heavy and/or light chain is derived from a particular source or species, while the remainder of the heavy and/or light chain is derived from a different source or species.

A "human antibody" is an antibody that possesses an amino acid sequence corresponding to that of an antibody produced by a human and/or has been made using any of the techniques for making human antibodies known to one of skill in the art. This definition of a human antibody specifically excludes a humanized antibody comprising non-human antigen-binding residues. Human antibodies can be produced using various techniques known in the art, including methods described in Cole et al, *Monoclonal Antibodies and Cancer Therapy*, Alan R. Liss, p. 77 (1985); Boerner et al, *J. Immunol,* 147(I):86-95 (1991). See also van Dijk and van de Winkel, *Curr. Opin. Pharmacol,* 5: 368-74 (2001). Human antibodies can be prepared by administering the antigen to a transgenic animal that has been modified to produce such antibodies in response to antigenic challenge, but whose endogenous loci have been disabled, e.g., immunized HuMab mice (see, e.g., Nils Lonberg et al., 1994, *Nature* 368:856-859, WO 98/24884, WO 94/25585, WO 93/1227, WO 92/22645, WO 92/03918 and WO 01/09187 regarding HuMab mice), xenomice (see, e.g., U.S. Pat. Nos. 6,075,181 and 6,150,584 regarding XENOMOUSE™ technology) or Trianni mice (see, e.g., WO 2013/063391, WO 2017/035252 and WO 2017/136734 regarding Trianni mice).

The term "humanized antibody" refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. Humanized antibodies are typically less immunogenic to humans, relative to non-humanized antibodies, and thus offer therapeutic benefits in certain situations. Those skilled in the art will be aware of humanized antibodies and will also be aware of suitable techniques for their generation. See for example, Hwang, W. Y. K., et al., *Methods* 36:35, 2005; Queen et al., *Proc. Natl. Acad. Sci. USA,* 86:10029-10033, 1989; Jones et al., *Nature,* 321:522-25, 1986; Riechmann et al., *Nature,* 332:323-27, 1988; Verhoeyen et al., *Science,* 239:1534-36, 1988; Orlandi et al., *Proc. Natl. Acad. Sci. USA,* 86:3833-37, 1989; U.S. Pat. Nos. 5,225,539; 5,530, 101; 5,585,089; 5,693,761; 5,693,762; 6,180,370; and Selick et al., WO 90/07861, each of which is incorporated herein by reference in its entirety.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, bispecific diabodies and triabodies. "Polyepitopic specificity" refers to the ability to specifically bind to two or more different epitopes on the same or different target(s).

"Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 μM to 0.001 pM, 3 μM to 0.001 pM, 1 μM to 0.001 pM, 0.5 μM to 0.001 pM or 0.1 μM to 0.001 pM. "Monospecific" refers to the ability to bind only one epitope. Multi-specific antibodies can have structures similar to full immunoglobulin molecules and include Fc regions, for example IgG Fc regions. Such structures can include, but are not limited to, IgG-Fv, IgG-(scFv)2, DVD-Ig, (scFv)2-(scFv)2-Fc and (scFv)2-Fc-(scFv)2. In case of IgG-(scFv)2, the scFv can be attached to either the N-terminal or the C-terminal end of either the heavy chain or the light chain.

As used herein, the term "bispecific antibodies" refers to monoclonal, often human or humanized, antibodies that have binding specificities for at least two different antigens. In the invention, one of the binding specificities can be directed towards CLDN18.2, the other can be for any other antigen, e.g., for a cell-surface protein, receptor, receptor subunit, tissue-specific antigen, virally derived protein, virally encoded envelope protein, bacterially derived protein, or bacterial surface protein, etc.

As used herein, the term "diabodies" refers to bivalent antibodies comprising two polypeptide chains, in which each polypeptide chain includes VH and VL domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain.

The term "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab)2; diabodies; linear antibodies; single-chain antibody molecules (e.g., scFv). Papain digestion of antibodies produces two identical antigen-binding fragments, called "Fab" fragments, and a residual "Fc" fragment, a designation reflecting the ability to crystallize readily. The Fab fragment consists of an entire light (L) chain (VL) along with the variable region domain of the heavy (H) chain (VH), and the first constant domain of one heavy chain (CH1). Pepsin treatment of an antibody yields a single large F(ab)2 fragment which roughly corresponds to two disulfide linked Fab fragments having divalent antigen-binding activity and is still capable of cross-linking antigen. Fab fragments differ from F(ab)2 fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The terms "antigen-binding domain" or "antigen-binding portion" of an antibody (or more simply "binding domain" or "binding portion") or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) F(ab')2 fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) *Nature* 341: 544-546), which consist of a VH domain; (vi) isolated complementarity determining regions (CDR), and (vii) combinations of two or more isolated CDRs which may optionally be joined by a synthetic linker.

"Fv" consists of a dimer of one heavy- and one light-chain variable region domain in tight, non-covalent association. From the folding of these two domains emanate six hyper-variable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

"Complementarity determining region" or "CDR" as the terms are used herein refer to short polypeptide sequences within the variable region of both heavy and light chain polypeptides that are primarily responsible for mediating specific antigen recognition. There are three CDRs (termed CDR1, CDR2, and CDR3) within each $V_L$ and each $V_H$.

As will be appreciated by those in the art, the exact numbering and placement of the CDRs can be different among different numbering systems. However, it should be understood that the disclosure of a variable heavy and/or variable light sequence includes the disclosure of the associated CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

In certain embodiments, the CDRs of an antibody can be determined according to the IMGT numbering system as described in Lefranc M-P, (1999) *The Ininunologist* 7: 132-136 and Lefranc M-P et al, (1999) *Nucleic Acids Res* 27: 209-212, each of which is herein incorporated by reference in its entirety. Unless stated otherwise herein, references to residue numbers in the variable domain of antibodies mean residue numbering by the IMGT numbering system.

In other embodiments, the CDRs of an antibody can be determined according to MacCallum R M et al. (1996) *J Mol Biol* 262: 732-745, herein incorporated by reference in its entirety. See also, e.g. Martin A. "Protein Sequence and Structure Analysis of Antibody Variable Domains," in Antibody Engineering, Kontermann and Diibel, eds., Chapter 31, pp. 422-439, Springer-Verlag, Berlin (2001), herein incorporated by reference in its entirety. In other embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

"Framework" or "framework region" or "FR" refers to variable domain residues other than the hypervariable region (HVR) residues. The FR of a variable domain generally consists of four FR domains: FR1, FR2, FR3, and FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup Ill as in Kabat et al., supra.

The "hinge region" is generally defined as stretching from 216-238 (EU numbering) or 226-251 (Kabat numbering) of human IgG1. The hinge can be further divided into three distinct regions, the upper, middle (e.g., core), and lower hinge.

The term "Fc region" herein is used to define a C-terminal region of an immunoglobulin heavy chain that contains at least a portion of the constant region and interacts with endogenous receptors present on the surface of cells of the immune system and some proteins of the complement system. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, the numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md. (1991).

The term "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For a review of methods for assessment of antibody purity, see, for example, Flatman et al., J. Chromatogr. B 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells because at least one component of the polypeptide natural environment will not be present.

An "epitope" is a term of art that indicates the site or sites of interaction between an antibody and its antigen(s). As described by (Janeway, C, Jr., P. Travers, et al. (2001). Immunobiology: the immune system in health and disease. Part II, Section 3-8. New York, Garland Publishing, Inc.): "An antibody generally recognizes only a small region on the surface of a large molecule such as a protein . . . [Certain epitopes] are likely to be composed of amino acids from different parts of the [antigen] polypeptide chain that have been brought together by protein folding. Antigenic determinants of this kind are known as conformational or discontinuous epitopes because the structure recognized is composed of segments of the protein that are discontinuous in the amino acid sequence of the antigen but are brought together in the three-dimensional structure. In contrast, an epitope composed of a single segment of polypeptide chain is termed a continuous or linear epitope" (Janeway, C., Jr., P. Travers, et al. (2001). Immunobiology: the immune system in health and disease. Part II, Section 3-8. New York, Garland Publishing, Inc.).

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more. The amino acid residues of an antibody that contact an antigen can be determined, for example, by determining the crystal structure of the antibody in complex with the antigen or by performing hydrogen/deuterium exchange. In some embodiments, residues of an antibody that are within 5 Å the antigen are considered to contact the antigen. In some embodiments, an antibody that binds to the same epitope as a reference antibody blocks binding of the reference antibody to its antigen in a competition assay by 50% or more, and conversely, the reference antibody blocks binding of the antibody to its antigen in a competition assay by 50% or more.

A "blocking" antibody or an "antagonist" antibody is one which inhibits or reduces biological activity of the antigen it binds. Certain blocking antibodies or antagonist antibodies substantially or completely inhibit the biological activity of the antigen.

With regard to the binding of an antibody to a target molecule, the term "specific binding" or "specifically binds to" or is "specific for" a particular polypeptide or an epitope on a particular polypeptide target means binding that is measurably different from a non-specific interaction. For example, as used herein the terms "specific binding," "specifically binds," and "selectively binds," refer to antibody binding to an epitope of human CLDN18.2 where the binding is measurably different from a non-specific interaction. Specific binding can be measured, for example, by determining binding of a molecule compared to the binding of a control molecule. For example, specific binding can be determined by competition with a control molecule that is similar to the target, for example, an excess of non-labeled target. In this case, specific binding is indicated if the binding of the labeled target to a probe is competitively inhibited by the excess unlabeled target. The term "specific binding" or "specifically binds to" or is "specific for" a particular polypeptide or an epitope on a particular polypeptide target as used herein can be exhibited, for example, by a molecule having a KD for the target of 10-4 M or lower, alternatively 10-5 M or lower, alternatively 10-6 M or lower, alternatively 10-7 M or lower, alternatively 10-8 M or lower, alternatively 10-9 M or lower, alternatively 10-10 M or lower, alternatively 10-11 M or lower, alternatively 10-12 M or lower or a KD in the range of 10-4 M to 10-6 M or 10-6 M to 10-10 M or 10-7 M to 10-9 M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "affinity," as used herein, means the strength of the binding of an antibody to an epitope. The affinity of an antibody is given by the dissociation constant Kd, defined as $[Ab] \times [Ag]/[Ab-Ag]$, where [Ab–Ag] is the molar concentration of the antibody-antigen complex, [Ab] is the molar concentration of the unbound antibody and [Ag] is the molar concentration of the unbound antigen. The affinity constant Ka is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

"EC50" with respect to an agent and a particular activity (e.g. binding to a cell, inhibition of enzymatic activity, activation or inhibition of an immune cell), refers to the efficient concentration of the agent which produces 50% of its maximum response or effect with respect to such activity. "EC100" with respect to an agent and a particular activity refers to the efficient concentration of the agent which produces its substantially maximum response with respect to such activity.

The term "effector functions" refer to those biological activities attributable to the Fc region of an antibody, which vary with the antibody isotype. Examples of antibody effector functions include C1q binding and complement-dependent cytotoxicity (CDC); Fc receptor binding; antibody-dependent cell-mediated cytotoxicity (ADCC); phagocytosis; down-regulation of cell surface receptors (e.g., B cell receptor); and B cell activation.

As used herein the term "Fc 7 receptor" refers to a family of endogenous receptors located in the membranes of immune cells including B lymphocytes, natural killer cells, macrophages, neutrophils, and mast cells which binds the Fc region of antibodies and is involved in antigen recognition.

As used herein, the term "specifically binds" when referring to a binding pair (e.g. antibody/cell surface molecule), indicates a binding reaction which is determinative of the presence of the protein, e.g., CLDN18.2, in a heterogeneous population of proteins and/or other biologics. Thus, under designated conditions, a specified antibody binds to a particular cell surface marker and does not bind in a significant amount to other proteins present on a cell surface or in a sample.

As used herein the term "specifically binds CLDN18.2" refers to the ability of an antibody, or antigen-binding fragment to recognize and bind endogenous claudin 18 isoform 2 as it occurs on the surface of normal or malignant cells, but not to claudin 18 isoform 1 (CLDN18.1), or to any other lineage-specific cell surface marker.

As used herein the term "endocytosis" refers to the process where eukaryotic cells internalize segments of the plasma membrane, cell-surface receptors, and components from the extracellular fluid. Endocytosis mechanisms include receptor-mediated endocytosis. The term "receptor-mediated endocytosis" refers to a biological mechanism by which a ligand, upon binding to its target, triggers membrane invagination and pinching, gets internalized and delivered into the cytosol or transferred to appropriate intracellular compartments.

As used herein the terms "antibody-based immunotherapy" and "immunotherapies" are used to broadly refer to any form of therapy that relies on the targeting specificity of an anti-CLDN18.2 antibody, bispecific molecule, antigen-binding domain, or fusion protein comprising a CLDN18.2 antibody or antibody fragments or CDRs thereof, to mediate a direct or indirect effect on a cell characterized by aberrant expression of CLDN18.2. The terms are meant to encompass methods of treatment using naked antibodies, bispecific antibodies (including T cell engaging, NK cell engaging and other immune cell/effector cell engaging formats) antibody drug conjugates, cellular therapies using T cells (CAR-T) or NK cells (CAR-NK) engineered to comprise a CLDN18.2-specific chimeric antigen receptor and oncolytic viruses comprising a CLDN18.2 specific binding agent, and gene therapies by delivering the antigen binding sequences of the anti-CLDN18.2 antibodies and express the corresponding antibody fragments in vivo.

It is noted here that, as used in this specification and the appended claims, the singular forms "a," "an," and "the" include plural reference unless the context clearly dictates otherwise.

Claudin 18 (CLDN18)

The claudin family of proteins were first cloned and named in 1998 as crucial structural and functional components of tight junctions. As a family, claudins are a multigene family of tetra-transmembrane proteins involved in the barrier functions of epithelial and endothelial cells and the maintenance of the cytoskeleton (Furuse et al., J. Cell. Biol. 141(7):1539-50, 1998). CLDN18 has different variants or conformations, including CLDN18 isoform 1 (CLDN18.1) and CLDN18 isoform 2 (CLDN18.2).

The first extracellular domain (ECD) of a claudin protein typically consists of about 50 amino acids, while the second one is smaller having about 22 amino acids (Hashimoto, et al. Drug Discovery Today 21(10):1711-1718, 2016). The N-terminal end is usually very short (e.g. about four to ten amino acids) while the C-terminal end ranges from 21 to about 63 amino acids and is required for localization of the proteins in tight junctions.

The observation that tight junction permeability is often higher in tumor tissues than in normal tissues, has led to speculation that claudin proteins on tumor cells may be more accessible than in normal tissues with intact tight junctions. This observation also makes claudin proteins attractive targets for therapeutic cancer interventions. In addition, published expression profiling results suggest that cancer therapies targeting CLDN18.2 will have favorable systemic toxicity profiles because normal turnover and homeostasis processes replenish gastrointestinal epithelial cells every two to seven days (Sahin et al). Transient gastrointestinal toxicity of limited duration is a common and manageable adverse event for cancer immunotherapeutics.

CLDN18.2 comprises four membrane spanning domains with two small extracellular loops (loop 1 embraced by hydrophobic region 1 and hydrophobic region 2; loop 2 embraced by hydrophobic regions 3 and 4). CLDN18.2 is a transmembrane protein, therefore epitopes present within, or formed by, its extracellular loops represent desirable targets for antibody-based cancer immunotherapy. However, given that CLDN18.1 is expressed by alveolar epithelial cells in normal lung tissue, which is a tissue that is highly relevant to toxicity, exclusive splice variant specificity was a recognized prerequisite for the use of CLDN18.2-specific antibodies for antibody-based cancer immunotherapy. Sahin et al were the first to report proof-of-concept results validating CLDN18.2 as a druggable target for cancer immunotherapies based on the isolation of antibodies (polyclonal and monoclonal) that exclusively bind to CLDN18.2 and not to CLDN18.1 (Sahin et al., Clin. Cancer Res. 14 (23) 7624-7634, 2008).

CLDN18.2 is expressed in a number of primary tumors and their metastasis, including gastric cancer, esophageal cancer, pancreatic cancer, lung cancer such as non-small cell lung cancer, ovarian cancer, colon cancer, hepatic cancer, head-neck cancer, and cancers of the gall bladder. Dysregulated expression of claudins are detected in many cancers and may contribute to tumorigenesis and cancer invasiveness (Singh et al., J Oncology 2010; 2010: 541957). The expression of CLDN18.2 is notably elevated in pancreatic ductal adenocarcinomas (PDAC) (Tanaka et al., J Histochem Cytochem. 2011; 59:942-952), esophageal tumors, non-small cell lung cancers (NSCLC), ovarian cancers (Sahin et al., Hu Cancer Biol. 2008; 14:7624-7634), and bile duct adenocarcinomas (Keira et al., Virchows Arch. 2015; 466: 265-277).

Despite the fact that gastric cancer contributes to significant cancer-related morbidity and mortality, the treatment options for gastric cancer are limited. Claudins are present in normal tissues, benign neoplasms, hyperplastic conditions and cancers (Ding et al., Cancer Manag. Res. 5:367-375 (2013)). The expression pattern of claudins is highly tissue-specific, and most tissues express multiple claudins. Claudin proteins can interact with claudins from adjacent cells in a homotypic or heterotypic fashion to form tight junctions (Ding et al.). Alterations in claudin expression and signaling pathways are known to be associated with cancer development and an association between the function of impaired tight junctions and tumor progression has been widely reported.

Anti-CLDN18.2 Antibodies

Anti-CLDN18 antibodies, in particular human and murine monoclonal anti-CLDN18.2 antibodies, that specifically bind to the first extracellular domain/loop of CLDN18.2 are provided. Binding of the CLDN18.2 monoclonal antibody or antigen binding fragment to CLDN18.2 can mediate complement-dependent cytotoxicity (CDC), antibody-dependent phagocytosis (ADPC), and/or antibody-dependent cellular cytotoxicity (ADCC) or other effects that result in the death of the targeted cancer cell. Alternatively, the antibody or antigen binding fragment thereof can, for example, serve to deliver a conjugated cytotoxic drug, and/or can form a bispecific antibody with another monoclonal antibody to mediate the death of the targeted cancer cell.

In an embodiment, the anti-CLDN18.2 antibodies or antibody fragments thereof comprise a VH having a set of CDRs (HCDR1, HCDR2, and HCDR3) disclosed in Table 1 or Table 2. For example, the anti-CLDN18 antibodies or antibody fragments thereof may comprise a set of CDRs corresponding to those CDRs in one or more of the anti-CLDN18.2 antibody heavy chains described in Table 2 (e.g., the CDRs of the Hu-1 antibody).

In another embodiment, the anti-CLDN18.2 antibodies comprise a VL having a set of CDRs (LCDR1, LCDR2, and LCDR3) as disclosed in Table 3 or Table 4. For example, the anti-CLDN18 antibodies or antibody fragments thereof may comprise a set of CDRs corresponding to those CDRs in one or more of the anti-CLDN18.2 antibody light chains described in Table 4 (e.g., the CDRs of the Hu-1 antibody).

In an alternative embodiment, the anti-CLDN18 antibodies or antibody fragments thereof comprise a VH having a set of CDRs (HCDR1, HCDR2, and HCDR3) as disclosed in Table 1, and a VL having a set of CDRs (LCDR1, LCDR2, and LCDR3) as disclosed in Table 3.

In an alternative embodiment, the anti-CLDN18 antibodies or antibody fragments thereof comprise a VH having a set of CDRs (HCDR1, HCDR2, and HCDR3) as disclosed in Table 2, and a VL having a set of CDRs (LCDR1, LCDR2, and LCDR3) as disclosed in Table 4.

In a particular embodiment the anti-CLDN18.2 antibody may comprise a set of six (6) CDRs derived from a single murine antibody (VH CDRs in Table 1 and VL CDRs in Table 3) or fully human antibody (VH CDRs in Table 2 and VL CDRs in Table 4). For example, the antibody may comprise a set of six CDR regions derived from the fully human anti-CLDN18.2 antibody "Hu-1." In this instance, the binding agent would comprise the amino acid sequences of SEQ ID NOS: 221-223 and SEQ ID NOS: 224-226, representing the CDR1, CDR2 and CDR3 of the variable heavy and the CDR1, CDR2 and CDR3 sequences of the variable light domains, respectively, of the Hu-1 antibody.

TABLE 1

CDR sequences of Murine Variable Heavy Chain Domains

| anti-CLDN18.2 mAb | CDR1 | CDR2 | CDR3 |
|---|---|---|---|
| Ms1 | SEQ ID NO: 47 | SEQ ID NO: 48 | SEQ ID NO: 49 |
| Ms2 | SEQ ID NO: 53 | SEQ ID NO: 54 | SEQ ID NO: 55 |
| Ms3 | SEQ ID NO: 59 | SEQ ID NO: 60 | SEQ ID NO: 61 |
| Ms4 | SEQ ID NO: 65 | SEQ ID NO: 66 | SEQ ID NO: 67 |
| Ms5 | SEQ ID NO: 71 | SEQ ID NO: 72 | SEQ ID NO: 73 |
| Ms6 | SEQ ID NO: 77 | SEQ ID NO: 78 | SEQ ID NO: 79 |
| Ms7 | SEQ ID NO: 83 | SEQ ID NO: 84 | SEQ ID NO: 85 |
| Ms8 | SEQ ID NO: 89 | SEQ ID NO: 90 | SEQ ID NO: 91 |
| Ms9 | SEQ ID NO: 95 | SEQ ID NO: 96 | SEQ ID NO: 97 |
| Ms10 | SEQ ID NO: 101 | SEQ ID NO: 102 | SEQ ID NO: 103 |
| Ms11 | SEQ ID NO: 107 | SEQ ID NO: 108 | SEQ ID NO: 109 |
| Ms12 | SEQ ID NO: 113 | SEQ ID NO: 114 | SEQ ID NO: 115 |
| Ms13 | SEQ ID NO: 119 | SEQ ID NO: 120 | SEQ ID NO: 121 |
| Ms14 | SEQ ID NO: 125 | SEQ ID NO: 126 | SEQ ID NO: 127 |
| Ms15 | SEQ ID NO: 131 | SEQ ID NO: 132 | SEQ ID NO: 133 |
| Ms16 | SEQ ID NO: 137 | SEQ ID NO: 138 | SEQ ID NO: 139 |
| Ms17 | SEQ ID NO: 143 | SEQ ID NO: 144 | SEQ ID NO: 145 |
| Ms18 | SEQ ID NO: 149 | SEQ ID NO: 150 | SEQ ID NO: 151 |
| Ms19 | SEQ ID NO: 155 | SEQ ID NO: 156 | SEQ ID NO: 157 |
| Ms20 | SEQ ID NO: 161 | SEQ ID NO: 162 | SEQ ID NO: 163 |
| Ms21 | SEQ ID NO: 167 | SEQ ID NO: 168 | SEQ ID NO: 169 |
| Ms22 | SEQ ID NO: 173 | SEQ ID NO: 174 | SEQ ID NO: 175 |
| Ms23 | SEQ ID NO: 179 | SEQ ID NO: 180 | SEQ ID NO: 181 |

TABLE 2

CDR sequences of Human Variable Heavy Chain Domains

| anti-CLDN18.2 mAb | CDR1 | CDR2 | CDR3 |
|---|---|---|---|
| Hu-1 | SEQ ID NO: 221 | SEQ ID NO: 222 | SEQ ID NO: 223 |
| Hu-2 | SEQ ID NO: 227 | SEQ ID NO: 228 | SEQ ID NO: 229 |
| Hu-3 | SEQ ID NO: 233 | SEQ ID NO: 234 | SEQ ID NO: 235 |
| Hu-4 | SEQ ID NO: 239 | SEQ ID NO: 240 | SEQ ID NO: 241 |
| Hu-5 | SEQ ID NO: 245 | SEQ ID NO: 246 | SEQ ID NO: 247 |
| Hu-6 | SEQ ID NO: 251 | SEQ ID NO: 252 | SEQ ID NO: 253 |
| Hu-7 | SEQ ID NO: 257 | SEQ ID NO: 258 | SEQ ID NO: 259 |
| Hu-8 | SEQ ID NO: 263 | SEQ ID NO: 264 | SEQ ID NO: 265 |
| Hu-9 | SEQ ID NO: 269 | SEQ ID NO: 270 | SEQ ID NO: 271 |
| Hu-10 | SEQ ID NO: 275 | SEQ ID NO: 276 | SEQ ID NO: 277 |
| Hu-11 | SEQ ID NO: 281 | SEQ ID NO: 282 | SEQ ID NO: 283 |
| Hu-12 | SEQ ID NO: 287 | SEQ ID NO: 288 | SEQ ID NO: 289 |
| Hu-13 | SEQ ID NO: 293 | SEQ ID NO: 294 | SEQ ID NO: 295 |
| Hu-14 | SEQ ID NO: 299 | SEQ ID NO: 300 | SEQ ID NO: 301 |
| Hu-16 | SEQ ID NO: 311 | SEQ ID NO: 312 | SEQ ID NO: 313 |
| Hu-17 | SEQ ID NO: 317 | SEQ ID NO: 318 | SEQ ID NO: 319 |
| Hu-18 | SEQ ID NO: 323 | SEQ ID NO: 324 | SEQ ID NO: 325 |

TABLE 3

CDR sequences of Murine Variable Light Chain Domains

| anti-CLDN18.2 mAb | CDR1 | CDR2 | CDR3 |
|---|---|---|---|
| Ms1 | SEQ ID NO: 50 | SEQ ID NO: 51 | SEQ ID NO: 52 |
| Ms2 | SEQ ID NO: 56 | SEQ ID NO: 57 | SEQ ID NO: 58 |
| Ms3 | SEQ ID NO: 62 | SEQ ID NO: 63 | SEQ ID NO: 64 |
| Ms4 | SEQ ID NO: 68 | SEQ ID NO: 69 | SEQ ID NO: 70 |
| Ms5 | SEQ ID NO: 74 | SEQ ID NO: 75 | SEQ ID NO: 76 |
| Ms6 | SEQ ID NO: 80 | SEQ ID NO: 81 | SEQ ID NO: 82 |
| Ms7 | SEQ ID NO: 86 | SEQ ID NO: 87 | SEQ ID NO: 88 |
| Ms8 | SEQ ID NO: 92 | SEQ ID NO: 93 | SEQ ID NO: 94 |
| Ms9 | SEQ ID NO: 98 | SEQ ID NO: 99 | SEQ ID NO: 101 |

TABLE 3-continued

CDR sequences of Murine Variable Light Chain Domains

| anti-CLDN18.2 mAb | CDR1 | CDR2 | CDR3 |
|---|---|---|---|
| Ms10 | SEQ ID NO: 104 | SEQ ID NO: 105 | SEQ ID NO: 106 |
| Ms11 | SEQ ID NO: 110 | SEQ ID NO: 111 | SEQ ID NO: 112 |
| Ms12 | SEQ ID NO: 116 | SEQ ID NO: 117 | SEQ ID NO: 118 |
| Ms13 | SEQ ID NO: 122 | SEQ ID NO: 123 | SEQ ID NO: 124 |
| Ms14 | SEQ ID NO: 128 | SEQ ID NO: 129 | SEQ ID NO: 130 |
| Ms15 | SEQ ID NO: 134 | SEQ ID NO: 135 | SEQ ID NO: 136 |
| Ms16 | SEQ ID NO: 140 | SEQ ID NO: 141 | SEQ ID NO: 142 |
| Ms17 | SEQ ID NO: 146 | SEQ ID NO: 147 | SEQ ID NO: 148 |
| Ms18 | SEQ ID NO: 152 | SEQ ID NO: 153 | SEQ ID NO: 154 |
| Ms19 | SEQ ID NO: 158 | SEQ ID NO: 159 | SEQ ID NO: 160 |
| Ms20 | SEQ ID NO: 164 | SEQ ID NO: 165 | SEQ ID NO: 166 |
| Ms21 | SEQ ID NO: 170 | SEQ ID NO: 171 | SEQ ID NO: 172 |
| Ms22 | SEQ ID NO: 176 | SEQ ID NO: 177 | SEQ ID NO: 178 |
| Ms23 | SEQ ID NO: 182 | SEQ ID NO: 183 | SEQ ID NO: 184 |

TABLE 4

CDR sequences of Human Variable Light Chain Domains

| anti-CLDN18.2 mAb | CDR1 | CDR2 | CDR3 |
|---|---|---|---|
| Hu-1 | SEQ ID NO: 224 | SEQ ID NO: 225 | SEQ ID NO: 226 |
| Hu-2 | SEQ ID NO: 230 | SEQ ID NO: 231 | SEQ ID NO: 232 |
| Hu-3 | SEQ ID NO: 236 | SEQ ID NO: 237 | SEQ ID NO: 238 |
| Hu-4 | SEQ ID NO: 242 | SEQ ID NO: 243 | SEQ ID NO: 244 |
| Hu-5 | SEQ ID NO: 248 | SEQ ID NO: 249 | SEQ ID NO: 250 |
| Hu-6 | SEQ ID NO: 254 | SEQ ID NO: 255 | SEQ ID NO: 256 |
| Hu-7 | SEQ ID NO: 260 | SEQ ID NO: 261 | SEQ ID NO: 262 |
| Hu-8 | SEQ ID NO: 266 | SEQ ID NO: 267 | SEQ ID NO: 268 |
| Hu-9 | SEQ ID NO: 272 | SEQ ID NO: 273 | SEQ ID NO: 274 |
| Hu-10 | SEQ ID NO: 278 | SEQ ID NO: 279 | SEQ ID NO: 280 |
| Hu-11 | SEQ ID NO: 284 | SEQ ID NO: 285 | SEQ ID NO: 286 |
| Hu-12 | SEQ ID NO: 290 | SEQ ID NO: 291 | SEQ ID NO: 292 |
| Hu-13 | SEQ ID NO: 296 | SEQ ID NO: 297 | SEQ ID NO: 298 |
| Hu-14 | SEQ ID NO: 302 | SEQ ID NO: 303 | SEQ ID NO: 304 |
| Hu-16 | SEQ ID NO: 314 | SEQ ID NO: 315 | SEQ ID NO: 316 |
| Hu-17 | SEQ ID NO: 320 | SEQ ID NO: 321 | SEQ ID NO: 322 |
| Hu-18 | SEQ ID NO: 326 | SEQ ID NO: 327 | SEQ ID NO: 328 |

In an embodiment, the antibody may be a monoclonal, chimeric, humanized or human antibody, or antigen-binding portions thereof, or bispecific or multispecific binding agent that specifically binds to human CLDN18 isoform 2.

In another embodiment, the anti-CLDN18.2 antibodies or antibody fragment comprise defined sets/combinations of complementarity determining region (CDR) sequences derived from the disclosed VH and/or VL domains of the anti-CLDN18.2 antibodies.

In an embodiment, the anti-CLDN8.2 antibody or antibody fragment thereof exhibits one or more of the following properties: binding preferentially to CLDN18 isoform 2 expressed by human tumor cells, not binding to CLDN18 isoform 1 (CLDN18.1), efficiently internalized from the surface of CLDN18.2 positive cells after binding, and capable of directing the killing of CLDN18.2 positive cells by inducing antibody-dependent cellular cytotoxicity (ADCC) mediated lysis.

In an embodiment, anti-CLDN18.2 specific antibodies or binding fragments thereof comprise a VH comprising a set of complementarity-determining regions CDR1, CDR2, and CDR3 selected from the group consisting of:

(i) CDR1: SEQ ID NO: 47, CDR2: SEQ ID NO: 48, CDR3: SEQ ID NO: 49;

(ii) CDR1: SEQ ID NO: 53, CDR2: SEQ ID NO: 54, CDR3: SEQ ID NO: 55;

(iii) CDR1: SEQ ID NO: 59, CDR2: SEQ ID NO: 60, CDR3: SEQ ID NO: 61;

(iv) CDR1: SEQ ID NO: 65, CDR2: SEQ ID NO: 66, CDR3: SEQ ID NO: 67;

(v) CDR1: SEQ ID NO: 71, CDR2: SEQ ID NO: 72, CDR3: SEQ ID NO: 73;

(vi) CDR1: SEQ ID NO: 77, CDR2: SEQ ID NO: 78, CDR3: SEQ ID NO: 79;

(vii) CDR1: SEQ ID NO: 83, CDR2: SEQ ID NO: 84, CDR3: SEQ ID NO: 85;

(viii) CDR1: SEQ ID NO: 89, CDR2: SEQ ID NO: 90, CDR3: SEQ ID NO: 91;

(ix) CDR1: SEQ ID NO: 95, CDR2: SEQ ID NO: 96, CDR3: SEQ ID NO: 97;

(x) CDR1: SEQ ID NO: 101, CDR2: SEQ ID NO: 102, CDR3: SEQ ID NO: 103;

(xi) CDR1: SEQ ID NO: 107, CDR2: SEQ ID NO: 108, CDR3: SEQ ID NO: 109;

(xii) CDR1: SEQ ID NO: 113, CDR2: SEQ ID NO: 114, CDR3: SEQ ID NO: 115;

(xiii) CDR1: SEQ ID NO: 119, CDR2: SEQ ID NO: 120, CDR3: SEQ ID NO: 121;

(xiv) CDR1: SEQ ID NO: 125, CDR2: SEQ ID NO: 126, CDR3: SEQ ID NO: 127;

(xv) CDR1: SEQ ID NO: 131, CDR2: SEQ ID NO: 132, CDR3: SEQ ID NO: 133;

(xvi) CDR1: SEQ ID NO: 137, CDR2: SEQ ID NO: 138, CDR3: SEQ ID NO: 139;

(xvii) CDR1: SEQ ID NO: 143, CDR2: SEQ ID NO: 144, CDR3: SEQ ID NO: 145;

(xviii) CDR1: SEQ ID NO: 149, CDR2: SEQ ID NO: 150, CDR3: SEQ ID NO: 151;

(xix) CDR1: SEQ ID NO: 155, CDR2: SEQ ID NO: 156, CDR3: SEQ ID NO: 157;

(xx) CDR1: SEQ ID NO: 161, CDR2: SEQ ID NO: 162, CDR3: SEQ ID NO: 163;

(xxi) CDR1: SEQ ID NO: 167, CDR2: SEQ ID NO: 168, CDR3: SEQ ID NO: 169;

(xxii) CDR1: SEQ ID NO: 173, CDR2: SEQ ID NO: 174, CDR3: SEQ ID NO: 175; and (xxiii) CDR1: SEQ ID NO: 179, CDR2: SEQ ID NO: 180, CDR3: SEQ ID NO: 181.

In an embodiment, anti-CLDN18.2 specific antibodies or binding fragments thereof comprise a VL comprising a set of complementarity-determining regions CDR1, CDR2, and CDR3 selected from the group consisting of:

(i) CDR1: SEQ ID NO: 50, CDR2: SEQ ID NO: 51, CDR3: SEQ ID NO: 52;

(ii) CDR1: SEQ ID NO: 56, CDR2: SEQ ID NO: 57, CDR3: SEQ ID NO: 58;

(iii) CDR1: SEQ ID NO: 62, CDR2: SEQ ID NO: 63, CDR3: SEQ ID NO: 64;

(iv) CDR1: SEQ ID NO: 68, CDR2: SEQ ID NO: 69, CDR3: SEQ ID NO: 70;

(v) CDR1: SEQ ID NO: 74, CDR2: SEQ ID NO: 75, CDR3: SEQ ID NO: 76;

(vi) CDR1: SEQ ID NO: 80, CDR2: SEQ ID NO: 81, CDR3: SEQ ID NO: 82;

(vii) CDR1: SEQ ID NO: 86, CDR2: SEQ ID NO: 87, CDR3: SEQ ID NO: 88;

(viii) CDR1: SEQ ID NO: 92, CDR2: SEQ ID NO: 93, CDR3: SEQ ID NO: 94;

(ix) CDR1: SEQ ID NO: 98, CDR2: SEQ ID NO: 99, CDR3: SEQ ID NO: 100;

(x) CDR1: SEQ ID NO: 104, CDR2: SEQ ID NO: 105, CDR3: SEQ ID NO: 106;

(xi) CDR1: SEQ ID NO: 110, CDR2: SEQ ID NO: 111, CDR3: SEQ ID NO: 112;

(xii) CDR1: SEQ ID NO: 116, CDR2: SEQ ID NO: 117, CDR3: SEQ ID NO: 118;

(xiii) CDR1: SEQ ID NO: 122, CDR2: SEQ ID NO: 123, CDR3: SEQ ID NO: 124;

(xiv) CDR1: SEQ ID NO: 128, CDR2: SEQ ID NO: 129, CDR3: SEQ ID NO: 130;

(xv) CDR1: SEQ ID NO: 134, CDR2: SEQ ID NO: 135, CDR3: SEQ ID NO: 136;

(xvi) CDR1: SEQ ID NO: 140, CDR2: SEQ ID NO: 141, CDR3: SEQ ID NO: 142;

(xvii) CDR1: SEQ ID NO: 146, CDR2: SEQ ID NO: 147, CDR3: SEQ ID NO: 148;

(xviii) CDR1: SEQ ID NO: 152, CDR2: SEQ ID NO: 153, CDR3: SEQ ID NO: 154;

(xix) CDR1: SEQ ID NO: 158, CDR2: SEQ ID NO: 159, CDR3: SEQ ID NO: 160;

(xx) CDR1: SEQ ID NO: 164, CDR2: SEQ ID NO: 165, CDR3: SEQ ID NO: 166;

(xxi) CDR1: SEQ ID NO: 170, CDR2: SEQ ID NO: 171, CDR3: SEQ ID NO: 172;

(xxii) CDR1: SEQ ID NO: 176, CDR2: SEQ ID NO: 177, CDR3: SEQ ID NO: 178; and (xxiii) CDR1: SEQ ID NO: 182, CDR2: SEQ ID NO: 183, CDR3: SEQ ID NO: 184.

In an embodiment, antibodies having the ability of binding to CLDN18.2 comprise a combination of VH and VL each comprising a set of complementarity-determining regions CDR1, CDR2 and CDR3 selected from the group consisting of:

(i) VH: CDR1: SEQ ID NO: 47, CDR2: SEQ ID NO: 48, CDR3: SEQ ID NO: 49, VL: CDR1: SEQ ID NO: 50, CDR2: SEQ ID NO: 51, CDR3: SEQ ID NO: 52;

(ii) VH: CDR1: SEQ ID NO: 53, CDR2: SEQ ID NO: 54, CDR3: SEQ ID NO: 55, VL: CDR1: SEQ ID NO: 56, CDR2: SEQ ID NO: 57, CDR3: SEQ ID NO: 58;

(iii) VH: CDR1: SEQ ID NO: 59, CDR2: SEQ ID NO: 60, CDR3: SEQ ID NO: 61, VL: CDR1: SEQ ID NO: 62, CDR2: SEQ ID NO: 63, CDR3: SEQ ID NO: 64;

(iv) VH: CDR1: SEQ ID NO: 65, CDR2: SEQ ID NO: 66, CDR3: SEQ ID NO: 67, VL: CDR1: SEQ ID NO: 68, CDR2: SEQ ID NO: 69, CDR3: SEQ ID NO: 70;

(v) VH: CDR1: SEQ ID NO: 71, CDR2: SEQ ID NO: 72, CDR3: SEQ ID NO: 73, VL: CDR1: SEQ ID NO: 74, CDR2: SEQ ID NO: 75, CDR3: SEQ ID NO: 76;

(vi) VH: CDR1: SEQ ID NO: 77, CDR2: SEQ ID NO: 78, CDR3: SEQ ID NO: 79, VL: CDR1: SEQ ID NO: 80, CDR2: SEQ ID NO: 81, CDR3: SEQ ID NO: 82;

(vii) VH: CDR1: SEQ ID NO: 83, CDR2: SEQ ID NO: 84, CDR3: SEQ ID NO: 85, VL: CDR1: SEQ ID NO: 86, CDR2: SEQ ID NO: 87, CDR3: SEQ ID NO: 88;

(viii) VH: CDR1: SEQ ID NO: 89, CDR2: SEQ ID NO: 90, CDR3: SEQ ID NO: 91, VL: CDR1: SEQ ID NO: 92, CDR2: SEQ ID NO: 93, CDR3: SEQ ID NO: 94;

(ix) VH: CDR1: SEQ ID NO: 95, CDR2: SEQ ID NO: 96, CDR3: SEQ ID NO: 97, VL: CDR1: SEQ ID NO: 98, CDR2: SEQ ID NO: 99, CDR3: SEQ ID NO: 100;

(x) VH: CDR1: SEQ ID NO: 101, CDR2: SEQ ID NO: 102, CDR3: SEQ ID NO: 103, VL: CDR1: SEQ ID NO: 104, CDR2: SEQ ID NO: 105, CDR3: SEQ ID NO: 106;

(xi) VH: CDR1: SEQ ID NO: 107, CDR2: SEQ ID NO: 108, CDR3: SEQ ID NO: 109, VL: CDR1: SEQ ID NO: 110, CDR2: SEQ ID NO: 111, CDR3: SEQ ID NO: 112;

(xii) VH: CDR1: SEQ ID NO: 113, CDR2: SEQ ID NO: 114, CDR3: SEQ ID NO: 115, VL: CDR1: SEQ ID NO: 116, CDR2: SEQ ID NO: 117, CDR3: SEQ ID NO: 118;

(xiii) VH: CDR1: SEQ ID NO: 119, CDR2: SEQ ID NO: 120, CDR3: SEQ ID NO: 121, VL: CDR1: SEQ ID NO: 122, CDR2: SEQ ID NO: 123, CDR3: SEQ ID NO: 124;

(xiv) VH: CDR1: SEQ ID NO: 125, CDR2: SEQ ID NO: 126, CDR3: SEQ ID NO: 127, VL: CDR1: SEQ ID NO: 128, CDR2: SEQ ID NO: 129, CDR3: SEQ ID NO: 130;

(xv) VH: CDR1: SEQ ID NO: 131, CDR2: SEQ ID NO: 132, CDR3: SEQ ID NO: 133, VL: CDR1: SEQ ID NO: 134, CDR2: SEQ ID NO: 135, CDR3: SEQ ID NO: 136;

(xvi) VH: CDR1: SEQ ID NO: 137, CDR2: SEQ ID NO: 138, CDR3: SEQ ID NO: 139, VL: CDR1: SEQ ID NO: 140, CDR2: SEQ ID NO: 141, CDR3: SEQ ID NO: 142;

(xvii) VH: CDR1: SEQ ID NO: 143, CDR2: SEQ ID NO: 144, CDR3: SEQ ID NO: 145, VL: CDR1: SEQ ID NO: 146, CDR2: SEQ ID NO: 147, CDR3: SEQ ID NO: 148;

(xviii) VH: CDR1: SEQ ID NO: 149, CDR2: SEQ ID NO: 150, CDR3: SEQ ID NO: 151, VL: CDR1: SEQ ID NO: 152, CDR2: SEQ ID NO: 153, CDR3: SEQ ID NO: 154;

(xix) VH: CDR1: SEQ ID NO: 155, CDR2: SEQ ID NO: 156, CDR3: SEQ ID NO: 157, VL: CDR1: SEQ ID NO: 158, CDR2: SEQ ID NO: 159, CDR3: SEQ ID NO: 160;

(xx) VH: CDR1: SEQ ID NO: 161, CDR2: SEQ ID NO: 162, CDR3: SEQ ID NO: 163, VL: CDR1: SEQ ID NO: 164, CDR2: SEQ ID NO: 165, CDR3: SEQ ID NO: 166;

(xxi) VH: CDR1: SEQ ID NO: 167, CDR2: SEQ ID NO: 168, CDR3: SEQ ID NO: 169, VL: CDR1: SEQ ID NO: 170, CDR2: SEQ ID NO: 171, CDR3: SEQ ID NO: 172;

(xxii) VH: CDR1: SEQ ID NO: 173, CDR2: SEQ ID NO: 174, CDR3: SEQ ID NO: 175, VL: CDR1: SEQ ID NO: 176, CDR2: SEQ ID NO: 177, CDR3: SEQ ID NO: 178; and (xxiii) VH: CDR1: SEQ ID NO: 179, CDR2: SEQ ID NO: 180, CDR3: SEQ ID NO: 181, VL: CDR1: SEQ ID NO: 182, CDR2: SEQ ID NO: 183, CDR3: SEQ ID NO: 184.

In an embodiment fully human anti-CLDN18.2 antibodies, or antigen binding fragments thereof, comprise a VH comprising a set of complementarity-determining regions CDR1, CDR2, and CDR3 selected from the group consisting of:

(i) CDR1: SEQ ID NO: 221, CDR2: SEQ ID NO: 222, CDR3: SEQ ID NO: 223;

(ii) CDR1: SEQ ID NO: 227, CDR2: SEQ ID NO: 228, CDR3: SEQ ID NO: 229;

(iii) CDR1: SEQ ID NO: 233, CDR2: SEQ ID NO: 234, CDR3: SEQ ID NO: 235;

(iv) CDR1: SEQ ID NO: 239, CDR2: SEQ ID NO: 240, CDR3: SEQ ID NO: 241;

(v) CDR1: SEQ ID NO: 245, CDR2: SEQ ID NO: 246, CDR3: SEQ ID NO: 247;

(vi) CDR1: SEQ ID NO: 251, CDR2: SEQ ID NO: 252, CDR3: SEQ ID NO: 253;

(vii) CDR1: SEQ ID NO: 257, CDR2: SEQ ID NO: 258, CDR3: SEQ ID NO: 259;

(viii) CDR1: SEQ ID NO: 263, CDR2: SEQ ID NO: 264, CDR3: SEQ ID NO: 265;

(ix) CDR1: SEQ ID NO: 269, CDR2: SEQ ID NO: 270, CDR3: SEQ ID NO: 271;

(x) CDR1: SEQ ID NO: 275, CDR2: SEQ ID NO: 276, CDR3: SEQ ID NO: 277;

(xi) CDR1: SEQ ID NO: 281, CDR2: SEQ ID NO: 282, CDR3: SEQ ID NO: 283;

(xii) CDR1: SEQ ID NO: 287, CDR2: SEQ ID NO: 288, CDR3: SEQ ID NO: 289;

(xiii) CDR1: SEQ ID NO: 293, CDR2: SEQ ID NO: 294, CDR3: SEQ ID NO: 295;

(xiv) CDR1: SEQ ID NO: 299, CDR2: SEQ ID NO: 300, CDR3: SEQ ID NO: 301;

(xv) CDR1: SEQ ID NO: 311, CDR2: SEQ ID NO: 312, CDR3: SEQ ID NO: 313;

(xvi) CDR1: SEQ ID NO: 317, CDR2: SEQ ID NO: 318, CDR3: SEQ ID NO: 319; and (xvii) CDR1: SEQ ID NO: 323, CDR2: SEQ ID NO: 324, CDR3: SEQ ID NO: 325.

In an embodiment, fully human anti-CLDN18.2 antibodies, or antigen binding fragments thereof, comprise a VL comprising a set of complementarity-determining regions CDR1, CDR2, and CDR3 selected from the group consisting of:

(i) CDR1: SEQ ID NO: 224, CDR2: SEQ ID NO: 225, CDR3: SEQ ID NO: 226;

(ii) CDR1: SEQ ID NO: 230, CDR2: SEQ ID NO: 231, CDR3: SEQ ID NO: 232;

(iii) CDR1: SEQ ID NO: 236, CDR2: SEQ ID NO: 237, CDR3: SEQ ID NO: 238;

(iv) CDR1: SEQ ID NO: 242, CDR2: SEQ ID NO: 243, CDR3: SEQ ID NO: 244;

(v) CDR1: SEQ ID NO: 248, CDR2: SEQ ID NO: 249, CDR3: SEQ ID NO: 250;

(vi) CDR1: SEQ ID NO: 254, CDR2: SEQ ID NO: 255, CDR3: SEQ ID NO: 256;

(vii) CDR1: SEQ ID NO: 260, CDR2: SEQ ID NO: 261, CDR3: SEQ ID NO: 262;

(viii) CDR1: SEQ ID NO: 266, CDR2: SEQ ID NO: 267, CDR3: SEQ ID NO: 268;

(ix) CDR1: SEQ ID NO: 272, CDR2: SEQ ID NO: 273, CDR3: SEQ ID NO: 274;

(x) CDR1: SEQ ID NO: 278, CDR2: SEQ ID NO: 279, CDR3: SEQ ID NO: 280;

(xi) CDR1: SEQ ID NO: 284, CDR2: SEQ ID NO: 285, CDR3: SEQ ID NO: 286;

(xii) CDR1: SEQ ID NO: 290, CDR2: SEQ ID NO: 291, CDR3: SEQ ID NO: 292;

(xiii) CDR1: SEQ ID NO: 296, CDR2: SEQ ID NO: 297, CDR3: SEQ ID NO: 298;

(xiv) CDR1: SEQ ID NO: 302, CDR2: SEQ ID NO: 303, CDR3: SEQ ID NO: 304;

(xv) CDR1: SEQ ID NO: 314, CDR2: SEQ ID NO: 315, CDR3: SEQ ID NO: 316;

(xvi) CDR1: SEQ ID NO: 320, CDR2: SEQ ID NO: 321, CDR3: SEQ ID NO: 322; and (xvii) CDR1: SEQ ID NO: 326, CDR2: SEQ ID NO: 327, CDR3: SEQ ID NO: 328.

SEQ ID NOs and the amino acid sequences of the variable domains (VH and VL) and CDRs of the murine anti-CLDN18.2 antibodies are provided in FIG. 1.

SEQ ID NOs and the amino acid sequences of the variable domains (VH and VL) and CDRs of the human anti-CLDN18.2 antibodies are provided in FIG. 2.

In an embodiment, antibodies having the ability of binding to CLDN18.2 comprise a combination of VH and VL each comprising a set of complementarity-determining regions CDR1, CDR2 and CDR3 selected from the group consisting of:

(i) VH: CDR1: SEQ ID NO: 221, CDR2: SEQ ID NO: 222, CDR3: SEQ ID NO: 223, VL: CDR1: SEQ ID NO: 224, CDR2: SEQ ID NO: 225, CDR3: SEQ ID NO: 226;

(ii) VH: CDR1: SEQ ID NO: 227, CDR2: SEQ ID NO: 228, CDR3: SEQ ID NO: 229, VL: CDR1: SEQ ID NO: 230, CDR2: SEQ ID NO: 231, CDR3: SEQ ID NO: 232;

(iii) VH: CDR1: SEQ ID NO: 233, CDR2: SEQ ID NO: 234, CDR3: SEQ ID NO: 235, VL: CDR1: SEQ ID NO: 236, CDR2: SEQ ID NO: 237, CDR3: SEQ ID NO: 238;

(iv) VH: CDR1: SEQ ID NO: 239, CDR2: SEQ ID NO: 240, CDR3: SEQ ID NO: 241, VL: CDR1: SEQ ID NO: 242, CDR2: SEQ ID NO: 243, CDR3: SEQ ID NO: 244;

(v) VH: CDR1: SEQ ID NO: 245, CDR2: SEQ ID NO: 246, CDR3: SEQ ID NO: 247, VL: CDR1: SEQ ID NO: 248, CDR2: SEQ ID NO: 249, CDR3: SEQ ID NO: 250;

(vi) VH: CDR1: SEQ ID NO: 251, CDR2: SEQ ID NO: 252, CDR3: SEQ ID NO: 253, VL: CDR1: SEQ ID NO: 254, CDR2: SEQ ID NO: 255, CDR3: SEQ ID NO: 256;

(vii) VH: CDR1: SEQ ID NO: 257, CDR2: SEQ ID NO: 258, CDR3: SEQ ID NO: 259, VL: CDR1: SEQ ID NO: 260, CDR2: SEQ ID NO: 261, CDR3: SEQ ID NO: 262;

(viii) VH: CDR1: SEQ ID NO: 263, CDR2: SEQ ID NO: 264, CDR3: SEQ ID NO: 265, VL: CDR1: SEQ ID NO: 266, CDR2: SEQ ID NO: 267, CDR3: SEQ ID NO: 268;

(ix) VH: CDR1: SEQ ID NO: 269, CDR2: SEQ ID NO: 270, CDR3: SEQ ID NO: 271, VL: CDR1: SEQ ID NO: 272, CDR2: SEQ ID NO: 273, CDR3: SEQ ID NO: 274;

(x) VH: CDR1: SEQ ID NO: 275, CDR2: SEQ ID NO: 276, CDR3: SEQ ID NO: 277. VL: CDR1: SEQ ID NO: 278, CDR2: SEQ ID NO: 279, CDR3: SEQ ID NO: 280;

(xi) VH: CDR1: SEQ ID NO: 281, CDR2: SEQ ID NO: 282, CDR3: SEQ ID NO: 283, VL: CDR1: SEQ ID NO: 284, CDR2: SEQ ID NO: 285, CDR3: SEQ ID NO: 286;

(xii) VH: CDR1: SEQ ID NO: 287, CDR2: SEQ ID NO: 288, CDR3: SEQ ID NO: 289, VL: CDR1: SEQ ID NO: 290, CDR2: SEQ ID NO: 291, CDR3: SEQ ID NO: 292;

(xiii) VH: CDR1: SEQ ID NO: 293, CDR2: SEQ ID NO: 294, CDR3: SEQ ID NO: 295, VL: CDR1: SEQ ID NO: 296, CDR2: SEQ ID NO: 297, CDR3: SEQ ID NO: 298;

(xiv) VH: CDR1: SEQ ID NO: 299, CDR2: SEQ ID NO: 300, CDR3: SEQ ID NO: 301, VL: CDR1: SEQ ID NO: 302, CDR2: SEQ ID NO: 303, CDR3: SEQ ID NO: 304;

(xv) VH: CDR1: SEQ ID NO: 311, CDR2: SEQ ID NO: 312, CDR3: SEQ ID NO: 313, VL: CDR1: SEQ ID NO: 314, CDR2: SEQ ID NO: 315, CDR3: SEQ ID NO: 316;

(xvi) VH: CDR1: SEQ ID NO: 317, CDR2: SEQ ID NO: 318, CDR3: SEQ ID NO: 319, VL: CDR1: SEQ ID NO: 320, CDR2: SEQ ID NO: 321, CDR3: SEQ ID NO: 322; and (xvii) VH: CDR1: SEQ ID NO: 323, CDR2: SEQ ID NO: 324, CDR3: SEQ ID NO: 325, VL: CDR1: SEQ ID NO: 326, CDR2: SEQ ID NO: 327, CDR3: SEQ ID NO: 328.

In an embodiments, the anti-CLDN18.2 antibodies or antibody fragments thereof comprise a variable heavy chain sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 185, 187, 189, 191, 193, 195, 197, 199, 201, 203, 205, 207, 209, 211, 215, 217, and 219 and/or a variable light chain sequence selected from the group consisting of: SEQ ID NOs: 2, 4, 6, 8, 10, 12, 14, 16, 18, 20, 22, 24, 26, 28, 30, 32, 34, 36, 38, 40, 42, 44, 46, 186, 188, 190, 192, 194, 196, 198, 200, 202, 204, 206, 208, 210, 212, 216, 218, and 220.

In an embodiment, the anti-CLDN18.2 antibody or antigen binding fragment thereof comprises a specific pair of variable heavy chain and variable light chain sequences, selected from the following combinations: a variable heavy chain sequence comprising SEQ ID NO: 1 and a variable light chain sequence comprising SEQ ID NO: 2; a variable heavy chain sequence comprising SEQ ID NO: 3 and a variable light chain sequence comprising SEQ ID NO: 4; a variable heavy chain sequence comprising SEQ ID NO: 5 and a variable light chain sequence comprising SEQ ID NO: 6; a variable heavy chain sequence comprising SEQ ID NO: 7 and a variable light chain sequence comprising SEQ ID NO: 8; a variable heavy chain sequence comprising SEQ ID NO: 9 and a variable light chain sequence comprising SEQ ID NO: 10; a variable heavy chain sequence comprising SEQ ID NO: 11 and a variable light chain sequence comprising SEQ ID NO: 12; a variable heavy chain sequence comprising SEQ ID NO: 13 and a variable light chain sequence comprising SEQ ID NO: 14; a variable heavy chain sequence comprising SEQ ID NO: 15 and a variable light chain sequence comprising SEQ ID NO: 16; a variable heavy chain sequence comprising SEQ ID NO: 17 and a variable light chain sequence comprising SEQ ID NO: 18; a variable heavy chain sequence comprising SEQ ID NO: 19 and a variable light chain sequence comprising SEQ ID NO: 20; a variable heavy chain sequence comprising SEQ ID NO: 21 and a variable light chain sequence comprising SEQ ID NO: 22; a variable heavy chain sequence comprising SEQ ID NO: 23 and a variable light chain sequence comprising SEQ ID NO: 24; a variable heavy chain sequence comprising SEQ ID NO: 25 and a variable light chain sequence comprising SEQ ID NO: 26; a variable heavy chain sequence comprising SEQ ID NO: 27 and a variable light chain sequence comprising SEQ ID NO: 28; a variable heavy chain sequence comprising SEQ ID NO: 29 and a variable light chain sequence comprising SEQ ID NO: 30; a variable heavy chain sequence comprising SEQ ID NO: 31 and a variable light chain sequence comprising SEQ ID NO: 32; a variable heavy chain sequence comprising SEQ ID NO: 33 and a variable light chain sequence comprising SEQ ID NO: 34; a variable heavy chain sequence comprising SEQ ID NO: 35 and a variable light chain sequence comprising SEQ ID NO: 36; a variable heavy chain sequence comprising SEQ ID NO: 37 and a variable light chain sequence comprising SEQ ID NO: 38; a variable heavy chain sequence comprising SEQ ID NO: 39 and a variable light chain sequence comprising SEQ ID NO: 40; a variable heavy chain sequence comprising SEQ ID NO: 41 and a variable light chain sequence comprising SEQ ID NO: 42; a variable heavy chain sequence comprising SEQ ID NO: 43 and a variable light chain sequence comprising SEQ ID NO:44; and a variable heavy chain sequence comprising SEQ ID NO:45 and a variable light chain sequence comprising SEQ ID NO:46.

In an alternative embodiment, fully human anti-CLDN18.2 antibodies, or antigen binding fragment thereof, comprise a specific pair of variable heavy chain and variable light chain sequences, selected from the following combinations: a variable heavy chain sequence comprising SEQ ID NO: 185 and a variable light chain sequence comprising SEQ ID NO: 186; a variable heavy chain sequence comprising SEQ ID NO: 187 and a variable light chain sequence comprising SEQ ID NO: 188; a variable heavy chain sequence comprising SEQ ID NO: 189 and a variable light chain sequence comprising SEQ ID NO: 190; a variable heavy chain sequence comprising SEQ ID NO: 191 and a variable light chain sequence comprising SEQ ID NO: 192; a variable heavy chain sequence comprising SEQ ID NO: 193 and a variable light chain sequence comprising SEQ ID NO: 194; a variable heavy chain sequence comprising SEQ ID NO: 195 and a variable light chain sequence comprising SEQ ID NO: 196; a variable heavy chain sequence comprising SEQ ID NO: 197 and a variable light chain sequence comprising SEQ ID NO: 198; a variable heavy chain sequence comprising SEQ ID NO: 199 and a variable light chain sequence comprising SEQ ID NO: 200; a variable heavy chain sequence comprising SEQ ID NO: 201 and a variable light chain sequence comprising SEQ ID NO: 202; a variable heavy chain sequence comprising SEQ ID NO: 203 and a variable light chain sequence comprising SEQ ID NO: 204; a variable heavy chain sequence comprising SEQ ID NO: 205 and a variable light chain sequence comprising SEQ ID NO: 206; a variable heavy chain sequence comprising SEQ ID NO: 207 and a variable light chain sequence comprising SEQ ID NO: 208; a variable heavy chain sequence comprising SEQ ID NO: 209 and a variable light chain sequence comprising SEQ ID NO: 210; a variable heavy chain sequence comprising SEQ ID NO: 211 and a variable light chain sequence comprising SEQ ID NO: 212; a variable heavy chain sequence comprising SEQ ID NO: 215 and a variable light chain sequence comprising SEQ ID NO: 216; a variable heavy chain sequence comprising SEQ ID NO: 217 and a variable light chain sequence comprising SEQ ID NO: 218; and a variable heavy chain sequence comprising SEQ ID NO: 219 and a variable light chain sequence comprising SEQ ID NO: 220.

In an alternative embodiment, the anti-CLDN18.2 antibodies or antibody fragments thereof comprise a pair of variable heavy chain and variable light chain sequences, selected from the following combinations: a variable heavy chain sequence that is 90%, 95%, or 99% identical to SEQ ID NO: 1 and a variable light chain sequence that is 90%, 95%, or 99% identical to SEQ ID NO: 2; a variable heavy chain sequence that is 90%, 95%, or 99% identical to SEQ ID NO: 3 and a variable light chain sequence that is 90%, 95%, or 99% identical to SEQ ID NO: 4; a variable heavy chain sequence that is 90%, 95%, or 99% identical to SEQ ID NO: 5 and a variable light chain sequence that is 90%, 95%, or 99% identical to SEQ ID NO: 6; a variable heavy chain sequence that is 90%, 95%, or 99% identical to SEQ ID NO: 7 and a variable light chain sequence that is 90%, 95%, or 99% identical to SEQ ID NO: 8; a variable heavy chain sequence that is 90%, 95%, or 99% identical to SEQ ID NO: 9 and a variable light chain sequence that is 90%, 95%, or 99% identical to SEQ ID NO: 10; a variable heavy chain sequence that is 90%, 95%, or 99% identical to SEQ ID NO: 11 and a variable light chain sequence that is 90%, 95%, or 99% identical to SEQ ID NO: 12; a variable heavy chain sequence that is 90%, 95%, or 99% identical to SEQ ID NO: 13 and a variable light chain sequence that is 90%, 95%, or 99% identical to SEQ ID NO: 14; a variable heavy chain sequence that is 90%, 95%, or 99% identical to SEQ ID NO: 15 and a variable light chain sequence that is 90%, 95%, or 99% identical to SEQ ID NO: 16; a variable heavy chain sequence that is 90%, 95%, or 99% identical to SEQ ID NO: 17 and a variable light chain sequence that is 90%, 95%, or 99% identical to SEQ ID NO: 18; a variable heavy chain sequence that is 90%, 95%, or 99% identical to SEQ ID NO: 19 and a variable light chain sequence that is 90%, 95%, or 99% identical to SEQ ID NO: 20; a variable heavy chain sequence that is 90%, 95%, or 99% identical to SEQ ID NO: 21 and a variable light chain sequence that is 90%, 95%, or 99% identical to SEQ ID NO: 22; a variable heavy chain sequence that is 90%, 95%, or 99% identical to SEQ ID NO: 23 and a variable light chain sequence that is 90%, 95%, or 99% identical to SEQ ID NO: 24; a variable heavy chain sequence that is 90%, 95%, or 99% identical to SEQ ID NO: 25 and a variable light chain sequence that is 90%, 95%, or 99% identical to SEQ ID NO: 26; a variable heavy chain sequence that is 90%, 95%, or 99% identical to SEQ ID NO: 27 and a variable light chain sequence that is 90%, 95%, or 99% identical to SEQ ID NO: 28; a variable heavy chain sequence that is 90%, 95%, or 99% identical to SEQ ID NO: 29 and a variable light chain sequence that is 90%, 95%, or 99% identical to SEQ ID NO: 30; a variable heavy chain sequence that is 90%, 95%, or 99% identical to SEQ ID NO: 31 and a variable light chain sequence that is 90%, 95%, or 99% identical to SEQ ID NO: 32; a variable heavy chain sequence that is 90%, 95%, or 99% identical to SEQ ID NO: 33 and a variable light chain sequence that is 90%, 95%, or 99% identical to SEQ ID NO: 34; a variable heavy chain sequence that is 90%, 95%, or 99% identical to SEQ ID NO: 35 and a variable light chain sequence that is 90%, 95%, or 99% identical to SEQ ID NO: 36; a variable heavy chain sequence that is 90%, 95%, or 99% identical to SEQ ID NO: 37 and a variable light chain sequence that is 90%, 95%, or 99% identical to SEQ ID NO: 38; a variable heavy chain sequence that is 90%, 95%, or 99% identical to SEQ ID NO: 39 and a variable light chain sequence that is 90%, 95%, or 99% identical to SEQ ID NO: 40; a variable heavy chain sequence that is 90%, 95%, or 99% identical to SEQ ID NO: 41 and a variable light chain sequence that is 90%, 95%, or 99% identical to SEQ ID NO: 42; a variable heavy chain sequence that is 90%, 95%, or 99% identical to SEQ ID NO: 43 and a variable light chain sequence that is 90%, 95%, or 99% identical to SEQ ID NO: 44; a variable heavy chain sequence that is 90%, 95%, or 99% identical to SEQ ID NO: 45 and a variable light chain sequence that is 90%, 95%, or 99% identical to SEQ ID NO: 46.

In another alternative embodiment, the anti-CLDN18.2 antibodies or antibody fragments thereof comprise a pair of variable heavy chain and variable light chain sequences, selected from the following combinations: a variable heavy chain sequence that is 90%, 95%, or 99% identical to SEQ ID NO: 185 and a variable light chain sequence that is 90%, 95%, or 99% identical to SEQ ID NO: 186; a variable heavy chain sequence that is 90%, 95%, or 99% identical to SEQ ID NO: 187 and a variable light chain sequence that is 90%, 95%, or 99% identical to SEQ ID NO: 188; a variable heavy chain sequence that is 90%, 95%, or 99% identical to SEQ ID NO: 189 and a variable light chain sequence that is 90%, 95%, or 99% identical to SEQ ID NO: 190; a variable heavy chain sequence that is 90%, 95%, or 99% identical to SEQ ID NO: 191 and a variable light chain sequence that is 90%, 95%, or 99% identical to SEQ ID NO: 192; a variable heavy chain sequence that is 90%, 95%, or 99% identical to SEQ ID NO: 193 and a variable light chain sequence that is 90%, 95%, or 99% identical to SEQ ID NO: 194; a variable heavy chain sequence that is 90%, 95%, or 99% identical to SEQ ID NO: 195 and a variable light chain sequence that is 90%, 95%, or 99% identical to SEQ ID NO: 196; a variable heavy chain sequence that is 90%, 95%, or 99% identical to SEQ ID NO: 197 and a variable light chain sequence that is 90%, 95%, or 99% identical to SEQ ID NO: 198; a variable heavy chain sequence that is 90%, 95%, or 99% identical to SEQ ID NO: 199 and a variable light chain sequence that is 90%, 95%, or 99% identical to SEQ ID NO: 200; a variable heavy chain sequence that is 90%, 95%, or 99% identical to SEQ ID NO: 201 and a variable light chain sequence that is 90%, 95%, or 99% identical to SEQ ID NO: 202; a variable heavy chain sequence that is 90%, 95%, or 99% identical to SEQ ID NO: 203 and a variable light chain sequence that is 90%, 95%, or 99% identical to SEQ ID NO: 204; a variable heavy chain sequence that is 90%, 95%, or 99% identical to SEQ ID NO: 205 and a variable light chain sequence that is 90%, 95%, or 99% identical to SEQ ID NO: 206; a variable heavy chain sequence that is 90%, 95%, or 99% identical to SEQ ID NO: 207 and a variable light chain sequence that is 90%, 95%, or 99% identical to SEQ ID NO: 208; a variable heavy chain sequence that is 90%, 95%, or 99% identical to SEQ ID NO: 209 and a variable light chain sequence that is 90%, 95%, or 99% identical to SEQ ID NO: 210; a variable heavy chain sequence that is 90%, 95%, or 99% identical to SEQ ID NO: 211 and a variable light chain sequence that is 90%, 95%, or 99% identical to SEQ ID NO: 212; a variable heavy chain sequence that is 90%, 95%, or 99% identical to SEQ ID NO: 215 and a variable light chain sequence that is 90%, 95%, or 99% identical to SEQ ID NO: 216; a variable heavy chain sequence that is 90%, 95%, or 99% identical to SEQ ID NO: 217 and a variable light chain sequence that is 90%, 95%, or 99% identical to SEQ ID NO: 218; a variable heavy chain sequence that is 90%, 95%, or 99% identical to SEQ ID NO: 219 and a variable light chain sequence that is 90%, 95%, or 99% identical to SEQ ID NO: 220.

In some embodiments, the antibody is a full-length antibody. In other embodiments, the antibody is an antibody fragment including, for example, an antibody fragment selected from the group consisting of: Fab, Fab', F(ab)2, Fv, domain antibodies (dAbs), and complementarity determining region (CDR) fragments, single-chain antibodies (scFv), chimeric antibodies, diabodies, triabodies, tetrabodies, miniantibodies, multispecific antibodies, bispecific antibodies and polypeptides that contain at least a portion of an immunoglobulin that is sufficient to confer CLDN18.2-specific binding to the polypeptide.

Thus, in one embodiment, the antibody fragment comprises at least one CDR as described herein. The antibody fragment may comprise at least two, three, four, five, or six CDRs as described herein. The antibody fragment further may comprise at least one variable region domain of an antibody described herein. The variable region domain may be of any size or amino acid composition and will generally comprise at least one CDR sequence responsible for specifically binding to human CLDN18.2, for example, CDR-H1, CDR-H2, CDR-H3, CDR-L1, CDR-L2, and/or CDR-L3 as described herein, and which is adjacent to or in frame with one or more framework sequences.

In some embodiments, the anti-CLDN8.2 antibody is a monoclonal antibody. In some embodiments, the anti-CLDN8.2 antibody is a human antibody. In alternative embodiments, the anti-CLDN8.2 antibody is a murine antibody. In some embodiments, the anti-CLDN8.2 antibody is a chimeric antibody, a bispecific antibody, or a humanized antibody.

In some embodiments, the anti-CLDN8.2 antibodies or antibody fragments thereof comprise one or more conservative amino acid substitutions. A person of skill in the art will recognize that a conservative amino acid substitution is a substitution of one amino acid with another amino acid that has similar structural or chemical properties, such as, for example, a similar side chain. Exemplary conservative substitutions are described in the art, for example, in Watson et al., Molecular Biology of the Gene, The Benjamin/Cummings Publication Company, 4th Ed. (1987).

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al. (1998) Acta Physiol Scand Suppl 643: 55-67; Sasaki et al. (1998) Adv Biophys 35: 1-24). Amino acid substitutions to the antibodies of the invention may be made by known methods for example by PCR mutagenesis (U.S. Pat. No. 4,683,195).

In one embodiment, the IL-CLDN18.2 antibody or antibody fragment thereof comprises all six of the CDR regions of the Ms1, Ms2, Ms3, Ms4, Ms5, Ms6, Ms7, Ms8, Ms9, Ms10, Ms11, Ms12, Ms13, Ms14, Ms15, Ms16, Ms17, Ms18, Ms19, Ms20, Ms21, Ms22 or, Ms23 antibodies formatted as a chimeric or a humanized antibody. In other embodiments, the CLDN18.2 antibody or antibody fragment thereof comprises all six of the CDR regions of one of the disclosed fully human antibodies.

In some embodiments, a variable region domain of an anti-CLDN18.2 antibody disclosed herein may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly, a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example, to provide a hinge region or a portion of a hinge region domain as found in a Fab fragment, or to provide further domains, such as antibody CH2 and CH3 domains.

Antigen binding fragments, monospecific or multispecific antibodies may be produced by recombinant DNA techniques or by enzymatic or chemical cleavage of intact antibodies. Examples of antibody fragments include but are not limited to Fv, Fab, Fab', Fab'-SH, F(ab)2; diabodies; linear antibodies; single-chain antibody molecules (e.g., scFv). "Single-chain Fv" also abbreviated as "sFv" or "scFv" are antibody fragments that comprise the VH and VL antibody domains connected into a single polypeptide chain. One or more of the disclosed anti-CLDN18 binding CDRs may be incorporated into a recombinant molecule either covalently or noncovalently to make it an antigen binding protein in the format of chimeric antibodies, diabodies, triabodies, tetrabodies, and polypeptides that contain at least a portion of an immunoglobulin that is sufficient to confer CLDN18 specific binding to the polypeptide.

Thus, in one embodiment, the binding agent comprises at least one CDR as described herein. The binding agent may comprise at least two, three, four, five, or six CDRs as described herein. The binding agent further may comprise at least one variable region domain of an antibody described herein. The variable region domain may be of any size or amino acid composition and will generally comprise at least one CDR sequence responsible for binding to human CLDN18.2, for example, CDR-H1, CDR-H2, CDR-H3 and/ or the light chain CDRs specifically described herein and which is adjacent to or in frame with one or more framework sequences.

In general terms, the variable (V) region domain may be any suitable arrangement of immunoglobulin heavy (VH) and/or light (VL) chain variable domains. Thus, for example, the V region domain may be monomeric and be a VH or VL domain, which is capable of independently binding human CLDN18.2 as described below. Alternatively, the V region domain may be dimeric and contain VH-VH, VH-VL, or VL-VL, dimers. The V region dimer comprises at least one VH and at least one VL chain that may be non-covalently associated (hereinafter referred to as FV). If desired, the chains may be covalently coupled either directly, for example via a disulfide bond between the two variable domains, or through a linker, for example, a peptide linker, to form a single-chain Fv (scFV).

A person of skill in the art will recognize that a human IgG immunoglobulin molecule (antibody) consists of four polypeptide chains, composed of two identical 50 kDa γ heavy (H) chains and two identical 25 kDa κ or λ light (L) chains, linked together by inter-chain disulfide bonds. Each heavy chain consists of an N-terminal variable domain (VH) and an Fc region comprising three constant domains (CH1, CH2, CH3), with an additional "hinge region" between CH1 and CH2. Each light chain consists of an N-terminal variable domain (VL) and a single constant domain (CL). Two types of light chains, kappa (κ) and lambda (λ), were also originally defined serologically, and subsequently by protein and gene sequences. Each H2L2 module expresses either two kappa or two lambda light chains to form H2κ2 or H2λ2 heterodimers.

The Fc-region of IgG heavy chain molecules also contains a binding epitope, located at the interface between the Fc CH2-CH3 domains for the neonatal Fc receptor (FcRn) that is responsible for placental transport and IgG half-life. Generally, the variable regions of an antibody (VH and VL domain) are involved in the recognition of an epitope on a target and the Fc fragment functions to confer the biological properties of the antibody. More specifically, the Fc region allows the antibody to be recognized by the immune effectors (including monocytes, macrophages, dendritic cells, and natural killer or NK cells) expressing Fcγ receptors, to activate the complement system, and to bind to the FcRn (neonatal Fc receptor).

Human IgG comprises four highly conserved subclasses: IgG1, IgG2, IgG3 and IgG4 that show over 90% homology in amino acid sequence, with subtype-specific differences that affect their binding to accessory molecules and receptors. The subclasses of IgG differ from each other in the sequence of their constant region, particularly in the hinge and upper CH2 domains that are involved in binding to both IgG-Fc receptors (Fc γ receptors) and the complement component C1q. As a result, the different IgG subclasses have different effector functions, both in terms of activating immune effector cells and activating the complement cascade. The types of FcγR-mediated effector cell responses include, but are not limited to, antibody-dependent cellular cytotoxicity (ADCC), antibody-dependent cellular phagocytosis (ADCP), the release of cytokines and antigen uptake for presentation.

In addition to isotypic variation, allelic variation is also found among the IgG subclasses. These polymorphic epitopes of immunoglobulins that can differ between individuals and ethnic groups were originally discovered on the basis of serological findings, as immunogenic determinants found on IgG from some individuals but not others. The allotypes are inherited in a codominant Mendelian way, and various sets of combinations are found in African, white, and Oriental populations.

One of the most commonly used sub-classes of the IgG isotype for therapeutic antibodies is an IgG1, which has four well-characterized allotypes. It has been reported that the use of IgG1 sequences comprising alternative allotypes can modify (increase or decrease) the binding affinity for FcRn receptor, and/or increases the stability of the complex formed by the modified antibody and FcRn, thereby affecting the pharmacokinetics of a therapeutic antibody (US2018/0362624, and, J. Immunol. 196(2):607 (2016), Ternant, D et al). Currently, IgG1 mAb therapeutics of the four predominant allotypes are licensed and in the marketplace. It is noted that those of ordinary skill in the art can readily determine a suitable IgG1 CH sequence for use with the VH regions of the invention.

In one aspect, the anti-CLDN18.2 antibodies provided herein comprise a specific pair of the variable heavy chain and variable light chain sequences in combination with a wild-type human IgG1 heavy chain constant region (CH) and wild-type human kappa light chain (CL) region. For example, and not for the purpose of limitation, the invention provides anti-CLDN18.2 antibodies comprising a heavy chain variable region (VH) of the invention in combination with a wild-type human IgG1 constant heavy chain (CH) immunoglobulin sequence selected from the sequences set forth in SEQ ID NOS: 331-334, and a wild-type human immunoglobulin light chain having a light chain variable region of the invention (VL) in combination with an immunoglobulin light chain constant region (CL). In some aspects, the CL region comprises a human kappa light chain region comprising the sequence set forth in SEQ ID NO: 335. FIGS. 11A and 11B provide sequence information for human IgG1 CH domains (FIG. 11A) and a human kappa chain domain (FIG. 11B) suitable for use in combination with the VH and VL sequences of the invention.

In another aspect, the anti-CLDN18.2 antibodies provided herein comprise a human IgG1 CH region comprising a modified CH that includes point mutations introduced into the sequence to enhance a desirable effector function such as ADCC or ADCP activity or to prolong the half-life or stability of the antibody. In one aspect the invention provides an anti-CLDN18.2 antibody engineered or manufactured in a manner intended to make it "fit-for-purpose" as a cancer immunotherapy due to an enhanced ADCC, ADCP and/or CDC activity. More specifically, one aspect of the invention features an anti-CLDN18.2 antibody characterized by low or no IgG-Fc core fucose. Potential advantages of a non-fucosylated anti-CLDN18.2 therapeutic antibody include the potential of achieving therapeutic efficacy at lower doses, inducing high cellular cytotoxicity against tumor cells that express low levels of CLDN18.2, and triggering high effector function in NK cells expressing CD16a low-affinity Fcγ receptors.

In one aspect, and not for the purpose of limitation, the invention features an anti-CLDN18.2 antibody characterized by low or no IgG core fucose (non- or afucosylated) antibodies. One of skill in the art will readily appreciate that this aspect of the invention may be a chimeric or humanized anti-CLDN18.2 antibody comprising variable regions (i.e., VH and VL) regions selected from the pairs of antibody sequences (VH and VL) or the sets of VH and VL CDRs, in FIG. 1. Alternatively, the anti-CLDN18.2 antibody characterized by low or no IgG core fucose can be a fully human sequence comprising variable regions selected from the pairs of antibody sequences (VH and VL) or the sets of VH and VL CDR in FIG. 2.

In one aspect, the antibodies of the invention feature non-fucosylated anti-CLDN18.2 antibodies, or anti-CLDN18.2 antibodies characterized by low core IgG fucose levels, comprising a pair of VH and VL sequences selected from SEQ ID NO: 1 and SEQ ID NO: 2, SEQ ID NO: 3 and SEQ ID NO:4, SEQ ID NO: 201 and SEQ ID NO: 202, and SEQ ID NO: 203 and SEQ ID NO: 204, respectively. In any particular antibody, the anti-CLDN18.2 specific variable regions can be in the format of a full-length IgG comprising a human IgG1 constant heavy chain immunoglobulin sequence selected from SEQ ID NOS: 331-334, and a human Ig kappa light chain constant region comprising the sequence set forth in SEQ ID NO: 335.

In an alternative aspect, the invention features a CLDN18.2 antibody comprising point mutations at targeted sites in the Fc region to enhance ADCC, and/or ADCP and/or CDC activities relative to the activity of the same antibody (e.g., same variable VH and VL regions or set of 6 set CDR sequences) comprising a wild-type human IgG1 CH sequence. One of skill in the art will readily appreciate that this aspect of the invention may be a chimeric or humanized anti-CLDN18.2 antibody comprising variable regions (i.e., VH and VL) regions selected from the pairs of antibody sequences (VH and VL) or the sets of VH and VL CDRs, in FIG. 1. Alternatively, the Fc-engineered anti-CLDN18.2 antibody comprising point mutations can be a fully human sequence comprising variable regions selected from the pairs of antibody sequences (VH and VL) or the sets of VH and VL CDR in FIG. 2.

In one aspect, the invention provides Fc-engineered anti-CLDN18.2 specific antibodies comprising a pair of VH and VL sequences selected from SEQ ID NO: 1 and SEQ ID NO: 2, SEQ ID NO: 3 and SEQ ID NO:4, SEQ ID NO: 201 and SEQ ID NO: 202, and SEQ ID NO: 203 and SEQ ID NO: 204, respectively. In any particular antibody, the anti-CLDN18.2 specific variable regions can be in the format of a full length IgG comprising a human IgG1 constant heavy chain immunoglobulin sequence selected from SEQ ID NOS: 331-334, and a human Ig kappa light chain constant region comprising the sequence set forth in SEQ ID NO: 335.

For example, and not for the purpose of limitation, the invention provides an Fc engineered fully human IgG1 anti-CLDN18.2 antibody comprising the VH sequence provided in SEQ ID NO: 201 combined with an engineered CH region that includes point mutations in the CH1 and/or CH2 and/or CH3 region designed to enhance a desirable biological activity; and a VL sequence provided in SEQ ID NO: 202 combined with a human kappa light chain immunoglobulin sequence, such as the sequence set forth in SEQ ID NO: 335. In one aspect, and not for the purpose of limitation, the invention features an anti-CLDN18.2 antibody, referred to herein as mAb NBL-014, comprising a recombinant heavy chain having the amino acid sequence SEQ ID NO: 336 and a light chain comprising the sequence set forth in SEQ ID NO: 337 (see FIG. 12). In an alternative embodiment, the invention provides an anti-CLDN18.2 antibody comprising a recombinant heavy chain having the amino acid sequence SEQ ID NO: 338 and a light chain comprising the sequence set forth in SEQ ID NO: 337, referred to herein as NBL-014 (see FIG. 12).

In an alternative aspect, the invention provides an Fc engineered fully human IgG1 anti-CLDN18.2 antibody comprising the VH sequence provided in SEQ ID NO: 203 combined with an engineered CH region that includes point mutations in the CH1 and/or CH2 and/or CH3 region designed to enhance a desirable biological activity; and a VL sequence provided in SEQ ID NO: 204 combined with a human kappa light chain immunoglobulin sequence, such as the sequence set forth in SEQ ID NO: 335.

In an alternative aspect, the invention provides Fc-modified, glycoengineered or protein-engineered (e.g. by the introduction of point mutations in the CH Fc region), anti-CLDN18.2 specific antibodies comprising a VH sequence that includes CDR1, CDR2 and CDR3 regions selected from the sets of VH and VL CDRs provided in FIGS. 1 and 2. More specifically the invention features engineered anti-CLDN18.2 antibodies a VH domain comprising a set of CDR1, CDR2, and CDR3 sequences selected from SEQ ID NO:S 47-49, SEQ ID NOS: 53-55, SEQ ID NOS: 269-271, and SEQ ID NOS: 275-277, combined with an engineered CH region that includes point mutations in the CH1 and/or CH2 and/or CH3 region designed to enhance a desirable biological activity, paired with a VL sequence comprising a set of CDR1, CDR2 and CDR3 sequences selected from SEQ ID NOS: 50-52, SEQ ID NOS: 56-58, SEQ ID NOS: 272-274, and SEQ ID NOS: 278-280 respectively, combined with a human kappa light chain immunoglobulin sequence.

The therapeutic value of the antibodies of the disclosure can be enhanced by conjugation to a cytotoxic drug or agent that improves its effectiveness and potency. In some embodiments the antibody is an antibody drug conjugate (ADC) comprising a CLDN18.2-specific antibody coupled to a cytotoxic effector agent such as a radioisotope, a drug, or a cytotoxin. Internalization by endocytosis indicates that an antibody is suitable for antibody drug conjugate (ADC) development. Anti-CLDN18.2 antibodies having these properties can also be applied, but are not limited to bispecific, chimeric antigen receptor T or NK cells, cell therapy, and combinational therapies for treating CLDN18.2-associated diseases or disorders.

The anti-CLDN18.2 antibodies of the disclosure can also be used for developing antibody-based immunotherapeutics that rely on CLDN18.2-specific binding to direct patient effector cells (e.g., T cells or NK cells) to tumors including bispecific T cell engaging antibodies, or bispecific molecules that redirect NK cells, or cell therapies, such as CAR-T therapy.

Methods of Producing Antibodies

Many suitable methods can be applied for antibody generation and are known to those of skill in the art. For example, a recipient may be immunized with cells that express claudin 18.2, soluble recombinant claudin 18.2 protein, or a fragment or a peptide conjugated with a carrier protein thereof. Any suitable method known to those of skill in the art may be used to elicit an antibody with desired biologic properties to inhibit claudin 18.2. Such methods can include a method of immunization that includes the use of adjuvants, other immune stimulants, repeat booster immunizations, and the use of one or more immunization routes.

Any suitable source of claudin 18.2 can be used as the immunogen for the generation of the non-human antibody or human antibody, specific for claudin 18.2 of the compositions and methods disclosed herein. Such forms include, but are not limited to cells expressing claudin 18.2 (endogenous' cells or cells that are transfected with claudin 18.2 gene) whole protein, peptide(s), and epitopes, generated through recombinant, synthetic, chemical or enzymatic degradation means known in the art.

Different forms of the antigens may be used to generate the antibody that is sufficient to generate a biologically active antibody. Thus, the eliciting antigen may be a single epitope, multiple epitopes, or the entire protein alone or in combination with one or more immunogenicity enhancing agents. In some cases, the eliciting antigen is an isolated full-length protein, a cell surface protein (e.g., immunizing with cells transfected with at least a portion of the antigen), or a soluble protein (e.g., immunizing with only the extracellular domain portion of the protein).

In some embodiments, the antigen is produced in a genetically modified cell. The DNA encoding the antigen may be genomic or non-genomic (e.g., cDNA), and may encode at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including, but not limited to adenoviral vectors, plasmids, and non-viral vectors, such as cationic lipids.

It is desirable to prepare monoclonal antibodies (mAbs) from various mammalian hosts, such as mice, rodents, primates, humans, etc. Description of techniques for preparing such monoclonal antibodies may be found in, e.g., Sties et al. (eds.) BASIC AND CLINICAL IMMUNOLOGY (4$^{th}$ ed.) Lance Medical Publication, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2D ed) Academic Press, New York, N.Y. Typically, spleen cells from an animal immunized with a desired antigen are immortalized, commonly by fusion with a myeloma cell. See Kohler and Milstein (196) Eur. J. Immunol. 6:511-519. Alternative methods of immortalization include transformation with Epstein Barr Virus, oncogene, or retroviruses, or other methods known in the art. See. e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or an antigen binding fragment thereof by screening a DNA library from human B cells according, e.g., to the general protocol outlined by Huse et al. (1989) Science 246: 1275-1281. Thus, monoclonal antibodies may be obtained by a variety of techniques familiar to researchers skilled in the art.

Other suitable techniques involve selection of libraries of antibodies in phage, yeast, virus or similar vector. See e.g., Huse et al. supra; and Ward et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,9396,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86: 10029-10023; or made in transgenic mice, see Nils Lonberg et al. (1994), Nature 368:856-859; and Mendez et al. (1997) Nature Genetics 15: 146-156; TRANSGENIC ANIMALS AND METHODS OF USE (WO2012US62118A), Medarex, Trianni, Abgenix, Ablexis, OminiAb, Harbour and other technologies.

In some embodiments, the ability of the produced antibody to bind an antigen (e.g., CLDN18) can be assessed using standard binding assays, such as ELISA, Western Blot, Immunofluorescent and flow cytometric analysis. In some aspects, the produced antibody may also be assessed for its ability to mediate the killing of target cells (e.g. tumor cells) expressing CLDN18 (e.g., antibody-dependent cell-mediated cytotoxicity (ADCC), complement-dependent cytotoxicity (CDC), antibody-dependent phagocytosis (ADCP) and/ or inhibition of cell proliferation).

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present disclosure. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-CLDN18 polypeptide (e.g., a heavy chain or light chain variable region), or its complement. Hybridizing nucleic acids of the type described herein can be used, for example, as a cloning probe, a primer, e.g., a PCR primer, or a diagnostic probe.

Polynucleotides, Vectors, and Host Cells

Other embodiments encompass isolated polynucleotides that comprise a sequence encoding an anti-CLDN18.2 antibody or antibody fragment thereof, vectors, and host cells comprising the polynucleotides, and recombinant techniques for production of the antibody. The isolated polynucleotides can encode any desired form of the anti-CLDN18.2 antibody including, for example, full-length monoclonal antibodies, Fab, Fab', F(ab')2, and Fv fragments, diabodies, linear antibodies, single-chain antibody molecules, and multispecific antibodies formed from antibody fragments.

Some embodiments include isolated polynucleotides comprising sequences that encode the heavy chain variable region of an antibody or antibody fragment having the amino acid sequence of SEQ ID NOs: 1, 3, 5, 7, 9, 11, 13, 15, 17, 19, 21, 23, 25, 27, 29, 31, 33, 35, 37, 39, 41, 43, 45, 185, 187, 189, 191, 193, 195, 197, 199, 201, 203, 205, 207, 209, 211, 215, 217, or 219. Some embodiments include isolated polynucleotides comprising sequences that encode the light chain variable region of an antibody or antibody fragment having the amino acid sequence of any of SEQ ID NOs: 2, 4, 6, 8, 10, 12, 14, 16, 18, 20, 22, 24, 26, 28, 30, 32, 34, 36, 38, 40, 42, 44, 46, 186, 188, 190, 192, 194, 196, 198, 200, 202, 204, 206, 208, 210, 212, 216, 218, or 220.

In an embodiment, the isolated polynucleotide sequence(s) encodes an antibody or antibody fragment having a light chain and a heavy chain variable region comprising the amino acid sequences of:

(a) a variable heavy chain sequence comprising SEQ ID NO: 1 and a variable light chain sequence comprising SEQ ID NO: 2;

(b) a variable heavy chain sequence comprising SEQ ID NO: 3 and a variable light chain sequence comprising SEQ ID NO: 4;

(c) a variable heavy chain sequence comprising SEQ ID NO: 5 and a variable light chain sequence comprising SEQ ID NO: 6;

(d) a variable heavy chain sequence comprising SEQ ID NO: 7 and a variable light chain sequence comprising SEQ ID NO: 8;

(e) a variable heavy chain sequence comprising SEQ ID NO: 9 and a variable light chain sequence comprising SEQ ID NO: 10;

(f) a variable heavy chain sequence comprising SEQ ID NO: 11 and a variable light chain sequence comprising SEQ ID NO: 12;

(g) a variable heavy chain sequence comprising SEQ ID NO: 13 and a variable light chain sequence comprising SEQ ID NO: 14;

(h) a variable heavy chain sequence comprising SEQ ID NO: 15 and a variable light chain sequence comprising SEQ ID NO: 16;

(i) a variable heavy chain sequence comprising SEQ ID NO: 17 and a variable light chain sequence comprising SEQ ID NO: 18;

(j) a variable heavy chain sequence comprising SEQ ID NO: 19 and a variable light chain sequence comprising SEQ ID NO: 20;

(k) a variable heavy chain sequence comprising SEQ ID NO: 21 and a variable light chain sequence comprising SEQ ID NO: 22;

(l) a variable heavy chain sequence comprising SEQ ID NO: 23 and a variable light chain sequence comprising SEQ ID NO: 24;

(m) a variable heavy chain sequence comprising SEQ ID NO: 25 and a variable light chain sequence comprising SEQ ID NO: 26;

(n) a variable heavy chain sequence comprising SEQ ID NO: 27 and a variable light chain sequence comprising SEQ ID NO: 28;

(o) a variable heavy chain sequence comprising SEQ ID NO: 29 and a variable light chain sequence comprising SEQ ID NO: 30;

(p) a variable heavy chain sequence comprising SEQ ID NO: 31 and a variable light chain sequence comprising SEQ ID NO: 32;

(q) a variable heavy chain sequence comprising SEQ ID NO: 33 and a variable light chain sequence comprising SEQ ID NO: 34;

(r) a variable heavy chain sequence comprising SEQ ID NO: 35 and a variable light chain sequence comprising SEQ ID NO: 36;

(s) a variable heavy chain sequence comprising SEQ ID NO: 37 and a variable light chain sequence comprising SEQ ID NO: 38;

(t) a variable heavy chain sequence comprising SEQ ID NO: 39 and a variable light chain sequence comprising SEQ ID NO: 40;

(u) a variable heavy chain sequence comprising SEQ ID NO: 41 and a variable light chain sequence comprising SEQ ID NO: 42;

(v) a variable heavy chain sequence comprising SEQ ID NO: 43 and a variable light chain sequence comprising SEQ ID NO: 44; or (w) and a variable heavy chain sequence comprising SEQ ID NO: 45 and a variable light chain sequence comprising SEQ ID NO: 46.

In another embodiment, the isolated polynucleotide sequence(s) encodes an antibody or antibody fragment having a light chain and a heavy chain variable region comprising the amino acid sequences of:

(aa) a variable heavy chain sequence comprising SEQ ID NO: 185 and a variable light chain sequence comprising SEQ ID NO: 186;

(bb) a variable heavy chain sequence comprising SEQ ID NO: 187 and a variable light chain sequence comprising SEQ ID NO: 188;

(cc) a variable heavy chain sequence comprising SEQ ID NO: 189 and a variable light chain sequence comprising SEQ ID NO: 190;

(dd) a variable heavy chain sequence comprising SEQ ID NO: 191 and a variable light chain sequence comprising SEQ ID NO: 192;

(ee) a variable heavy chain sequence comprising SEQ ID NO: 193 and a variable light chain sequence comprising SEQ ID NO: 194;

(ff) a variable heavy chain sequence comprising SEQ ID NO: 195 and a variable light chain sequence comprising SEQ ID NO: 196;

(gg) a variable heavy chain sequence comprising SEQ ID NO: 197 and a variable light chain sequence comprising SEQ ID NO: 198;

(hh) a variable heavy chain sequence comprising SEQ ID NO: 199 and a variable light chain sequence comprising SEQ ID NO: 200;

(ii) a variable heavy chain sequence comprising SEQ ID NO: 201 and a variable light chain sequence comprising SEQ ID NO: 202;

(jj) a variable heavy chain sequence comprising SEQ ID NO: 203 and a variable light chain sequence comprising SEQ ID NO: 204;

(kk) a variable heavy chain sequence comprising SEQ ID NO: 205 and a variable light chain sequence comprising SEQ ID NO: 206;

(ll) a variable heavy chain sequence comprising SEQ ID NO: 207 and a variable light chain sequence comprising SEQ ID NO: 208;

(mm) a variable heavy chain sequence comprising SEQ ID NO: 209 and a variable light chain sequence comprising SEQ ID NO: 210;

(nn) a variable heavy chain sequence comprising SEQ ID NO: 211 and a variable light chain sequence comprising SEQ ID NO: 212;

(oo) a variable heavy chain sequence comprising SEQ ID NO: 215 and a variable light chain sequence comprising SEQ ID NO: 216;

(pp) a variable heavy chain sequence comprising SEQ ID NO: 217 and a variable light chain sequence comprising SEQ ID NO: 218; or (qq) a variable heavy chain sequence comprising SEQ ID NO: 219 and a variable light chain sequence comprising SEQ ID NO: 220.

In an alternative embodiment, the isolated polynucleotide sequence(s) encodes an antibody or antibody fragment having a light chain and a heavy chain variable region comprising the amino acid sequences of:

(aa) a variable heavy chain sequence that is 90%, 95%, or 99% identical to SEQ ID NO: 185 and a variable light chain sequence that is 90%, 95%, or 99% identical to SEQ ID NO: 186;

(bb) a variable heavy chain sequence that is 90%, 95%, or 99% identical to SEQ ID NO: 187 and a variable light chain sequence that is 90%, 95%, or 99% identical to SEQ ID NO: 188;

(cc) a variable heavy chain sequence that is 90%, 95%, or 99% identical to SEQ ID NO: 189 and a variable light chain sequence that is 90%, 95%, or 99% identical to SEQ ID NO: 190;

(dd) a variable heavy chain sequence that is 90%, 95%, or 99% identical to SEQ ID NO: 191 and a variable light chain sequence that is 90%, 95%, or 99% identical to SEQ ID NO: 192;

(ee) a variable heavy chain sequence that is 90%, 95%, or 99% identical to SEQ ID NO: 193 and a variable light chain sequence that is 90%, 95%, or 99% identical to SEQ ID NO: 194;

(ff) a variable heavy chain sequence that is 90%, 95%, or 99% identical to SEQ ID NO: 195 and a variable light chain sequence that is 90%, 95%, or 99% identical to SEQ ID NO: 196;

(gg) a variable heavy chain sequence that is 90%, 95%, or 99% identical to SEQ ID NO: 197 and a variable light chain sequence that is 90%, 95%, or 99% identical to SEQ ID NO: 198;

(hh) a variable heavy chain sequence that is 90%, 95%, or 99% identical to SEQ ID NO: 199 and a variable light chain sequence that is 90%, 95%, or 99% identical to SEQ ID NO: 200;

(ii) a variable heavy chain sequence that is 90%, 95%, or 99% identical to SEQ ID NO: 201 and a variable light chain sequence that is 90%, 95%, or 99% identical to SEQ ID NO: 202;

(jj) a variable heavy chain sequence that is 90%, 95%, or 99% identical to SEQ ID NO: 203 and a variable light chain sequence that is 90%, 95%, or 99% identical to SEQ ID NO: 204;

(kk) a variable heavy chain sequence that is 90%, 95%, or 99% identical to SEQ ID NO: 205 and a variable light chain sequence that is 90%, 95%, or 99% identical to SEQ ID NO: 206;

(ll) a variable heavy chain sequence that is 90%, 95%, or 99% identical to SEQ ID NO: 207 and a variable light chain sequence that is 90%, 95%, or 99% identical to SEQ ID NO: 208;

(mm) a variable heavy chain sequence that is 90%, 95%, or 99% identical to SEQ ID NO: 209 and a variable light chain sequence that is 90%, 95%, or 99% identical to SEQ ID NO: 210;

(nn) a variable heavy chain sequence that is 90%, 95%, or 99% identical to SEQ ID NO: 211 and a variable light chain sequence that is 90%, 95%, or 99% identical to SEQ ID NO: 212;

(oo) a variable heavy chain sequence that is 90%, 95%, or 99% identical to SEQ ID NO: 215 and a variable light chain sequence that is 90%, 95%, or 99% identical to SEQ ID NO: 216;

(pp) a variable heavy chain sequence that is 90%, 95%, or 99% identical to SEQ ID NO: 217 and a variable light chain sequence that is 90%, 95%, or 99% identical to SEQ ID NO: 218; or (qq) a variable heavy chain sequence that is 90%, 95%, or 99% identical to SEQ ID NO: 219 and a variable light chain sequence that is 90%, 95%, or 99% identical to SEQ ID NO: 220.

In an alternative embodiment, the isolated polynucleotide sequence(s) encodes an antibody or antibody fragment having a light chain and a heavy chain variable region comprising the amino acid sequences of:

(a) a variable heavy chain sequence that is 90%, 95%, or 99% identical to SEQ ID NO: 1 and a variable light chain sequence that is 90%, 95%, or 99% identical to SEQ ID NO: 2;

(b) a variable heavy chain sequence that is 90%, 95%, or 99% identical to SEQ ID NO: 3 and a variable light chain sequence that is 90%, 95%, or 99% identical to SEQ ID NO: 4;

(c) a variable heavy chain sequence that is 90%, 95%, or 99% identical to SEQ ID NO: 5 and a variable light chain sequence that is 90%, 95%, or 99% identical to SEQ ID NO: 6;

(d) a variable heavy chain sequence that is 90%, 95%, or 99% identical to SEQ ID NO: 7 and a variable light chain sequence that is 90%, 95%, or 99% identical to SEQ ID NO: 8;

(e) a variable heavy chain sequence that is 90%, 95%, or 99% identical to SEQ ID NO: 9 and a variable light chain sequence that is 90%, 95%, or 99% identical to SEQ ID NO: 10;

(f) a variable heavy chain sequence that is 90%, 95%, or 99% identical to SEQ ID NO: 11 and a variable light chain sequence that is 90%, 95%, or 99% identical to SEQ ID NO: 12;

(g) a variable heavy chain sequence that is 90%, 95%, or 99% identical to SEQ ID NO: 13 and a variable light chain sequence that is 90%, 95%, or 99% identical to SEQ ID NO: 14;

(h) a variable heavy chain sequence that is 90%, 95%, or 99% identical to SEQ ID NO: 15 and a variable light chain sequence that is 90%, 95%, or 99% identical to SEQ ID NO: 16;

(i) a variable heavy chain sequence that is 90%, 95%, or 99% identical to SEQ ID NO: 17 and a variable light chain sequence that is 90%, 95%, or 99% identical to SEQ ID NO: 18;

(j) a variable heavy chain sequence that is 90%, 95%, or 99% identical to SEQ ID NO: 19 and a variable light chain sequence that is 90%, 95%, or 99% identical to SEQ ID NO: 20;

(k) a variable heavy chain sequence that is 90%, 95%, or 99% identical to SEQ ID NO: 21 and a variable light chain sequence that is 90%, 95%, or 99% identical to SEQ ID NO: 22;

(l) a variable heavy chain sequence that is 90%, 95%, or 99% identical to SEQ ID NO: 23 and a variable light chain sequence that is 90%, 95%, or 99% identical to SEQ ID NO: 24;

(m) a variable heavy chain sequence that is 90%, 95%, or 99% identical to SEQ ID NO: 25 and a variable light chain sequence that is 90%, 95%, or 99% identical to SEQ ID NO: 26;

(n) a variable heavy chain sequence that is 90%, 95%, or 99% identical to SEQ ID NO: 27 and a variable light chain sequence that is 90%, 95%, or 99% identical to SEQ ID NO: 28;

(o) a variable heavy chain sequence that is 90%, 95%, or 99% identical to SEQ ID NO: 29 and a variable light chain sequence that is 90%, 95%, or 99% identical to SEQ ID NO: 30;

(p) a variable heavy chain sequence that is 90%, 95%, or 99% identical to SEQ ID NO: 31 and a variable light chain sequence that is 90%, 95%, or 99% identical to SEQ ID NO: 32;

(q) a variable heavy chain sequence that is 90%, 95%, or 99% identical to SEQ ID NO: 33 and a variable light chain sequence that is 90%, 95%, or 99% identical to SEQ ID NO: 34;

(r) a variable heavy chain sequence that is 90%, 95%, or 99% identical to SEQ ID NO: 35 and a variable light chain sequence that is 90%, 95%, or 99% identical to SEQ ID NO: 36;

(s) a variable heavy chain sequence that is 90%, 95%, or 99% identical to SEQ ID NO: 37 and a variable light chain sequence that is 90%, 95%, or 99% identical to SEQ ID NO: 38;

(t) a variable heavy chain sequence that is 90%, 95%, or 99% identical to SEQ ID NO: 39 and a variable light chain sequence that is 90%, 95%, or 99% identical to SEQ ID NO: 40;

(u) a variable heavy chain sequence that is 90%, 95%, or 99% identical to SEQ ID NO: 41 and a variable light chain sequence that is 90%, 95%, or 99% identical to SEQ ID NO: 42;

(v) a variable heavy chain sequence that is 90%, 95%, or 99% identical to SEQ ID NO: 43 and a variable light chain sequence that is 90%, 95%, or 99% identical to SEQ ID NO: 44; or (w) a variable heavy chain sequence that is 90%, 95%, or 99% identical to SEQ ID NO: 45 and a variable light chain sequence that is 90%, 95%, or 99% identical to SEQ ID NO: 46.

The polynucleotide(s) that comprise a sequence encoding an anti-CLDN18.2 antibody or antibody fragment thereof can be fused to one or more regulatory or control sequence, as known in the art, and can be contained in suitable expression vectors or host cells as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single-chain antibody.

For recombinant production, a polynucleotide encoding the antibody is inserted into a replicable vector for cloning (amplification of the DNA) or for expression. Many suitable vectors for expressing the recombinant antibody are available. The vector components generally include but are not limited to, one or more of the following: a signal sequence, an origin of replication, one or more marker genes, an enhancer element, a promoter, and a transcription termination sequence.

The anti-CLDN18.2 antibodies or antibody fragments thereof can also be produced as fusion polypeptides, in which the antibody or fragment is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-CLDN18.2 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the anti-CLDN18.2 antibody.

Expression and cloning vectors contain a nucleic acid sequence that enables the vector to replicate in one or more selected host cells. Generally, in cloning vectors, this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2–υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

Antibody-Based Immunotherapy

The goal of antibody-based immunotherapy using tumor-antigen-targeting antibodies is to eliminate cancer cells without harming normal tissue. Therefore, the efficacy and safety of antibody-based immunotherapies in oncology vary depending in large part on the intended mechanism of action, the relevant effector function of the immune system and the nature of the tumor-associated target antigen. The optimal target antigen should be accessible and expressed homogenously and exclusively on the surface of cancer cells. If the intended mechanism of action is antibody-dependent cell-mediated cytotoxicity (ADCC) or complement-mediated cytotoxicity (CDC), then in order to maximize antibody Fc region interactions with components of the complement system or immune effector cells, the antigen-mAb complex should not be rapidly internalized.

A critical feature of monoclonal antibodies is their high specificity and their ability to either directly reduce proliferation and/or induce apoptosis in target tumor cells, or to mark them for immune-effector mediated cell killing (complement-dependent cytotoxicity (CDC), antibody-dependent cellular cytotoxicity (ADCC)) (Kubota, T. et al. (2009) Cancer Sci. 100 (9), 1566-1572). Conjugation to cytotoxic drugs can expand the utility of monoclonal antibodies and improve their potency and effectiveness (Goldmacher, V. S. et al. (2011) Ther. Deliv. 2 (3), 397-416; Sievers, E. L. (2013) Annu. Rev. Med. 64, 15-29).

Antibody-dependent cell-mediated cytotoxicity (ADCC) describes the cell-killing ability of effector cells, which preferably requires the target cell being marked by an antibody. Effector cells may include B cells, T cells, killer cells, NK cells, macrophages, monocytes, eosinophils, neutrophils, polymorphonuclear cells, granulocytes, mast cells, and/or basophils; more specifically effector cells are T cells or NK cells. In certain aspects, ADCC occurs when antibodies bind to antigens on tumor cells, and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

More specifically, there are six structurally distinct types of human Fcγ receptors (FcγRI or CD64, FcγRIIa/CD32a, FcγRIIb/CD32b, FcγRIIc/CD32c, FcγRIIIa/CD16a, and FcγRIIIb/CD16b) expressed on leukocytes of both the myeloid and lymphoid lineage. Fcγ receptors are divided into two types: activating receptors (CD64, CD32a, CD32c, CD16a, and CD16b) that lead to immune cell activation through immunoreceptor tyrosine-based activation motifs (ITAM) on cytosolic tails or on co-receptor molecules, and an inhibitory receptor (CD32b) that signals through immunoreceptor tyrosine-based inhibitory motifs (ITIM).

Single-nucleotide polymorphisms (SNPs) in FCGR2A (H131R) and FCGR3A (V158F) are associated with improved outcomes attributed to a higher antibody binding affinity for human IgG1 and IgG2 therapeutic antibodies which results in increased ADCC activity (Vargas, F. A. et al, Cancer Cell 33: 649-663 (2018), Musolino, A. et al., J. Clin. Oncol. 26: 1789-1796 (2008), Zhang, W. et al, J. Clin. Oncol. 25:3712-3718 (2007), Nordstrom, J. L. et al, Breast Cancer Res. 13:R123 (2011)). The activating CD16A FcγR occurs in two variants, or alleles, with high (158V) or low (158F) affinity for the Fc domain of IgG1. A majority (approximately 85%) of the population carries the 158F genotype, either in the homozygous form or as heterozygous with 158V. Thus, FcgR genotypes most frequently associated with greater beneficial responses occur in a minority of the population. This provides a strong rationale for engineering the Fe domain of therapeutic antibodies developed for the treatment of cancer to better interact with low-binding alleles of activating FcγRs to expand, without regard to FcγR genotype, with the goal of developing therapeutics capable of conferring a benefit to a greater percentage of patients.

A critical step in the activation of cytotoxic cells is the binding of mAbs to FcγRIIIa (CD16A) on immune effector cells, and the strength of this interaction is determined by antibody isotype, the glycosylation pattern of the antibody Fc region and FcγRIIIa polymorphisms. Numerous publications have reported findings that demonstrate the role of FcγR-mediated effector function in antibody-based cancer therapies derived from clinical studies. The study results indicate an association between clinical response (e.g., antibody efficacy) and specific alloforms of activating human FcγRs. Patients that carry the 158F allele have been reported to show diminished clinical responses to certain therapeutic antibodies, including trastuzumab, rituximab, cetuximab, infliximab and ipilimumab and other therapeutic antibodies that utilize ADCC as a major mechanism of action. Antibodies engineered to have improved FcgR binding profiles have been reported to drive superior anti-tumor responses and confer greater clinical benefit.

The discovery of activating and inhibitory FcγRs resulted in translational research efforts focused on designing therapeutic antibodies that were "fit for purpose" based on having FcγR binding activities characterized by an activating/inhibiting (A:I) ratio designed to activate immune effector cells to perform particular functions. Immunotherapy of cancer with monoclonal antibodies (mAb) promotes the elimination of tumor cells by a variety of mechanisms including ADCC, ADCP and/or CDC activities. In practice, the therapeutic activity of several approved mAbs depends on the binding of the Fcγ regions to low-affinity Fcγ receptors expressed on effector cells.

Several publications report the successful use of protein engineering strategies to design variant human IgG1 Fc domains (CH regions) with optimized FcgR binding profiles and activating/inhibiting (A:I) ratios suitable to optimize cell-mediated effector functions. In particular, efforts have focused on increasing the affinity of the Fc domain for the low-affinity receptor FcγIIIa. A number of mutations within the Fc domain have been identified that either directly or indirectly enhance binding of Fc receptors and as a result significantly enhance cellular cytotoxicity (Lazar, G. A. PNAS 103:4005-4010 (2006), Shields, R. L. et al, J. Biol. Chem. 276:6591-6604 (2001) Stewart, R. et al., Protein Engineering Design and Selection 24: 671-678 (2011)). Researchers at Genentech identified the mutations S239D/A330L/I332E, MedImmune identified the mutation F243L (Stewart et al) and Xencor identified G236A (Richards, J. O. et al, Mol. Cancer Ther. 7:2517-2575 (2008)).

Several different companies, including, Xencor, Applied Molecular Evolution, Medimmune, Genentech and Macrogenics have described antibody variants, comprising at least one amino acid modification relative to a wild-type Fc region, wherein the variant Fc region binds FcγRIIIA and/or FcγRIIA with a greater affinity, relative to a comparable molecule comprising the wild-type Fc region. Xencor has developed the Xmab platform technology and published results of IgG1 Fc variants comprising S239D/I332E point mutations and S239D/A330L/I332E as optimized Fc variants with desirable A:J ratios. Applied Molecular Evolution has identified IgG variants comprising P247I and A339Q point mutations. Macrogenics has described variant human IgG1 Fc regions comprising mutations at V305I, F243L, R292P, Y300L, and P396L (variant 18) (Stavenhagen, J. B. et al, Cancer Res. 67:8882-8990 (2007)) or L235V, F243L, R292P, Y300L, and P396L (Nordstrom, J. L. et al, Breast Cancer Res. 13:R123 (2011)).

Nordstrom et al. reported that response to trastuzumab (HERCEPTIN™) in metastatic breast cancer correlates with the expression of the high binding variant (158V) of the activating Fcγ receptor CD16A. Using a chimeric anti-HER2 monoclonal antibody MGAH22 (with specificity and affinity similar to trastuzumab) that comprised a human IgG1 Fc domain engineered for increased binding to both alleles of human CD16A, Nordstrom demonstrated that the engineered Fc domain conferred enhanced ADCC against all HER2-positive tumor cells tested, including cells resistant to trastuzumab's anti-proliferative activity or expressing low HER2 levels. The greatest improvement occurs with effector cells isolated from donors homozygous or heterozygous for CD16A-158F, the low-binding allele.

The Fc variations incorporated into MGHA22 were incorporated into the clinical-stage antibody product candidate margetuximab which has been engineered to have an increased ability to bind to the activating Fc-γ receptor (CD16A) and a decreased ability to bind to the Fc-γ inhibitory receptor CD32B on immune effector cells. Macrogenics has recently published preliminary data from the first randomized Phase 3 study that was designed to examine the potential benefit of Fc modification and the role of Fc-gamma receptor genotypes on anti-HER2 antibody efficacy. The SOPHIA study (NCT02492711) is a randomized, open-label Phase 3 clinical trial evaluating margetuximab plus chemotherapy compared to trastuzumab plus chemotherapy in patients with HER2-positive metastatic breast cancer. The study met its first sequential primary endpoint of progression-free survival (PFS). The median PFS of patients treated with margetuximab and chemotherapy was 5.8 months compared to 4.9 months in patients treated with trastuzumab and chemotherapy. At the time of the primary PFS analysis, overall survival (OS) data based on 158 events were immature. The median OS at that time was prolonged by 1.7 months in patients treated with margetuximab and chemotherapy compared to patients treated with trastuzumab and chemotherapy. For the exploratory subpopulation of patients carrying the CD16A 158F allele, the median OS was prolonged by 6.8 months in the margetuximab arm compared to the trastuzumab arm (Macrogenics Press Release).

Glycoengineering strategies have also been used to develop therapeutic antibodies with optimized effector functions tailored to the treatment of cancer. It is known that FcγRs interact with the carbohydrates on the CH2 domain and that the composition of these glycans has a substantial effect on effector function activity. A highly conserved glycan at position 297 in the Fc-region infers structural changes to the Fc-region required for binding to the Fcγ receptor. Subtle differences in the glycan composition at this site can affect the Fc-structure and may also alter the interaction with Fcγ R by direct contact. Perhaps the best example of this is non-fucosylated antibodies that exhibit increased binding to CD16A and exhibit greatly enhanced ADCC activity (Niwa, R et al, Clin. Cancer Res. 10:6248-6255 (2004), Ferrara, C. et al, J. Biol. Chem 281:5032-5036 (2006)).

The efficacy of therapeutic antibodies is critically dependent on appropriate posttranslational modifications. In particular, glycosylation of the antibody Fc is essential for Fc receptor-mediated activity. Among the effector functions of antibody therapeutics, ADCC has been identified clinically as an important mechanism of anti-cancer antibodies. It is well known in the art that the absence of IgG-Fc core fucose vastly increases binding to Fcγ RIIa (CD16a) and results in higher ADCC potency (e.g., lower EC50), a finding that has been successfully used to improve the efficacy of therapeutic antibodies. Glycoengineering strategies include producing antibodies under conditions that will provide low or no fucosylation (e.g., non-fucosylated mAb) in order to enhance ADCC by increasing FcGRIIIa binding.

One of skill in the art will acknowledge that BioWa/Kyowa Hakko Kirin and GlycArt/Roche, have each developed proprietary cell lines that yield defucosylated antibodies. To achieve this result, BioWa/Kyowa Kirin Hakko established α-1,6-fucosyltransferase (FUT8) enzyme knockout Chinese hamster ovary cell line (POTELLIGENT® technology), while GlycArt/Roche chose to over-express heterologous β-1,4-N-acetylglucosaminyltransferase III in antibody-producing cells (GlycoMab™ technology, U.S. Pat. No. 6,602,684).

Glycoengineered antibodies with improved ADCC activities have been approved by the Food and Drug Administration (FDA) and are currently marketed in the United States, including mogamulizumab (POTELIGEO™), obinutuzumab (GAZYVA™) and benralizumab (FASENRA™). Mogamulizumab is an afucosylated anti-CCR4 antibody that is produced in a cell line with a mutation in the FUT8 (a-1,6-fucosyltransferase) gene using the POTELLIGENT™ technology platform developed by Biowa. In mammals, most core-fucosylation on N-glycans is formed by α-1,6 linkage. FUT8 is the only α-1,6 fucosyltransferase that catalyzes the transfer of fucose residues from GDP-fucose to the innermost GlcNAc of the tri-mannosyl core structure via the α-1,6 linkage. Benralizumab is an anti-IL5 receptor antibody that is also manufactured using the POTELLIGENT™ technology platform and has been reported to be capable of inducing a >1000-fold amplification of antibody-dependent cell mediated ADCC (Pelaia, C et al, BioMed Research Int., Article ID 4839230 (2018).

Obinutuzumab is a type II anti-CD20 mAb characterized by having a low fucose content as a consequence of the addition of a B-1,4-N-acetylglucosaminyl-transferase (GnIII) gene in the production cell line (Glycart GLYCO-MAB™ technology). The modification has the effect of adding bisecting N-acetylglucosamine (GlcNac) to the N-glycan structures, the presence of which interferes with fucosylation leading to the production of highly enriched bisected non-fucosylated glycosylation variants. The glyco-engineering strategy used to manufacture obinutuzumab confers a unique mechanism of action that relies on enhanced ADCC and ADCP, with reduced reliance on the primary mechanism of action used by two other anti-CD20 antibodies (Rituximab and ofatumumab) that rely primarily on CDC (Tobinai, K et al, Adv. Ther. 34(2): 324-356 (2017)). A person skilled in the art will also recognize that it is possible to produce antibodies with low fucose content by using a decoy substrate of glycosyltransferases, such as 2-deoxy-2-fluoro-1-fucose (2FF,) or a fucosyltransferase inhibitor such as 2F-peracetyl-fucose to cause reduced incorporation of fucose in the glycan of antibodies expressed in mammalian cells (Dekkers, G, et al, Scientific Reports 6, article number 36964 (2016)). It has been reported that antibodies produced using fucosyltransferase inhibitor showed a significant decrease in the relative percentage of fucosylated glycan species (G0f, G1f, and G2f) and that the percentage of fucosylation can be decreased from 86% to 19% in the presence of the inhibitor (Ho, D. et al. Fucosylation of a Therapeutic Antibody: Effects on Antibody-dependent Cell-mediated cytotoxicity (ADCC) Potency and Efficacy, Bioprocess International, Apr. 12, 2016).

Complement-dependent cytotoxicity (CDC) is another cell-killing method that can be directed by antibodies. IgM is the most effective isotype for complement activation, but IgG1 and IgG3 are also both very effective at directing CDC via the classical complement activation pathway.

In some aspects, antibodies described herein are used in combination with or are conjugated to, a therapeutic moiety or agent, such as a cytotoxin, a drug, or a radioisotope. In certain aspects, an antibody described herein is used in combination with a chemotherapeutic agent. In certain aspects, an antibody-drug conjugate (ADC) comprises an antibody described herein conjugated (e.g., covalently attached) to a therapeutic moiety or agent.

Examples of therapeutic agents that may be used in conjugation with an antibody, include antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). In certain aspects, the therapeutic agent is a cytotoxic agent or a radiotoxic agent. In another aspect, the therapeutic agent is a photosensitizing agent, suitable for use in photodynamic therapy, such as porfimer sodium. In some aspects, the therapeutic agent is an immunosuppressant. In some aspects, the therapeutic agent is GM-CSF. In some aspects, the therapeutic agent is doxorubicin, cisplatin, bleomycin, sulfate, carmustine, chlorambucil, cyclophosphamide or ricin A.

Examples of a cytotoxin or cytotoxic agent include any agent that is detrimental to and, in particular, kills cells, such as taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In some aspects, an antibody described herein can be conjugated to a radioisotope, such as iodine-131, yttrium-90 or indium-111, to generate cytotoxic radiopharmaceuticals for treating a CLD18-related disorder, such as cancer.

Techniques for conjugating a therapeutic moiety to antibodies are well known to those of skill in the art, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

In some embodiments, ADCs are designed to kill cancer cells in a target-dependent manner. The first step in this process is the binding of the antibody to its antigen. Upon ADC binding, the entire antigen-ADC complex is internalized and the cytotoxic payload is released into the tumor cell resulting in cell death. Factors that influence the therapeutic index for ADCs include the tumor specificity of the targeting antibody, the expression level of the tumor target antigen, the cytotoxic drug and the linker (Panowksi, S. et al. (2014) MAbs 6 (1), 34-45). If the intended mechanism of action of a therapeutic antibody is downregulation of the tumor-associated antigen, or if the antibody is an ADC designed to deliver a toxin into the cancer cell then internalization is a desirable characteristic of the antibody used to deliver the toxic payload to the targeted tumor cell.

In some aspects, an ADC comprises any agent that exerts a therapeutic effect on cancer cells and an anti-CLDN18.2 antibody or derivative thereof as described herein. Conjugation of the drug does not alter or significantly alter the binding characteristics, in particular, the specificity of the antibody. In certain aspects, the drug is a cytotoxic or cytostatic agent (e.g., any agent that is detrimental to and/or kills cancer cells). Examples of classes of such cytotoxic agents include anti-tubulin agents, DNA minor groove binders (e.g., enediynes and lexitropsins), DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, nitrosoureas, platinols, pre-forming compounds, purine antimetabolites, puromycins, radiation sensitizers, steroids, taxanes (e.g., paclitaxel and docetaxel), topoisomerase inhibitors, vinca alkaloids, or the like. Additional examples of such cytotoxic agents are described in US Publication No. 2018/0117174.

The generation of antibody-drug conjugates can be accomplished by any technique known to the skilled artisan. Antibody-drug conjugates can be prepared by binding the drug to an antibody in accordance with a conventional technique. An antibody and a drug may be directly bound to each other via their own linker groups or indirectly via a linker or other substance. Examples of linkers that may be used in forming an ADC are described in US Publication No. 2018/0117174.

One example of an anti-CLDN18.2 antibody being used in immunotherapy is iMAb362, a chimeric IgG1 monoclonal antibody, specific for an epitope in the first extracellular domain of CLDN18.2. iMAb362, its murine parental antibody, and other anti-CLDN18-specific antibodies are disclosed in patents and patent applications belonging to the WO2007/059997, WO2014/075788, and WO2016/166122 patent families.

Preclinically, iMAb362 was shown to inhibit tumor growth and to kill cancer cells by both indirect (complement-dependent cytotoxicity, antibody-dependent cellular cytotoxicity) and direct (antiproliferative and proapoptotic effects) mechanisms of action. Astellas Pharma has published reports indicating that preclinical characterization of iMAb362 antibody-drug conjugate (ADC) comprising the antimitotic drug monomethyl auristatin E, with a valine-citrulline linker (iMAb-vcMMAE) is ongoing (Kreuzberg, M et al, Annals of Oncology 28(5) v122-v141, abstract 377P, WO2016/165762).

The phase IIb FAST trial enrolled patients with advanced or recurrent gastric or gastroesophageal junction adenocarcinoma (NCT01630083). Eligibility for enrollment required patients to have CLDN18.2-positive tumors (i.e., $2^+/3^+$ intensity in $\geq 40\%$ of tumor cells by immunohistochemistry). The trial evaluated the role of iMAb362 in combination with chemotherapy versus chemotherapy alone in a first-line setting. According to the final results, the addition of antibody iMAB362 to chemotherapy (EOX, epirubicin, oxaliplatin and capecitabine) increased the median overall survival by five months (8.4 vs 13.2 months, P=0.0001) in patients with advanced gastric, esophageal or gastroesophageal junction adenocarcinoma (Schuler, M et al., Annals of Oncology, 27 (6): vi207-vi242, abstract 6140 (2016)). The combination therapy also significantly improved progression-free survival and response rate. Reports indicate that when the results are stratified by CLDN18.2 expression levels, the best outcomes were seen among the high expressers ($\geq 2^+$ intensity in $\geq 70\%$) whose median overall survival was 9.0 months vs. 16.7 months, P<0.0005). The results confirm that the addition of an anti-CLDN18.2 antibody to first-line chemotherapy provides a clinically relevant benefit in patients with advanced/recurrent gastric cancer.

Compositions and Methods of Treatment

The disclosure also provides compositions including, for example, pharmaceutical compositions that comprise an anti-CLDN18.2 antibody or antibody fragment thereof. Such compositions have numerous therapeutic uses for the treatment of diseases or disorders (e.g., diseases or disorders involving cells expressing CLDN18.2). In some aspects, the compositions described herein are administered to patients, e.g., in vivo, to treat or prevent a disease associated with dysregulated expression of CLDN18.2. Preferred patients include human patients having an epithelial cell-derived primary or metastatic cancer.

The antibodies can be administered either alone or in combination with other compositions that are useful for treating an immune-mediated inflammatory disorder or an autoimmune disease. In some embodiments, compositions including, for example, pharmaceutical compositions, comprising the anti-CLDN18.2 antibody can further comprise a therapeutic agent, either conjugated or unconjugated to the anti-CLDN18.2 antibody or antibody fragment.

In some aspects, the present invention provides a composition, e.g., a pharmaceutical composition, containing one or more antibodies of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In some aspects, the pharmaceutical composition is administered to a subject to treat cancer.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of the active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A composition of the present invention can be administered by a variety of methods known in the art. As will be appreciated by the skilled artisan, the route and/or mode of administration will vary depending upon the desired results. The active compounds can be prepared with carriers that will protect the compound against rapid releases, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

Dosage levels of the active ingredients in the pharmaceutical compositions may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions described herein may be administered in effective amounts. An "effective amount" refers to the amount which achieves a desired reaction or the desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease.

In some aspects, the treatment of cancer represents a field where combination strategies are especially desirable since frequently the combined action of two, three, four or even more cancer drugs/therapies generates synergistic effects which are considerably stronger than the impact of a monotherapeutic approach. The agents and compositions (e.g., pharmaceutical compositions) provided herein may be used alone or in combination with conventional therapeutic regimens such as surgery, irradiation, chemotherapy and/or bone marrow transplantation (autologous, syngeneic, allogeneic or unrelated). The agents and compositions may also be used in combination with one or more of cytokines, chemokines, costimulatory molecules, or fusion proteins, bacterial treatments, kinase inhibitors, toll-like receptors, angiogenesis inhibitors, small molecule targeted therapy drugs, virus-based vaccines, multi-epitope strategies, adoptive T cell transfer, and peptide-based target therapies. See U.S. Pat. No. 10,093,736. Thus, in another embodiment of the present invention, a cancer treatment may be effectively combined with various other drugs.

In some aspects, the agents and compositions described herein are administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by dysregulated CLDN18.2 expression.

For example, in one embodiment, the agents and compositions described herein can be used to treat a patient with a cancer disease, e.g., a cancer disease such as described herein characterized by the presence of cancer cells expressing CLDN18.2. In some aspects, a cancer disease is gastric cancer, esophageal cancer, pancreatic cancer, lung cancer, ovarian cancer, colon cancer, hepatic cancer, head-neck cancer, cancer of the gallbladder, or metastases thereof.

In an embodiment of the provided treatment method, the subject in need of therapy is also administered a therapeutic agent selected from the group consisting of an antineoplastic agent, a chemotherapeutic agent, a growth inhibitory agent, a cytotoxic agent, and an immune checkpoint inhibitor.

In an embodiment of the provided treatment methods, an antibody, antibody fragment, or bispecific antibody comprising an anti-CLDN18.2 binding agent of the present invention is co-administered with a chemotherapeutic agent, which may be a cytotoxic agent. For example, epitubicin, oxaliplatin, and/or 5-FU can be administered to patients receiving anti-Claudin 18.2 therapy.

The combination of therapeutic agents discussed herein can be administered concurrently as components of a bispecific or multispecific binding agent or fusion protein or as a single composition in a pharmaceutically acceptable carrier. Alternatively, a combination of therapeutics can be administered concurrently as separate compositions with each agent in a pharmaceutically acceptable carrier. In another embodiment, the combination of therapeutic agents can be administered sequentially.

In one embodiment, the treatment method of the invention further comprises administering an agent capable of stabilizing or increasing expression of Claudin 18.2 at the cell surface of a cancer cell. For example, an agent stabilizing or increasing expression of Claudin 18.2 may be oxaliplatin and/or 5-FU.

In some aspects, conventional viral and non-viral based gene transfer methods can be used to introduce nucleic acids encoding the antibodies or derivatives thereof, as described herein, in mammalian cells or target tissues. Such methods can be used to administer nucleic acids encoding the antibodies to cells in vitro. In some embodiments, the nucleic acids encoding the antibodies or derivatives thereof are administered for in vivo or ex vivo gene therapy uses. In other embodiments, gene delivery techniques are used to study the activity of the antibodies in cell-based or animal models. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the disclosure include lipofection, microinjection, biolistics, virosomes, liposomes, immunoliposomes, polycation or lipid: nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid: nucleic acid complexes, including targeted liposomes such as immunolipid complexes, is well known to one of skill in the art.

The use of RNA or DNA viral based systems for the delivery of nucleic acids encoding the antibodies described herein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the disclosure could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene.

Additionally, high transduction efficiencies have been observed in many different cell types and target tissues.

All patents and publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The broad scope of this disclosure is best understood with reference to the following examples, which are not intended to limit the disclosures to the specific embodiments. The specific embodiments described herein are offered by way of example only, and the disclosure is to be limited by the terms of the appended claims, along with the full scope of the equivalents to which such claims are entitled.

EXAMPLES

General Methods

Methods for protein purification including immunoprecipitation, chromatography, and electrophoresis are described. Coligan et al. (2000) Current Protocols in Protein Science, Vol. 1, John Wiley and Sons, Inc., New York. Chemical analysis, chemical modification, post-translational modification, production of fusion proteins, and glycosylation of proteins are described. See, e.g., Coligan et al. (2000) Current Protocols in Protein Science, Vol. 2, John Wiley and Sons, Inc., New York; Ausubel et al. (2001) Current Protocols in Molecular Biology, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391. Production, purification, and fragmentation of polyclonal and monoclonal antibodies are described. Coligan et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra.

Hybridoma supernatant was purified via HiTrap protein G column (GE, cat. No. 17040401) according to the manufacturer's procedures. Briefly, hybridoma supernatant was equilibrated with DPBS (Gibco, cat. No. 14190-136) for 5 CV and loaded via syringe/infusion pump (Legato 200, KDS) at ambient temperature and 3 minute residence time. The column was washed with 5 CV of DPBS and elution was performed with 4 CV of pH 2.8 elution buffer (Fisher Scientific, cat. No. PI21004). Elution was fractionated, and fractions were neutralized with 1M Tris-HCL, pH 8.5 (Fisher Scientific, cat No. 50-843-270) and assayed by A280 (DropSense96, Trinean). Peak fractions were pooled, and buffer exchanged into DPBS. Centrifugal filters (EMD Millipore, cat. No. UFC803024) were equilibrated in DPBS at 4,000×g for 2 mins. Purified sample was loaded, DPBS was added and the sample was spun at 4,000×g for 5-10 minute spins until total DPBS volume reached ≥6 DV. The final pool was analyzed by A280.

Standard methods in molecular biology are described. Maniatis et al. (1982) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif. Standard methods also appear in Ausbel et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Stable cell lines expressing CLDN18.2 or CLDN18.1 were generated by transfecting a selected host cell (i.e., CHO-K1, NIH/3T3 or HEK293 cells, all purchased from ATCC) with pcDNA3.1-based plasmids expressing *Homo sapiens* claudin18, transcript variant 2 (CLDN18.2) or *Homo sapiens* claudin18, transcript variant 1 (CLDN18.1) using lipid-based transfection using Lipofectamine 3000 (Invitrogen, cat #L3000015).

Expression was confirmed using appropriate antibodies 24 h and 48 h after transfection using flow cytometry to assay for surface expression. Antibiotic selection was used to select the integrated cell, after 7-10 days of geneticin selection limiting dilution was performed on the surviving cells in 96-well plate while keeping the transfectants under selection pressure (Geneticin).

After 10-14 days, single colonies were picked up for screening using flow cytometry with CLDN18.2 or CLDN18.1-specific antibodies (CLDN18.2 in-house version of a positive control antibody synthesized using publicly available sequence information for a monoclonal antibody reported in US 2018/0117174 as being specific for CLDN18.2 (and not specific for CLDN18.1) (referred to herein as a "positive control" antibody); CLDN18.1 Claudin 18 polyclonal antibody (Invitrogen, cat #38-8000)). The top 3-5 highly expressed clones were chosen for further development. After a couple of passages, the expression level was confirmed by flow cytometry and image assay to make sure it is stable. Specific gene expression was also confirmed by PCR.

The sequences for the heavy and light chain variable regions for hybridoma clones were determined as described below. Total RNA was extracted from 1-2×10⁶ hybridoma cells using the RNeasy Plus Mini Kit from Qiagen (Germantown, Md., USA). cDNA was generated by performing 5' RACE reactions using the SMARTer RACE 5'/3' Kit from Takara (Mountainview, Calif., USA). PCR was performed using the Q5 High-Fidelity DNA Polymerase from NEB (Ipswitch, Mass., USA) to amplify the variable regions from the heavy and light chains using the Takara Universal Primer Mix in combination with gene-specific primers for the 3' mouse constant region of the appropriate immunoglobulin. The amplified variable regions for the heavy and light chains were run on 2% agarose gels, the appropriate bands excised and then gel purified using the Mini Elute Gel Extraction Kit from Qiagen. The purified PCR products were cloned using the Zero Blunt PCR Cloning Kit from Invitrogen (Carlsbad, Calif., USA), transformed into Stellar Competent *E. coli* cells from Takara and plated onto LB Agar+50 ug/ml kanamycin plates. Direct colony Sanger sequencing was performed by GeneWiz (South Plainfield, N.J., USA). The resulting nucleotide sequences were analyzed using IMGT V-QUEST to identify productive rearrangements and analyze translated protein sequences. CDR determination was based on IMGT numbering.

Methods for flow cytometry, including fluorescence-activated cell sorting detection systems (FACS®), are available. See, e.g., Owens et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) Catalogue, Molecular Probes, Inc., Eugene, Oreg.; Sigma-Aldrich (2003) Catalogue, St. Louis, Mo.

The in-house positive control CLDN18.2-specific antibody zolbetuximab (formerly designated claudiximab) referred to herein as "PC1", was made by a CRO based on the public information for their VH and VL sequences (VH sequence: SEQ ID NO: 32 of US 2018/0117174; VL sequence: SEQ ID NO: 39 of US 2018/0117174). The PC1 antibody was used to confirm CLDN18.2 expression by the transfectant and tumor cell lines used in the examples and to establish the binding and functional assays used to evaluate and characterize the anti-CLDN18.2-specific antibodies disclosed herein.

Briefly, plasmids containing the control and benchmark antibody sequences were transfected using the ExpiCHO™ Expression System (Catalog Number: A29133, ThermoFisher Scientific, USA) according to the manufacturer's protocol. The cells were cultured at 37° C. and 8% $CO_2$ on day 1 and then at 32° C. and 5% $CO_2$ post-transfection in media provided in the kit. Antibodies were purified by clarifying the ExpiCHO™ culture medium by centrifugation at 1,000 g for 10 min followed by 5,000 g for 30 min. The supernatant was then filtered using a 0.45μηι filter followed by a 0.22μηι filter. Subsequently, the supernatant was subjected to affinity purification using protein A/G resins (Life Technologies, Carlsbad, Calif.; Catalog #20424) according to the manufacturer's protocol. Prior to ELISA purification, antibody titer in the culture medium was roughly determined to ensure the amount of medium loaded occupied less than 80% of the resin binding capacity. After incubation, the resins were washed with PBS and eluted with Elution Buffer (Life Technologies, Catalog #21004). The elution fractions were immediately adjusted to physiologic pH by adding Tris Buffer, pH 8.0. The purified antibodies were subsequently subjected to buffer exchange and protein concentration using Amicon Ultra-15 Centrifugal Filter Unit (Life Technologies, Catalog #UFC900324) in PBS buffer. Antibody concentration was determined by BCA Protein Assay. SDS-PAGE and Coomassie-staining were carried out to test the antibody purity. The purified protein was aliquoted and stored at −80° C. for long-time storage or kept at 4° C. for immediate use.

The integrity of the antibody was validated by SDS-PAGE followed by Coomassie staining under non-reducing vs reducing conditions; under non-reducing conditions, one dominating band around 150 kDa, whereas under reducing conditions, two bands were observed, 50 kDa and 25 kDa.

Standard techniques for characterizing ligand/receptor interactions are available. See, e.g., Coligan et al. (2001) Current Protocols in Immunology, Vol. 4, John Wiley, Inc., New York. Standard methods of antibody functional characterization appropriate for the characterization of antibodies with particular mechanisms of action are also well known to those of skill in the art.

Software packages and databases for determining, e.g., antigenic fragments, leader sequences, protein folding, functional domains, CDR annotation, glycosylation sites, and sequence alignments, are available.

Example 1: Generation of Anti-CLDN18.2 Antibodies

Mouse anti-Claudin 18.2 antibodies were generated by immunizing Balb/c mice with HEK293 cells transfected with the human Claudin 18.2 gene.

Human anti-Claudin 18.2 antibodies were generated by immunizing human Ig transgenic mice, Trianni mouse strain (WO2013/063391) with HEK293 cells transfected with human Claudin 18.2 gene.

Mice (Balb/c or human Ig transgenic) were immunized with either intraperitoneally (IP) or subcutaneously (SC). The immune response was monitored by retroorbital bleeds. The plasma was screened by FACS or Imaging (as described below), and mice with sufficient titers of anti-claudin 18.2 were used for fusions. Mice were boosted intraperitoneally or intravenously with the immunogens before sacrifice and removal of the spleen and lymph nodes.

To select Balb/c or human Ig transgenic mice producing antibodies that bound Claudin 18.2, sera from immunized mice were screened by flow cytometry (FACS) for binding to a cell line expressing claudin 18.2 (CHO, HEK293 or 3T3-claudin 18.2 cell lines) and not to control cell line that does not express claudin 18.2. Briefly, claudin 18.2-CHO (HEK or 3T3 cells) were incubated with dilutions of serum from immunized mice. Cells were washed, and specific antibody binding was detected with PE-labeled anti-mouse IgG Ab. Flow cytometric analysis was performed on a flow cytometry instrument (Intellicyte, IQue plus, Sartorius). In addition, mice serum was tested by Imaging. Briefly, claudin 18.2-Cho (HEK or 3T3 cells) were incubated with dilutions of serum from immunized mice. Cells were washed, fixed with paraformaldehyde, washed, specified antibody binding was detected with secondary Alexa488 goat anti-mouse antibody and Hoechst (Invitrogen, Calsbad, Calif.). Plates were scanned and analyzed on an imaging machine (Cytation 5, Biotek, Winooski, Vt.). Hybridoma supernatants were tested for anti-claudin 18.2 specific binding by FACS and Imaging as described above.

To generate hybridomas producing human and mouse antibodies of the invention, splenocytes and lymph node cells were isolated from an immunized mouse and fused to an appropriate immortalized cell line, such as a mouse myeloma cell line. The resulting hybridomas were screened for the production of antigen-specific antibodies. For example, single-cell suspensions of splenocytes, lymph node cells from immunized mice were fused to the equal number of Sp2/0 non-secreting mouse IgG myeloma cells (ATCC, CRL 1581) by electrofusion. Cells were plated in flat-bottom 96-well tissue culture plates, followed by 2 weeks of incubation in the selection medium (HAT medium), then switched to hybridoma culture media. Approximately 10-14 days after cell plating, supernatants from individual wells were screened by FACS or Imaging as described above. The antibody-secreting hybridomas were transferred to 24-well plates, screened again, and if still positive for anti-claudin 18.2, the positive hybridomas were subcloned by limiting dilution or sorting using a single cell sorter. The stable subclones were then cultured in vitro to generate small amounts of antibodies to be used for purification and for characterization.

Example 2: Specificity of Anti-Claudin18.2 Antibodies

The binding specificity of the anti-claudin antibodies was evaluated using an immunofluorescence imaging assay.

The specific cellular binding affinity of anti-Claudin18.2 antibodies was tested on CHO-CLDN18.2 (transfected CHO cell expressing recombinant human CLDN18.2) and CHO-CLDN18.1 (transfected CHO cell expressing recombinant human CLDN18.1) cells. The cells were plated in complete media containing F12 with 10% FBS, then incubated overnight at 37° C., anti-Claudin18.2 antibodies were serial diluted and added to the assay plates, incubated at 4° C. for 2 hours, followed by fixing cells and further staining the cells for 30 minutes with Alexa Fluor® 488 Goat Anti-Human IgG (H+L) secondary antibody, invitrogen Cat #A-11013 for detection. The binding was assessed by imaging the cells and quantifying the fluorescence intensity using a Biotek Cytation.

Figure 3A:
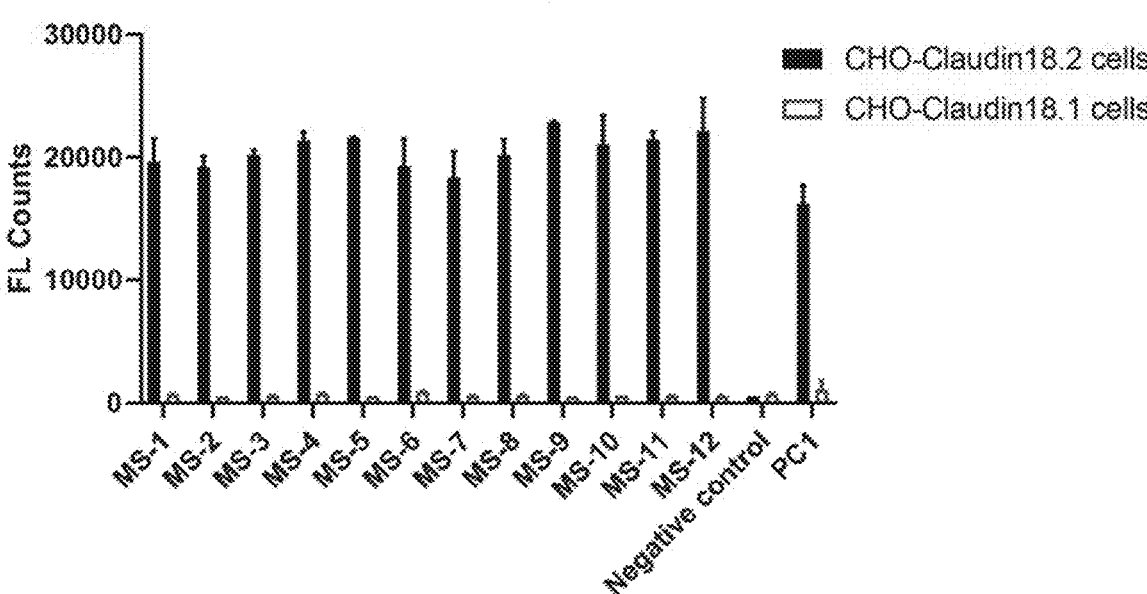
Figure 3B:
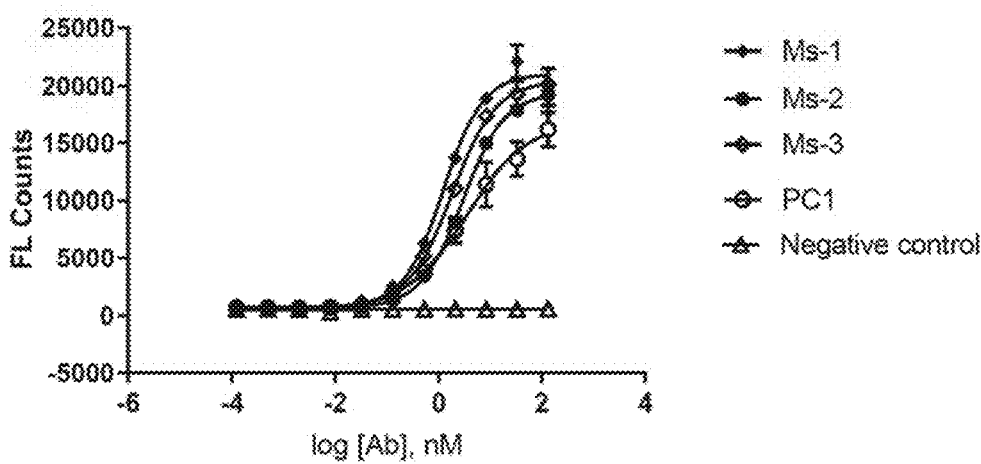

As demonstrated in FIG. 3A, the group of purified murine anti-Claudin 18.2 antibodies binds to the CHO-CLDN18.2 cells, but not the CHO-CLDN18.1 cells when using 10 μg/ml of antibodies in the study, FIG. 3B shows the representative data of dose-dependent binding of Ms-1, Ms-2 and Ms-3 to CHO-CLDN18.2 cells with EC50 values of 1.2 nM, 2.8 nM, and 1.8 nM respectively. The control Ab PC1 has an EC50 value of 3.2 nM, consistent with literature reports. The negative control antibody doesn't bind to the CHO-CLDN18.2 cells.

Figure 3C:
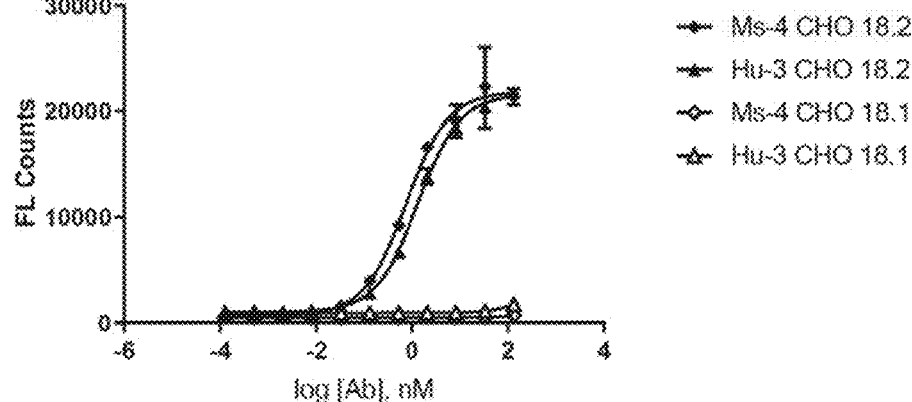

The binding affinity of lead panel antibodies was also tested in a CHO CLDN18.1 cell line stably expressing Claudin18.1. None of the antibodies showed active binding activity at the highest testing concentration of 133.4 nM. Data from representative clones are shown in FIG. 3C. Both clones Ms-4 and Hu-3 exhibited dose-dependent binding to CHO-CLDN18.2 cells with EC50 values of 0.75 nM and 1.34 nM, while not binding to CHO-CLDN18.1 cell.

The complete set of dose-dependent binding data of the murine anti-Claudin18.2 lead panel is summarized in Table 5. The group of purified murine anti-Claudin 18.2 antibodies binds to the CHO-CLDN18.2 cells with EC50 values ranging from 0.8-3.3 nM.

TABLE 5

| Specificity of Murine anti-CLDN18.2 Antibodies | | |
| mAb | CHO-18.2 binding, EC50 nM | PATU8988S binding |
| --- | --- | --- |
| Ms1 | 1.2 | +++ |
| Ms2 | 3.0 | ++ |
| Ms3 | 1.8 | +++ |
| Ms4 | 0.8 | ++++ |
| Ms5 | 1.7 | +++ |
| Ms6 | 1.2 | +++ |
| Ms7 | 1.4 | +++ |
| Ms8 | 1.5 | +++ |
| Ms9 | 1.5 | +++ |
| Ms10 | 1.3 | +++ |
| Ms11 | 3.3 | ++ |
| Ms12 | 2.0 | +++ |
| Ms13 | 1.2 | +++ |
| Ms14 | 1.1 | ++ |
| Ms15 | 1.8 | +++ |
| Ms16 | 0.8 | ++++ |
| Ms17 | 1.4 | +++ |

TABLE 5-continued

| Specificity of Murine anti-CLDN18.2 Antibodies | | |
| mAb | CHO-18.2 binding, EC50 nM | PATU8988S binding |
| --- | --- | --- |
| Ms18 | 1.3 | +++ |
| Ms19 | 2.3 | +++ |
| Ms20 | 1.3 | +++ |
| Ms21 | 1.5 | +++ |
| Ms22 | 2.6 | +++ |

Similarly, as shown in FIG. 4A, representative purified human anti-Claudin 18.2 antibodies bind to the CHO-CLDN18.2 cells, but not the CHO-CLDN18.1 cells when using 10 μg/ml of antibodies in the study.

The complete set of dose-dependent binding data of the human anti-Claudin18.2 lead panel is summarized in Table 6. The group of 17 purified Claudin 18.2 antibodies binds to the CHO CLDN18.2 with EC50 values ranging from 0.77 nM to 19 nM. Representative clone data is demonstrated in FIG. 4B. Clones Hu-2, Hu-9, and Hu-10 exhibited binding EC50 of 1.5, 1.1 and 1.5 nM.

TABLE 6

| Specificity of Human anti-CLDN18.2 Antibodies | | |
| mAb | CHO-18.2 binding, EC50 nM | PATU8988S binding |
| --- | --- | --- |
| Hu-1 | 3.6 | ++ |
| Hu-2 | 1.5 | +++ |
| Hu-3 | 1.3 | +++ |
| Hu-4 | 5.2 | ++ |
| Hu-5 | 4.5 | + |
| Hu-6 | 1.5 | +++ |
| Hu-7 | 1.0 | ++++ |
| Hu-8 | 3.7 | ++ |
| Hu-9 | 1.1 | ++++ |
| Hu-10 | 1.5 | ++++ |
| Hu-11 | 17 | ++ |
| Hu-12 | 1.2 | ++++ |
| Hu-13 | 5.6 | ++ |
| Hu-14 | 19 | + |
| Hu-16 | 12 | + |
| Hu-17 | 6.2 | + |
| Hu-18 | 0.8 | + |

Example 3: Binding Affinity of Claudin18.2 Antibodies to Tumor Cell Lines Expressing Claudin18.2

Target protein density and glycosylation status vary from cell type to cell type. The binding affinity and activity of affinity dependent mechanisms, such as ADCC and CDC, are significantly impacted by the target density and glycosylation status. Effects determined using cell lines that endogenously express Claudin18.2 have more translational relevance to the efficacy of anti-Claudin18.2 antibodies.

Tumor cells were plated in complete media containing RPMI1640 with +10% FBS, then incubated overnight at 37° C., Claudin18.2 antibodies were serial diluted and added to the assay plates, incubated at 4° C. for 2 hours, followed by fixing cells and further staining the cells for 30 minutes with Alexa Fluor® 488 Goat Anti-Human IgG (H+L) secondary antibody (invitrogen Cat #A-11013) for detection. The binding was assessed by imaging the cells and quantifying the fluorescence intensity using a Biotek Cytation.

Figure 5:
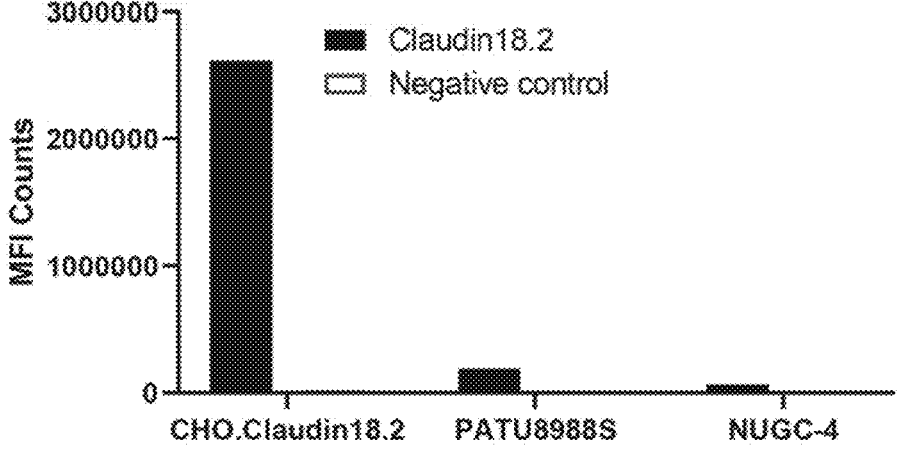

The relative expression level of different types of cells is provided in FIG. 5. Evaluation of the Claudin18.2 expression level in recombinant CHO-Claudin18.2 cells engineered to overexpress Claudin18.2 side by side with the gastric tumor cell line NUGC-4 and the pancreatic tumor cell line PATU8988S reveals that the CHO-Claudin18.2 expression level is more than 100-fold higher than the endogenous expression level of NUGC-4 and PATU8988S cells.

The disclosed anti-CLDN18.2 antibodies demonstrate binding to the pancreatic tumor cell line PATU8988S (see Tables 5 and 6, above) with EC50 values ranging from less than 2 nM to about 100 nM. The strength of the binding are reported in Table 5 and Table 6 in four categories, the strongest binding with EC50 values less than 2 nM are defined as "++++", binding EC50 values between 2 nM and 20 nM are defined as "+++", binding EC50 values between 20 nM and 100 nM are marked as "++", and weak binding EC50 about 100 nM were indicated as "+".

Figure 6A:
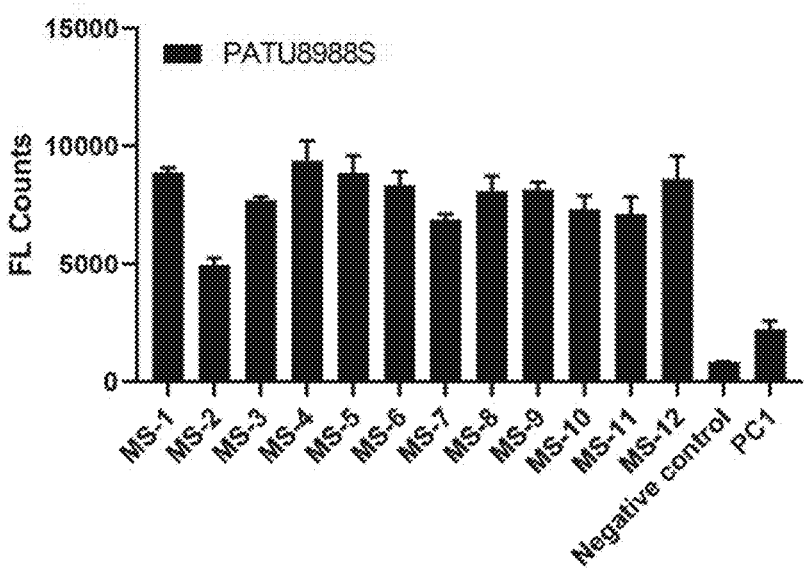
Figure 6B:
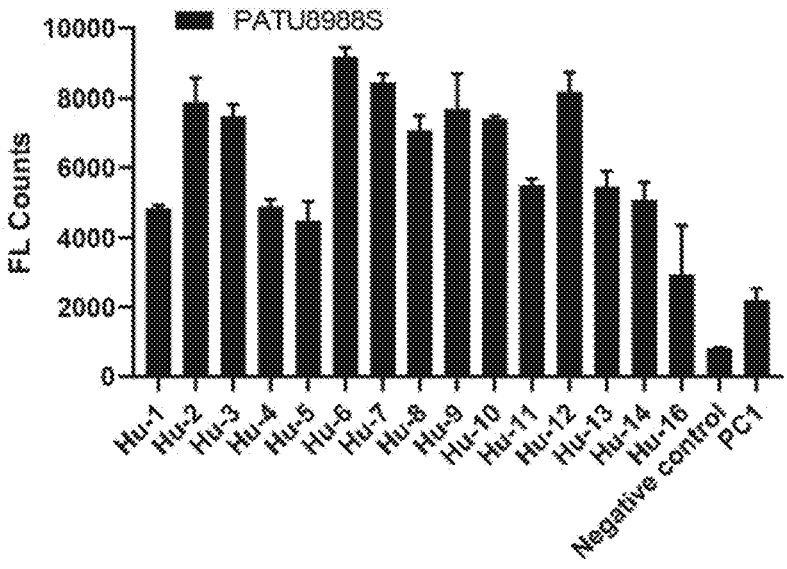

As shown in FIGS. 6A and 6B, the binding of anti-claudin18.2 antibody panels exhibited better binding affinities to PATU8988S cells than the in-house positive control PC1. When 20 µg/ml antibodies were used to stain the cells, the binding fluorescence intensity of PC1 is significantly lower than the fluorescence intensity of Ms1-10 and Hu1-16 antibodies.

Figure 7:
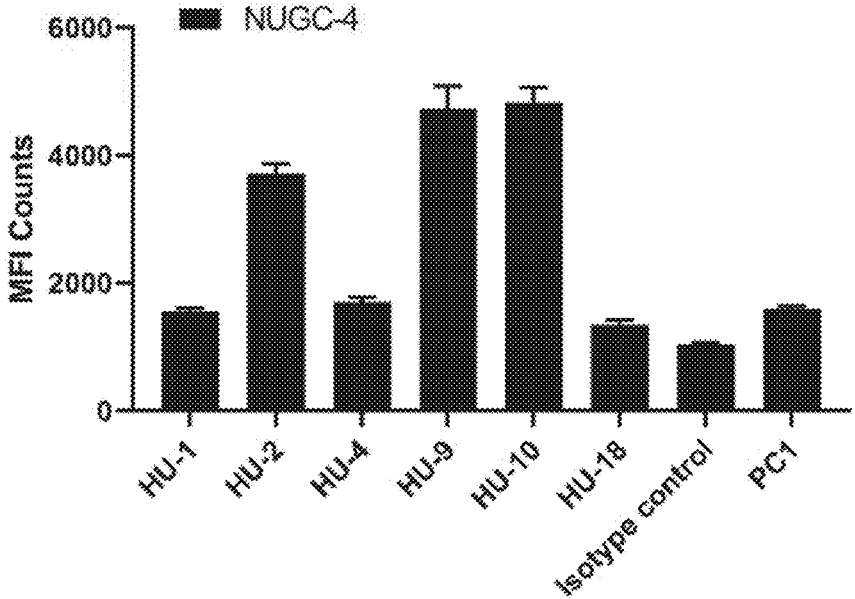
FIG. 7 is a bar graph showing the binding of human anti-Claudin18.2 antibodies to tumor cell line NUGC-4.

Similarly, the binding affinity of the antibodies Hu-2, Hu-9 and Hu-10 in the human antibody panel exhibited better binding affinities to the human gastric tumor cell line NUGC-4, shown by representative data in FIG. 7.

Figure 8:
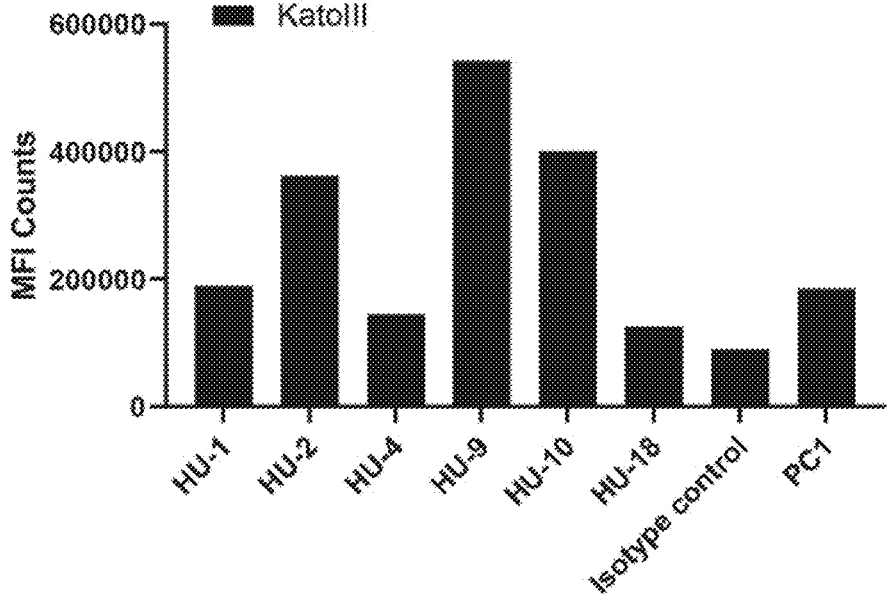
FIG. 8 is a bar graph showing the binding of human anti-Claudin18.2 antibodies to tumor cell line KatoIII.

To further evaluate anti-claudin18.2 Ab binding affinity to tumor cells, another human gastric tumor cell line, KATOIII that endogenously expresses claudin18.2 was used in a flow cytometry binding assay (FIG. 8). Briefly, KatoIII cells were plated in complete media containing RPMI1640 with +10% FBS, Claudin18.2 antibodies were serial diluted and added to the assay plates, incubated at 4° C. for 2 hours, followed by fixing cells and further staining the cells for 30 minutes with Alexa Fluor® 488 Goat Anti-Human IgG (H+L) secondary antibody (Invitrogen Cat #A-11013) for detection.

Antibody binding was assessed by flow cytometry instrument IQUE plus (Sartorius, Göttingen, Germany). As shown in FIG. 8, when 6.67 µg/ml antibodies were used to stain the cells, the binding fluorescence intensity of the PC1 antibody in-house iMAb362 is significantly lower than the fluorescence intensity of Hu-2, Hu-9, and Hu-10 antibodies.

Example 4: Antibody-Dependent Cellular Cytotoxicity (ADCC)

Antibody-dependent cellular cytotoxicity (ADCC) of Claudin18.2 antibodies bound to Claudin18.2 positive cells was measured by a bioluminescence assay to determine the activity of the antibodies that specifically bind and activate mouse FcγRIV. Cells stably expressing CLDN18.2, either recombinant protein expressed by transfected CHO cells or a human cell line expressing endogenous CLDN18.2, or negative cells were plated in complete media containing F12+10% FBS, the cells were incubated overnight at 37° C. Claudin18.2 antibodies were then serial diluted and added together with effector cells. Cell viability was detected using a Promega bioluminescence assay following the manufacturer's instruction (Promega, cat #M1201).

As shown in Table 7, representative human Claudin 18.2 antibodies, which have human variable regions with mouse IgG2a Fc, induced ADCC with EC50 values ranging from 0.77 nM to 7.09 nM. Representative data is demonstrated in FIG. 9. Antibodies Hu-2, Hu-7, and Hu-9 exhibited ADCC EC50 of 3.51, 3.52, and 1.10 nM. An unrelated Mouse IgG2a antibody that is not specific for CLDN18.2 shows no activity in the assay. The PC1 antibody engineered to comprise a human IgG1 Fc, had an EC50 of 0.66 nM in a similar assay when adding human effector cells (Data not shown).

TABLE 7

| Antibody dependent cellular cytotoxicity (ADCC) Activity | |
| --- | --- |
| mAb | CHO-18.2 EC50 nM |
| Hu-1 | 0.77 |
| Hu-2 | 3.51 |
| Hu-3 | 3.11 |
| Hu-4 | 2.39 |
| Hu-5 | 7.09 |
| Hu-6 | 4.80 |
| Hu-7 | 3.52 |
| Hu-8 | 1.42 |
| Hu-9 | 1.10 |
| Hu-10 | 1.25 |
| Hu-11 | 1.51 |
| Hu-12 | 2.26 |
| Hu-13 | 1.17 |
| Hu-14 | 1.51 |
| Hu-16 | 3.09 |

Example 5: Endocytosis Screening

Endocytosis of the disclosed CLDN18.2-specific antibodies bound to Claudin18.2 positive cells was measured by a cytotoxicity based endocytosis assay that used the co-internalization of the target bound antibody together with an anti-Human IgG Fc-MMAF Antibody.

Cells stably expressing Claudin 18.2 or negative cells were plated in complete media containing F12+10% FBS, the cells were incubated overnight at 37° C. Claudin18.2 antibodies were then serial diluted and added together with anti-Human IgG Fc-MMAF antibody to the assay plates and incubated at 37° C. for 72 hours. Cell viability was detected using a Promega Cell-titer Glo bioluminescence assay (Promega, cat #7570) following the manufacturer's instruction.

As demonstrated in Table 8, the lead panel of purified murine Claudin 18.2 antibodies induced endocytosis derived cell toxicity in CHO CLDN18.2 cells with EC50 values ranging from 0.71-2.55 nM.

Similarly, as shown in Table 9, the Trianni panel of purified human Claudin 18.2 antibodies induced endocytosis derived cell toxicity in CHO CLDN18.2 with EC50 values ranging from 0.85 nM to 13.39 nM. Representative clone data is demonstrated in FIG. 10. Clones Hu-2, Hu-7, Hu-9, and Hu-11 exhibited endocytosis derived cytotoxicity EC50 of 1.43, 1.65, 0.85 and 1.31 nM, respectively.

The lead panel antibodies also exhibited endocytosis derived cell cytotoxicity in a pancreatic tumor cell line PATU8988S which endogenously expresses Claudin18.2, but did not exhibit endocytosis derived cell killing activity in a CHO CLDN18.1 cell line stably expressing Claudin18.1 (data not shown).

TABLE 8

| Endocytosis of Murine anti-Claudin18.2 mAbs | |
| --- | --- |
| Clone name | CHO-18.2 EC50 nM |
| Ms1 | 1.09 |
| Ms2 | 2.55 |
| Ms3 | 1.14 |
| Ms4 | 0.98 |
| Ms5 | 1.43 |
| Ms6 | 1.26 |
| Ms7 | 1.12 |
| Ms8 | 1.08 |
| Ms9 | 1.10 |
| Ms10 | 0.96 |
| Ms11 | 1.30 |
| Ms12 | 1.07 |
| Ms13 | 0.71 |
| Ms14 | 1.02 |
| Ms15 | 1.15 |
| Ms16 | 1.00 |
| Ms17 | 0.81 |
| Ms18 | 1.39 |
| Ms19 | 1.36 |
| Ms20 | 1.07 |
| Ms21 | 0.95 |
| Ms22 | 1.61 |

TABLE 9

| Endocytosis of Human anti-Claudin18.2 mAbs | |
| --- | --- |
| Clone name | CHO-18.2 EC50 nM |
| Hu-1 | 1.61 |
| Hu-2 | 1.43 |
| Hu-3 | 1.23 |
| Hu-4 | 1.55 |
| Hu-5 | 13.39 |
| Hu-6 | 1.69 |
| Hu-7 | 1.65 |
| Hu-8 | 1.00 |
| Hu-9 | 0.85 |
| Hu-10 | 0.85 |
| Hu-11 | 1.31 |
| Hu-12 | 2.01 |
| Hu-13 | 2.16 |
| Hu-14 | 1.51 |
| Hu-16 | 3.09 |

Example 6: Enhanced Antibody-Dependent Cellular Cytotoxicity (ADCC)

The ADCC activity of Claudin18.2 antibodies bound to Claudin18.2 positive cells was measured by a bioluminescence assay to determine the activity of the antibodies that specifically bind and activate human FcγRIIIa. CHO cells stably expressing CLDN18.2, or negative cells, were plated in complete media containing F12+10% FBS, the cells were incubated overnight at 37° C. Claudin18.2 antibodies were then serial diluted and added together with effector cells. Cell viability was detected using a Promega biolumines-cence assay following the manufacturer's instruction (Promega, cat #7010).

As shown in FIG. 13A, the unmodified anti-Claudin18.2 antibody NBL-014 and the Fc modified antibodies NBL-014P, comprising point mutations introduced to enhance ADCC activity, and NBL-014G, an Fc-modified variant produced in HEK cells under conditions selected to express an antibody characterized by low, or no IgG core fucose (e.g., non- or afucosylated), induced enhanced ADCC activity in CHO-claudin 18.2 cells and PATU8988S cells.

In high target density CHO-claudin18.2 cells, NBL-014P and NBL-014G exhibited EC50 values of 0.06 nM to 0.02 nM, 10-fold and 35-fold better than the unmodified parental NBL-014 antibody, which has an ADCC EC50 of 0.73 nM (FIG. 13A).

An alternative ADCC assay was also used to evaluate the anti-claudin18.2 antibody's ADCC activity by directly mea-suring the % target cell lysis using effector cell line NK92MI-CD16a. Briefly, CHO-Claudin18.2 target cells were stained with CFSE per manufacture's instruction, the cells were then seeded into a U-bottom 384 well plate, at 800 k/mL in RPMI medium (no antibiotics). Serial diluted Ab and isotype control were added into the plate. NK92MI cells were harvested and counted, and diluted to indicated con-centration, 320 k/mL, then 10 ul/well was added to have a final 1:5 ratio of NK92MI vs. tumor cells, incubated at 37° C., 5% $CO_2$ for 4 hours at 37° C. 5% $CO_2$, then taken out at room temp for 10 min. Dead cell dye 7-AAD (1:100) was added and mixed in the well, allowed to sit for 10 min, and the plate was then run on the FACS to determine the cell death/killing ability (gate on CFSE positive to define dead cell 7-AAD+).

As shown in FIG. 13B, the Fc modified antibodies NBL-014P and NBL-014G induced modestly enhanced ADCC activity in this assay format.

Example 7: Enhanced ADCC Activity in Tumor Cells Endogenously Expressing Claudin18.2

Compared to CHO-claudin18.2 cells overexpressing Claudin18.2, the human tumor cell lines PATU8988S and NUGC-4 endogenously express much less Claudin18.2 (FIG. 5). The anti-Claudin 18.2 antibodies were tested for their ADCC activity using the human tumor cell lines as target cells. The ADCC activity of Claudin18.2 antibodies was measured by a bioluminescence assay to determine the activity of the antibodies that specifically bind and activate human FcγRIIIa. Human cell lines expressing endogenous CLDN18.2 were plated in complete media containing RPMI1640+10% FBS, the cells were incubated overnight at 37° C.

Claudin18.2 antibodies were then serial diluted and added together with effector cells. Cell viability was detected using a Promega bioluminescence assay following the manufac-turer's instruction (Promega, cat #7010). In the PATU8988S cell line ADCC assay, NBL-014P and NBL-014G showed ADCC EC50 values of 0.06 nM, and 0.04 nM respectively, which are enhanced relative to the ADCC activity of paren-tal clone NBL-014 (EC50 of 0.12 nM, see FIG. 13A). Moreover, in this pancreatic cell model, the maximum of the ADCC effect upshifted ~33 fold over the parental antibody NBL-014's maximum ADCC response (FIG. 14B).

In NUGC-4 cell line, NBL-014P and NBL-014G showed ADCC EC50 of 0.04 nM, and 0.06 nM respectively, also enhanced from the parental clone NBL-014, which has an ADCC EC50 of 0.40 nM. Moreover, in this gastric cell assay the maximum of the ADCC effect upshifted ~3 fold over the parental antibody NBL-014's maximum ADCC response (FIG. 14A).

Example 8: Complement-Dependent Cellular Cytotoxicity (CDC) of Anti-Claudin18.2 Antibodies The capability of anti-claudin18.2 antibodies to induce CDC activity was first evaluated using the CHO cell line overexpressing claudin18.2. This flow cytometer-based CDC assay was done using pooled human serum from PeproTech (Rockyhill, N.J.). CHO-Claudin18.2 cells were seeded in a 384-well plate at 8,000 cells per well. 10 ul of selected antibodies were added, at a serial dilution starting with a concentration of 10 μg/ml. The plate was left to incubate for 15 minutes at 37° C. After the incubation, 10 ul of human serum was added to wells, with the final dilution at 1/16th per volume. The plate was then left to incubate for 2.5 hours at 37° C. 7AAD viability dye was added 10 minutes prior to iQue plus (flow cytometer) acquisition.

In high target density CHO-claudin18.2 cells, NBL-014P and NBL-014G exhibited potent EC50 values of 0.15 nM to 0.30 nM, similar to its un-engineered form NBL-014, which has a CDC EC50 of 0.22 nM (FIG. 15). Relative to the CDC activity of PC1 (in-house iMAb36) (EC50 value of 1.76), the observed EC50 activity of NBL-014 represents approximately a ~10 fold improvement.

The CDC activity of anti-claudin18.2 antibodies was further evaluated in the human tumor cell lines PATU8988S endogenously expressing claudin18.2. As Shown in FIG. 16, NBL-014, NBL-014P and NBL-014G all induced strong CDC activity in PATU8988S, with NBL-014P having the highest CDC % killing.

Example 9: Antibody-Dependent Cellular Phagocytosis (ADCP) of Anti-Claudin18.2 Antibodies The ability of anti-claudin18.2 antibodies to induce ADCP was assessed using a Promega bioluminescence assay. The assay uses CHO cells overexpressing claudin18.2 or NUGC cells as target cells. The effector cells were co-cultured with target cells in the presence of anti-claudin18.2 antibodies. The antibody binds to the target on target cells which in turn activate FcγRIIa on effector cells, resulting in NFAT-RE-mediated luciferase activity, that can be quantified using a Bio-Glo Luciferase Assay system.

Briefly, CHO-claudin18.2 or NUGC-4 cells were plated in assay buffer in white 384-well plates, 12000/20 ul/well (0.6M/ml). The effector cells were thawed and resuspended to 1M/ml and 10 ul was added to the assay plate (10000/well). Antibodies were diluted in assay buffer and added 10 l/well on top of the target cell. The cell plate was incubated overnight. On the next day, 20 ul of luc substrate was directly added according to manufacturer's instruction, the plate was spun down and read immediately.

The ADCP activity of anti-claudin18.2 antibodies NBL-014, NBL-014G and NBL-014P were shown in FIG. 17A (CHO-claudin18.2 cells) and FIG. 17B (NUGC-4 cells). When using a high-density CLDN18.2 target cell, the activity from the Fc engineered Abs was similar to that of their parental antibodies, while the ADCP activity of the in-house PC1 antibody (iMAb362) exhibited a high response but less potent activity.

Use of the human tumor cell line NUGC-4 (endogenous expression of CLDN18.2) to evaluate ADCP activity results in data indicating that the in-house PC1 antibody is 100 times less potent, but that its maximum activity is higher than NBL-014, NBL-014P and NBL-014G.

Based on these results, it appears that the ADCP activity of NBL-014 is potent regardless of the Claudin18.2 expression level, and that neither of the Fc modifications (protein-engineering or glycol-engineering) changed the potency of the observed activity. The EC50 values of NBL-014G and NBL-014P are similar to their parent clone NBL-014. In both cell lines tested, the CHO-Claudin18.2 and NUGC-4, NBL-14, NBL-14G and NBL-14P demonstrated better ADCP activity in terms of EC50 values than PC1. However, the ADCP effect at high antibody concentration of 10 μg/ml of PC1 has two-fold higher response than NBL-014.

Example 10: Anti-Tumor Efficacy of Anti-Claudin18.2 Antibodies in a PATU8988S-Overexpressing Claudin18.2 Subcutaneous Tumor Model of Pancreatic Cancer 6-7 week old female BALB/c nude mice were injected with $5 \times 10^6$ viable PATU8988S-overexpressing Claudin18.2 cells in 0.1 ml PBS subcutaneously into the right flank. Three days later, mice were randomly sorted into groups (N=10) and treatment by intraperitoneal injection was initiated (Day 0). Group 1 received PBS control; Group 2 received 200 ug of isotype antibody control, Group 3 received 200 ug of NBL-014, and Group 4 received 200 ug of PC1 antibody. Treatment was administered two times weekly for 4 weeks.

Body weights were measured twice weekly. Tumor volumes were determined at different time points using the formula $V=\frac{1}{2} \times L \times W \times W$, where L is the long dimension and W is the short dimension of the xenograft. Any mice with tumors over 2500 mm³ were sacrificed.

As shown in FIG. 18A, the tested antibody NBL-014 and PC1 inhibited tumor size growth. On day 34 of the study, the mice were sacrified and the tumors were taken out to measure the weight. Both NBL-014 and in-house PC1 antibody (iMAb362) showed potent anti-tumor efficacy using tumor weight as the indicator (FIG. 18B).

Example 11: Anti-Tumor Efficacy of Anti-Claudin18.2 Antibodies in a NUGC-4 Subcutaneous Model of Gastric Cancer 6-7 week old female BALB/c nude mice were injected with $5 \times 10^6$ viable NUGC-4 cells in 0.1 ml PBS subcutaneously into the right flank. Three days later, mice were randomly sorted into groups (N=10) and treatment by intraperitoneal injection was initiated (Day 0). Group 1 received PBS control; Group 2 received 200 ug of NBL-014, and Group 3 received 200 ug of PC1 antibody The treatment was administered two times weekly for 5 weeks.

Body weights were measured twice weekly. Tumor volumes were determined at different time points using the formula $V=\frac{1}{2} \times L \times W \times W$, where L is the long dimension and W is the short dimension of the xenograft. Any mice with tumors over 2500 mm³ were sacrificed.

As shown in FIG. 19, the tested antibody NBL-014 inhibited tumor growth. On day 35 of the study, both NBL-014 and PC1 showed significant anti-tumor efficacy. NBL-014 exhibited better anti-tumor activity than in-house PC1 antibody (iMAb362).

Example 12: Anti-Tumor Efficacy of Fc Engineered Anti-Claudin18.2 Antibody in PBMC Humanized NUGC-4 Subcutaneous Model of Gastric Cancer To investigate the therapeutic potential of an Fc engineered anti-Clandin18.2 antibody, NOG-MHC I/II-2 KO (NOD.Cg-B2m$^{em1Tac}$ Prkdc$^{scid}$ H2-Ab1$^{tm1Doi}$ Il2rg$^{tm1Sug}$/JicTac) mice from Jackson laboratory were chosen to use because of the extended treatment window without GVHD on-set.

Briefly, 6-7 week old female NOG dko mice were inoculated with $5 \times 10^6$ viable NUGC-4 cells in 0.1 ml PBS subcutaneously into the right flank. Three days later, peripheral blood mononuclear cells (PBMCs) were thawed and counted. $1 \times 10^7$ PBMC diluted in 300 ul PBS was engrafted to each mouse through the tail vein. The mice were randomly sorted into groups, and treatment by intraperitoneal injection of antibodies was initiated (Day 0). Group 1 received PBS with PBMC; Group 2 received 200 ug of NBL-014, which has an engineered human IgG1 Fc.

The treatment was administered two times weekly for 5 weeks. The PBMC engraft was repeated 4 times once a week. The body weights of the mice were measured twice weekly. Tumor volumes were determined at different time points using the formula $V = \frac{1}{2} * L \times W \times W$, where L is the long dimension and W is the short dimension of the xenograft. Any mice with tumors over 2500 mm3 were sacrificed.

As Shown in FIGS. 20A and 20B, the group received NBL-014 showed significantly reduced tumor volume (FIG. 20A) and tumor weight (FIG. 20B) relative to the control group.

---

What is claimed is:

1. An antibody drug conjugate comprising an isolated fully human anti-human CLDN18.2 antibody or antigen-binding fragment thereof conjugated to one or more therapeutic agents, wherein the antibody does not bind to human CLDN18.1 and the antibody comprises:

(a) a heavy chain variable region comprising CDR1: SEQ ID NO: 221, CDR2: SEQ ID NO: 222, CDR3: SEQ ID NO: 223 and a light chain variable region comprising CDR1: SEQ ID NO: 224, CDR2: SEQ ID NO: 225, CDR3: SEQ ID NO: 226;

(b) a heavy chain variable region comprising CDR1: SEQ ID NO: 227, CDR2: SEQ ID NO: 228, CDR3: SEQ ID NO: 229 and a light chain variable region comprising CDR1: SEQ ID NO: 230, CDR2: SEQ ID NO: 231, CDR3: SEQ ID NO: 232;

(c) a heavy chain variable region comprising CDR1: SEQ ID NO: 233, CDR2: SEQ ID NO: 234, CDR3: SEQ ID NO: 235 and a light chain variable region comprising CDR1: SEQ ID NO: 236, CDR2: SEQ ID NO: 237, CDR3: SEQ ID NO: 238;

(d) a heavy chain variable region comprising CDR1: SEQ ID NO: 251, CDR2: SEQ ID NO: 252, CDR3: SEQ ID NO: 253 and a light chain variable region comprising CDR1: SEQ ID NO: 254, CDR2: SEQ ID NO: 255, CDR3: SEQ ID NO: 256;

(e) a heavy chain variable region comprising CDR1: SEQ ID NO: 257, CDR2: SEQ ID NO: 258, CDR3: SEQ ID NO: 259 and a light chain variable region comprising CDR1: SEQ ID NO: 260, CDR2: SEQ ID NO: 261, CDR3: SEQ ID NO: 262;

(f) a heavy chain variable region comprising CDR1: SEQ ID NO: 269, CDR2: SEQ ID NO: 270, CDR3: SEQ ID NO: 271 and a light chain variable region comprising CDR1: SEQ ID NO: 272, CDR2: SEQ ID NO: 273, CDR3: SEQ ID NO: 274;

(g) a heavy chain variable region comprising CDR1: SEQ ID NO: 275, CDR2: SEQ ID NO: 276, CDR3: SEQ ID NO: 277 and a light chain variable region comprising CDR1: SEQ ID NO: 278, CDR2: SEQ ID NO: 279, CDR3: SEQ ID NO: 280; or (h) a heavy chain variable region comprising CDR1: SEQ ID NO: 287, CDR2: SEQ ID NO: 288, CDR3: SEQ ID NO: 289 and a light chain variable region comprising CDR1: SEQ ID NO: 290, CDR2: SEQ ID NO: 291, CDR3: SEQ ID NO: 292.

2. The antibody drug conjugate of claim 1, wherein the therapeutic agent is selected from the group consisting of a radioisotope, a drug, and a cytotoxin.

3. The antibody drug conjugate of claim 1, wherein the therapeutic agent is selected from the group consisting of antimetabolites, alkylating agents, anthracyclines, antibiotics, anti-mitotic agents, photosensitizing agent, and immunosuppressant.

4. The antibody drug conjugate of claim 1, wherein the therapeutic agent comprises a cytotoxic agent.

5. The antibody drug conjugate of claim 4, wherein the cytotoxic agent is selected from the group consisting of anti-tubulin agents, DNA minor groove binders, DNA replication inhibitors, alkylating agents, anthracyclines, antibiotics, antifolates, antimetabolites, chemotherapy sensitizers, duocarmycins, etoposides, fluorinated pyrimidines, iono-phores, nitrosoureas, platinols, pre-forming compounds, purine antimetabolites, puromycins, radiation sensitizers, steroids, taxanes, topoisomerase inhibitors, and vinca alka-loids.

6. An antibody drug conjugate comprising an isolated fully human anti-human CLDN18.2 antibody or antigen-binding fragment thereof conjugated to one or more thera-peutic agents, wherein the antibody does not bind to human CLDN18.1 and the antibody comprises:

(a) a heavy chain variable region sequence of SEQ ID NO: 185 and a light chain variable region sequence of SEQ ID NO: 186;

(b) a heavy chain variable region sequence of SEQ ID NO: 187 and a light chain variable region sequence of SEQ ID NO: 188;

(c) a heavy chain variable region sequence of SEQ ID NO: 189 and a light chain variable region sequence of SEQ ID NO: 190;

(d) a heavy chain variable region sequence of SEQ ID NO: 195 and a light chain variable region sequence of SEQ ID NO: 196;

(e) a heavy chain variable region sequence of SEQ ID NO: 197 and a light chain variable region sequence of SEQ ID NO: 198;

(f) a heavy chain variable region sequence of SEQ ID NO: 201 and a light chain variable region sequence of SEQ ID NO: 202;

(g) a heavy chain variable region sequence of SEQ ID NO: 203 and a light chain variable region sequence of SEQ ID NO: 204; or (h) a heavy chain variable region sequence of SEQ ID NO: 207 and a light chain variable region sequence of SEQ ID NO: 208.

7. The antibody drug conjugate of claim 6, wherein the therapeutic agent is selected from the group consisting of a radioisotope, a drug, and a cytotoxin.

8. The antibody drug conjugate of claim 6, wherein the therapeutic agent is selected from the group consisting of antimetabolites, alkylating agents, anthracyclines, antibiot-ics, anti-mitotic agents, photosensitizing agent, and immu-nosuppressant.

9. The antibody drug conjugate of claim 6, wherein the therapeutic agent comprises a cytotoxic agent.

10. The antibody drug conjugate of claim 9, wherein the cytotoxic agent is selected from the group consisting of anti-tubulin agents, DNA minor groove binders, DNA rep-lication inhibitors, alkylating agents, anthracyclines, antibi-otics, antifolates, antimetabolites, chemotherapy sensitizers, duocarmycins, etoposides, fluorinated pyrimidines, iono-phores, nitrosoureas, platinols, pre-forming compounds, purine antimetabolites, puromycins, radiation sensitizers, steroids, taxanes, topoisomerase inhibitors, and vinca alka-loids.

* * * * *